US012721841B2

(12) United States Patent
Kanoh et al.

(10) Patent No.: US 12,721,841 B2
(45) **Date of Patent: *Sep. 1, 2026**

(54) COMPOSITION CONTAINING ARYLAMIDE DERIVATIVE

(71) Applicant: Chugai Seiyaku Kabushiki Kaisha, Tokyo (JP)

(72) Inventors: Takeo Kanoh, Tokyo (JP); Shinichi Nakae, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 626 days.

This patent is subject to a terminal disclaimer.

(21) Appl. No.: 18/016,691

(22) PCT Filed: Jul. 21, 2021

(86) PCT No.: PCT/JP2021/027316

§ 371 (c)(1), (2) Date: Jan. 18, 2023

(87) PCT Pub. No.: WO2022/019329

PCT Pub. Date: Jan. 27, 2022

(65) Prior Publication Data

US 2023/0270730 A1 Aug. 31, 2023

(30) Foreign Application Priority Data

Jul. 22, 2020 (JP) ................................ 2020-125822

(51) Int. Cl.

*A61K 31/44* (2006.01)
*A61K 9/20* (2006.01)

(52) U.S. Cl.

CPC ............ *A61K 31/44* (2013.01); *A61K 9/2013* (2013.01); *A61K 9/2018* (2013.01); *A61K 9/2054* (2013.01)

(58) Field of Classification Search

CPC ..................................................... A61K 31/44

See application file for complete search history.

(56) References Cited

U.S. PATENT DOCUMENTS

| | | | | |
|---|---|---|---|---|
| 11,964,950 | B2 | 4/2024 | Isshiki et al. | |
| 2007/0112038 | A1* | 5/2007 | Marlow ............... | C07D 413/14 546/288 |
| 2023/0002333 | A1 | 1/2023 | Isshiki et al. | |
| 2024/0246922 | A1 | 7/2024 | Isshiki et al. | |
| 2024/0327355 | A1 | 10/2024 | Kuwata et al. | |

FOREIGN PATENT DOCUMENTS

| | | | |
|---|---|---|---|
| EP | 1 674 452 | A | 6/2006 |
| EP | 1 780 197 | A | 5/2007 |
| EP | 1 982 982 | A | 10/2008 |
| EP | 4 094 804 | A | 11/2022 |
| JP | 2007-511613 | | 5/2007 |
| JP | 2013-508320 | | 3/2013 |
| WO | WO 00/041994 | A1 | 7/2000 |
| WO | WO 2005/028426 | | 3/2005 |
| WO | WO 2005/051300 | | 6/2005 |
| WO | WO 2006/011466 | | 2/2006 |
| WO | WO 2007/091736 | | 8/2007 |
| WO | WO 2011/047796 | | 4/2011 |
| WO | WO 2014/081025 | A1 | 5/2014 |
| WO | WO 2021/149776 | | 7/2021 |
| WO | WO 2022/258612 | A1 | 12/2022 |
| WO | WO 2023/003014 | A1 | 1/2023 |

OTHER PUBLICATIONS

Zhong, L., Zhu, X., Yu, B., & Su, W. "Influence of alkalizers on dissolution properties of telmisartan in solid dispersions prepared by cogrinding." Drug Development and Industrial Pharmacy, 2013, 40(12), 1660-1669.*

Hartung, "Optimization of allosteric MEK inhibitors. Part 1: Venturing into underexplored SAR territories." Bioorganic & Medicinal Chemistry Letters, 2013, 23(8), 2384-2390.*

Blumenschein Jr. et al., "A Randomized Phase II Study of the MEK1/MEK2 Inhibitor Trametinib (GSK1120212) Compared with Docetaxel in KRAS-Mutant Advanced Non-Small Cell Lung Cancer (NSCLC)," Annals of Oncology, 2015, 26(5):894-901.

Chenard-Poirier et al., "Results from the Biomarker-Driven Basket Trial of RO5126766 (CH5127566), a Potent RAF/MEK Inhibitor, in RAS- or RAF-Mutated Malignancies Including Multiple Myeloma," Journal of Clinical Oncology, 2017, vol. 35, No. 15, Supplement, Abstract No. 2506.

Cheng et al., "Current Development Status of MEK Inhibitors," Molecules, 2017, vol. 22, e1551.

Flaherty et al., "Combined BRAF and MEK Inhibition in Melanoma with Braf V600 Mutations," The New England Journal of Medicine, 2012, vol. 367, pp. 1694-1703.

Flaherty et al., "Improved Survival with MEK Inhibition in BRAF-Mutated Melanoma," The New England Journal of Medicine, 2012, vol. 367, pp. 107-114.

International Pharmaceutical Excipients Council Japan, "Japanese Pharmaceutical Excipients Directory 2016," Yakuji Nippo, Limited, Feb. 18, 2016, pp. 555-556 and 566-567.

(Continued)

*Primary Examiner* — David K O'Dell

(74) *Attorney, Agent, or Firm* — Fish & Richardson P.C.

(57) ABSTRACT

The present disclosure provides, for example, a composition comprising: 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt; and a dispersant (e.g., methylcellulose) and/or a basic compound (e.g., meglumine). According to the present disclosure, there is provided a composition comprising a specific aryl amide derivative that has RAF/MEK complex-stabilizing activity and/or MEK-inhibiting activity and is useful for the treatment or prevention of a cell proliferative disorder, particularly a cancer, the composition having good properties with respect to the dissolution and/or stability of the aryl amide derivative in the composition.

23 Claims, 22 Drawing Sheets

(56) References Cited

OTHER PUBLICATIONS

Ishii et al., "Enhanced Inhibition of ERK Signaling by a Novel Allosteric MEK Inhibitor, CH5126766, that Suppresses Feedback Reactivation of RAF Activity," Cancer Research 2013, 73(13):4050-4060.

Jänne et al., "Selumetinib Plus Docetaxel Compared with Docetaxel Alone and Progression-Free Survival in Patients with KRAS-Mutant Advanced Non-Small Cell Lung Cancer: The SELECT-1 Randomized Clinical Trial," JAMA, 2017, 317(18):1844-1853.

Lito et al., "Disruption of CRAF-Mediated MEK Activation is Required for Effective MEK Inhibition in KRAS Mutant Tumors," Cancer Cell, 2014, 25(5):697-710.

Ryan et al., "Therapeutic Strategies to Target RAS-Mutant Cancers," Nature Reviews Clinical Oncology, 2018, vol. 15, pp. 709-720.

Zhao et al., "The Clinical Development of MEK Inhibitors," Nature Reviews Clinical Oncology, 2014, vol. 11, pp. 385-400.

International Search Report for PCT/JP2021/027316, mailed Aug. 31, 2021, 7 pages (with English translation).

International Preliminary Report on Patentability for PCT/JP2021/027316, dated Jan. 24, 2023, 12 pages (with English translation).

* cited by examiner

COMPOSITION CONTAINING ARYLAMIDE DERIVATIVE

CROSS-REFERENCE TO RELATED APPLICATIONS

This application is the National Stage of International Application No. PCT/JP2021/027316, filed on Jul. 21, 2021, which claims the benefit of Japanese Application No. 2020-125822, filed on Jul. 22, 2020.

TECHNICAL FIELD

The present disclosure relates to compositions comprising an aryl amide derivative.

BACKGROUND ART

MEK (mitogen-activated protein kinase kinase) is a serine/threonine kinase in the MAPK signaling pathway and is known to transmit signals intracellularly and to be closely involved in cell proliferation (see non patent document 1). MEK inhibitors that have been reported include PD0325901, CH4987655, trametinib, cobimetinib and selumetinib (see patent document 1 and non patent document 2), and their use either alone or in combination with RAF inhibitors has been reported to exhibit clinical effects against RAF-mutant cancers, such as BRAF-mutant malignant melanoma (see non patent documents 3 and 4).

It is also known that the clinical effects of some MEK inhibitors against RAS-mutant cancers such as RAS-mutant non-small cell lung cancer are less than satisfactory. In fact, it has been reported that selumetinib and trametinib showed poor effects in clinical trials for KRAS-mutant non-small cell lung cancer (see non patent documents 5 and 6).

CH5126766 (see patent document 2 and non patent documents 7 and 8), which is known not only as a MEK inhibitor but also as a RAF/MEK complex stabilizer, has been reported to exhibit a clinical effect against RAS-mutant non-small cell lung cancer (see non patent document 9). CH5126766 also reportedly stabilizes the RAF/MEK complex and inhibits increased MEK phosphorylation (feedback activation of the MAPK signaling pathway) (see non patent documents 7, 8 and 10). This feedback activation is thought to be one reason for the less than satisfactory clinical effects of some MEK inhibitors against RAS-mutant cancers (see non patent document 10).

CITATION LIST

Patent Literature

Patent document 1: WO 2006/011466

Patent document 2: WO 2007/091736

Non Patent Literature

Non patent document 1: Nature. 2018, vol. 15, p. 709-720

Non patent document 2: Molecules. 2017, vol. 22, el 551

Non patent document 3: N. Engl. J. Med. 2012, vol. 367, p. 107-114

Non patent document 4: N. Engl. J. Med. 2012, vol. 367, p. 1694-1703

Non patent document 5: JAMA. 2017, vol. 317, no. 18, p. 1844-1853

Non patent document 6: Ann. Oncol. 2015, vol. 26, no. 5, p. 894-901

Non patent document 7: Cancer Res. 2013, vol. 73, no. 13, p. 4050-4060

Non patent document 8: Cancer Cell. 2014, vol. 25, no. 5, p. 697-710

Non patent document 9: J. Clin. Oncol. 2017, vol. 35, no. 15, suppl., 2506

Non patent document 10: Nat. Rev. Clin. Oncol. 2014, vol. 11, p. 385-400

SUMMARY OF INVENTION

Technical Problem

Several RAF/MEK complex stabilizers or MEK inhibitors that are useful for the treatment or prevention of cell proliferative disorders (particularly cancers) are known, but at the current time the options available are still not sufficient to satisfy the varied needs of consumers.

In this situation, it has been found that specific aryl amide derivatives (compounds, salts or solvates according to (A1) to (A16) and (B1) to (B3) below) have RAF/MEK complex-stabilizing activity and/or MEK-inhibiting activity, and are useful for the treatment or prevention of cell proliferative disorders, particularly cancers. The present inventors have aimed to develop a formulation of such an aryl amide derivative.

However, with regard to a composition consisting of such an aryl amide derivative and, for example, lactose hydrate, the present inventors have found that when the composition is treated with an acidic solution, the dissolution of the aryl amide derivative into artificial intestinal fluid remarkably decreases, i.e., that when the composition is administered orally to a living organism, the aryl amide derivative may not be well absorbed in the living organism. Also, with regard to a composition consisting of such an aryl amide derivative and, for example, mannitol, the present inventors have found that the aryl amide derivative in the composition is easily degraded.

It is an object of the present disclosure to provide a composition comprising such an aryl amide derivative, the composition having good properties with respect to the dissolution and/or stability of the aryl amide derivative in the composition.

Solution to Problem

The present inventors have made intensive research to achieve the above object, and as a result, have found that the copresence of a dispersant in a composition could result in improved dissolution of the aryl amide derivative in the composition and the copresence of a basic compound in a composition could result in improved stability of the aryl amide derivative in the composition. The present inventors have thus completed inventions of the present disclosure.

The present disclosure provides a composition comprising an aryl amide derivative according to any one of (A1) to (A16) and (B1) to (B3) below and a dispersant.

The present disclosure also provides a composition comprising an aryl amide derivative according to any one of (A1) to (A16) and (B1) to (B3) below and a basic compound.

The present disclosure also provides a composition comprising an aryl amide derivative according to any one of (A1) to (A16) and (B1) to (B3) below, a dispersant, and a basic compound.

In the cases where a dispersant is contained, the composition of the present disclosure has good properties with respect to the dissolution of the aryl amide derivative in the composition. Specifically, for example, it exhibits high performance with respect to the dissolution of the aryl amide derivative into artificial intestinal fluid (e.g., FaSSIF (fasted state simulated intestinal fluid) or FeSSIF (fed state simulated intestinal fluid)) even after being treated with an acidic solution (e.g., Japanese Pharmacopoeia 1st fluid for dissolution test or FaSSGF (fasted state simulated gastric fluid)) for 60 minutes. That is, it is inferred that when the composition is administered orally to a living organism, the aryl amide derivative is well absorbed in the living organism.

In the cases where a basic compound is contained, the composition of the present disclosure has good properties with respect to the stability of the aryl amide derivative in the composition. Specifically, for example, when the composition is stored tightly stoppered at 80° C. for 2 weeks or at 40° C. for 3 months, the aryl amide derivative in the composition is not easily degraded and exhibits high storage stability. For example, in the case of the aryl amide derivative according to (A14) below, the content of a hydrolysis product thereof (the compound of formula (X) shown in Test Example 12 below) is, for example, 3.0% by weight or less with respect to the content of the aryl amide derivative even after it has been stored at 80° C. for 2 weeks.

Examples of the dispersant in the composition of the present disclosure include methylcellulose, polyvinyl alcohol, hydroxypropylcellulose, copolyvidone, hydroxypropylmethylcellulose, methacrylic acid copolymer, polyvinylpyrrolidone, and hypromellose acetate succinate, with methylcellulose, polyvinyl alcohol, and hydroxypropylcellulose being preferred, and methylcellulose being particularly preferred.

The content of the dispersant in the composition of the present disclosure is, for example, 0.1 to 20 parts by weight, preferably 0.2 to 10 parts by weight and more preferably 1 to 10 parts by weight, relative to 1 part by weight of the aryl amide derivative.

Examples of the basic compound in the composition of the present disclosure include meglumine, arginine, histidine, magnesium oxide, calcium silicate, and magnesium stearate, with meglumine and arginine being preferred, and meglumine being particularly preferred.

The content of the basic compound in the composition of the present disclosure is, for example, 0.2 to 40 parts by weight, preferably 0.5 to 20 parts by weight and more preferably 1 to 10 parts by weight, relative to 1 part by weight of the aryl amide derivative.

The aryl amide derivative contained in the composition of the present disclosure is described below.

In one aspect, the aryl amide derivative of the present disclosure is a compound, salt or solvate according to any one of (A1) to (A6) below.

(A1) A compound represented by general formula (1) below or a pharmaceutically acceptable salt thereof, or a pharmaceutically acceptable solvate of said compound or salt:

[Chemical Formula 1]

(1)

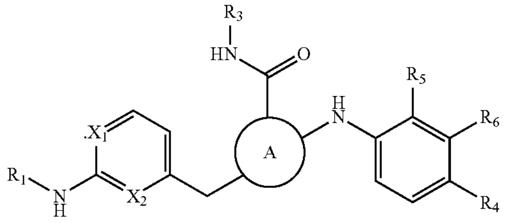

wherein:

ring A is a group represented by general formula (2), (3), (4) or (5) below (where the bonds denoted by *,  and * are bonded to $-NH-$, $-CONH-$ and $-CH_2-$, respectively):

[Chemical Formula 2]

(2)

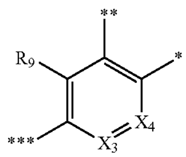

(3)

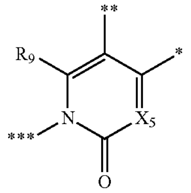

(4)

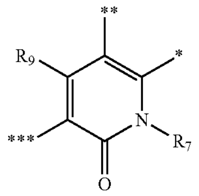

(5)

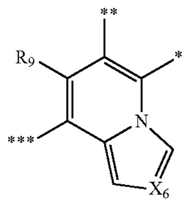

$X_1$, $X_2$, $X_3$, $X_4$, $X_5$ and $X_6$ are each independently $-CR_2=$ or $-N=$;

$R_2$ is a hydrogen atom, a halogen atom, or a C1-6 alkyl group;

$R_1$ is $-S(=O)_2-NH-R_8$ or $-S(=O)_2-R_8$;

$R_8$ is a hydrogen atom, a C1-6 alkyl group (the C1-6 alkyl group being optionally substituted with a halogen atom, a hydroxy group, a C1-6 alkoxy group, a C3-6 cycloalkyl group or a C3-6 heterocycloalkyl group), a monocyclic or bicyclic C3-6 cycloalkyl group (the C3-6 cycloalkyl group being optionally substituted with a C1-6 alkyl group or a C1-6 alkoxy group), or a monocyclic or bicyclic C3-6 heterocycloalkyl group;

$R_3$ is a hydrogen atom, a C1-6 alkyl group (the C1-6 alkyl group being optionally substituted with a halogen atom, a hydroxy group or a C1-6 alkoxy group), a C3-6 cycloalkyl group (the C3-6 cycloalkyl group being optionally substituted with a halogen atom or a C1-6 alkyl group), or a C1-6 alkoxy group (the C1-6 alkoxy group being optionally substituted with a halogen atom, a hydroxy group or a C1-6 alkoxy group);

$R_5$ is a halogen atom or a C1-6 alkyl group;

$R_6$ is a hydrogen atom, a halogen atom or a C1-6 alkyl group and $R_4$ is a hydrogen atom, a halogen atom, a C1-6 alkyl group, a C2-7 alkenyl group, a C2-7 alkynyl group, a C3-6 cycloalkyl group or a C1-6 alkylthio group, or $R_6$ and $R_4$ form an unsaturated hetero 5-membered ring together with the carbon atoms to which they are bonded;

$R_7$ is a hydrogen atom or a C1-6 alkyl group; and $R_9$ is a hydrogen atom, a halogen atom, or a C1-6 alkyl group.

(A2) The compound, salt or solvate according to (A1), wherein:

ring A is a group represented by general formula (2) or (4);

$R_8$ is a hydrogen atom, a C1-6 alkyl group (the C1-6 alkyl group being optionally substituted with a halogen atom, a hydroxy group or a C1-6 alkoxy group), or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_6$ is a hydrogen atom, a halogen atom or a C1-6 alkyl group and $R_4$ is a halogen atom or a cyclopropyl group; and $R_7$ is a hydrogen atom or a methyl group.

(A3) The compound, salt or solvate according to (A1), wherein the compound represented by general formula (1) is a compound represented by formula (6) below:

[Chemical Formula 3]

(6)

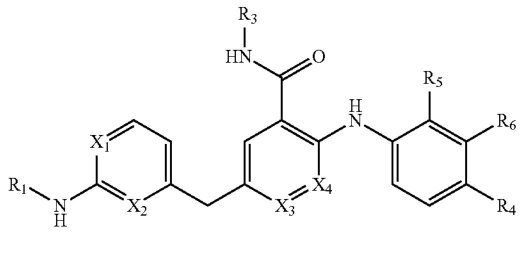

wherein:

$X_1$, $X_2$, $X_3$ and $X_4$ are each independently $—CR_2=$ or $—N=$;

$R_2$ is a hydrogen atom, a halogen atom, or a C1-6 alkyl group;

$R_1$ is $—S(=O)_2—NH—R_5$ or $—S(=O)_2—R_8$;

$R_8$ is a hydrogen atom, a C1-6 alkyl group (the C1-6 alkyl group being optionally substituted with a halogen atom, a hydroxy group or a C1-6 alkoxy group), or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_5$ is a halogen atom or a C1-6 alkyl group; and $R_6$ is a hydrogen atom, a halogen atom or a C1-6 alkyl group and $R_4$ is a halogen atom or a cyclopropyl group.

(A4) The compound, salt or solvate according to any one of (A1) to (A3), wherein:

$R_2$ is a hydrogen atom or a halogen atom;

$R_8$ is a C1-6 alkyl group (the C1-6 alkyl group being optionally substituted with a halogen atom or a C1-6 alkoxy group) or a monocyclic C3-6 cycloalkyl group (the C3-6 cycloalkyl group being optionally substituted with a C1-6 alkyl group);

$R_z$ is a hydrogen atom, a C1-6 alkyl group, a C3-6 cycloalkyl group, or a C1-6 alkoxy group (the C1-6 alkoxy group being optionally substituted with a hydroxy group);

$R_5$ is a halogen atom; and $R_6$ is a hydrogen atom and $R_4$ is a halogen atom or a cyclopropyl group.

(A5) The compound, salt or solvate according to any one of (A1) to (A3), wherein:

$R_2$ is a hydrogen atom or a fluorine atom;

$R_8$ is a C1-4 alkyl group (the C1-4 alkyl group being optionally substituted with a fluorine atom or a C1-4 alkoxy group) or a cyclopropyl group (the cyclopropyl group being optionally substituted with a C1-4 alkyl group);

$R_3$ is a hydrogen atom, a C1-4 alkyl group, a cyclopropyl group, or a C1-4 alkoxy group (the C1-4 alkoxy group being optionally substituted with a hydroxy group);

$R_5$ is a fluorine atom; and $R_6$ is a hydrogen atom and $R_4$ is an iodine atom or a cyclopropyl group.

(A6) The compound, salt or solvate according to any one of (A1) to (A3), wherein:

$R_2$ is a fluorine atom;

$R_1$ is $—S(=O)_2—NH—R_8$;

$R_8$ is a C1-4 alkyl group;

$R_3$ is a hydrogen atom or a cyclopropyl group;

$R_5$ is a fluorine atom; and $R_6$ is a hydrogen atom and $R_4$ is an iodine atom or a cyclopropyl group.

In another aspect, the aryl amide derivative of the present disclosure is a compound, salt or solvate according to any one of (A7) to (A10) below. The compounds, salts or solvates of (A7) below include the compounds, salts or solvates of (A1) to (A6).

(A7) A compound represented by general formula (11) below or a pharmaceutically acceptable salt thereof, or a pharmaceutically acceptable solvate of said compound or salt:

[Chemical Formula 4]

(11)

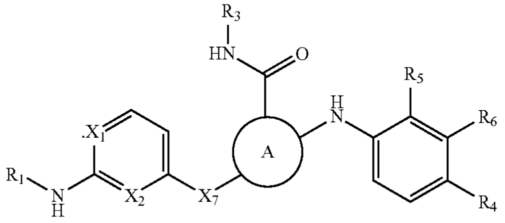

wherein:

ring A is a group represented by general formula (2), (3), (4) or (5) below (where the bonds denoted by *,  and * are bonded to —NH—, —CONH— and —$X_7$—, respectively):

[Chemical Formula 5]

(2)

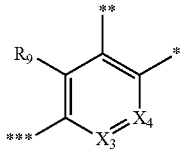

(3)

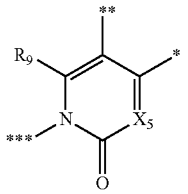

(4)

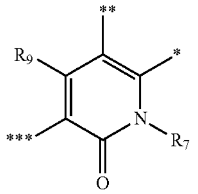

(5)

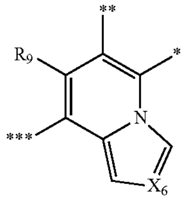

$X_1$, $X_2$, $X_3$, $X_4$, $X_5$ and $X_6$ are each independently —$CR_2$═ or —N═;

$R_2$ is a hydrogen atom, a halogen atom, or a C1-6 alkyl group;

$X_7$ is —$(CH_2)_m$— or —O— and m is 1, 2 or 3;

$R_1$ is —S(═O)$_2$—NH—$R_8$ or —S(═O)$_2$—$R_8$;

$R_8$ is a hydrogen atom, a C1-6 alkyl group (the C1-6 alkyl group being optionally substituted with a halogen atom, a hydroxy group, a C1-6 alkoxy group, a C3-6 cycloalkyl group or a C3-6 heterocycloalkyl group), a monocyclic or bicyclic C3-6 cycloalkyl group (the C3-6 cycloalkyl group being optionally substituted with a C1-6 alkyl group or a C1-6 alkoxy group), or a monocyclic or bicyclic C3-6 heterocycloalkyl group;

$R_3$ is a hydrogen atom, a C1-6 alkyl group (the C1-6 alkyl group being optionally substituted with a halogen atom, a hydroxy group or a C1-6 alkoxy group), a C3-6 cycloalkyl group (the C3-6 cycloalkyl group being optionally substituted with a halogen atom or a C1-6 alkyl group), or a C1-6 alkoxy group (the C1-6 alkoxy group being optionally substituted with a halogen atom, a hydroxy group or a C1-6 alkoxy group);

$R_5$ is a hydrogen atom, a halogen atom, or a C1-6 alkyl group;

$R_6$ is a hydrogen atom, a halogen atom or a C1-6 alkyl group and $R_4$ is a hydrogen atom, a halogen atom, a C1-6 alkyl group, a C2-7 alkenyl group, a C2-7 alkynyl group, a C3-6 cycloalkyl group or a C1-6 alkylthio group, or $R_6$ and $R_4$ form an unsaturated hetero 5-membered ring together with the carbon atoms to which they are bonded;

$R_7$ is a hydrogen atom or a C1-6 alkyl group; and $R_9$ is a hydrogen atom, a halogen atom, or a C1-6 alkyl group.

(A8) The compound, salt or solvate according to (A7), wherein:

ring A is a group represented by general formula (2) or (4);

$X_7$ is —$CH_2$—;

$R_8$ is a hydrogen atom, a C1-6 alkyl group (the C1-6 alkyl group being optionally substituted with a halogen atom, a hydroxy group or a C1-6 alkoxy group), or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_5$ is a halogen atom or a C1-6 alkyl group;

$R_6$ is a hydrogen atom, a halogen atom or a C1-6 alkyl group and $R_4$ is a halogen atom or a cyclopropyl group; and $R_7$ is a hydrogen atom or a methyl group.

(A9) The compound, salt or solvate according to (A7), wherein the compound represented by general formula (11) is a compound represented by general formula (6) below:

[Chemical Formula 6]

(6)

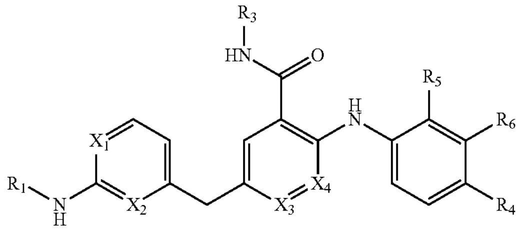

wherein:

$X_1$, $X_2$, $X_3$ and $X_4$ are each independently —$CR_2$═ or —N═;

$R_2$ is a hydrogen atom, a halogen atom, or a C1-6 alkyl group;

$R_1$ is —S(═O)$_2$—NH—$R_8$ or —S(═O)$_2$—$R_8$;

$R_8$ is a hydrogen atom, a C1-6 alkyl group (the C1-6 alkyl group being optionally substituted with a halogen atom, a hydroxy group or a C1-6 alkoxy group), or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_5$ is a halogen atom or a C1-6 alkyl group; and $R_6$ is a hydrogen atom, a halogen atom or a C1-6 alkyl group and $R_4$ is a halogen atom or a cyclopropyl group.

(A10) The compound, salt or solvate according to any one of (A7) to (A9), wherein:

$R_2$ is a hydrogen atom or a halogen atom;

$R_8$ is a C1-6 alkyl group (the C1-6 alkyl group being optionally substituted with a halogen atom or a C1-6 alkoxy group) or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_5$ is a halogen atom; and $R_6$ is a hydrogen atom and $R_4$ is a halogen atom or a cyclopropyl group.

In another aspect, the aryl amide derivative of the present disclosure is a compound, salt or solvate according to any one of (A11) to (A16) below. The compounds, salts or solvates of (A7) include the compounds, salts or solvates of (A11) to (A16) below.

(A11) A compound or a pharmaceutically acceptable salt thereof, or a pharmaceutically acceptable solvate of said compound or salt, said compound being selected from among:

N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), 2-(4-cyclopropyl-2-fluoroanilino)-3,4-difluoro-5-[[3-fluoro-2-(methylsulfamoylamino)pyridin-4-yl]methyl]benzamide (compound A-1), N-cyclopropyl-5-[[2-(ethylsulfamoylamino)-3-fluoropyridin-4-yl]methyl]-3,4-difluoro-2-(2-fluoro-4-iodoanilino)benzamide (compound A-4), N-cyclopropyl-3,4-difluoro-5-[[3-fluoro-2-(2-fluoroethylsulfamoylamino)pyridin-4-yl]methyl]-2-(2-fluoro-4-iodoanilino)benzamide (compound A-6), 3,4-difluoro-2-(2-fluoro-4-iodoanilino)-5-[[3-fluoro-2-(methylsulfamoylamino)pyridin-4-yl]methyl]-N-[(2-methylpropan-2-yl)oxy]benzamide (compound A-8), 3,4-difluoro-2-(2-fluoro-4-iodoanilino)-5-[[3-fluoro-2-(methylsulfamoylamino)pyridin-4-yl]methyl]-N-methoxybenzamide (compound A-13), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(propan-2-ylsulfamoylamino)pyridin-4-yl]methyl]benzamide (compound A-31), 3,4-difluoro-2-(2-fluoro-4-iodoanilino)-5-[[3-fluoro-2-(2-methoxyethylsulfamoylamino)pyridin-4-yl]methyl]benzamide (compound A-33), 3,4-difluoro-2-(2-fluoro-4-iodoanilino)-5-[[3-fluoro-2-(2-methylpropylsulfainoylamino)pyridin-4-yl]methyl]benzamide (compound A-34), 3,4-difluoro-2-(2-fluoro-4-iodoanilino)-5-[[3-fluoro-2-[(1-methylcyclobutyl)sulfamoylamino]pyridin-4-yl]methyl]benzamide (compound A-35), 3,4-difluoro-2-(2-fluoro-4-iodoanilino)-5-[[3-fluoro-2-(propylsulfamoylamino)pyridin-4-yl]methyl]benzamide (compound A-41), 3,4-difluoro-2-(2-fluoro-4-iodoanilino)-5-[[3-fluoro-2-(methylsulfamoylamino)pyridin-4-yl]methyl]-N-(2-hydroxyethoxy)benzamide (compound B-1), 5-[[3-(ethylsulfonylamino)-2-fluorophenyl]methyl]-3,4-difluoro-2-(2-fluoro-4-iodoanilino)benzamide (compound D-4), 5-[[3-(ethylsulfonylamino)-2-fluorophenyl]methyl]-3,4-difluoro-2-(2-fluoro-4-iodoanilino)-N-methoxybenzamide (compound E-1), 3,4-difluoro-2-(2-fluoro-4-iodoanilino)-5-[[2-fluoro-3-(methylsulfamoylamino)phenyl]methyl]benzamide (compound E-7), 3,4-difluoro-2-(2-fluoro-4-iodoanilino)-5-[[2-fluoro-3-(methanesulfonamide)phenyl]methyl]benzamide (compound E-13), 4-fluoro-2-(2-fluoro-4-iodoanilino)-5-[[3-fluoro-2-(methylsulfamoylamino)pyridin-4-yl]methyl]benzamide (compound I-1), N-cyclopropyl-2-(2-fluoro-4-iodoanilino)-5-[[3-fluoro-2-(methylsulfamoylamino)pyridin-4-yl]methyl]-1-methyl-6-oxopyridine-3-carboxamide (compound J-5), 3,4-difluoro-2-(2-fluoro-4-iodoanilino)-5-[[3-fluoro-2-[(1-methylcyclobutyl)sulfamoylamino]pyridin-4-yl]methyl]-N-methoxybenzamide (compound A-15), 3,4-difluoro-5-[[3-fluoro-2-(methylsulfamoylamino)pyridin-4-yl]methyl]-2-(2-fluoro-4-methylsulfanylanilino)benzamide (compound A-18), 2-(4-ethynyl-2-fluoroanilino)-3,4-difluoro-5-[[3-fluoro-2-(propylsulfamoylamino)pyridin-4-yl]methyl]benzamide (compound A-20), 2-(4-bromo-2-fluoroanilino)-3,4-difluoro-5-[[3-fluoro-2-(methylsulfamoylamino)pyridin-4-yl]methyl]benzamide (compound A-27), 2-(2-chloro-4-iodoanilino)-5-[[3-(ethylsulfonylamino)-2-fluorophenyl]methyl]-3,4-difluoro-N-methoxybenzamide (compound E-9), 3,4-difluoro-2-(2-fluoro-4-iodoanilino)-5-[[2-fluoro-3-(oxan-4-ylsulfonylamino)phenyl]methyl]benzamide (compound E-23), 2-[4-(difluoromethylsulfanyl)-2-fluoroanilino]-3,4-difluoro-5-[[3-fluoro-2-(methylsulfamoylamino)pyridin-4-yl]methyl]benzamide (compound H-1), 3,4-difluoro-2-[(4-fluoro-1-benzothiophen-5-yl)amino]-5-[[3-fluoro-2-(methylsulfamoylamino)pyridin-4-yl]methyl]benzamide (compound H-3), 3,4-difluoro-2-(2-fluoro-4-iodoanilino)-5-[3-fluoro-2-(methylsulfamoylamino)pyridin-4-yl]oxybenzamide (compound H-4), 2-(2-fluoro-4-iodoanilino)-5-[[3-fluoro-2-(methylsulfamoylamino)pyridin-4-yl]methyl]-N-methoxy-1-methyl-6-oxopyridine-3-carboxamide (compound J-8), 2-(2-fluoro-4-iodoanilino)-5-[[3-fluoro-2-(methylsulfamoylamino)pyridin-4-yl]methyl]-1-methyl-N-[(2-methylpropan-2-yl)oxy]-6-oxopyridine-3-carboxamide (compound J-10), 5-[[2-(ethylsulfamoylamino)-3-fluoropyridin-4-yl]methyl]-2-(2-fluoro-4-iodoanilino)-1-methyl-6-oxopyridine-3-carboxamide (compound J-14), 5-(2-fluoro-4-iodoanilino)-2-[[3-fluoro-2-(methylsulfamoylamino)pyridin-4-yl]methyl]pyridine-4-carboxamide (compound L-1), 5-(2-fluoro-4-iodoanilino)-8-[[3-fluoro-2-(methylsulfamoylamino)pyridin-4-yl]methyl]imidazo[1,5-a]pyridine-6-carboxamide (compound M-1), 5-fluoro-4-(2-fluoro-4-iodoanilino)-1-[[3-fluoro-2-(methylsulfamoylamino)pyridin-4-yl]methyl]-6-oxopyridine-3-carboxamide (compound N-1), 5-fluoro-4-(2-fluoro-4-iodoanilino)-1-[[3-fluoro-2-(propylsulfamoylamino)pyridin-4-yl]methyl]-6-oxopyridine-3-carboxamide (compound N-2), 4-(2-fluoro-4-iodoanilino)-1-[[3-fluoro-2-(methylsulfamoylamino)pyridin-4-yl]methyl]-5-methyl-6-oxopyridine-3-carboxamide (compound P-1), and 1-[[2-(ethylsulfonylamino)-3-fluoropyridin-4-yl]methyl]-4-(2-fluoro-4-iodoanilino)-5-methyl-6-oxopyridine-3-carboxamide (compound P-2).

(A12) A compound or a pharmaceutically acceptable salt thereof, or a pharmaceutically acceptable solvate of said compound or salt, said compound being selected from among:

N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), 2-(4-cyclopropyl-2-fluoroanilino)-3,4-difluoro-5-[[3-fluoro-2-(methylsulfamoylamino)pyridin-4-yl]methyl]benzamide (compound A-1), N-cyclopropyl-5-[[2-(ethylsulfamoylamino)-3-fluoropyridin-4-yl]methyl]-3,4-difluoro-2-(2-fluoro-4-iodoanilino)benzamide (compound A-4), N-cyclopropyl-3,4-difluoro-5-[[3-fluoro-2-(2-fluoroethylsulfamoylamino)pyridin-4-yl]methyl]-2-(2-fluoro-4-iodoanilino)benzamide (compound A-6), 3,4-difluoro-2-(2-fluoro-4-iodoanilino)-5-[[3-fluoro-2-(methylsulfamoylamino)pyridin-4-yl]methyl]-N-[(2-methylpropan-2-yl)oxy]benzamide (compound A-8), 3,4-difluoro-2-(2-fluoro-4-iodoanilino)-5-[[3-fluoro-2-(methylsulfamoylamino)pyridin-4-yl]methyl]-N-methoxybenzamide (compound A-13), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(propan-2-ylsulfamoylamino)pyridin-4-yl]methyl]benzamide (compound A-31), 3,4-difluoro-2-(2-fluoro-4-iodoanilino)-5-[[3-fluoro-2-(2-methoxyethylsulfamoylamino)pyridin-4-yl]methyl]benzamide (compound A-33), 3,4-difluoro-2-(2-fluoro-4-iodoanilino)-5-[[3-fluoro-2-(2-methyl propylsulfamoylamino)pyridin-4-yl]methyl]benzamide (compound A-34), 3,4-difluoro-2-(2-fluoro-4-iodoanilino)-5-[[3-fluoro-2-[(1-methylcyclobutyl)sulfamoylamino]pyridin-4-yl]methyl]benzamide (compound A-35), 3,4-difluoro-2-(2-fluoro-4-iodoanilino)-5-[[3-fluoro-2-(propylsulfamoylamino)pyridin-4-yl]methyl]benzamide (compound A-41), 3,4-difluoro-2-(2-fluoro-4-iodoanilino)-5-[[3-fluoro-2-(methylsulfamoylamino)pyridin-4-yl]methyl]-N-(2-hydroxyethoxy)benzamide (compound B-1), 5-[[3-(ethylsulfonylamino)-2-fluorophenyl]methyl]-3,4-difluoro-2-(2-fluoro-4-iodoanilino)benzamide (compound D-4), 5-[[3-(ethylsulfonylamino)-2-fluorophenyl]methyl]-3,4-difluoro-2-(2-fluoro-4-iodoanilino)-N-methoxybenzamide (compound E-1), 3,4-difluoro-2-(2-fluoro-4-iodoanilino)-5-[[2-fluoro-3-(methylsulfamoylamino)phenyl]methyl]benzamide (compound E-7), 3,4-difluoro-2-(2-fluoro-4-iodoanilino)-5-[[2-fluoro-3-(methanesulfonamide)phenyl]methyl]benzamide (compound E-13), 4-fluoro-2-(2-fluoro-4-iodoanilino)-5-[[3-fluoro-2-(methylsulfamoylamino)pyridin-4-yl]methyl]benzamide (compound I-1), and N-cyclopropyl-2-(2-fluoro-4-iodoanilino)-5-[[3-fluoro-2-(methylsulfamoylamino)pyridin-4-yl]methyl]-1-methyl-6-oxopyridine-3-carboxamide (compound J-5).

(A13) A compound or a pharmaceutically acceptable salt thereof, or a pharmaceutically acceptable solvate of said compound or salt, said compound being selected from among:

N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), and 2-(4-cyclopropyl-2-fluoroanilino)-3,4-difluoro-5-[[3-fluoro-2-(methylsulfamoylamino)pyridin-4-yl]methyl]benzamide (compound A-1).

(A14)

2-(4-Cyclopropyl-2-fluoroanilino)-3,4-difluoro-5-[[3-fluoro-2-(methylsulfamoylamino)pyridin-4-yl]methyl]benzamide (compound A-1) or a pharmaceutically acceptable salt thereof, or a pharmaceutically acceptable solvate of said compound or salt.

(A15)

2-(4-Cyclopropyl-2-fluoroanilino)-3,4-difluoro-5-[[3-fluoro-2-(methylsulfamoylamino)pyridin-4-yl]methyl]benzamide (compound A-1) or a sodium salt or potassium salt thereof, or a pharmaceutically acceptable solvate of said compound or salt.

(A16) A sodium salt of 2-(4-cyclopropyl-2-fluoroanilino)-3,4-difluoro-5-[[3-fluoro-2-(methylsulfamoylamino)pyridin-4-yl]methyl]benzamide (compound A-1).

The compounds, salts or solvates of (A1) to (A16) exhibit high RAF/MEK complex-stabilizing activity and can be used as active ingredients in therapeutic or prophylactic agents for cell proliferative disorders, particularly cancers (more specifically, RAS-mutant cancers). Therefore, a composition comprising a compound, salt or solvate of any one of (A1) to (A16) and a dispersant and/or a basic compound can be used as a pharmaceutical composition. Also, a composition comprising a compound, salt or solvate of any one of (A1) to (A16) and a dispersant and/or a basic compound can be used as a pharmaceutical composition for the treatment or prevention of a cell proliferative disorder, particularly a cancer.

In another aspect, the aryl amide derivative of the present disclosure is a compound, salt or solvate according to any one of (B1) to (B3) below.

(B1) A compound represented by general formula (1) below or a pharmaceutically acceptable salt thereof, or a pharmaceutically acceptable solvate of said compound or salt:

[Chemical Formula 7]

(1)

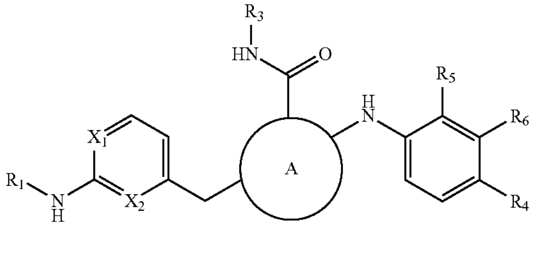

wherein:

ring A is a group represented by general formula (2), (3) or (4) below (where the bonds denoted by *,  and * are bonded to —NH—, —CONH— and —$CH_2$—, respectively):

[Chemical Formula 8]

(2)

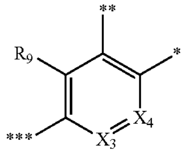

(3)

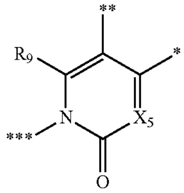

(4)

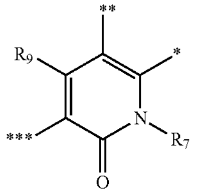

$X_1$, $X_2$, $X_3$, $X_4$ and $X_5$ are each independently —$CR_2$═ or —N═;

$R_2$ is a hydrogen atom, a halogen atom, or a C1-4 alkyl group;

$R_1$ is —S(═O)$_2$—NH—$R_8$ or —S(═O)$_2$—R;

$R_8$ is a C1-4 alkyl group (the C1-4 alkyl group being optionally substituted with a halogen atom, a hydroxy group, a C1-4 alkoxy group, a C3-6 cycloalkyl group or a C3-6 heterocycloalkyl group) or a C3-6 cycloalkyl group (the C3-6 cycloalkyl group being optional substituted with a C1-4 alkyl group);

$R_3$ is a hydrogen atom, a C3-6 cycloalkyl group, or a C1-6 alkoxy group;

$R_5$ is a halogen atom;

$R_6$ is a hydrogen atom and $R_4$ is a halogen atom or a C3-6 cycloalkyl group;

$R_7$ is a C1-4 alkyl group; and $R_y$ is a hydrogen atom.

(B2) A compound or a pharmaceutically acceptable salt thereof, or a pharmaceutically acceptable solvate of said compound or salt, said compound being selected from among:

2-(4-cyclopropyl-2-fluoroanilino)-3,4-difluoro-5-[[3-fluoro-2-(methylsulfamoylamino)pyridin-4-yl]methyl]benzamide (compound A-1), (+/−)-3,4-difluoro-5-[[3-fluoro-2-(2-hydroxypropylsulfamoylamino)pyridin-4-yl]methyl]-2-(2-fluoro-4-iodoanilino)benzamide (compound A-17), 3,4-difluoro-2-(2-fluoro-4-iodoanilino)-5-[[3-fluoro-2-(oxetan-3-ylmethylsulfamoylamino)pyridin-4-yl]methyl]benzamide (compound A-21), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(2-methoxyethylsulfamoylamino)pyridin-4-yl]methyl]benzamide (compound A-33), 5-[[2-(ethylsulfamoylamino)-3-fluoropyridin-4-yl]methyl]-3,4-difluoro-2-(2-fluoro-4-iodoanilino)benzamide (compound A-40), 3,4-difluoro-5-[[3-fluoro-2-(2-fluoroethylsulfamoylamino)pyridin-4-yl]methyl]-2-(2-fluoro-4-iodoanilino)benzamide (compound A-42), 5-[[2-(ethylsulfonylamino)-3-fluoropyridin-4-yl]methyl]-3,4-difluoro-2-(2-fluoro-4-iodoanilino)-N-methoxybenzamide (compound B-16), 3,4-difluoro-2-(2-fluoro-4-iodoanilino)-5-[[2-(methylsulfamoylamino)pyridin-4-yl]methyl]benzamide (compound C-3), 2-(2-fluoro-4-iodoanilino)-5-[[3-fluoro-2-(methylsulfamoylamino)pyridin-4-yl]methyl]-1-methyl-N-[(2-methylpropan-2-yl)oxy]-6-oxopyridine-3-carboxamide (compound J-10), 5-(2-fluoro-4-iodoanilino)-2-[[3-fluoro-2-(methylsulfamoylamino)pyridin-4-yl]methyl]pyridine-4-carboxamide (compound L-1), 5-fluoro-4-(2-fluoro-4-iodoanilino)-1-[[3-fluoro-2-(methylsulfamoylamino)pyridin-4-yl]methyl]-6-oxopyridine-3-carboxamide (compound N-1), 1-[[2-(ethylsulfonylamino)-3-fluoropyridin-4-yl]methyl]-4-(2-fluoro-4-iodoanilino)-5-methyl-6-oxopyridine-3-carboxamide (compound P-2), 1-[[2-(ethylsulfonylamino)-3-fluoropyridin-4-yl]methyl]-4-(2-fluoro-4-iodoanilino)-N-methoxy-5-methyl-6-oxopyridine-3-carboxamide (compound P-5), and N-cyclopropyl-4-(2-fluoro-4-iodoanilino)-1-[[3-fluoro-2-(methylsulfamoylamino)pyridin-4-yl]methyl]-5-methyl-6-oxopyridine-3-carboxamide (compound P-6).

(B3) A compound or a pharmaceutically acceptable salt thereof, or a pharmaceutically acceptable solvate of said compound or salt, said compound being selected from among:

(+/−)-3,4-difluoro-5-[[3-fluoro-2-(2-hydroxypropylsulfamoylamino)pyridin-4-yl]methyl]-2-(2-fluoro-4-iodoanilino)benzamide (compound A-17), 3,4-difluoro-2-(2-fluoro-4-iodoanilino)-5-[[3-fluoro-2-(oxetan-3-ylmethylsulfamoylamino)pyridin-4-yl]methyl]benzamide (compound A-21), 5-[[2-(ethylsulfamoylamino)-3-fluoropyridin-4-yl]methyl]-3,4-difluoro-2-(2-fluoro-4-iodoanilino)benzamide (compound A-40), 3,4-difluoro-5-[[3-fluoro-2-(2-fluoroethylsulfamoylamino)pyridin-4-yl]methyl]-2-(2-fluoro-4-iodoanilino)benzamide (compound A-42), 5-[[2-(ethylsulfonylamino)-3-fluoropyridin-4-yl]methyl]-3,4-difluoro-2-(2-fluoro-4-iodoanilino)-N-methoxybenzamide (compound B-16), 3,4-difluoro-2-(2-fluoro-4-iodoanilino)-5-[[2-(methylsulfamoylamino)pyridin-4-yl]methyl]benzamide (compound C-3), 1-[[2-(ethylsulfonylamino)-3-fluoropyridin-4-yl]methyl]-4-(2-fluoro-4-iodoanilino)-N-methoxy-5-methyl-6-oxopyridine-3-carboxamide (compound P-5), and N-cyclopropyl-4-(2-fluoro-4-iodoanilino)-1-[[3-fluoro-2-(methylsulfamoylamino)pyridin-4-yl]methyl]-5-methyl-6-oxopyridine-3-carboxamide (compound P-6).

The compounds, salts or solvates of (B1) to (B3) exhibit high MEK-inhibiting activity and can be used as active ingredients in therapeutic or prophylactic agents for cell proliferative disorders, particularly cancers (more specifically, RAF-mutant cancers). Therefore, a composition comprising a compound, salt or solvate of any one of (B1) to (B3) and a dispersant and/or a basic compound can be used as a pharmaceutical composition. Also, a composition comprising a compound, salt or solvate of any one of (B1) to (B3) and a dispersant and/or a basic compound can be used as a pharmaceutical composition for the treatment or prevention of a cell proliferative disorder, particularly a cancer.

Inventions provided by the present disclosure include the compositions or methods according to D1 to D19 below, for example.

D1: A composition comprising: a compound represented by general formula (1) shown in (A1) above or a pharmaceutically acceptable salt thereof, or a pharmaceutically acceptable solvate of said compound or salt; and a dispersant.

D2: The composition according to D1, wherein said dispersant is at least one selected from the group consisting of methylcellulose, polyvinyl alcohol, hydroxypropylcellulose, copolyvidone, hydroxypropylmethylcellulose, methacrylic acid copolymer, polyvinylpyrrolidone, and hypromellose acetate succinate.

D3: The composition according to D1 or D2, wherein said dispersant is methylcellulose.

D4: The composition according to any one of D1 to D3, wherein the content of said dispersant is 0.1 to 20 parts by weight relative to 1 part by weight of said compound of general formula (1), said salt or said solvate.

D5: The composition according to any one of D1 to D4, wherein the dissolution of said compound of general formula (1), said salt or said solvate into FaSSIF after said composition has been treated with Japanese Pharmacopoeia 1st fluid for dissolution test for 60 minutes is improved compared with the case where said dispersant is not contained.

D6: The composition according to any one of D1 to D5, further comprising a basic compound.

D7: A composition comprising: a compound represented by general formula (1) shown in (A1) above or a pharmaceutically acceptable salt thereof, or a pharmaceutically acceptable solvate of said compound or salt, and a basic compound.

D8: The composition according to D6 or D7, wherein said basic compound is at least one selected from the group consisting of meglumine, arginine, histidine, magnesium oxide, calcium silicate, and magnesium stearate.

D9: The composition according to any one of D6 to D8, wherein said basic compound is meglumine.

D10: The composition according to any one of D6 to D9, wherein the content of said basic compound is 0.2 to 40 parts by weight relative to 1 part by weight of said compound of general formula (1), said salt or said solvate.

D11: The composition according to any one of D6 to D10, wherein the stability exhibited by said compound of general formula (1), said salt or said solvate when said composition is stored tightly stoppered at 80° C. for 2 weeks is improved compared with the case where said basic compound is not contained.

D12: The composition according to any one of D1 to D11, wherein:

ring A is a group represented by general formula (2) or (4) shown in (A1) above;

$R_8$ is a hydrogen atom, a C1-6 alkyl group (the C1-6 alkyl group being optionally substituted with a halogen atom, a hydroxy group or a C1-6 alkoxy group), or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_6$ is a hydrogen atom, a halogen atom or a C1-6 alkyl group and $R_4$ is a halogen atom or a cyclopropyl group; and $R_7$ is a hydrogen atom or a methyl group.

D13: The composition according to any one of D1 to D12, wherein said compound of general formula (1) is 2-(4-cyclopropyl-2-fluoroanilino)-3,4-difluoro-5-[[3-fluoro-2-(methylsulfamoylamino)pyridin-4-yl]methyl]benzamide.

D14: The composition according to any one of D1 to D13, further comprising a pharmaceutically acceptable excipient.

D15: The composition according to any one of D1 to D14, wherein the content of said compound of general formula (1), said salt or said solvate is 10% by weight or less with respect to the weight of said composition.

D16: The composition according to any one of D1 to D15, wherein the content of said compound of general formula (1), said salt or said solvate is 7% by weight or less with respect to the weight of said composition.

D17: The composition according to any one of D1 to D16, wherein the content of said compound of general formula (1), said salt or said solvate is 5% by weight or less with respect to the weight of said composition.

D18: The composition according to any one of D1 to D17, in the form of a capsule or a tablet.

D19: A method for producing the composition according to any one of D1 to D18, the method comprising providing a mixture containing: said compound of general formula (1), said salt or said solvate; and said dispersant and/or said basic compound.

Inventions provided by the present disclosure also include the compositions according to E1 to E7 below, for example.

E1: A composition comprising 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt, together with a compound represented by formula (X) shown in Test Example 12 below, wherein the content of said compound of formula (X) is 3.0% by weight or less with respect to the content of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

E2: A composition comprising 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt, together with a compound represented by formula (X) shown in Test Example 12 below, wherein the peak area of said compound of formula (X) that is obtained by high-performance liquid chromatography (HPLC) analysis of said composition is 3.0% or less with respect to the peak area of said 2-(4-cyclopropyl-2-fluoroanilino)-3,4-difluoro-5-[[3-fluoro-2-(methylsulfamoylamino)pyridin-4-yl]methyl]benzamide, said salt or said solvate that is obtained by said HPLC analysis.

E3: A composition comprising 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt, and a basic compound, together with a compound represented by formula (X) shown in Test Example 12 below, wherein the content of said compound of formula (X) is 3.0% by weight or less with respect to the content of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

E4: A composition comprising 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt, and a basic compound, together with a compound represented by formula (X) shown in Test Example 12 below, wherein the peak area of said compound of formula (X) that is obtained by high-performance liquid chromatography (HPLC) analysis of said composition is 3.0% or less with respect to the peak area of said 2-(4-cyclopropyl-2-fluoroanilino)-3,4-difluoro-5-[[3-fluoro-2-(methylsulfamoylamino)pyridin-4-yl]methyl]benzamide, said salt or said solvate that is obtained by said HPLC analysis.

E5: The composition according to E3 or E4, wherein said basic compound is at least one selected from the group consisting of meglumine, arginine, histidine, magnesium oxide, calcium silicate, and magnesium stearate.

E6: The composition according to any one of E3 to E5, wherein said basic compound is meglumine.

E7: The composition according to any one of E3 to E6, wherein the content of said basic compound is 0.2 to 40 parts by weight relative to 1 part by weight of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Inventions provided by the present disclosure also include the compositions according to Q1 to Q24 below, for example.

Q1: A composition comprising: 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt; and a dispersant.

Q2: A composition comprising: a sodium salt of 2-(4-cyclopropyl-2-fluoroanilino)-3,4-difluoro-5-[[3-fluoro-2-(methylsulfamoylamino)pyridin-4-yl]methyl]benzamide; and a dispersant.

Q3: The composition according to Q1 or Q2, wherein said dispersant is at least one selected from the group consisting of methylcellulose, polyvinyl alcohol, and hydroxypropylcellulose.

Q4: The composition according to any one of Q1 to Q3, wherein said dispersant is methylcellulose.

Q5: The composition according to any one of Q1 to Q4, wherein the content of said dispersant is 0.1 to 20 parts by weight relative to 1 part by weight of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Q6: The composition according to any one of Q1 to Q5, wherein the content of said dispersant is 0.2 to 10 parts by weight relative to 1 part by weight of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Q7: The composition according to any one of Q1 to Q6, wherein the content of said dispersant is 1 to 10 parts by weight relative to 1 part by weight of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Q8: The composition according to any one of Q1 to Q7, further comprising a basic compound.

Q9: A composition comprising: 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt; and a basic compound.

Q10: A composition comprising: a sodium salt of 2-(4-cyclopropyl-2-fluoroanilino)-3,4-difluoro-5-[[3-fluoro-2-(methylsulfamoylamino)pyridin-4-yl]methyl]benzamide; and a basic compound.

Q11: The composition according to any one of Q8 to Q10, wherein said basic compound is at least one selected from the group consisting of meglumine and arginine.

Q12: The composition according to any one of Q8 to Q11, wherein said basic compound is meglumine.

Q13: The composition according to any one of Q8 to Q12, wherein the content of said basic compound is 0.2 to 40 parts by weight relative to 1 part by weight of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Q14: The composition according to any one of Q8 to Q13, wherein the content of said basic compound is 0.5 to 20 parts by weight relative to 1 part by weight of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Q15: The composition according to any one of Q8 to Q14, wherein the content of said basic compound is 1 to 10 parts by weight relative to 1 part by weight of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Q16: The composition according to any one of Q1 to Q15, further comprising an excipient.

Q17: The composition according to Q16, wherein said excipient is mannitol.

Q18: The composition according to any one of Q1 to Q17, further comprising a lubricant.

Q19: The composition according to Q18, wherein said lubricant is magnesium stearate.

Q20: The composition according to any one of Q1 to Q19, wherein the content of said 2-(4-cyclopropyl-2-fluoroanilino)-3,4-difluoro-5-[[3-fluoro-2-(methylsulfamoylamino)pyridin-4-yl]methyl]benzamide, said salt or said solvate is 10% by weight or less with respect to the weight of said composition.

Q21: The composition according to any one of Q1 to Q20, wherein the content of said 2-(4-cyclopropyl-2-fluoroanilino)-3,4-difluoro-5-[[3-fluoro-2-(methylsulfamoylamino)pyridin-4-yl]methyl]benzamide, said salt or said solvate is 7% by weight or less with respect to the weight of said composition.

Q22: The composition according to any one of Q1 to Q21, wherein the content of said 2-(4-cyclopropyl-2-fluoroanilino)-3,4-difluoro-5-[[3-fluoro-2-(methylsulfamoylamino)pyridin-4-yl]methyl]benzamide, said salt or said solvate is 5% by weight or less with respect to the weight of said composition.

Q23: The composition according to any one of Q1 to Q22, in the form of a capsule or a tablet.

Q24: The composition according to any one of Q1 to Q23, which is a pharmaceutical formulation.

Inventions provided by the present disclosure also include the uses or methods according to F1 to F6 below, for example.

F1: Use of the composition according to any one of D1 to D18, E1 to E7, and Q1 to Q24 in the manufacture of a medicament for treating a patient in need of treatment with said compound of general formula (1), said 2-(4-cyclopropyl-2-fluoroanilino)-3,4-difluoro-5-[[3-fluoro-2-(methylsulfamoylamino)pyridin-4-yl]methyl]benzamide, said salt or said solvate.

F2: A method for treating a patient in need of treatment with said compound of general formula (1), said 2-(4-cyclopropyl-2-fluoroanilino)-3,4-difluoro-5-[[3-fluoro-2-(methylsulfamoylamino)pyridin-4-yl]methyl]benzamide, said salt or said solvate, the method comprising administering the composition according to any one of D1 to D18, E1 to E7, and Q1 to Q24 to said patient.

F3: Use of the composition according to any one of D1 to D18, E1 to E7, and Q1 to Q24 in the manufacture of a medicament for the treatment or prevention of a cell proliferative disorder.

F4: The use according to F3, wherein said cell proliferative disorder is a cancer.

F5: A method for treating or preventing a cell proliferative disorder in a patient, the method comprising administering the composition according to any one of D1 to D18, E1 to E7, and Q1 to Q24 to said patient.

F6: The method according to F5, wherein said cell proliferative disorder is a cancer.

Inventions provided by the present disclosure also include the uses according to G1 to G8 below, for example.

G1: Use of a dispersant for the manufacture of a composition comprising a compound represented by general formula (1) shown in (A1) above or a pharmaceutically acceptable salt thereof, or a pharmaceutically acceptable solvate of said compound or salt.

G2: Use of a basic compound for the manufacture of a composition comprising a compound represented by general formula (1) shown in (A1) above or a pharmaceutically acceptable salt thereof, or a pharmaceutically acceptable solvate of said compound or salt.

G3: Use of a dispersant and a basic compound for the manufacture of a composition comprising a compound represented by general formula (1) shown in (A1) above or a pharmaceutically acceptable salt thereof, or a pharmaceutically acceptable solvate of said compound or salt.

G4: The use according to G1 or G3, wherein said dispersant is at least one selected from the group consisting of methylcellulose, polyvinyl alcohol, hydroxypropylcellulose, copolyvidone, hydroxypropylmethylcellulose, methacrylic acid copolymer, polyvinylpyrrolidone, and hypromellose acetate succinate.

G5: The use according to G4, wherein said dispersant is methylcellulose.

G6: The use according to G2 or G3, wherein said basic compound is at least one selected from the group consisting of meglumine, arginine, histidine, magnesium oxide, calcium silicate, and magnesium stearate.

G7: The use according to G6, wherein said basic compound is meglumine.

G8: The use according to any one of G1 to G7, wherein said compound of general formula (1) is 2-(4-cyclopropyl-2-fluoroanilino)-3,4-difluoro-5-[[3-fluoro-2-(methylsulfamoylamino)pyridin-4-yl]methyl]benzamide.

Inventions provided by the present disclosure also include the methods according to K1 to K10 below, for example.

K1: A method for improving the dissolution of a compound represented by general formula (1) shown in (A1) above or a pharmaceutically acceptable salt thereof, or a pharmaceutically acceptable solvate of said compound or salt in a composition, the method comprising allowing a dispersant to be copresent in said composition.

K2: The method according to K1, wherein said dissolution is the dissolution of said compound of general formula (1), said salt or said solvate into FaSSIF after said composition has been treated with Japanese Pharmacopoeia 1st fluid for dissolution test for 60 minutes.

K3: The method according to K1 or K2, wherein said dispersant is at least one selected from the group consisting of methylcellulose, polyvinyl alcohol, hydroxypropylcellulose, copolyvidone, hydroxypropylmethylcellulose, methacrylic acid copolymer, polyvinylpyrrolidone, and hypromellose acetate succinate.

K4: The method according to any one of K1 to K3, wherein said dispersant is methylcellulose.

K5: The method according to any one of K1 to K4, wherein said composition further comprises a basic compound.

K6: The method according to K5, wherein said basic compound is at least one selected from the group consisting of meglumine, arginine, histidine, magnesium oxide, calcium silicate, and magnesium stearate.

K7: The method according to K5 or K6, wherein said basic compound is meglumine.

K8: The method according to any one of K1 to K7, wherein said composition further comprises an excipient.

K9: The method according to K8, wherein said excipient is mannitol.

K10: The method according to any one of K1 to K9, wherein said compound of general formula (1) is 2-(4-cyclopropyl-2-fluoroanilino)-3,4-difluoro-5-[[3-fluoro-2-(methylsulfamoylamino)pyridin-4-yl]methyl] benzamide.

Inventions provided by the present disclosure also include the methods according to L1 to L10 below, for example.

L1: A method for improving the stability of a compound represented by general formula (1) shown in (A1) above or a pharmaceutically acceptable salt thereof, or a pharmaceutically acceptable solvate of said compound or salt in a composition, the method comprising allowing a basic compound to be copresent in said composition.

L2: The method according to L1, wherein said stability is the stability exhibited by said compound of general formula (1), said salt or said solvate when said composition is stored tightly stoppered at 80° C. for 2 weeks.

L3: The method according to L1 or L2, wherein said basic compound is at least one selected from the group consisting of meglumine, arginine, histidine, magnesium oxide, calcium silicate, and magnesium stearate.

L4: The method according to any one of L1 to L3, wherein said basic compound is meglumine.

L5: The method according to any one of L1 to L4, wherein said composition further comprises a dispersant.

L6: The method according to L5, wherein said dispersant is at least one selected from the group consisting of methylcellulose, polyvinyl alcohol, hydroxypropylcellulose, copolyvidone, hydroxypropylmethylcellulose, methacrylic acid copolymer, polyvinylpyrrolidone, and hypromellose acetate succinate.

L7: The method according to L5 or L6, wherein said dispersant is methylcellulose.

L8: The method according to any one of L1 to L7, wherein said composition further comprises an excipient.

L9: The method according to L8, wherein said excipient is mannitol.

L10: The method according to any one of L1 to L9, wherein said compound of general formula (1) is 2-(4-cyclopropyl-2-fluoroanilino)-3,4-difluoro-5-[[3-fluoro-2-(methylsulfamoylamino)pyridin-4-yl]methyl] benzamide.

Advantageous Effects of Invention

According to the present disclosure, there is provided a composition comprising a specific aryl amide derivative that has RAF/MEK complex-stabilizing activity and/or MEK-inhibiting activity and is useful for the treatment or prevention of a cell proliferative disorder, particularly a cancer, the composition having good properties with respect to the dissolution and/or stability of the aryl amide derivative in the composition.

DESCRIPTION OF EMBODIMENTS

Figure 1:
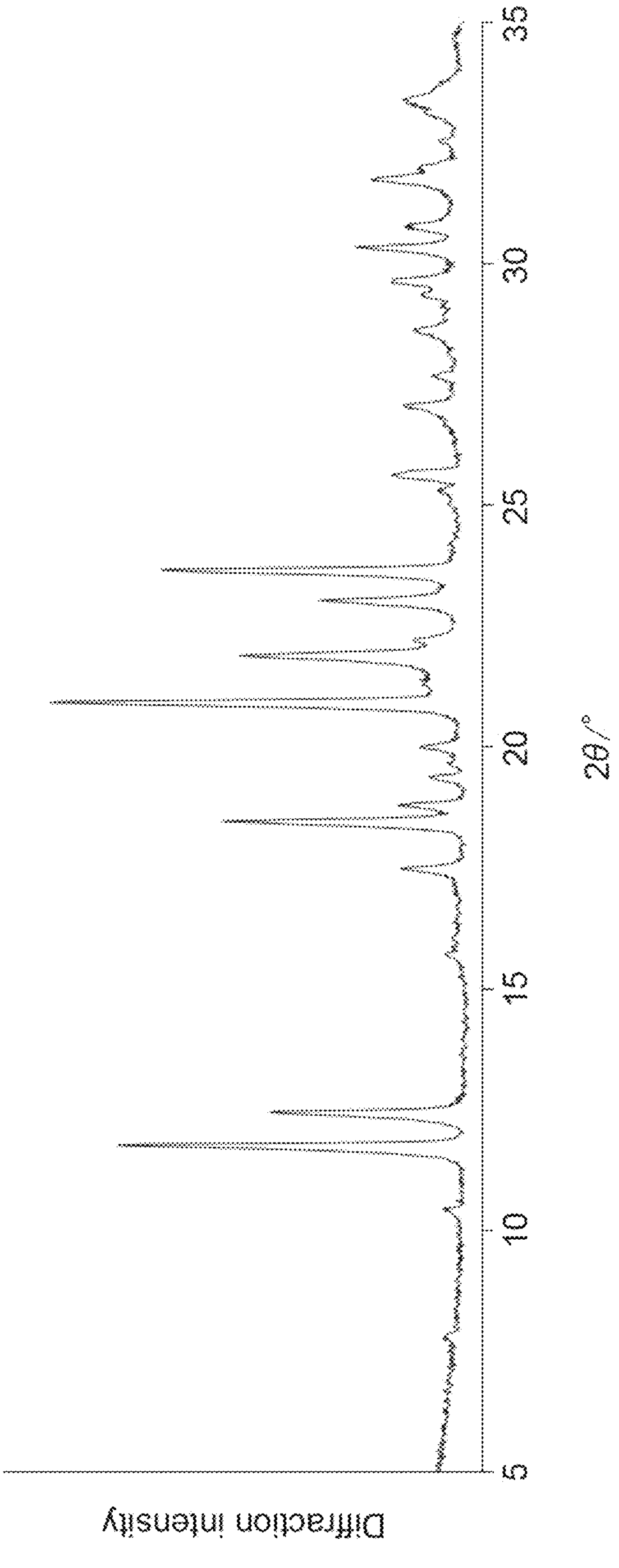
FIG. 1 shows a powder X-ray diffraction pattern of sample A-1a (Form I).

Exemplary embodiments of the present disclosure are described below.

As used in the present disclosure, "halogen atom" refers to a fluorine atom, a chlorine atom, a bromine atom, or an iodine atom.

As used in the present disclosure, "C1-6 alkyl group" means a straight- or branched-chain alkyl group of 1 to 6 carbon atoms. Examples include methyl, ethyl, n-propyl, isopropyl, n-butyl, sec-butyl, tert-butyl, 1-methylpropyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl groups.

As used in the present disclosure, "C2-7 alkenyl group" means a straight- or branched-chain alkenyl group of 2 to 7 carbon atoms. Examples include vinyl, allyl, 1-butenyl, 2-butenyl, 3-butenyl, pentenyl, pentadienyl, hexenyl, hexadienyl, heptenyl, heptadienyl, and heptatrienyl groups.

As used in the present disclosure, "C2-7 alkynyl group" means a straight- or branched-chain alkynyl group of 2 to 7 carbon atoms. Examples include ethynyl, 1-propynyl, 2-propynyl, 1-butynyl, 2-butynyl, 3-butynyl, pentynyl, pentadiynyl, hexynyl, hexadiynyl, heptynyl, heptadiynyl, and heptatriynyl groups.

As used in the present disclosure, "C1-6 alkoxy group" means an alkyloxy group having a straight- or branched-chain alkyl group of 1 to 6 carbon atoms. Examples include methoxy, ethoxy, n-propoxy, isopropoxy, n-butoxy, sec-butoxy, tert-butoxy, n-pentoxy, and n-hexoxy groups.

As used in the present disclosure, "C1-6 alkylthio group" means an alkylthio group having a straight- or branched-chain alkyl group of 1 to 6 carbon atoms. Examples include methylthio, ethylthio, n-propylthio, isopropylthio, n-butylthio, sec-butylthio, tert-butylthio, n-pentylthio, and n-hexylthio groups.

As used in the present disclosure, "C3-6 cycloalkyl group" means a cyclic alkyl group of 3 to 6 atoms composing a ring. While it may be either monocyclic or bicyclic, it means a monocyclic one unless otherwise specified. Examples of monocyclic groups include cyclopropyl, cyclobutyl, cyclopentyl, and cyclohexyl groups.

Examples of bicyclic groups include bicyclo[1.1.1]pentanyl and bicyclo[2.1.1]hexyl groups.

As used in the present disclosure, "C3-6 heterocycloalkyl group" means a C3-6 cycloalkyl group wherein at least one of the carbon atoms composing the ring is replaced by a nitrogen atom, an oxygen atom or a sulfur atom. While it may be either monocyclic or bicyclic, it means a monocyclic one unless otherwise specified.

Examples of monocyclic groups include tetrahydrofuranyl, tetrahydropyranyl, pyrrolidinyl, piperidinyl, piperazinyl, and morpholinyl groups. Examples of bicyclic groups include oxabicyclo[3.1.0]hexan-6-yl and azabicyclo[2.1.1]hexanyl groups.

As used in the present disclosure, "unsaturated hetero 5-membered ring" means an unsaturated 5-membered ring containing at least one heteroatom selected from among nitrogen, oxygen and sulfur atoms. Examples include furan, thiophene, pyrrole, imidazole, and thiazole.

In the present disclosure, examples of pharmaceutically acceptable salts include: inorganic acid salts such as hydrochlorides, hydrobromides, hydroiodides, sulfates, and phosphates; sulfonates such as methanesulfonates, benzenesulfonates, and toluenesulfonates; carboxylates such as formates, acetates, oxalates, maleates, fumarates, citrates, malates, succinates, malonates, gluconates, mandelates, benzoates, salicylates, fluoroacetates, trifluoroacetates, tartrates, propionates, and glutarates; alkali metal salts such as lithium salts, sodium salts, potassium salts, cesium salts, and rubidium salts; alkaline earth metal salts such as magnesium salts and calcium salts; and ammonium salts such as ammonium salts, alkylammonium salts, dialkylammonium salts, trialkylammonium salts, and tetraalkylammonium salts. Among them, alkali metal salts such as lithium salts, sodium salts, potassium salts, cesium salts and rubidium salts are preferred, and sodium salts and potassium salts are more preferred.

In the present disclosure, a "pharmaceutically acceptable solvate" is a solvate with, for example, water, an alcohol (e.g., methanol, ethanol, 1-propanol or 2-propanol), acetone, dimethylformamide, or dimethylacetamide. The solvate may be a solvate with a single solvent or may be a solvate with multiple solvents. Hydrates are examples of preferred solvates.

A first aspect of the present disclosure provides a composition comprising a compound represented by general formula (1) below or a pharmaceutically acceptable salt thereof, or a pharmaceutically acceptable solvate of said compound or salt, and a dispersant and/or a basic compound:

[Chemical Formula 9]

(1)

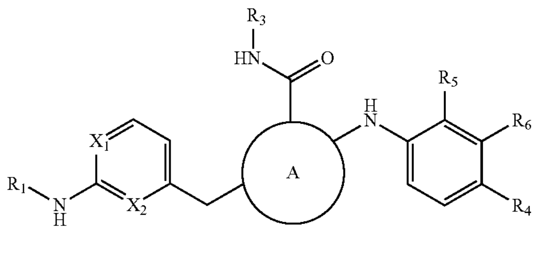

wherein:

ring A is a group represented by general formula (2) (3), (4) or (5) below (where the bonds denoted by *,  and * are bonded to —NH—, —CONH— and —$CH_2$—, respectively):

[Chemical Formula 10]

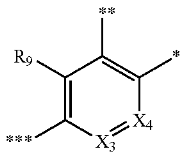
(2)

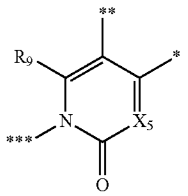
(3)

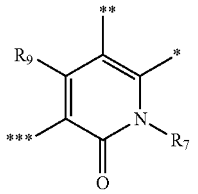
(4)

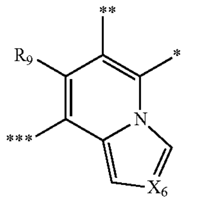
(5)

$X_1$, $X_2$, $X_3$, $X_4$, $X_5$ and $X_6$ are each independently —$CR_2$═ or —N═;

$R_2$ is a hydrogen atom, a halogen atom, or a C1-6 alkyl group;

$R_1$ is —S(═O)$_2$—NH—R % or —S(═O)$_2$—$R_8$;

$R_5$ is a hydrogen atom, a C1-6 alkyl group (the C1-6 alkyl group being optionally substituted with a halogen atom, a hydroxy group, a C1-6 alkoxy group, a C3-6 cycloalkyl group or a C3-6 heterocycloalkyl group), a monocyclic or bicyclic C3-6 cycloalkyl group (the C3-6 cycloalkyl group being optionally substituted with a C1-6 alkyl group or a C1-6 alkoxy group), or a monocyclic or bicyclic C3-6 heterocycloalkyl group;

$R_3$ is a hydrogen atom, a C1-6 alkyl group (the C1-6 alkyl group being optionally substituted with a halogen atom, a hydroxy group or a C1-6 alkoxy group), a C3-6 cycloalkyl group (the C3-6 cycloalkyl group being optionally substituted with a halogen atom or a C1-6 alkyl group), or a C1-6 alkoxy group (the C1-6 alkoxy group being optionally substituted with a halogen atom, a hydroxy group or a C1-6 alkoxy group);

$R_5$ is a halogen atom or a C1-6 alkyl group;

$R_6$ is a hydrogen atom, a halogen atom or a C1-6 alkyl group and $R_4$ is a hydrogen atom, a halogen atom, a C1-6 alkyl group, a C2-7 alkenyl group, a C2-7 alkynyl group, a C3-6 cycloalkyl group or a C1-6 alkylthio group, or $R_6$ and $R_4$ form an unsaturated hetero 5-membered ring together with the carbon atoms to which they are bonded;

$R_7$ is a hydrogen atom or a C1-6 alkyl group; and $R_9$ is a hydrogen atom, a halogen atom, or a C1-6 alkyl group.

The compounds, salts or solvates of the first aspect exhibit high RAF/MEK complex-stabilizing activity and can be used for the treatment or prevention of cell proliferative disorders, particularly cancers (more specifically, RAS-mutant cancers). Many of them have high MEK-inhibiting activity, and such compounds, salts or solvates are also suitable for RAF-mutant cancers.

Ring A is preferably a group represented by general formula (2) or (4), and more preferably a group represented by general formula (2).

$R_2$ is preferably a hydrogen or halogen atom, more preferably a hydrogen or fluorine atom, and even more preferably a fluorine atom.

$R_1$ is preferably —S(═O)$_2$—NH—$R_8$.

$R_8$ is preferably a hydrogen atom, a C1-6 alkyl group (the C1-6 alkyl group being optionally substituted with a halogen atom, a hydroxy group or a C1-6 alkoxy group) or a monocyclic C3-6 cycloalkyl group (the C3-6 cycloalkyl group being optionally substituted with a C1-6 alkyl group), more preferably a C1-6 alkyl group (the C1-6 alkyl group being optionally substituted with a halogen atom or a C1-6 alkoxy group) or a monocyclic C3-6 cycloalkyl group (the C3-6 cycloalkyl group being optionally substituted with a C1-6 alkyl group), more preferably a C1-4 alkyl group (the C1-4 alkyl group being optionally substituted with a fluorine atom or a C1-4 alkoxy group) or a cyclopropyl group (the cyclopropyl group being optionally substituted with a C1-4 alkyl group), and even more preferably a C1-4 alkyl group.

$R_3$ is preferably a hydrogen atom, a C1-6 alkyl group, a C3-6 cycloalkyl group or a C1-6 alkoxy group (the C1-6 alkoxy group being optionally substituted with a hydroxy group), more preferably a hydrogen atom, a C1-4 alkyl group, a cyclopropyl group or a C1-4 alkoxy group (the C1-4 alkoxy group being optionally substituted with a hydroxy group), and even more preferably a hydrogen atom or a cyclopropyl group.

$R_5$ is preferably a halogen atom and more preferably a fluorine atom.

$R_6$ is preferably a hydrogen atom, a halogen atom or a C1-6 alkyl group, and more preferably a hydrogen atom.

$R_4$ is preferably a halogen atom or a cyclopropyl group, and more preferably an iodine atom or a cyclopropyl group.

$R_7$ is preferably a hydrogen atom or a methyl group.

The compound represented by general formula (1) is preferably a compound represented by general formula (6) below:

[Chemical Formula 11]

(6)

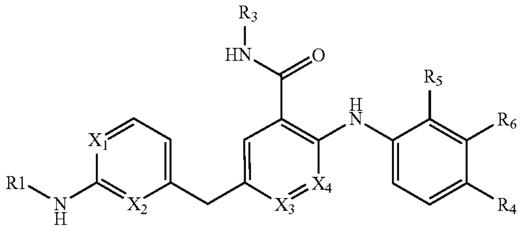

wherein:

$X_1$, $X_2$, $X_3$ and $X_4$ are each independently —$CR_2$= or —N=;

$R_2$ is a hydrogen atom, a halogen atom, or a C1-6 alkyl group;

$R_1$ is —S(=O)$_2$—NH—$R_8$ or —S(=O)$_2$—$R_8$;

$R_8$ is a hydrogen atom, a C1-6 alkyl group (the C1-6 alkyl group being optionally substituted with a halogen atom, a hydroxy group or a C1-6 alkoxy group), or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_5$ is a halogen atom or a C1-6 alkyl group; and $R_6$ is a hydrogen atom, a halogen atom or a C1-6 alkyl group and $R_4$ is a halogen atom or a cyclopropyl group.

Examples of Compounds Represented by Formula (1) Include:

N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), 2-(4-cyclopropyl-2-fluoroanilino)-3,4-difluoro-5-[[3-fluoro-2-(methylsulfamoylamino)pyridin-4-yl]methyl]benzamide (compound A-1), N-cyclopropyl-5-[[2-(ethylsulfamoylamino)-3-fluoropyridin-4-yl]methyl]-3,4-difluoro-2-(2-fluoro-4-iodoanilino)benzamide (compound A-4), N-cyclopropyl-3,4-difluoro-5-[[3-fluoro-2-(2-fluoroethylsulfamoylamino)pyridin-4-yl]methyl]-2-(2-fluoro-4-iodoanilino)benzamide (compound A-6), 3,4-difluoro-2-(2-fluoro-4-iodoanilino)-5-[[3-fluoro-2-(methylsulfamoylamino)pyridin-4-yl]methyl]-N-[(2-methylpropan-2-yl)oxy]benzamide (compound A-8), 3,4-difluoro-2-(2-fluoro-4-iodoanilino)-5-[[3-fluoro-2-(methylsulfamoylamino)pyridin-4-yl]methyl]-N-methoxybenzamide (compound A-13), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(propan-2-ylsulfamoylamino)pyridin-4-yl]methyl]benzamide (compound A-31), 3,4-difluoro-2-(2-fluoro-4-iodoanilino)-5-[[3-fluoro-2-(2-methoxyethylsulfamoylamino)pyridin-4-yl]methyl]benzamide (compound A-33), 3,4-difluoro-2-(2-fluoro-4-iodoanilino)-5-[[3-fluoro-2-(2-methyl propylsulfamoylamino)pyridin-4-yl]methyl]benzamide (compound A-34), 3,4-difluoro-2-(2-fluoro-4-iodoanilino)-5-[[3-fluoro-2-[(1-methylcyclobutyl)sulfamoylamino]pyridin-4-yl]methyl]benzamide (compound A-35), 3,4-difluoro-2-(2-fluoro-4-iodoanilino)-5-[[3-fluoro-2-(propylsulfamoylamino)pyridin-4-yl]methyl]benzamide (compound A-41), 3,4-difluoro-2-(2-fluoro-4-iodoanilino)-5-[[3-fluoro-2-(methylsulfamoylamino)pyridin-4-yl]methyl]-N-(2-hydroxyethoxy)benzamide (compound B-1), 5-[[3-(ethylsulfonylamino)-2-fluorophenyl]methyl]-3,4-difluoro-2-(2-fluoro-4-iodoanilino)benzamide (compound D-4), 5-[[3-(ethylsulfonylamino)-2-fluorophenyl]methyl]-3,4-difluoro-2-(2-fluoro-4-iodoanilino)-N-methoxybenzamide (compound E-1), 3,4-difluoro-2-(2-fluoro-4-iodoanilino)-5-[[2-fluoro-3-(methylsulfamoylamino)phenyl]methyl]benzamide (compound E-7), 3,4-difluoro-2-(2-fluoro-4-iodoanilino)-5-[[2-fluoro-3-(methanesulfonamide)phenyl]methyl]benzamide (compound E-13), 4-fluoro-2-(2-fluoro-4-iodoanilino)-5-[[3-fluoro-2-(methylsulfamoylamino)pyridin-4-yl]methyl]benzamide (compound 1-1), N-cyclopropyl-2-(2-fluoro-4-iodoanilino)-5-[[3-fluoro-2-(methylsulfamoylamino)pyridin-4-yl]methyl]-1-methyl-6-oxopyridine-3-carboxamide (compound J-5), 3,4-difluoro-2-(2-fluoro-4-iodoanilino)-5-[[3-fluoro-2-[(1-methylcyclobutyl)sulfamoylamino]pyridin-4-yl]methyl]-N-methoxybenzamide (compound A-15), 3,4-difluoro-5-[[3-fluoro-2-(methylsulfamoylamino)pyridin-4-yl]methyl]-2-(2-fluoro-4-methylsulfanylanilino)benzamide (compound A-18), 2-(4-ethynyl-2-fluoroanilino)-3,4-difluoro-5-[[3-fluoro-2-(propylsulfamoylamino)pyridin-4-yl]methyl]benzamide (compound A-20), 2-(4-bromo-2-fluoroanilino)-3,4-difluoro-5-[[3-fluoro-2-(methylsulfamoylamino)pyridin-4-yl]methyl]benzamide (compound A-27), 2-(2-chloro-4-iodoanilino)-5-[[3-(ethylsulfonylamino)-2-fluorophenyl]methyl]-3,4-difluoro-N-methoxybenzamide (compound E-9), 3,4-difluoro-2-(2-fluoro-4-iodoanilino)-5-[[2-fluoro-3-(oxan-4-ylsulfonylamino)phenyl]methyl]benzamide (compound E-23), 2-[4-(difluoromethylsulfanyl)-2-fluoroanilino]-3,4-difluoro-5-[[3-fluoro-2-(methylsulfamoylamino)pyridin-4-yl]methyl]benzamide (compound H-1), 3,4-difluoro-2-[(4-fluoro-1-benzothiophen-5-yl)amino]-5-[[3-fluoro-2-(methylsulfamoylamino)pyridin-4-yl]methyl]benzamide (compound H-3), 2-(2-fluoro-4-iodoanilino)-5-[[3-fluoro-2-(methylsulfamoylamino)pyridin-4-yl]methyl]-N-methoxy-1-methyl-6-oxopyridine-3-carboxamide (compound J-8), 2-(2-fluoro-4-iodoanilino)-5-[[3-fluoro-2-(methylsulfamoylamino)pyridin-4-yl]methyl]-1-methyl-N-[(2-methylpropan-2-yl)oxy]-6-oxopyridine-3-carboxamide (compound J-10), 5-[[2-(ethylsulfamoylamino)-3-fluoropyridin-4-yl]methyl]-2-(2-fluoro-4-iodoanilino)-1-methyl-6-oxopyridine-3-carboxamide (compound J-14), 5-(2-fluoro-4-iodoanilino)-2-[[3-fluoro-2-(methylsulfamoylamino)pyridin-4-yl]methyl]pyridine-4-carboxamide (compound L-1), 5-(2-fluoro-4-iodoanilino)-8-[[3-fluoro-2-(methylsulfamoylamino)pyridin-4-yl]methyl]imidazo[1,5-a]pyridine-6-carboxamide (compound M-1), 5-fluoro-4-(2-fluoro-4-iodoanilino)-1-[[3-fluoro-2-(methylsulfamoylamino)pyridin-4-yl]methyl]-6-oxopyridine-3-carboxamide (compound N-1), 5-fluoro-4-(2-fluoro-4-iodoanilino)-1-[[3-fluoro-2-(propylsulfamoylamino)pyridin-4-yl]methyl]-6-oxopyridine-3-carboxamide (compound N-2), 4-(2-fluoro-4-iodoanilino)-1-[[3-fluoro-2-(methylsulfamoylamino)pyridin-4-yl]methyl]-5-methyl-6-oxopyridine-3-carboxamide (compound P-1), and 1-[[2-(ethylsulfonylamino)-3-fluoropyridin-4-yl]methyl]-4-(2-fluoro-4-iodoanilino)-5-methyl-6-oxopyridine-3-carboxamide (compound P-2).

Among these compounds,

N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), 2-(4-cyclopropyl-2-fluoroanilino)-3,4-difluoro-5-[[3-fluoro-2-(methylsulfamoylamino)pyridin-4-yl]methyl]benzamide (compound A-1), N-cyclopropyl-5-[[2-(ethylsulfamoylamino)-3-fluoropyridin-4-yl]methyl]-3,4-difluoro-2-(2-fluoro-4-iodoanilino)benzamide (compound A-4), N-cyclopropyl-3,4-difluoro-5-[[3-fluoro-2-(2-fluoroethylsulfamoylamino)pyridin-4-yl]methyl]-2-(2-fluoro-4-iodoanilino)benzamide (compound A-6), 3,4-difluoro-2-(2-fluoro-4-iodoanilino)-5-[[3-fluoro-2-(methylsulfamoylamino)pyridin-4-yl]methyl]-N-[(2-methylpropan-2-yl)oxy]benzamide (compound A-8), 3,4-difluoro-2-(2-fluoro-4-iodoanilino)-5-[[3-fluoro-2-(methylsulfamoylamino)pyridin-4-yl]methyl]-N-methoxybenzamide (compound A-13), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(propan-2-ylsulfamoylamino)pyridin-4-yl]methyl]benzamide (compound A-31), 3,4-difluoro-2-(2-fluoro-4-iodoanilino)-5-[[3-fluoro-2-(2-methoxyethylsulfamoylamino)pyridin-4-yl]methyl]benzamide (compound A-33), 3,4-difluoro-2-(2-fluoro-4-iodoanilino)-5-[[3-fluoro-2-(2-methyl propylsulfamoylamino)pyridin-4-yl]methyl]benzamide (compound A-34), 3,4-difluoro-2-(2-fluoro-4-iodoanilino)-5-[[3-fluoro-2-[(1-methylcyclobutyl)sulfamoylamino]pyridin-4-yl]methyl]benzamide (compound A-35), 3,4-difluoro-2-(2-fluoro-4-iodoanilino)-5-[[3-fluoro-2-(propylsulfamoylamino)pyridin-4-yl]methyl]benzamide (compound A-41), 3,4-difluoro-2-(2-fluoro-4-iodoanilino)-5-[[3-fluoro-2-(methylsulfamoylamino)pyridin-4-yl]methyl]-N-(2-hydroxyethoxy)benzamide (compound B-1), 5-[[3-(ethylsulfonylamino)-2-fluorophenyl]methyl]-3,4-difluoro-2-(2-fluoro-4-iodoanilino)benzamide (compound D-4), 5-[[3-(ethylsulfonylamino)-2-fluorophenyl]methyl]-3,4-difluoro-2-(2-fluoro-4-iodoanilino)-N-methoxybenzamide (compound E-1), 3,4-difluoro-2-(2-fluoro-4-iodoanilino)-5-[[2-fluoro-3-(methylsulfamoylamino)phenyl]methyl]benzamide (compound E-7), 3,4-difluoro-2-(2-fluoro-4-iodoanilino)-5-[[2-fluoro-3-(methanesulfonamide)phenyl]methyl]benzamide (compound E-13), 4-fluoro-2-(2-fluoro-4-iodoanilino)-5-[[3-fluoro-2-(methylsulfamoylamino)pyridin-4-yl]methyl]benzamide (compound I-1), and N-cyclopropyl-2-(2-fluoro-4-iodoanilino)-5-[[3-fluoro-2-(methylsulfamoylamino)pyridin-4-yl]methyl]-1-methyl-6-oxopyridine-3-carboxamide (compound J-5)

are preferred in terms of, for example, MEK-inhibiting activity, RAF-inhibiting activity, cell proliferation-inhibiting activity and/or metabolic stability, with N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), and 2-(4-cyclopropyl-2-fluoroanilino)-3,4-difluoro-5-[[3-fluoro-2-(methylsulfamoylamino)pyridin-4-yl]methyl]benzamide (compound A-1)

being more preferred, and 2-(4-cyclopropyl-2-fluoroanilino)-3,4-difluoro-5-[[3-fluoro-2-(methylsulfamoylamino)pyridin-4-yl]methyl]benzamide (compound A-1)

being particularly preferred.

A pharmaceutically acceptable salt of 2-(4-cyclopropyl-2-fluoroanilino)-3,4-difluoro-5-[[3-fluoro-2-(methylsulfamoylamino)pyridin-4-yl]methyl]benzamide (compound A-1) that is preferred is, for example, a sodium salt or a potassium salt, with a sodium salt being particularly preferred.

A second aspect of the present disclosure provides a composition comprising a compound represented by general formula (11) below or a pharmaceutically acceptable salt thereof, or a pharmaceutically acceptable solvate of said compound or salt, and a dispersant and/or a basic compound:

[Chemical Formula 12]

(11)

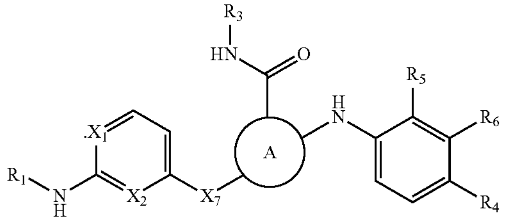

wherein:

ring A is a group represented by general formula (2) (3), (4) or (5) below (where the bonds denoted by *,  and * are bonded to —NH—, —CONH— and —$X_7$—, respectively):

[Chemical Formula 13]

(2)

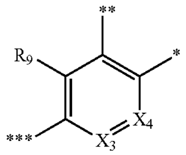

(3)

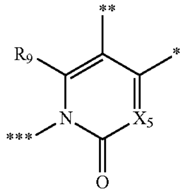

(4)

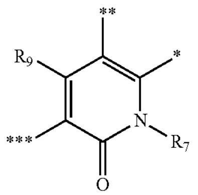

(5)

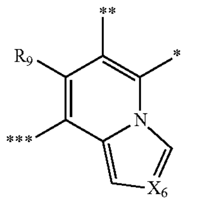

$X_1$, $X_2$, $X_3$, $X_4$, $X_5$ and $X_6$ are each independently $—CR_2═$ or $—N═$;

$R_2$ is a hydrogen atom, a halogen atom, or a C1-6 alkyl group;

$X_7$ is $—(CH_2)_m—$ or —O— and m is 1, 2 or 3;

$R_1$ is $—S(═O)_2—NH—R_8$ or $—S(═O)_2—R_8$;

$R_8$ is a hydrogen atom, a C1-6 alkyl group (the C1-6 alkyl group being optionally substituted with a halogen atom, a hydroxy group, a C1-6 alkoxy group, a C3-6 cycloalkyl group or a C3-6 heterocycloalkyl group), a monocyclic or bicyclic C3-6 cycloalkyl group (the C3-6 cycloalkyl group being optionally substituted with a C1-6 alkyl group or a C1-6 alkoxy group), or a monocyclic or bicyclic C3-6 heterocycloalkyl group;

$R_3$ is a hydrogen atom, a C1-6 alkyl group (the C1-6 alkyl group being optionally substituted with a halogen atom, a hydroxy group or a C1-6 alkoxy group), a C3-6 cycloalkyl group (the C3-6 cycloalkyl group being optionally substituted with a halogen atom or a C1-6 alkyl group), or a C1-6 alkoxy group (the C1-6 alkoxy group being optionally substituted with a halogen atom, a hydroxy group or a C1-6 alkoxy group);

$R_5$ is a hydrogen atom, a halogen atom, or a C1-6 alkyl group;

$R_6$ is a hydrogen atom, a halogen atom or a C1-6 alkyl group and $R_4$ is a hydrogen atom, a halogen atom, a C1-6 alkyl group, a C2-7 alkenyl group, a C2-7 alkynyl group, a C3-6 cycloalkyl group or a C1-6 alkylthio group, or $R_6$ and $R_4$ form an unsaturated hetero 5-membered ring together with the carbon atoms to which they are bonded;

$R_7$ is a hydrogen atom or a C1-6 alkyl group; and $R_9$ is a hydrogen atom, a halogen atom, or a C1-6 alkyl group.

The compounds, salts or solvates of the second aspect exhibit high RAF/MEK complex-stabilizing activity and can be used for the treatment or prevention of cell proliferative disorders, particularly cancers (more specifically, RAS-mutant cancers). Many of them have high MEK-inhibiting activity, and such compounds, salts or solvates are also suitable for RAF-mutant cancers.

Ring A is preferably a group represented by general formula (2) or (4), and more preferably a group represented by general formula (2).

$R_2$ is preferably a hydrogen or halogen atom, more preferably a hydrogen or fluorine atom, and even more preferably a fluorine atom.

$X_7$ is preferably $—CH_2—$.

$R_1$ is preferably $—S(═O)_2—NH—R_8$.

$R_8$ is preferably a hydrogen atom, a C1-6 alkyl group (the C1-6 alkyl group being optionally substituted with a halogen atom, a hydroxy group or a C1-6 alkoxy group) or a monocyclic C3-6 cycloalkyl group (the C3-6 cycloalkyl group being optionally substituted with a C1-6 alkyl group), more preferably a C1-6 alkyl group (the C1-6 alkyl group being optionally substituted with a halogen atom or a C1-6 alkoxy group) or a monocyclic C3-6 cycloalkyl group (the C3-6 cycloalkyl group being optionally substituted with a C1-6 alkyl group), more preferably a C1-4 alkyl group (the C1-4 alkyl group being optionally substituted with a fluorine atom or a C1-4 alkoxy group) or a cyclopropyl group (the cyclopropyl group being optionally substituted with a C1-4 alkyl group), and even more preferably a C1-4 alkyl group.

$R_3$ is preferably a hydrogen atom, a C1-6 alkyl group, a C3-6 cycloalkyl group or a C1-6 alkoxy group (the C1-6 alkoxy group being optionally substituted with a hydroxy group), more preferably a hydrogen atom, a C1-4 alkyl group, a cyclopropyl group or a C1-4 alkoxy group (the C1-4 alkoxy group being optionally substituted with a hydroxy group), and even more preferably a hydrogen atom or a cyclopropyl group.

$R_5$ is preferably a halogen atom or a C1-6 alkyl group, more preferably a halogen atom, and even more preferably a fluorine atom.

$R_6$ is preferably a hydrogen atom, a halogen atom or a C1-6 alkyl group, and more preferably a hydrogen atom.

$R_4$ is preferably a halogen atom or a cyclopropyl group, and more preferably an iodine atom or a cyclopropyl group.

$R_7$ is preferably a hydrogen atom or a methyl group.

The compound represented by general formula (11) is preferably a compound represented by general formula (6) below:

[Chemical Formula 14]

(6)

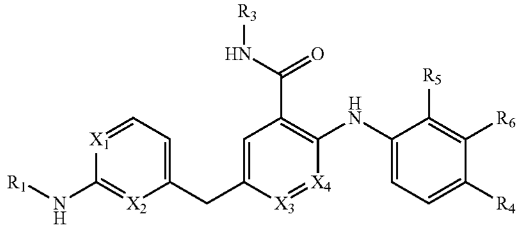

wherein:

$X_1$, $X_2$, $X_3$ and $X_4$ are each independently —$CR_2$= or —N=;

$R_2$ is a hydrogen atom, a halogen atom, or a C1-6 alkyl group;

$R_1$ is —S(=O)$_2$—NH—$R_8$ or —S(=O)$_2$—$R_8$;

$R_8$ is a hydrogen atom, a C1-6 alkyl group (the C1-6 alkyl group being optionally substituted with a halogen atom, a hydroxy group or a C1-6 alkoxy group), or a monocyclic C3-6 cycloalkyl group (the C3-6 cycloalkyl group being optionally substituted with a C1-6 alkyl group);

$R_3$ is a hydrogen atom, a C1-6 alkyl group, a C3-6 cycloalkyl group, or a C1-6 alkoxy group (the C1-6 alkoxy group being optionally substituted with a hydroxy group);

$R_5$ is a halogen atom or a C1-6 alkyl group; and $R_6$ is a hydrogen atom, a halogen atom or a C1-6 alkyl group and R is a halogen atom or a cyclopropyl group.

Examples of Compounds Represented by Formula (11) Include:

N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), 2-(4-cyclopropyl-2-fluoroanilino)-3,4-difluoro-5-[[3-fluoro-2-(methylsulfamoylamino)pyridin-4-yl]methyl]benzamide (compound A-1), N-cyclopropyl-5-[[2-(ethylsulfamoylamino)-3-fluoropyridin-4-yl]methyl]-3,4-difluoro-2-(2-fluoro-4-iodoanilino)benzamide (compound A-4), N-cyclopropyl-3,4-difluoro-5-[[3-fluoro-2-(2-fluoroethylsulfamoylamino)pyridin-4-yl]methyl]-2-(2-fluoro-4-iodoanilino)benzamide (compound A-6), 3,4-difluoro-2-(2-fluoro-4-iodoanilino)-5-[[3-fluoro-2-(methylsulfamoylamino)pyridin-4-yl]methyl]-N-[(2-methylpropan-2-yl)oxy]benzamide (compound A-8), 3,4-difluoro-2-(2-fluoro-4-iodoanilino)-5-[[3-fluoro-2-(methylsulfamoylamino)pyridin-4-yl]methyl]-N-methoxybenzamide (compound A-13), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(propan-2-ylsulfamoylamino)pyridin-4-yl]methyl]benzamide (compound A-31), 3,4-difluoro-2-(2-fluoro-4-iodoanilino)-5-[[3-fluoro-2-(2-methoxyethylsulfamoylamino)pyridin-4-yl]methyl]benzamide (compound A-33), 3,4-difluoro-2-(2-fluoro-4-iodoanilino)-5-[[3-fluoro-2-(2-methyl propylsulfamoylamino)pyridin-4-yl]methyl]benzamide (compound A-34), 3,4-difluoro-2-(2-fluoro-4-iodoanilino)-5-[[3-fluoro-2-[(1-methylcyclobutyl)sulfamoylamino]pyridin-4-yl]methyl]benzamide (compound A-35), 3,4-difluoro-2-(2-fluoro-4-iodoanilino)-5-[[3-fluoro-2-(propylsulfamoylamino)pyridin-4-yl]methyl]benzamide (compound A-41), 3,4-difluoro-2-(2-fluoro-4-iodoanilino)-5-[[3-fluoro-2-(methylsulfamoylamino)pyridin-4-yl]methyl]-N-(2-hydroxyethoxy)benzamide (compound B-1), 5-[[3-(ethylsulfonylamino)-2-fluorophenyl]methyl]-3,4-difluoro-2-(2-fluoro-4-iodoanilino)benzamide (compound D-4), 5-[[3-(ethylsulfonylamino)-2-fluorophenyl]methyl]-3,4-difluoro-2-(2-fluoro-4-iodoanilino)-N-methoxybenzamide (compound E-1), 3,4-difluoro-2-(2-fluoro-4-iodoanilino)-5-[[2-fluoro-3-(methylsulfamoylamino)phenyl]methyl]benzamide (compound E-7), 3,4-difluoro-2-(2-fluoro-4-iodoanilino)-5-[[2-fluoro-3-(methanesulfonamide)phenyl]methyl]benzamide (compound E-13), 4-fluoro-2-(2-fluoro-4-iodoanilino)-5-[[3-fluoro-2-(methylsulfamoylamino)pyridin-4-yl]methyl]benzamide (compound I-1), N-cyclopropyl-2-(2-fluoro-4-iodoanilino)-5-[[3-fluoro-2-(methylsulfamoylamino)pyridin-4-yl]methyl]-1-methyl-6-oxopyridine-3-carboxamide (compound J-5), 3,4-difluoro-2-(2-fluoro-4-iodoanilino)-5-[[3-fluoro-2-[(1-methylcyclobutyl)sulfamoylamino]pyridin-4-yl]methyl]-N-methoxybenzamide (compound A-15), 3,4-difluoro-5-[[3-fluoro-2-(methylsulfamoylamino)pyridin-4-yl]methyl]-2-(2-fluoro-4-methylsulfanylanilino)benzamide (compound A-18), 2-(4-ethynyl-2-fluoroanilino)-3,4-difluoro-5-[[3-fluoro-2-(propylsulfamoylamino)pyridin-4-yl]methyl]benzamide (compound A-20), 2-(4-bromo-2-fluoroanilino)-3,4-difluoro-5-[[3-fluoro-2-(methylsulfamoylamino)pyridin-4-yl]methyl]benzamide (compound A-27), 2-(2-chloro-4-iodoanilino)-5-[[3-(ethylsulfonylamino)-2-fluorophenyl]methyl]-3,4-difluoro-N-methoxybenzamide (compound E-9), 3,4-difluoro-2-(2-fluoro-4-iodoanilino)-5-[[2-fluoro-3-(oxan-4-ylsulfonylamino)phenyl]methyl]benzamide (compound E-23), 2-[4-(difluoromethylsulfanyl)-2-fluoroanilino]-3,4-difluoro-5-[[3-fluoro-2-(methylsulfamoylamino)pyridin-4-yl]methyl]benzamide (compound H-1), 3,4-difluoro-2-[(4-fluoro-1-benzothiophen-5-yl)amino]-5-[[3-fluoro-2-(methylsulfamoylamino)pyridin-4-yl]methyl]benzamide (compound H-3), 3,4-difluoro-2-(2-fluoro-4-iodoanilino)-5-[3-fluoro-2-(methylsulfamoylamino)pyridin-4-yl]oxybenzamide (compound H4), 2-(2-fluoro-4-iodoanilino)-5-[[3-fluoro-2-(methylsulfamoylamino)pyridin-4-yl]methyl]-N-methoxy-1-methyl-6-oxopyridine-3-carboxamide (compound J-8), 2-(2-fluoro-4-iodoanilino)-5-[[3-fluoro-2-(methylsulfamoylamino)pyridin-4-yl]methyl]-1-methyl-N-[(2-methylpropan-2-yl)oxy]-6-oxopyridine-3-carboxamide (compound J-10), 5-[[2-(ethylsulfamoylamino)-3-fluoropyridin-4-yl]methyl]-2-(2-fluoro-4-iodoanilino)-1-methyl-6-oxopyridine-3-carboxamide (compound J-14), 5-(2-fluoro-4-iodoanilino)-2-[[3-fluoro-2-(methylsulfamoylamino)pyridin-4-yl]methyl]pyridine-4-carboxamide (compound L-1), 5-(2-fluoro-4-iodoanilino)-8-[[3-fluoro-2-(methylsulfamoylamino)pyridin-4-yl]methyl]imidazo[1,5-a]pyridine-6-carboxamide (compound M-1), 5-fluoro-4-(2-fluoro-4-iodoanilino)-1-[[3-fluoro-2-(methylsulfamoylamino)pyridin-4-yl]methyl]-6-oxopyridine-3-carboxamide (compound N-1), 5-fluoro-4-(2-fluoro-4-iodoanilino)-1-[[3-fluoro-2-(propylsulfamoylamino)pyridin-4-yl]methyl]-6-oxopyridine-3-carboxamide (compound N-2), 4-(2-fluoro-4-iodoanilino)-1-[[3-fluoro-2-(methylsulfamoylamino)pyridin-4-yl]methyl]-5-methyl-6-oxopyridine-3-carboxamide (compound P-1), and 1-[[2-(ethylsulfonylamino)-3-fluoropyridin-4-yl]methyl]-4-(2-fluoro-4-iodoanilino)-5-methyl-6-oxopyridine-3-carboxamide (compound P-2).

Among these compounds,

N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), 2-(4-cyclopropyl-2-fluoroanilino)-3,4-difluoro-5-[[3-fluoro-2-(methylsulfamoylamino)pyridin-4-yl]methyl]benzamide (compound A-1), N-cyclopropyl-5-[[2-(ethylsulfamoylamino)-3-fluoropyridin-4-yl]methyl]-3,4-difluoro-2-(2-fluoro-4-iodoanilino)benzamide (compound A-4), N-cyclopropyl-3,4-difluoro-5-[[3-fluoro-2-(2-fluoroethylsulfamoylamino)pyridin-4-yl]methyl]-2-(2-fluoro-4-iodoanilino)benzamide (compound A-6), 3,4-difluoro-2-(2-fluoro-4-iodoanilino)-5-[[3-fluoro-2-(methylsulfamoylamino)pyridin-4-yl]methyl]-N-[(2-methylpropan-2-yl)oxy]benzamide (compound A-8), 3,4-difluoro-2-(2-fluoro-4-iodoanilino)-5-[[3-fluoro-2-(methylsulfamoylamino)pyridin-4-yl]methyl]-N-methoxybenzamide (compound A-13), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(propan-2-ylsulfamoylamino)pyridin-4-yl]methyl]benzamide (compound A-31), 3,4-difluoro-2-(2-fluoro-4-iodoanilino)-5-[[3-fluoro-2-(2-methoxyethylsulfamoylamino)pyridin-4-yl]methyl]benzamide (compound A-33), 3,4-difluoro-2-(2-fluoro-4-iodoanilino)-5-[[3-fluoro-2-(2-methylpropylsulfainoylamino)pyridin-4-yl]methyl]benzamide (compound A-34), 3,4-difluoro-2-(2-fluoro-4-iodoanilino)-5-[[3-fluoro-2-[(1-methylcyclobutyl)sulfamoylamino]pyridin-4-yl]methyl]benzamide (compound A-35), 3,4-difluoro-2-(2-fluoro-4-iodoanilino)-5-[[3-fluoro-2-(propylsulfamoylamino)pyridin-4-yl]methyl]benzamide (compound A-41), 3,4-difluoro-2-(2-fluoro-4-iodoanilino)-5-[[3-fluoro-2-(methylsulfamoylamino)pyridin-4-yl]methyl]-N-(2-hydroxyethoxy)benzamide (compound B-1), 5-[[3-(ethylsulfonylamino)-2-fluorophenyl]methyl]-3,4-difluoro-2-(2-fluoro-4-iodoanilino)benzamide (compound D-4), 5-[[3-(ethylsulfonylamino)-2-fluorophenyl]methyl]-3,4-difluoro-2-(2-fluoro-4-iodoanilino)-N-methoxybenzamide (compound E-1), 3,4-difluoro-2-(2-fluoro-4-iodoanilino)-5-[[2-fluoro-3-(methylsulfamoylamino)phenyl]methyl]benzamide (compound E-7), 3,4-difluoro-2-(2-fluoro-4-iodoanilino)-5-[[2-fluoro-3-(methanesulfonamide)phenyl]methyl]benzamide (compound E-13), 4-fluoro-2-(2-fluoro-4-iodoanilino)-5-[[3-fluoro-2-(methylsulfamoylamino)pyridin-4-yl]methyl]benzamide (compound I-1), and N-cyclopropyl-2-(2-fluoro-4-iodoanilino)-5-[[3-fluoro-2-(methylsulfamoylamino)pyridin-4-yl]methyl]-1-methyl-6-oxopyridine-3-carboxamide (compound J-5)

are preferred in terms of, for example, MEK-inhibiting activity, RAF-inhibiting activity, cell proliferation-inhibiting activity and/or metabolic stability, with N-cyclopropyl-3,4-difluoro-2-(2-fluoro-4-iodoanilino)-5-[[3-fluoro-2-(methylsulfamoylamino)pyridin-4-yl]methyl]benzamide (compound A-2), 2-(2-fluoro-4-iodoanilino)-5-[[3-fluoro-2-(methylsulfamoylamino)pyridin-4-yl]methyl]-1-methyl-6-oxopyridine-3-carboxamide (compound J-1), and 2-(4-cyclopropyl-2-fluoroanilino)-3,4-difluoro-5-[[3-fluoro-2-(methylsulfamoylamino)pyridin-4-yl]methyl]benzamide (compound A-1)

being more preferred, and 2-(4-cyclopropyl-2-fluoroanilino)-3,4-difluoro-5-[[3-fluoro-2-(methylsulfamoylamino)pyridin-4-yl]methyl]benzamide (compound A-1) being particularly preferred.

A pharmaceutically acceptable salt of 2-(4-cyclopropyl-2-fluoroanilino)-3,4-difluoro-5-[[3-fluoro-2-(methylsulfamoylamino)pyridin-4-yl]methyl]benzamide (compound A-1) that is preferred is, for example, a sodium salt or a potassium salt, with a sodium salt being particularly preferred.

A third aspect of the present disclosure provides a composition comprising a compound represented by general formula (1) below or a pharmaceutically acceptable salt thereof, or a pharmaceutically acceptable solvate of said compound or salt, and a dispersant and/or a basic compound:

[Chemical Formula 15]

(1)

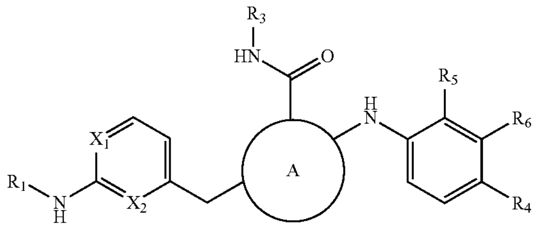

wherein:

ring A is a group represented by general formula (2), (3) or (4) below (where the bonds denoted by *,  and * are bonded to —NH—, —CONH— and —$CH_2$—, respectively):

[Chemical Formula 16]

(2)

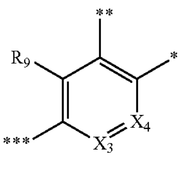

-continued (3)

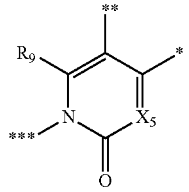

(4)

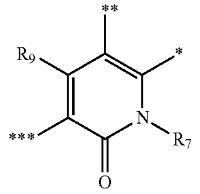

$X_1$, $X_2$, $X_3$, $X_4$ and $X_5$ are each independently —$CR_2$═ or —N═;

$R_2$ is a hydrogen atom, a halogen atom, or a C1-4 alkyl group;

$R_1$ is —S(═O)$_2$—NH—$R_8$ or —S(═O)$_2$—$R_8$;

$R_8$ is a C1-4 alkyl group (the C1-4 alkyl group being optionally substituted with a halogen atom, a hydroxy group, a C1-4 alkoxy group, a C3-6 cycloalkyl group or a C3-6 heterocycloalkyl group) or a C3-6 cycloalkyl group (the C3-6 cycloalkyl group being optional substituted with a C1-4 alkyl group);

$R_3$ is a hydrogen atom, a C3-6 cycloalkyl group, or a C1-6 alkoxy group;

$R_5$ is a halogen atom;

$R_6$ is a hydrogen atom and $R_4$ is a halogen atom or a C3-6 cycloalkyl group;

$R_7$ is a C1-4 alkyl group; and $R_9$ is a hydrogen atom.

The compounds, salts or solvates of the third aspect exhibit high MEK-inhibiting activity and can be used for the treatment or prevention of cell proliferative disorders, particularly cancers (more specifically, RAF-mutant cancers).

The following are examples of compounds of the third aspect that are preferred in terms of, for example, MEK-inhibiting activity and metabolic stability:

2-(4-cyclopropyl-2-fluoroanilino)-3,4-difluoro-5-[[3-fluoro-2-(methylsulfamoylamino)pyridin-4-yl]methyl]benzamide (compound A-1), (+/−)-3,4-difluoro-5-[[3-fluoro-2-(2-hydroxypropylsulfamoylamino)pyridin-4-yl]methyl]-2-(2-fluoro-4-iodoanilino)benzamide (compound A-17), 3,4-difluoro-2-(2-fluoro-4-iodoanilino)-5-[[3-fluoro-2-(oxetan-3-ylmethylsulfamoylamino)pyridin-4-yl]methyl]benzamide (compound A-21), 3,4-difluoro-2-(2-fluoro-4-iodoanilino)-5-[[3-fluoro-2-(methylsulfamoylamino)pyridin-4-yl]methyl]benzamide (compound A-25), 5-[[2-(cyclopropylsulfamoylamino)-3-fluoropyridin-4-yl]methyl]-3,4-difluoro-2-(2-fluoro-4-iodoanilino)benzamide (compound A-30), 3,4-difluoro-2-(2-fluoro-4-iodoanilino)-5-[[3-fluoro-2-(2-methoxyethylsulfamoylamino)pyridin-4-yl]methyl]benzamide (compound A-33), 5-[[2-(ethylsulfamoylamino)-3-fluoropyridin-4-yl]methyl]-3,4-difluoro-2-(2-fluoro-4-iodoanilino)benzamide (compound A-40), 3,4-difluoro-5-[[3-fluoro-2-(2-fluoroethylsulfamoylamino)pyridin-4-yl]methyl]-2-(2-fluoro-4-iodoanilino)benzamide (compound A-42), 5-[[2-(ethylsulfonylamino)-3-fluoropyridin-4-yl]methyl]-3,4-difluoro-2-(2-fluoro-4-iodoanilino)-N-methoxybenzamide (compound B-16), 3,4-difluoro-2-(2-fluoro-4-iodoanilino)-5-[[2-(methylsulfamoylamino)pyridin-4-yl]methyl]benzamide (compound C-3), 2-(2-fluoro-4-iodoanilino)-5-[[3-fluoro-2-(methylsulfamoylamino)pyridin-4-yl]methyl]-1-methyl-N-[(2-methylpropan-2-yl)oxy]-6-oxopyridine-3-carboxamide (compound J-10), 5-(2-fluoro-4-iodoanilino)-2-[[3-fluoro-2-(methylsulfamoylamino)pyridin-4-yl]methyl]pyridine-4-carboxamide (compound L-1), 5-fluoro-4-(2-fluoro-4-iodoanilino)-1-[[3-fluoro-2-(methylsulfamoylamino)pyridin-4-yl]methyl]-6-oxopyridine-3-carboxamide (compound N-1), 1-[[2-(ethylsulfonylamino)-3-fluoropyridin-4-yl]methyl]-4-(2-fluoro-4-iodoanilino)-5-methyl-6-oxopyridine-3-carboxamide (compound P-2), 1-[[2-(ethylsulfonylamino)-3-fluoropyridin-4-yl]methyl]-4-(2-fluoro-4-iodoanilino)-N-methoxy-5-methyl-6-oxopyridine-3-carboxamide (compound P-5), and N-cyclopropyl-4-(2-fluoro-4-iodoanilino)-1-[[3-fluoro-2-(methylsulfamoylamino)pyridin-4-yl]methyl]-5-methyl-6-oxopyridine-3-carboxamide (compound P-6).

As used herein, “Japanese Pharmacopoeia” means The Japanese Pharmacopoeia, Seventeenth Edition. Also, “Japanese Pharmacopoeia 1st fluid for dissolution test” means 1st fluid for dissolution test described in The Japanese Pharmacopoeia, Seventeenth Edition.

The following are examples of abbreviations used throughout the present specification and their meanings.

Boc: tert-Butoxycarbonyl
COMU: (1-Cyano-2-ethoxy-2-oxoethylideneaminooxy)dimethylamino-morpholino-carbenium hexafluorophosphate
DBU: Diazabicycloundecene
DCC: N,N'-Dicyclohexylcarbodiimide
DCM: Dichloromethane
DIPEA: N,N-Diisopropylethylamine
DMA: N,N-Dimethylacetamide
DMF: N,N-Dimethylformamide
DMSO: Dimethyl sulfoxide
EDC: 1-Ethyl-3-(3-dimethylaminopropyl)carbodiimide
EDC HCl: 1-(3-Dimethylaminopropyl)-3-ethylcarbodiimide hydrochloride
EtOH: Ethanol
HATU: O-(7-Azabenzotriazol-1-yl)-N,N,N',N'-tetramethyluronium hexafluorophosphate
HOAt: 1-Hydroxy-7-azabenzotriazole
HOOBt: 3,4-Dihydro-3-hydroxy-4-oxo-1,2,3-benzotriazine
LDA: Lithium diisopropylamide
MeOH: Methanol
NMP: N-Methyl-2-pyrrolidone
TBS: tert-Butyldimethylsilyl
TFA: Trifluoroacetic acid
THF: Tetrahydrofuran
Xantphos: 4,5-bis(Diphenylphosphino)-9,9-dimethylxanthene Examples of preferred methods for producing compounds of the present disclosure will now be described. The definitions for $X_1$, $R_1$, $R_2$, $R_3$, $R_4$, $R_5$ and $R_7$ are the same as above unless the context indicates otherwise. $R_a$ represents, for example, a 4-methylphenyl group or a 2-nitrophenyl group, and $R_b$ represents, for example, a Boc group or a 2,4-dimethoxybenzyl group.

(General Production Process-1)
General production process-1 is a preferred production process for compounds represented by general formula (6) wherein $X_2$, $X_3$ and $X_4$ (which may be the same or different) are —$CR_2$= and $R_6$, is a hydrogen atom.
[Chemical Formula 17]
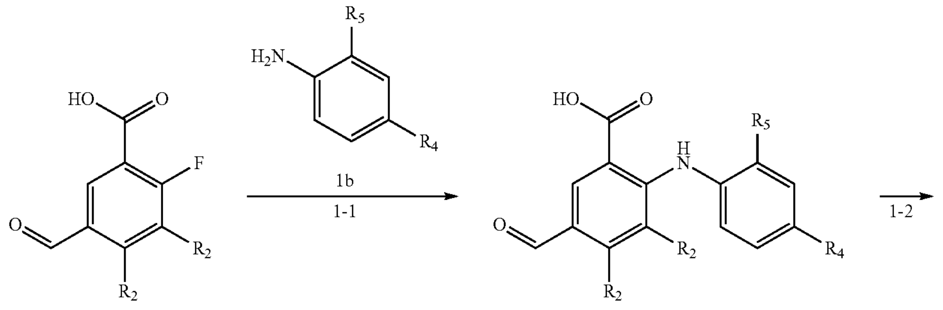
1a 1c
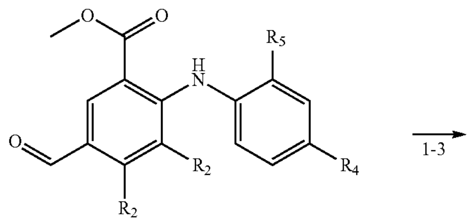
1d
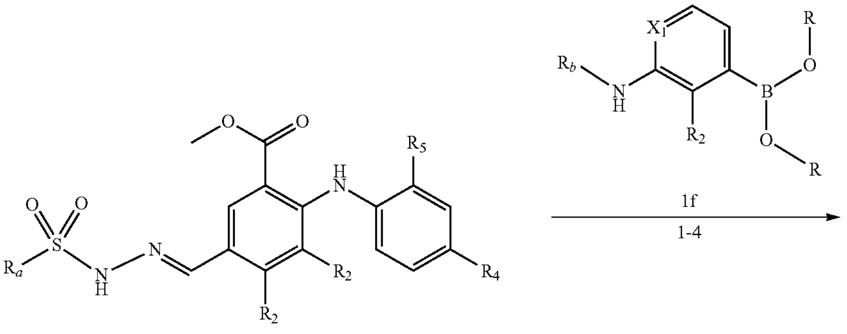
1e
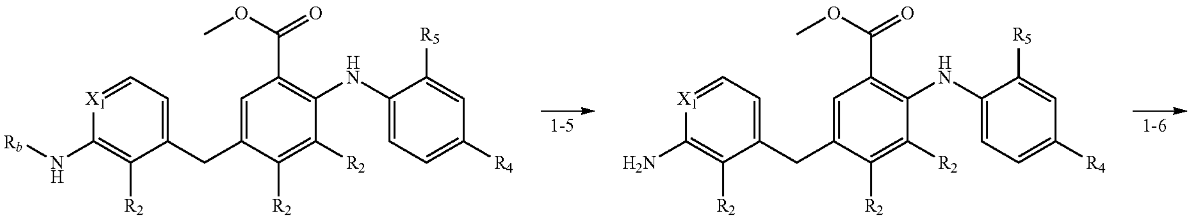
1g 1h
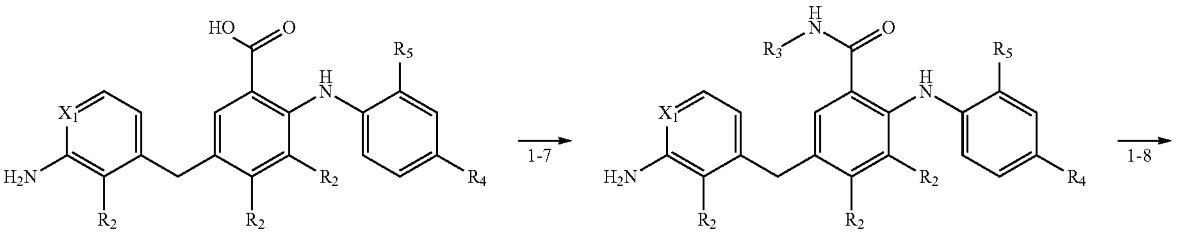
1i 1j -continued

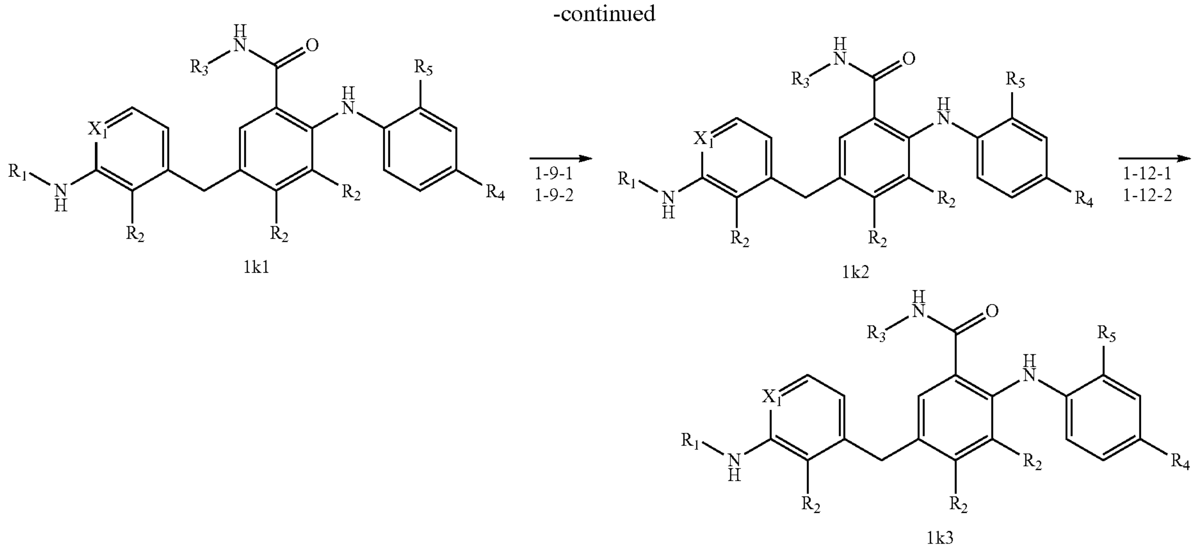

1k1

1k2

1k3

[Chemical Formula 18]

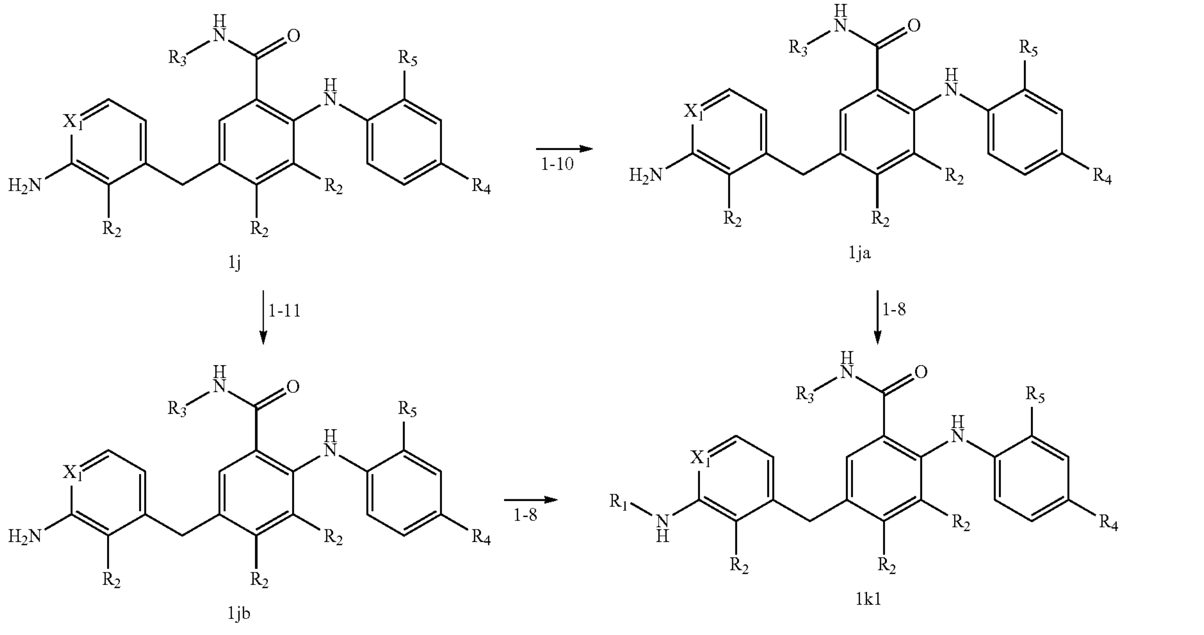

1j

1ja

1jb

1k1

Step 1-1:

$S_NAr$ Reaction Between Aniline Derivative 1b and Fluorobenzene Derivative 1a

An aniline derivative 1b is reacted with a fluorobenzene derivative 1a in the presence of a base. Examples of the base include organic lithium reagents, with lithium bis(trimethylsilyl)amide and lithium diisopropylamide being preferred. Examples of the solvent include polar aprotic solvents such as THF, 1,4-dioxane and NMP, with THF being preferred.

Step 1-2:

Methylation of Benzoic Acid Derivative 1c

A benzoic acid derivative 1c is reacted with a methylating reagent. Examples of the methylating reagent include diazomethane derivatives, with diazomethyltrimethylsilane being preferred. Examples of the solvent include alcohols, nonpolar solvents, and mixed solvents thereof, with mixed solvents of toluene and methanol and mixed solvents of THE and methanol being preferred.

Step 1-3:

Hydrazonation of Aldehyde Derivative 1d

An aldehyde derivative 1d is reacted with an arylsulfonyl hydrazide. Examples of the arylsulfonyl hydrazide include methylbenzenesulfonyl hydrazides and nitrobenzenesulfonyl hydrazides, with 4-methylbenzenesulfonyl hydrazide and 2-nitrobenzenesulfonyl hydrazide being preferred. Examples of the solvent include polar solvents such as alcohols, with methanol and ethanol being preferred.

Step 1-4:

Coupling of Hydrazone Derivative 1e and Arylboronic Acid Derivative 1f

A hydrazone derivative 1e is reacted with an arylboronic acid derivative if in the presence of a base. Examples of the base include carbonic acid salts and amines, with potassium carbonate and DIPEA being preferred. Examples of the solvent include polar solvents such as 1,4-dioxane, DMF, NMP and THF, with 1,4-dioxane being preferred. The reaction temperature is preferably 80° C. or higher.

Step 1-5:

Deprotection of Methyl Benzoate Derivative 1g

A methyl benzoate derivative 1g is placed under acidic conditions for removal of the protecting group $R_b$. Examples of the acid include sulfuric acid, hydrochloric acid, methanesulfonic acid and trifluoroacetic acid, with trifluoroacetic acid being preferred. Examples of the solvent include alcohols and nonpolar solvents such as DCM, with DCM being preferred.

Step 1-6:

Hydrolysis of Ester Derivative 1h

An ester derivative 1h is reacted with a hydroxide. Examples of the hydroxide include lithium hydroxide, potassium hydroxide and sodium hydroxide, with lithium hydroxide being preferred. Examples of the solvent include polar solvents such as alcohols and THF, water, and mixed solvents thereof, with aqueous THF being preferred.

Step 1-7:

Amidation of Benzoic Acid Derivative 1i

A benzoic acid derivative 1i is reacted with the corresponding amine or amine hydrochloride in the presence of a condensation agent.

The corresponding amine or amine hydrochloride may optionally have a Boc group. Examples of the condensation agent include DCC, EDC or EDC·HCl, HATU, COMU, and propylphosphonic anhydride (cyclic trimer), and HOOBt or HOAt, for example, may be further added as appropriate. For example, it is preferred to use a combination of EDC or EDC·HCl and HOOBt or to use HATU. In some cases, a base such as DIPEA or triethylamine, for example, may also be used in addition to the condensation agent, the base preferably being DIPEA. Examples of the solvent include polar solvents such as DMF, DMA, NMP, methanol and ethanol, and mixed solvents thereof, with DMF being preferred.

Step 1-8:

Sulfamidation or Sulfonamidation of Amine Derivative 1j, 1Ja or 1jb Sulfamidation:

An amine derivative 1j, 1ja or 1jb is reacted with the corresponding sulfamoyl chloride or 4-nitrophenyl sulfamate in the presence of a base. The corresponding sulfamoyl chloride or 4-nitrophenyl sulfamate may optionally have a Boc group. Examples of the base include amines, with pyridine, triethylamine, DIPEA and imidazole being preferred. Examples of the solvent include polar solvents such as DMF, DMA, NMP, THF, 1,4-dioxane, acetonitrile and pyridine, nonpolar solvents such as dichloromethane and dichloroethane, and mixed solvents thereof, with DMF, DMA, THF and dichloromethane being preferred.

Sulfonamidation:

An amine derivative 1j, 1ja or 1jb is reacted with the corresponding sulfonyl chloride in the presence of a base. Examples of the base include amines, with pyridine, triethylamine, DIPEA and imidazole being preferred. Examples of the solvent include polar solvents such as DMF, DMA, NMP, THF, 1,4-dioxane, acetonitrile and pyridine, nonpolar solvents such as dichloromethane and dichloroethane, and mixed solvents thereof, with dichloromethane and pyridine being preferred.

Step 1-9-1:

Boc Deprotection of Sulfamide or Sulfonamide Derivative 1k1

When $R_1$ or $R_3$ of a sulfamide or sulfonamide derivative 1k1 has a Boc group, the Boc group is removed by placing the compound 1k1 under acidic conditions. Examples of the acid include sulfuric acid, hydrochloric acid, methanesulfonic acid and trifluoroacetic acid. Alternatively, Boc deprotection may be carried out by producing an acid with, for example, chlorotrimethylsilane (TMSCl) in an alcohol. Examples of the solvent include alcohols and nonpolar solvents such as DCM. The combination of the acid and solvent is preferably, for example, a combination of TMSCl and 2,2,2-trifluoroethanol or a combination of trifluoroacetic acid and DCM.

Step 1-9-2:

Alkylation, Alkenylation, Alkynylation or Thioetherification of Sulfamide or Sulfonamide Derivative 1k1

When $R_4$ or $R_5$ of a sulfamide or sulfonamide derivative 1k1 is a halogen, it may be subjected to alkylation, alkenylation, alkynylation or thioetherification by the following method, for example.

Method 1 (Alkylation or Alkenylation by Suzuki/Miyaura Cross-Coupling):

The compound 1k1 is reacted with the corresponding boronic acid, boronic acid ester or borate in the presence of Pd. This can be carried out by the method described in Chem. Rev. 1995, vol. 95, no. 7, p. 2457 or ACC. Chem. Res., vol. 40, p. 275, for example. Preferred examples of the base include inorganic salts such as carbonates and hydroxides and amines such as triethylamine and DIPEA, with sodium carbonate, potassium carbonate and triethylamine being preferred. Examples of the solvent include polar solvents such as THF, 1,4-dioxane, DMF, DMA, NMP, methanol, ethanol, 2-propanol and water, and mixed solvents thereof, with mixed solvents of THE and 2-propanol and mixed solvents of THF and water being preferred. Examples of the Pd and its ligands include ones mentioned in Chem. Rev. 1995, vol. 95, no. 7, p. 2457, ACC. Chem. Res., vol. 40, p. 275 and ACC. Chem. Res., vol. 41, p. 1461, with $PdCl_2(PPh_3)_2$, $Pd(PPh_3)_4$ and [1,1'-bis(diphenylphosphino)ferrocene]palladium(II) dichloride being preferred. The reaction temperature is preferably 80° C. or higher.

Method 2 (Alkylation or Alkenylation by Negishi Cross-Coupling):

The compound 1k1 is reacted with the corresponding organic zinc reagent in the presence of Pd or Ni. This can be carried out by the method described in Tetrahedron. 1992, vol. 48, no. 44, p. 9577 or Aldrichimica Acta. 2005, vol. 38, p. 71, for example. Examples of the solvent include polar solvents such THF, 1,4-dioxane, DMF, DMA and NMP, and mixed solvents thereof, with THF being preferred. Examples of the Pd and Ni include ones mentioned in Tetrahedron. 1992, vol. 48, no. 44, p. 9577 and Aldrichimica Acta. 2005, vol. 38, p. 71, as well as $PdCl_2(PPh_3)_2$, $Pd(PPh_3)_4$ and [1,1'-bis(diphenylphosphino)ferrocene]palladium(II) dichloride, with $PdCl_2(PPh_3)_2$, $Pd(PPh_3)_4$ and [1,1'-bis(diphenylphosphino)ferrocene]palladium(II) dichloride being preferred.

Method 3 (Alkynylation by Sonogashira Cross-Coupling):

The compound 1k1 is reacted with the corresponding alkyne in the presence of Pd and Cu. This can be carried out by the method described in Chem. Soc. Rev. 2011, vol. 40, p. 5048, for example. The corresponding alkyne may have a silyl group, and may be, for example, trimethylsilylacetylene. Examples of the base include amines such as triethylamine, DIPEA, DBU and piperidine and inorganic bases such as NaOAc, with triethylamine and DIPEA being preferred. Examples of the Pd catalyst include $PdCl_2(PPh_3)_2$, $Pd(PPh_3)_4$, [1,1'-bis(diphenylphosphino)ferrocene]palladium(II) dichloride, Pd $(OAc)_2$ and $Pd_2(dba)_3$, with $PdCl_2(PPh_3)_2$, $Pd(PPh_3)_4$ and [1,1'-bis(diphenylphosphino)ferrocene]palladium(II) dichloride being preferred. Examples of the Cu include copper iodide, copper bromide and copper chloride, with copper iodide being preferred. Examples of the solvent include polar solvents such as THF, 1,4-dioxane, DMF, DMA, NMP, DMSO, methanol, ethanol and 2-propanol, and mixed solvents thereof, with THF being preferred.

Method 4 (Thioetherification):

The compound 1k1 is reacted with the corresponding mercaptane or a mercaptane salt in the presence of Pd. Examples of the base include amines such as triethylamine, DIPEA, DBU and piperidine, with triethylamine and DIPEA being preferred. Examples of the Pd catalyst include zero-valent Pd complexes such as $Pd(PPh_3)_4$, with [(4,5-bis(diphenylphosphino)-9,9-dimethylxanthene)-2-(2'-amino-1,1'-biphenyl)]palladium(II) methanesulfonate being preferred. Examples of the solvent include polar solvents such as THF, 1,4-dioxane, DMF, DMA, NMP, DMSO, methanol, ethanol and 2-propanol, and mixed solvents thereof, with 1,4-dioxane being preferred.

Step 1-10:

Bromination or Chlorination of Amine Derivative 1j

When $R_4$ or $R_5$ of an amine derivative 1j is a halogen, the compound 1j may be reacted with copper bromide or copper chloride for bromination or chlorination. Examples of the solvent include polar solvents such THF, 1,4-dioxane, DMF, DMA and NMP, with DMF being preferred.

Step 1-11:

TBS Protection of Amine Derivative 1j

When $R_3$ of an amine derivative 1j has a hydroxy group, the compound 1j may be reacted with tert-butyldimethylchlorosilane (TBSCl) in the presence of a base for TBS protection. Examples of the base include bases such as triethylamine, DIPEA and imidazole, with triethylamine being preferred. Examples of the solvent include polar solvents such THF, 1,4-dioxane, DMF, DMA and NMP, with DMF being preferred.

Step 1-12-1:

TBS Deprotection of Sulfamide or Sulfonamide Derivative 1k2

When $R_3$ of a sulfamide or sulfonamide derivative 1k2 has a TBS group, the compound 1k2 is reacted with tetrabutylammonium fluoride to remove the TBS group. Examples of the solvent include polar solvents such as THF, 1,4-dioxane and DMF, with THE being preferred.

Step 1-12-2:

Desilylation of Sulfamide or Sulfonamide Derivative 1k2

When $R_4$ or $R_5$ of a sulfamide or sulfonamide derivative 1k2 has a silyl group, the compound 1k2 is reacted with a base for removal of the silyl group. Examples of the base include carbonic acid salts, with potassium carbonate being preferred. Examples of the solvent include alcohols such as methanol and ethanol, with methanol being preferred.

(General Production Process-2)

General production process-2 is another preferred process for producing compound 1k1.

[Chemical Formula 19]

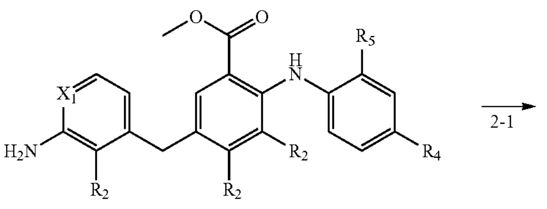

1h

-continued

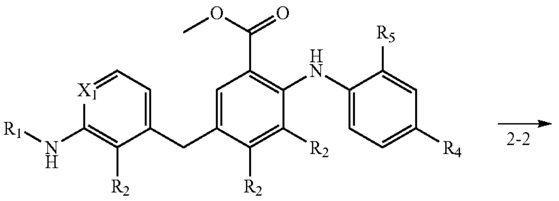

2a

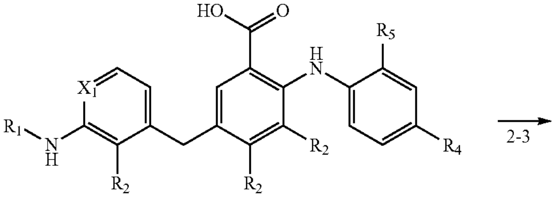

2b

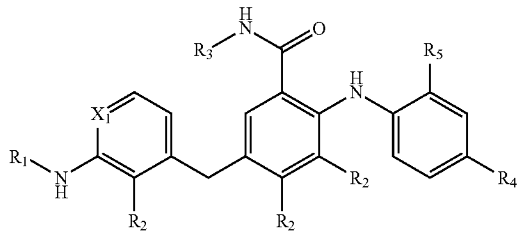

Step 2-1:

Sulfamidation or sulfonamidation of the amine derivative 1h is carried out in the same manner as step 1-8.

Step 2-2:

Hydrolysis of the ester derivative 2a is carried out in the same manner as step 1-6.

Step 2-3:

Amidation of the benzoic acid derivative 2b is carried out in the same manner as step 1-7. Before carrying out amidation, depending on the case, Boc deprotection, alkylation, alkenylation, alkynylation, thioetherification, bromination or chlorination of the benzoic acid derivative 2b may also be carried out in the same manner as step 1-9-1, 1-9-2 or 1-10.

(General Production Process-3)

General production process-3 is another preferred process for producing compound 1k1.

[Chemical Formula 20]

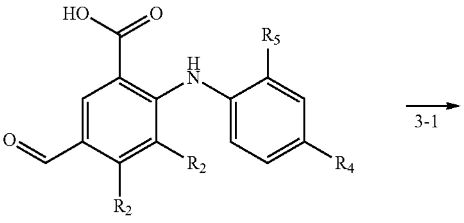

1c

-continued

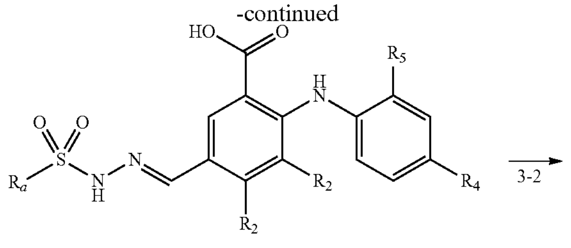

3a

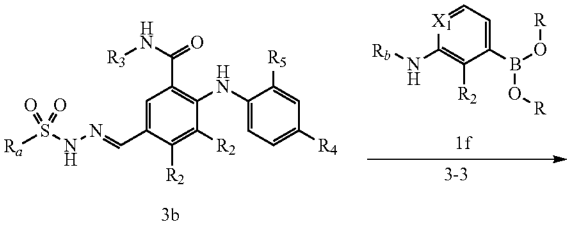

3b

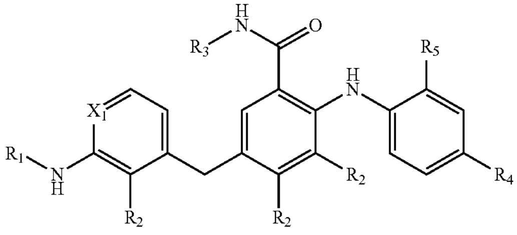

1kl

Step 3-1:

Hydrazonation of an aldehyde derivative 1c may be carried out in the same manner as step 1-3.

Step 3-2:

Amidation of the benzoic acid derivative 3a is carried out in the same manner as step 1-7.

Step 3-3:

Coupling between the hydrazone derivative 3b and aryl-boronic acid derivative if, removal of the protecting group $R_b$ and sulfamidation or sulfonamidation of the amine derivative may be carried out in the same manner as steps 1-4, 1-5 and 1-8, respectively.

(General Production Process-4)

General production process-4 is a preferred process for building the backbone of a compound represented by general formula (1) wherein ring A is a group represented by general formula (4), $X_1$ is —N═, $X_2$ is —CF═, and $R_6$ and $R_9$ are hydrogen atoms.

[Chemical Formula 21]

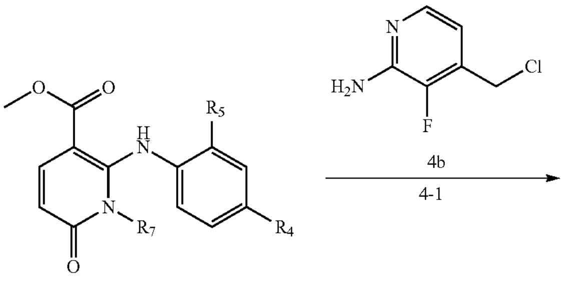

4a

-continued

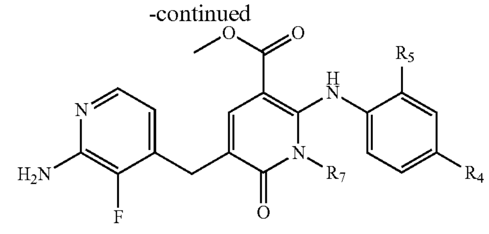

4c

Step 4-1:

Alkylation of Compound 4a

Compound 4a is reacted with compound 4b in the presence of a base. Examples of the base include phosphates and metal alkoxides such as sodium tert-butoxide, with tripotassium phosphate being preferred. Potassium iodide or tetrabutylammonium iodide, for example, may be added to accelerate the reaction, with tetrabutylammonium iodide being preferred as such an additive. Examples of the solvent include polar solvents such as NMP and 1,3-dimethyl-2-imidazolidinone, with 1,3-dimethyl-2-imidazolidinone being preferred. The reaction temperature is preferably 40° C. or higher.

The starting compounds and reagents used for production of the compounds of the present disclosure may also form salts or solvates, so long as the desired reactions are not inhibited.

When a compound of the present disclosure is obtained in free form, it may be converted to a pharmaceutically acceptable salt or solvate by a common method. Conversely, when a compound of the present disclosure is obtained in the form of a pharmaceutically acceptable salt or solvate, it may be converted to the free form.

Isolation or purification of the compounds, salts or solvates of the present disclosure can be carried out using, for example, distillation, recrystallization or chromatography. When isomers (such as enantiomers, diastereomers, or conformational isomers) exist, isolation or purification of the compounds can be carried out using, for example, recrystallization, a diastereomer salt method, enzymatic resolution, or chromatography (e.g., thin-layer chromatography, column chromatography, high-performance liquid chromatography, or gas chromatography).

Examples of the dispersant in the composition of the present disclosure include methylcellulose, polyvinyl alcohol, hydroxypropylcellulose, copolyvidone, hydroxypropylmethylcellulose, methacrylic acid copolymer, polyvinylpyrrolidone, and hypromellose acetate succinate, with methylcellulose, polyvinyl alcohol, and hydroxypropylcellulose being preferred, and methylcellulose being particularly preferred. In one aspect, the composition of the present disclosure comprises at least one dispersant selected from the group consisting of methylcellulose, polyvinyl alcohol, hydroxypropylcellulose, copolyvidone, hydroxypropylmethylcellulose, methacrylic acid copolymer, polyvinylpyrrolidone, and hypromellose acetate succinate.

The content of the dispersant in the composition of the present disclosure is, for example, 0.1 to 20 parts by weight, preferably 0.2 to 10 parts by weight and more preferably 1 to 10 parts by weight, relative to 1 part by weight of the compound, salt or solvate of any of the first to third aspects.

Examples of the basic compound in the composition of the present disclosure include meglumine, arginine, histidine, magnesium oxide, calcium silicate, and magnesium stearate, with meglumine and arginine being preferred, and meglumine being particularly preferred. In one aspect, the composition of the present disclosure comprises at least one basic compound selected from the group consisting of meglumine, arginine, histidine, magnesium oxide, calcium silicate, and magnesium stearate.

The content of the basic compound in the composition of the present disclosure is, for example, 0.2 to 40 parts by weight, preferably 0.5 to 20 parts by weight and more preferably 1 to 10 parts by weight, relative to 1 part by weight of the compound, salt or solvate of any of the first to third aspects.

The composition of the present disclosure may consist of a compound, salt or solvate of any of the first to third aspects, and a dispersant and/or a basic compound, or may comprise another pharmaceutically acceptable ingredient, for example, at least one ingredient selected from the group consisting of excipients, lubricants (coating agents), binders, disintegrants, flavoring agents, bases, diluents, surfactants, and emulsifiers.

Examples of excipients include starches (starch, potato starch, cornstarch, etc.), lactose hydrate, crystalline cellulose, mannitol, and calcium hydrogen phosphate.

Examples of lubricants (coating agents) include ethylcellulose, shellac, talc, magnesium stearate, carnauba wax, and paraffin.

Examples of binders include macrogol, as well as the same compounds mentioned as excipients.

Examples of disintegrants include croscarmellose sodium and sodium carboxymethyl starch, as well as the same compounds mentioned as excipients.

Examples of flavoring agents include commonly used sweeteners, acidulants and fragrances.

Examples of bases include: fats such as lard; vegetable oils such as olive oil and sesame oil; higher alcohols such as stearyl alcohol and cetanol; animal oils; lanolin acid; vaseline; paraffin; bentonite; glycerin; and glycol oil.

Examples of solvents or diluents for liquid formulations include phenol, chlorocresol, purified water, and distilled water.

Examples of surfactants or emulsifiers include polysorbate 80, polyoxyl 40 stearate, and lauromacrogol.

The composition of the present disclosure can be produced, for example, by mixing a compound, salt or solvate of any of the first to third aspects and a dispersant and/or a basic compound or by mixing a compound, salt or solvate of any of the first to third aspects, a dispersant and/or a basic compound, and another pharmaceutically acceptable ingredient (e.g., an aforementioned excipient, lubricant (coating agent), binder, disintegrant, flavoring agent, base, diluent, surfactant, or emulsifier). That is, in one aspect, there is provided a method for producing a composition comprising a compound represented by general formula (1) shown in (A1) above or a pharmaceutically acceptable salt thereof, or a pharmaceutically acceptable solvate of said compound or salt, and a dispersant and/or a basic compound, the method comprising providing a mixture containing said compound of general formula (1), said salt or said solvate, and said dispersant and/or said basic compound.

In one preferred aspect, the composition of the present disclosure comprises: 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt; and a dispersant and/or a basic compound. In one more preferred aspect, the composition of the present disclosure comprises: a sodium salt or potassium salt of 2-(4-cyclopropyl-2-fluoroanilino)-3,4-difluoro-5-[[3-fluoro-2-(methylsulfamoylamino)pyridin-4-yl]methyl]benzamide; and a dispersant and/or a basic compound. In one even more preferred aspect, the composition of the present disclosure comprises: a sodium salt of 2-(4-cyclopropyl-2-fluoroanilino)-3,4-difluoro-5-[[3-fluoro-2-(methylsulfamoylamino)pyridin-4-yl]methyl]benzamide; and a dispersant and/or a basic compound.

In one aspect, the composition of the present disclosure comprises 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt, together with a compound represented by formula (X) shown in Test Example 12 below. In one embodiment, the content of said compound of formula (X) is, for example, 3.0% by weight or less with respect to the content of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

Also, in one embodiment, the content of said compound of formula (X) is, for example, 0.02% by weight or more with respect to the content of said 2-(4-cyclopropyl-2-fluoroanilino)-3,4-difluoro-5-[[3-fluoro-2-(methylsulfamoylamino)pyridin-4-yl]methyl]benzamide, said salt or said solvate.

In one aspect, the composition of the present disclosure comprising a compound, salt or solvate of any of the first to third aspects and a dispersant and/or a basic compound is a pharmaceutical composition comprising the compound, salt or solvate as an active ingredient.

Also, in another aspect, the composition of the present disclosure comprising a compound, salt or solvate of any of the first to third aspects and a dispersant and/or a basic compound is a pharmaceutical composition for the treatment or prevention of a cell proliferative disorder, particularly a cancer, the pharmaceutical composition comprising the compound, salt or solvate as an active ingredient.

The subject to be administered a compound, salt or solvate of the present disclosure is an animal, preferably a mammal (for example, a mouse, a rat, a rabbit, a dog, a monkey (for example, a cynomolgus monkey), or a human), and most preferably a human. The human may be an adult (18 years or older) or a child (younger than 18). In the case of a child, it is preferably one of age at least 6 months or older, for example.

When a compound, salt or solvate of the present disclosure is to be used for the treatment or prevention of a cell proliferative disorder, the dose and dose interval may be determined as appropriate depending on, for example, the severity of symptoms, the age and body weight of the subject, the presence or absence of a concomitant drug, and the route of administration. For example, when the subject is a human, a compound, salt or solvate of the present disclosure will usually be administered once every day to every three weeks at a dose of 0.00001 to 5000 mg per kilogram of body weight, preferably 0.01 to 100 mg per kilogram of body weight. When it is administered daily, the dose mentioned above may be divided into 2 to 4 separate doses.

With regard to the route of administration to a subject, there may be used, for example: systemic administration such as oral administration, rectal administration, intravenous administration, intramuscular administration, subcutaneous administration, intracisternal administration, vaginal administration, intraperitoneal administration, intravesical administration, or inhalation administration; or topical administration in the form of an ointment, gel or cream. Oral administration is preferred.

A compound, salt or solvate of the present disclosure will usually be used in the form of a pharmaceutical formulation (dosage form). Therefore, in one aspect, the composition of the present disclosure is a formulation, for example, a pharmaceutical formulation. Examples of such formulations include tablets, capsules, granules, powders, fine granules, pills, and aqueous or nonaqueous solutions or suspensions. A solution or suspension can be filled and stored in a container suited for dispensing into individual doses.

The different formulations mentioned above can be produced by known methods by mixing compounds, salts or solvates of the present disclosure, dispersants and/or basic compounds, and other pharmaceutically acceptable additives. Examples of such additives include aforementioned excipients, lubricants (coating agents), binders, disintegrants, flavoring agents, bases, diluents, surfactants, and emulsifiers.

The preferred quantity of a compound, salt or solvate of the present disclosure in a formulation will differ depending on the dosage form, but will usually be 0.01% to 100% by weight with respect to the total weight of the formulation.

Examples of cell proliferative disorders to be treated or prevented using a compound, salt or solvate of the present disclosure include cancers, rheumatism and inflammation, among which cancers are preferred.

Examples of cancers include: blood and lymphoid cancers, such as leukemias (e.g., acute myelocytic leukemia, acute lymphocytic leukemia, chronic myelocytic leukemia, and chronic lymphocytic leukemia), malignant lymphomas (e.g., Hodgkin's disease and non-Hodgkin's lymphoma), multiple myeloma, and myelodysplastic syndrome; central nervous system cancers, such as brain tumor and glioma; and solid cancers, such as head and neck cancers (e.g., pharyngeal cancer, laryngeal cancer, and tongue cancer), esophageal cancer, gastric cancer, colorectal cancers (e.g., cecal cancer, colon cancer, and rectal cancer), lung cancers (e.g., small cell lung cancer and non-small cell lung cancer), thyroid cancer, breast cancer, gallbladder cancer, pancreatic cancer, liver cancer, prostate cancer, ovarian cancer, uterine cancer (e.g., endometrial cancer and cervical cancer), testicular cancer, renal cell carcinoma, bladder cancer, renal pelvic cancer, ureteral cancer, malignant melanoma, and skin cancers (e.g., basal cell carcinoma, squamous cell carcinoma, extramammary Paget's disease, Merkel cell carcinoma, sweat gland carcinomas (e.g., apocrine adenocarcinoma and eccrine adenocarcinoma), sebaceous carcinoma, and trichoepithelioma).

The cancer may be one with a gene mutation or without a gene mutation, or one where the presence or absence of mutation is unclear. Examples of genes to be mutated include EGFR, FGFR, ALK, ROS1, PI3K, BRAF, HRAS, KRAS, and NRAS.

When a compound, salt or solvate of the first or second aspect is to be used, the cancer is preferably a RAS-mutant cancer, for example, and more preferably a KRAS-mutant solid cancer (particularly KRAS-mutant non-small cell lung cancer), for example. According to one embodiment, it is used for a RAF-mutant cancer, particularly for a RAF-mutant and RAS-mutant cancer.

When a compound, salt or solvate of the third aspect is to be used, the cancer is preferably a RAF-mutant cancer, for example, and more preferably a BRAF-mutant solid cancer (particularly BRAF-mutant malignant melanoma), for example.

EXAMPLES

The present disclosure will now be explained in greater detail based on examples (production examples and test examples), with the understanding that the invention is in no way limited to the examples.

Production Examples

NMR analysis was conducted using an AVANCE III HD400 (400 MHz) by Bruker Co. The NMR data were shown in ppm (parts per million) (S) and the deuterium lock signal from the sample solvent was used as a reference.

The mass spectrum data were obtained using an ultra-high performance liquid chromatography (Nexera UC)-equipped single quadrupole mass spectrometer (LCMS-2020) by Shimadzu Corp. or an Acquity ultra-high performance liquid chromatography (UPLC or UPLC I-Class)-equipped single quadrupole mass spectrometer (SQD or SQD2) by Waters Co.

High-performance liquid chromatography was carried out using one of the analysis conditions A to G listed in Table 1 below. In Table 1, "TFA" stands for trifluoroacetic acid, "FA" for formic acid, and "AA" for ammonium acetate.

TABLE 1

| Analysis conditions | Apparatus | Column | Column temperature | Detection wavelength (PDA) |
|---|---|---|---|---|
| A | Nexera UC LCMS-2020 | Ascentis Express C18 2.1 mm I.D. × 50 mm L, 2.7 μm | 35° C. | 210-400 nm |
| B | Nexera UC LCMS-2020 | XSelect CSH C18 2.1 mm I.D. × 50 mm L, 2.5 μm | 35° C. | 210-400 nm |
| C | Acquity SQD/SQD2 | Ascentis Express C18 2.1 mm I.D. × 50 mm L, 2.7 μm | 35° C. | 210-400 nm |
| D | Acquity SQD/SQD2 | Ascentis Express C18 2.1 mm I.D. × 50 mm L, 2.7 μm | 35° C. | 210-400 nm |
| E | Acquity SQD/SQD2 | Ascentis Express C18 2.1 mm I.D. × 50 mm L, 5 μm | 35° C. | 210-400 nm |
| F | Acquity SQD/SQD2 | Ascentis Express C18 2.1 mm I.D. × 50 mm L, 2.7 μm | 35° C. | 210-400 nm |
| G | Acquity SQD/SQD2 | Ascentis Express C18 2.1 mm I.D. × 50 mm L, 2.7 μm | 35° C. | 210-400 nm |

TABLE 1-continued

| Analysis conditions | Mobile phase | Gradient Time after injection (min) | A/B | Flow rate (mL/min) |
|---|---|---|---|---|
| A | A) 0.05% TFA/$CH_3CN$ | 0-1.5 | 5/95 → 100/0 | 1 |
| | B) 0.05% TFA/$H_2O$ | 1.5-2.0 | 100/0 | |
| B | A) 0.1% FA/$CH_3CN$ | 0-1.75 | 5/95 → 100/0 | 1 |
| | B) 0.1% FA/$H_2O$ | 1.75-2.00 | 100/0 | |
| C | A) 0.1% FA/$CH_3CN$ | 0-1.0 | 5/95 → 100/0 | 1 |
| | B) 0.1% FA/$H_2O$ | 1.0-1.4 | 100/0 | |
| D | A) 0.1% FA/$CH_3CN$ | 0-1.0 | 40/60 → 100/0 | 1 |
| | B) 0.1% FA/$H_2O$ | 1.0-1.4 | 100/0 | |
| E | A) MeOH | 0-1.0 | 5/95 → 100/0 | 0.9 |
| | B) 10 mM AA/$H_2O$ | 1.0-1.4 | 100/0 | |
| F | A) 0.05% TFA/$CH_3CN$ | 0-1.0 | 5/95 → 100/0 | 1 |
| | B) 0.05% TFA/$H_2O$ | 1.0-1.4 | 100/0 | |
| G | A) 0.05% FA/$CH_3CN$ | 0-1.0 | 5/95 → 100/0 | 1 |
| | B) 0.05% FA/$H_2O$ | 1.0-1.4 | 100/0 | |

Microwave reaction was conducted using an Initiator by Biotage Co. A snap cap reaction vial was used for the microwave reaction.

Commercially available reagents were used directly without further purification.

All of the nonaqueous reactions were conducted in anhydrous solvents.

Concentration under reduced pressure and solvent distillation were carried out using a rotary evaporator.

As used herein, "room temperature" means a temperature of about 20° C. to about 25° C.

As used in the production examples below, "production example for compound A-1" means Production Example A-1-1 and "production example for compound a9" means Production Example a9-1.

Compound a1:

Methyl 3,4-difluoro-2-(2-fluoro-4-iodoanilino)-5-formylbenzoate

[Chemical Formula 22]

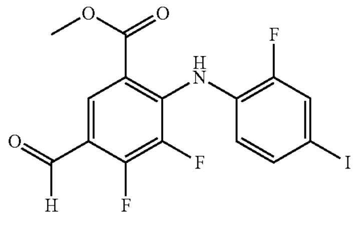

A mixed suspension of 3,4-difluoro-2-((2-fluoro-4-iodophenyl)amino)-5-formylbenzoic acid (5.50 g, 13.1 mmol) in toluene (44 mL) and MeOH (11 mL) was cooled to 0° C., a 10% diazomethyltrimethylsilane hexane solution (21.8 mL, 13.1 mmol) was added, and the mixture was stirred for 64 hours at room temperature. Acetic acid (0.748 mL) was added to the reaction mixture, which was then concentrated under reduced pressure. The resulting residue was purified by trituration (hexane/ethyl acetate) to give the title compound (5.01 g, 88%) as a colorless solid.

LCMS m/z: 436 $[M+H]^+$

HPLC retention time: 1.00 min (analysis conditions D)

Compound a2:

Methyl 3,4-difluoro-2-(2-fluoro-4-iodoanilino)-5-[(E)-[(4-methylphenyl)sulfonylhydrazinylidene]methyl]benzoate

[Chemical Formula 23]

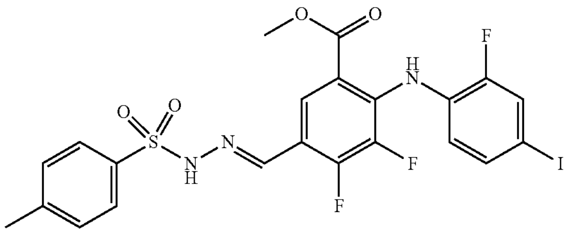

4-Methylbenzenesulfonyl hydrazide (2.14 g, 11.5 mmol) was added to a suspension of methyl 3,4-difluoro-2-(2-fluoro-4-iodoanilino)-5-formylbenzoate (compound a1, 5.00 g, 11.5 mmol) in EtOH (100 mL), and the mixture was stirred for 3 hours at room temperature. The reaction mixture was concentrated under reduced pressure, and then hexane (150 mL) was added. The mixture was cooled to 0° C. and filtered, and then washed with hexane (30 mL) to give the title compound (7.05 g, quant.) as a solid.

LCMS m/z: 604 $[M+H]^+$

HPLC retention time: 1.06 min (analysis conditions D)

Compound a3:

N-(2,4-Dimethoxybenzyl)-3-fluoro-4-iodopyridine-2-amine

[Chemical Formula 24]

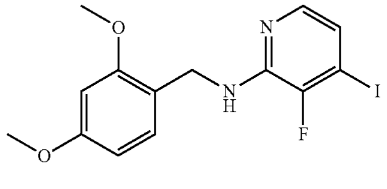

Triethylamine (3.63 mL, 26.0 mmol) and 1-(2,4-dimethoxyphenyl)methaneamine (3.26 mL, 21.7 mmol) were added to a solution of 2,3-difluoro-4-iodopyridine (2.09 g, 8.67 mmol) in NMP (32 mL), and the mixture was stirred for 1.5 hours at 100° C. Water was added to the reaction mixture, and extraction was performed with ethyl acetate. The organic layer was washed with 13% brine, dried over anhydrous sodium sulfate and, after filtering off the drying agent, concentrated under reduced pressure. The resulting residue was purified by silica gel column chromatography (hexane/ethyl acetate) to give the title compound (3.20 g, 95%) as an oil.

LCMS m/z: 389 $[M+H]^+$

HPLC retention time: 0.94 min (analysis conditions C)

Compound a4:

[2-[(2,4-Dimethoxyphenyl)methylamino]-3-fluoropyridin-4-yl]boronic Acid

[Chemical Formula 25]

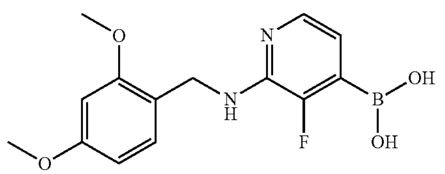

A 1,4-dioxane solution (27 mL) of N-(2,4-dimethoxybenzyl)-3-fluoro-4-iodopyridine-2-amine (compound a3, 2.70 g, 6.96 mmol), [1,1-bis(diphenylphosphino)ferrocene]dichloropalladium(II) dichloromethane addition product (568 mg, 0.696 mmol), potassium acetate (2.05 g, 20.9 mmol) and bis(pinacolato)diboron (2.65 g, 10.4 mmol) was stirred under a nitrogen atmosphere for 5 hours at 90° C. and then for 19 hours at 110° C. The reaction mixture was concentrated under reduced pressure, and the resulting residue was purified by reversed-phase column chromatography (0.1% formic acid aqueous solution/0.1% formic acid acetonitrile solution) to give the title compound (2.07 g, 97%) as an oil.

LCMS m/z: 307 $[M+H]^+$

HPLC retention time: 0.44 min (analysis conditions C)

Compound a5:

Methyl 5-[[2-[(2,4-dimethoxyphenyl)methylamino]-3-fluoropyridin-4-yl]methyl]-3,4-difluoro-2-(2-fluoro-4-iodoanilino)benzoate

[Chemical Formula 26]

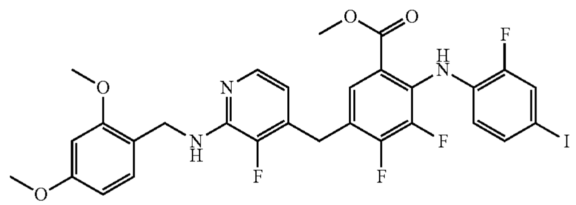

A 1,4-dioxane suspension (59 mL) of methyl 3,4-difluoro-2-(2-fluoro-4-iodoanilino)-5-[(E)-[(4-methylphenyl)sulfonylhydrazinylidene]methyl]benzoate (compound a2, 1.30 g, 2.16 mmol), [2-[(2,4-dimethoxyphenyl)methylamino]-3-fluoropyridin-4-yl]boronic acid (compound a4, 1.98 g, 6.46 mmol) and potassium carbonate (357 mg, 2.59 mmol) was stirred under a nitrogen atmosphere for 2.5 hours at 100° C. and then for 3 hours at 110° C. Ethyl acetate was added to the reaction mixture, which was then washed with water and 13% brine. The organic layer was dried over anhydrous sodium sulfate and, after filtering off the drying agent, concentrated under reduced pressure. The resulting residue was purified by silica gel column chromatography (hexane/ethyl acetate) to give the title compound (524 mg, 36%) as a foam.

LCMS m/z: 682 $[M+H]^+$

HPLC retention time: 1.03 min (analysis conditions D)

Compound a6:

Methyl 5-[(2-amino-3-fluoropyridin-4-yl)methyl]-3,4-difluoro-2-(2-fluoro-4-iodoanilino)benzoate

[Chemical Formula 27]

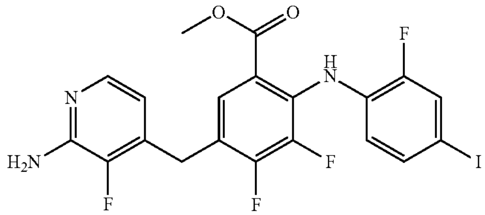

A DCM solution (16 mL) of methyl 5-[[2-[(2,4-dimethoxyphenyl)methylamino]-3-fluoropyridin-4-yl]methyl]-3,4-difluoro-2-(2-fluoro-4-iodoanilino)benzoate (compound a5, 523 mg, 0.768 mmol) was cooled to 0° C., trifluoroacetic acid (15.7 mL) was added, and the mixture was stirred for 1 hour at room temperature. The reaction mixture was concentrated under reduced pressure, and the resulting residue was purified by reversed-phase column chromatography (0.05% trifluoroacetic acid aqueous solution/0.05% trifluoroacetic acid acetonitrile solution) to give the title compound (321 mg, 79%) as an oil.

LCMS m/z: 532 $[M+H]^+$

HPLC retention time: 0.55 min (analysis conditions D)

Compound a7:

5-((2-Amino-3-fluoropyridin-4-yl)methyl)-3,4-difluoro-2-((2-fluoro-4-iodophenyl)amino)benzoic acid hydrochloride

[Chemical Formula 28]

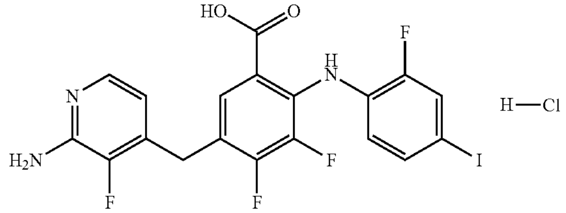

A mixed solution of methyl 5-[(2-amino-3-fluoropyridin-4-yl)methyl]-3,4-difluoro-2-(2-fluoro-4-iodoanilino)benzoate (compound a6, 4.00 g, 7.53 mmol) in THF (64 mL) and water (32 mL) was cooled to 0° C., lithium hydroxide monohydrate (948 mg, 22.6 mmol) was added, and the mixture was stirred for 3.5 hours at room temperature. After cooling to 0° C., 5 M hydrochloric acid (15.1 mL) was added to the reaction mixture, which was then concentrated under reduced pressure. The resulting residue was washed with water and TBME to give the title compound (4.20 g, quant.) as a violet compound.

LCMS m/z: 518 $[M+H]^+$

HPLC retention time: 0.68 min (analysis conditions C)

Compound a8:

5-((2-Amino-3-fluoropyridin-4-ylmethyl)-3,4-difluoro-2-((2-fluoro-4-iodophenyl)amino)benzamide

[Chemical Formula 29]

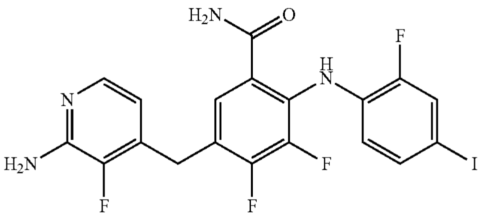

An anhydrous DMF solution (3.6 mL) of 5-((2-amino-3-fluoropyridin-4-yl)methyl)-3,4-difluoro-2-((2-fluoro-4-iodophenyl)amino)benzoic acid hydrochloride (compound a7, 200 mg, 0.361 mmol) was cooled to 0° C., HOOBt (67.8 mg, 0.415 mmol) and EDC·HCl (80.0 mg, 0.415 mmol) were added, and the mixture was stirred for 1.5 hours at room temperature. After further adding HOOBt (8.8 mg, 0.054 mmol) and EDC·HCl (10.4 mg, 0.054 mmol) and stirring at room temperature for 1 hour, a 7 M ammonia MeOH solution (0.103 mL, 0.722 mmol) and DIPEA (0.189 mL, 1.08 mmol) were added at 0° C. and the mixture was stirred for 30 minutes at room temperature. Water and a saturated sodium hydrogen carbonate aqueous solution were added at 1:1 to the reaction mixture, and extraction was performed with ethyl acetate. The organic layer was dried over anhydrous sodium sulfate and, after filtering off the drying agent, concentrated under reduced pressure. The resulting residue was dissolved in ethyl acetate (1 mL), and hexane (10 mL) was added. The obtained solid was filtered and washed with hexane to give the title compound (162 mg, 87%) as a colorless solid.

LCMS m/z: 517 $[M+H]^+$

HPLC retention time: 0.64 min (analysis conditions C)

Compound a9:

5-((2-Amino-3-fluoropyridin-4-yl)methyl)-2-((4-cyclopropyl-2-fluorophenyl)amino)-3,4-difluorobenzamide

[Chemical Formula 30]

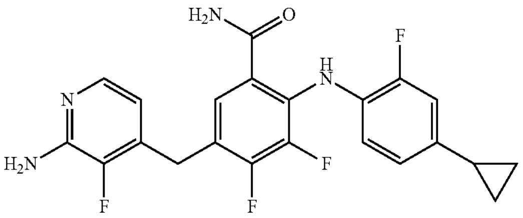

Production Example a9-1

Tetrakis(triphenylphosphine)palladium(0) (11.2 mg, 9.68 μmol) and 0.5 M cyclopropylzinc bromide (1.94 mL, 0.969 mmol) were added to an anhydrous THF solution (1.9 mL) of 5-((2-amino-3-fluoropyridin-4-yl)methyl)-3,4-difluoro-2-((2-fluoro-4-iodophenyl)amino)benzamide (compound a8, 100 mg, 0.194 mmol), and the mixture was stirred for 2.5 hours at room temperature under a nitrogen atmosphere. Ethyl acetate (5 mL) was added to the reaction mixture, which was then filtered with Celite and washed with ethyl acetate (3 mL). The filtrate was washed with water and saturated brine, and the organic layer was dried over anhydrous sodium sulfate and, after filtering off the drying agent, concentrated under reduced pressure. Dichloromethane/hexane (1/10, 11 mL) was added to the resulting residue, and the solid was filtered off and washed with hexane (3 mL) to give compound a9 (63.4 mg, 76%) as a colorless solid.

LCMS m/z: 431 $[M+H]^+$

HPLC retention time: 0.61 min (analysis conditions C)

Compound r1:

4-Nitrophenyl Methylsulfamate

[Chemical Formula 31]

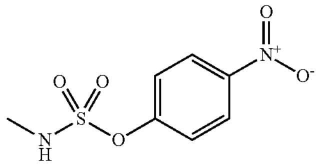

A dichloromethane solution (60 mL) of 4-nitrophenol (5.00 g, 35.9 mmol) and triethylamine (11.3 mL, 81.0 mmol) was cooled to −78° C., a dichloromethane solution (15 mL) of methylsulfamoyl chloride (5.82 g, 44.9 mmol) was added, and the mixture was stirred for 1.5 hours at −78° C. The reaction mixture was concentrated under reduced pressure, and the resulting residue was purified by silica gel column chromatography (hexane/ethyl acetate) and reversed-phase column chromatography (0.1% formic acid aqueous solution/0.1% formic acid acetonitrile solution) to give the title compound (5.51 g, 66%) as a colorless solid.

HPLC retention time: 0.63 min (analysis conditions C)

$^1$H-NMR (400 MHz, $CDCl_3$) δ: 8.31 (2H, m), 7.46 (2H, m), 4.68 (1H, m), 3.00 (3H, d, J=5.4 Hz).

Compound A-1:

2-(4-Cyclopropyl-2-fluoroanilino)-3,4-difluoro-5-[[3-fluoro-2-(methylsulfamoylamino)pyridin-4-yl]methyl]benzamide

[Chemical Formula 32]

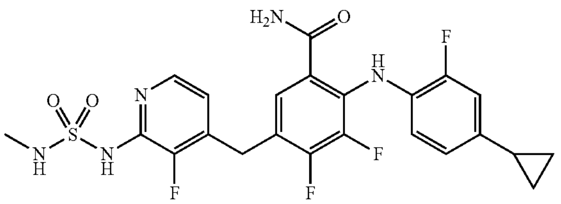

Production Example A-1-1

After dissolving 5-((2-amino-3-fluoropyridin-4-yl)methyl)-2-((4-cyclopropyl-2-fluorophenyl)amino)-3,4-difluorobenzamide (compound a9, 2.47 g, 5.74 mmol) in anhydrous DMF (28.7 mL), pyridine (2.78 mL, 34.4 mmol) and 4-nitrophenyl methylsulfamate (compound r1, 4.00 g, 17.2 mmol) were added and the mixture was stirred for 2.5 hours at 40° C. The reaction mixture was cooled to room temperature, and water (24.7 mL) was added. After further adding acetonitrile (3 mL) and water (19.8 mL) and stirring for 10 minutes, the solid was filtered out. The obtained solid was washed with water/acetonitrile (1/1, 49.4 mL) to give compound A-1 (2.56 g, 85%) as a colorless solid.

LCMS m/z: 524 $[M+H]^+$

HPLC retention time: 1.13 min (analysis conditions A)

Compound a10:

5-((2-Amino-3-fluoropyridin-4-yl)methyl)-N-cyclopropyl-3,4-difluoro-2-((2-fluoro-4-iodophenyl)amino)benzamide

[Chemical Formula 33]

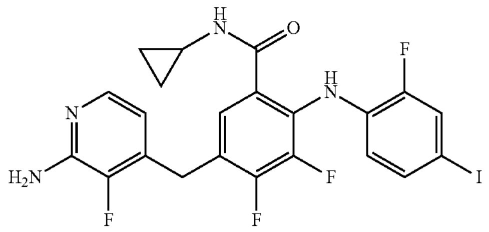

After dissolving 5-((2-amino-3-fluoropyridin-4-yl)methyl)-3,4-difluoro-2-((2-fluoro-4-iodophenyl)amino)benzoic acid hydrochloride (compound a7, 100 mg, 0.193 mmol) in anhydrous DMF (1 mL), HOOBt (63.1 mg, 0.387 mmol) and EDC·HCl (74.1 mg, 0.387 mmol) were added at room temperature. After stirring at room temperature for 3 hours, aminocyclopropane (33.1 mg, 0.580 mmol) and DIPEA (0.101 mL, 0.580 mmol) were added and the mixture was stirred for 1 hour at room temperature. The reaction mixture was purified by reversed-phase column chromatography (0.1% formic acid aqueous solution/0.1% formic acid acetonitrile solution) to give the title compound (103 mg, 96%) as a brown solid.

LCMS m/z: 557 $[M+H]^+$

HPLC retention time: 0.73 min (analysis conditions C)

Compound A-2:

N-Cyclopropyl-3,4-difluoro-2-(2-fluoro-4-iodoanilino)-5-[[3-fluoro-2-(methylsulfamoylamino)pyridin-4-yl]methyl]benzamide

[Chemical Formula 34]

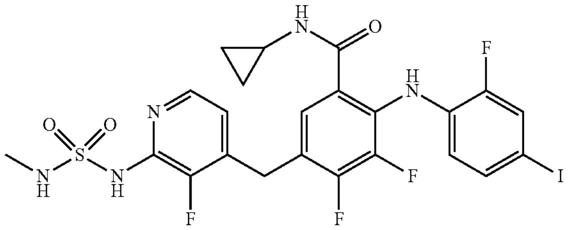

The title compound was synthesized from 5-((2-amino-3-fluoropyridin-4-yl)methyl)-N-cyclopropyl-3,4-difluoro-2-((2-fluoro-4-iodophenyl)amino)benzamide (compound a10) under the same conditions as the production example for compound A-1.

LCMS m/z: 650 $[M+H]^+$

HPLC retention time: 1.65 min (analysis conditions B)

Compound r2:

1-Chlorosulfonyloxy-4-nitrobenzene

[Chemical Formula 35]

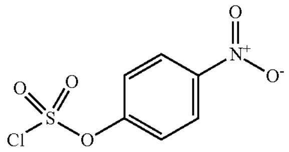

An $Et_2O$ suspension (96 mL) of 4-nitrophenol (12.0 g, 86 mmol) and pyridine (6.98 mL, 86 mmol) was cooled to −78° C., and then an $Et_2O$ solution (96 mL) of sulfuryl chloride (6.98 mL, 86 mmol) was added over a period of 10 minutes and the mixture was stirred for 6.5 hours at room temperature. The reaction mixture was filtered and washed with $Et_2O$ (15 mL), and then the filtrate was concentrated under reduced pressure. The resulting residue was purified by silica gel column chromatography (hexane/DCM) to give the title compound (19.8 g, 97%) as a yellow oil.

HPLC retention time: 0.77 min (analysis conditions C)

$^1$H-NMR (400 MHz, $CDCl_3$) δ: 8.41 (2H, m), 7.61 (2H, m).

Compound r3:

4-Nitrophenyl N-[(2,4-dimethoxyphenyl)methyl]sulfamate

[Chemical Formula 36]

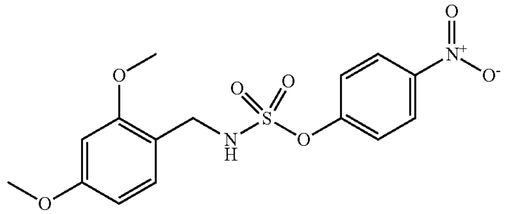

A DCM solution (36 mL) of 1-chlorosulfonyloxy-4-nitrobenzene (compound r2, 1.78 g, 7.48 mmol) was cooled to −78° C., a DCM solution (53 mL) of 2,4-dimethoxybenzylamine (1.00 g, 5.98 mmol), 4-nitrophenol (1.04 g, 7.48 mmol) and triethylamine (5.00 mL, 35.9 mmol) was added over a period of 10 minutes, and the mixture was stirred for 4 hours at room temperature. The reaction mixture was concentrated under reduced pressure, and the resulting residue was purified by reversed-phase column chromatography (0.1% formic acid aqueous solution/0.1% formic acid acetonitrile solution) and silica gel column chromatography (hexane/ethyl acetate) to give the title compound (1.28 g, 58%) as a colorless solid.

LCMS m/z: 367 $[M-H]^-$

HPLC retention time: 0.81 min (analysis conditions C)

Compound r4:

4-Nitrophenyl Sulfamate

[Chemical Formula 37]

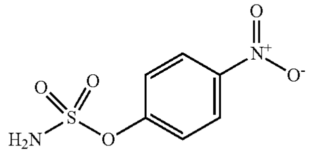

The title compound was synthesized from 4-nitrophenyl N-[(2,4-dimethoxyphenyl)methyl]sulfamate (compound r3) under the same conditions as the production example for compound a6.

LCMS m/z: 217 $[M-H]^-$

HPLC retention time: 0.53 min (analysis conditions C)

Compound r5:

4-Nitrophenyl N-ethylsulfamate

[Chemical Formula 38]

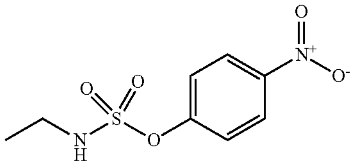

The title compound was synthesized from 1-chlorosulfonyloxy-4-nitrobenzene (compound r2) and the corresponding amine under the same conditions as the production example for compound r3.

LCMS m/z: 245 $[M-H]^-$

HPLC retention time: 0.68 min (analysis conditions C)

Compound r6:

4-Nitrophenyl N-cyclopropylsulfamate

[Chemical Formula 39]

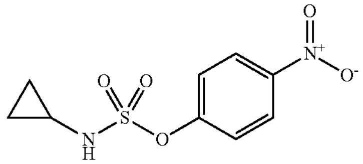

The title compound was synthesized from 1-chlorosulfonyloxy-4-nitrobenzene (compound r2) and the corresponding amine under the same conditions as the production example for compound r3.

LCMS m/z: 257 $[M-H]^-$

HPLC retention time: 0.70 min (analysis conditions C)

Compound r7:

4-Nitrophenyl N-(2-fluoroethyl)sulfamate

[Chemical Formula 40]

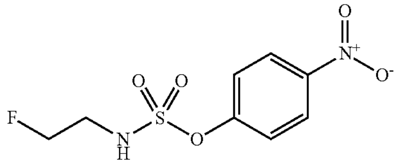

The title compound was synthesized from 1-chlorosulfonyloxy-4-nitrobenzene (compound r2) and the corresponding amine under the same conditions as the production example for compound r3.

LCMS m/z: 263 $[M-H]^-$

HPLC retention time: 0.65 min (analysis conditions C)

Compound r11:

4-Nitrophenyl N-[2-[tert-butyl(dimethyl)silyl]oxypropyl]sulfamate

[Chemical Formula 41]

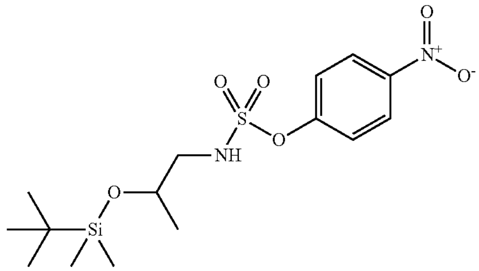

The title compound was synthesized from 1-chlorosulfonyloxy-4-nitrobenzene (compound r2) and the corresponding amine under the same conditions as the production example for compound r3.

LCMS m/z: 389 [M−H]⁻

HPLC retention time: 1.03 min (analysis conditions C)

Compound r8:

4-Nitrophenyl N-(2-methoxyethyl)sulfamate

[Chemical Formula 42]

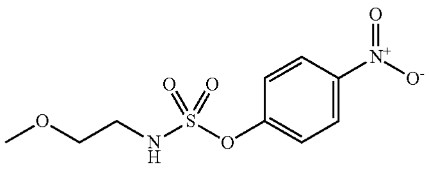

The title compound was synthesized from 1-chlorosulfonyloxy-4-nitrobenzene (compound r2) and the corresponding amine under the same conditions as the production example for compound r3.

LCMS m/z: 277 $[M+H]^+$

HPLC retention time: 0.64 min (analysis conditions C)

Compound r9:

4-Nitrophenyl N-(1-methylcyclobutyl)sulfamate

[Chemical Formula 43]

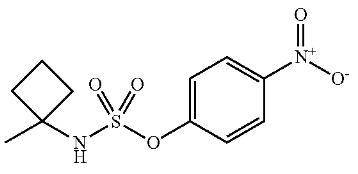

The title compound was synthesized from 1-chlorosulfonyloxy-4-nitrobenzene (compound r2) and the corresponding amine under the same conditions as the production example for compound r3.

LCMS m/z: 287 $[M+H]^+$

HPLC retention time: 0.78 min (analysis conditions C)

Compound r10:

4-Nitrophenyl N-[1-(methoxymethyl)cyclopropyl] sulfamate

[Chemical Formula 44]

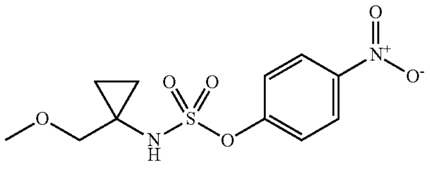

The title compound was synthesized from 1-chlorosulfonyloxy-4-nitrobenzene (compound r2) and the corresponding amine under the same conditions as the production example for compound r3.

LCMS m/z: 303 $[M+H]^+$

HPLC retention time: 0.67 min (analysis conditions C)

Compound r12:

4-Nitrophenyl N-propylsulfamate

[Chemical Formula 45]

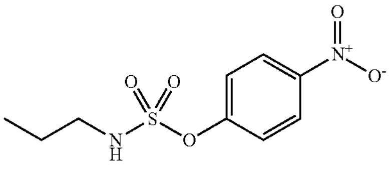

The title compound was synthesized from 1-chlorosulfonyloxy-4-nitrobenzene (compound r2) and the corresponding amine under the same conditions as the production example for compound r3.

LCMS m/z: 261 $[M+H]^+$

HPLC retention time: 0.72 min (analysis conditions C)

Compound r13:

4-Nitrophenyl N-(oxetan-3-ylmethyl)sulfamate

[Chemical Formula 46]

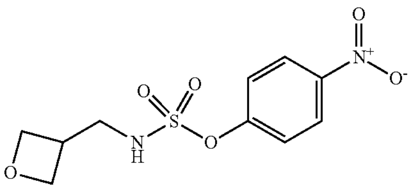

The title compound was synthesized from 1-chlorosulfonyloxy-4-nitrobenzene (compound r2) and the corresponding amine under the same conditions as the production example for compound r3.

LCMS m/z: 289 $[M+H]^+$

HPLC retention time: 0.59 min (analysis conditions C)

Compound r14:

4-Nitrophenyl N-(3-oxabicyclo[3.1.0]hexan-6-yl) sulfamate

[Chemical Formula 47]

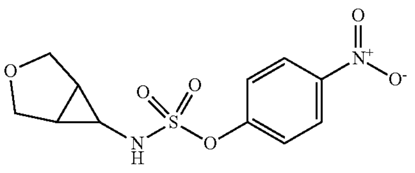

The title compound was synthesized from 1-chlorosulfonyloxy-4-nitrobenzene (compound r2) and the corresponding amine under the same conditions as the production example for compound r3.

LCMS m/z: 301 $[M+H]^+$

HPLC retention time: 0.63 min (analysis conditions C)

Compound r15:

4-Nitrophenyl N-(1-methylcyclopropyl)sulfamate

[Chemical Formula 48]

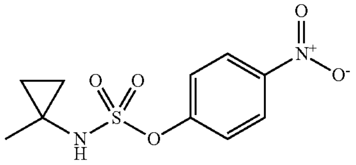

The title compound was synthesized from 1-chlorosulfonyloxy-4-nitrobenzene (compound r2) and the corresponding amine under the same conditions as the production example for compound r3.

LCMS m/z: 273 $[M+H]^+$

HPLC retention time: 0.73 min (analysis conditions C)

Compound r16:

4-Nitrophenyl N-[[(2R)-oxolan-2-yl]methyl] sulfamate

[Chemical Formula 49]

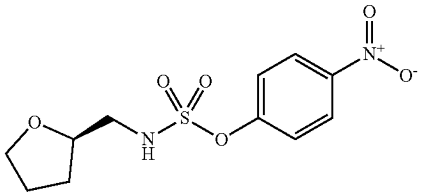

The title compound was synthesized from 1-chlorosulfonyloxy-4-nitrobenzene (compound r2) and the corresponding amine under the same conditions as the production example for compound r3.

LCMS m/z: 303 $[M+H]^+$

HPLC retention time: 0.67 min (analysis conditions C)

Compound r17:

4-Nitrophenyl N-(1-methoxy-2-methylpropan-2-yl)sulfamate

[Chemical Formula 50]

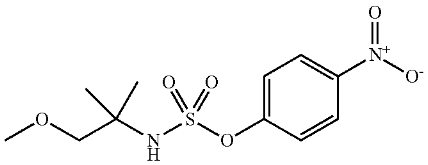

The title compound was synthesized from 1-chlorosulfonyloxy-4-nitrobenzene (compound r2) and the corresponding amine under the same conditions as the production example for compound r3.

HPLC retention time: 0.76 min (analysis conditions C)

$^1$H-NMR (400 MHz, DMSO-$d_6$) δ: 8.59 (1H, s), 8.34 (2H, m), 7.58 (2H, m), 3.30 (2H, s), 3.27 (3H, s), 1.28 (6H, s).

Compound A-3:

N-Cyclopropyl-3,4-difluoro-2-(2-fluoro-4-iodoanilino)-5-[[3-fluoro-2-(sulfamoylamino)pyridin-4-yl] methyl]benzamide

[Chemical Formula 51]

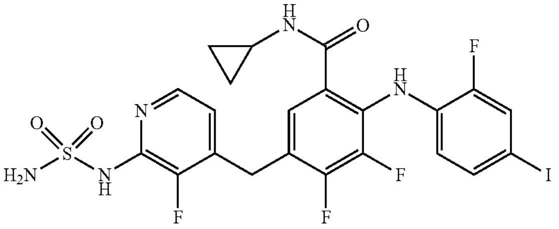

The title compound was synthesized from 5-((2-amino-3-fluoropyridin-4-yl)methyl)-N-cyclopropyl-3,4-difluoro-2-((2-fluoro-4-iodophenyl)amino)benzamide (compound a10) and the corresponding 4-nitrophenyl sulfamate under the same conditions as the production example for compound A-1.

LCMS m/z: 636 $[M+H]^+$

HPLC retention time: 1.58 min (analysis conditions B)

Compound A-4:

N-Cyclopropyl-5-[[2-(ethylsulfamoylamino)-3-fluoropyridin-4-yl]methyl]-3,4-difluoro-2-(2-fluoro-4-iodoanilino)benzamide

[Chemical Formula 52]

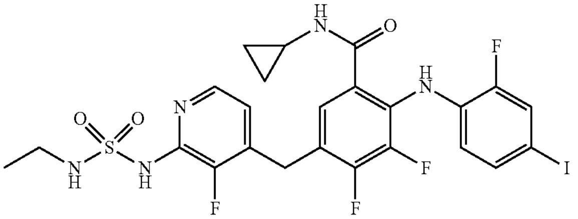

The title compound was synthesized from 5-((2-amino-3-fluoropyridin-4-yl)methyl)-N-cyclopropyl-3,4-difluoro-2-((2-fluoro-4-iodophenyl)amino)benzamide (compound a10) and the corresponding 4-nitrophenyl sulfamate under the same conditions as the production example for compound A-1.

LCMS m/z: 664 $[M+H]^+$

HPLC retention time: 1.70 min (analysis conditions B)

Compound A-5:

N-Cyclopropyl-5-[[2-(cyclopropylsulfamoylamino)-3-fluoropyridin-4-yl]methyl]-3,4-difluoro-2-(2-fluoro-4-iodoanilino)benzamide

[Chemical Formula 53]

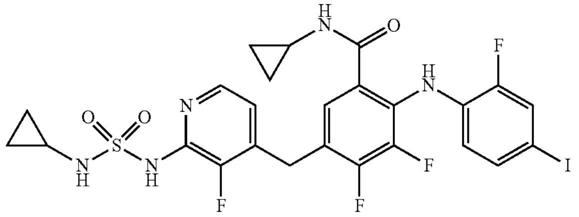

The title compound was synthesized from 5-((2-amino-3-fluoropyridin-4-yl)methyl)-N-cyclopropyl-3,4-difluoro-2-((2-fluoro-4-iodophenyl)amino)benzamide (compound a10) and the corresponding 4-nitrophenyl sulfamate under the same conditions as the production example for compound A-1.

LCMS m/z: 676 $[M+H]^+$

HPLC retention time: 1.70 min (analysis conditions B)

Compound A-6:

N-Cyclopropyl-3,4-difluoro-5-[[3-fluoro-2-(2-fluoroethylsulfamoylamino)pyridin-4-yl]methyl]-2-(2-fluoro-4-iodoanilino)benzamide

[Chemical Formula 54]

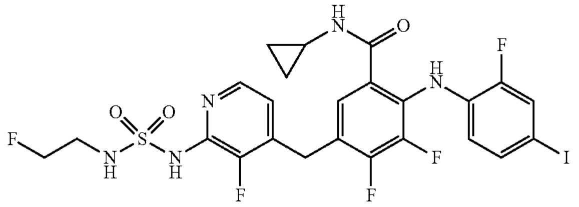

The title compound was synthesized from 5-((2-amino-3-fluoropyridin-4-yl)methyl)-N-cyclopropyl-3,4-difluoro-2-((2-fluoro-4-iodophenyl)amino)benzamide (compound a10) and the corresponding 4-nitrophenyl sulfamate under the same conditions as the production example for compound A-1.

LCMS m/z: 682 $[M+H]^+$

HPLC retention time: 1.66 min (analysis conditions B)

Compound A-7:

3,4-Difluoro-2-(2-fluoro-4-iodoanilino)-5-[[3-fluoro-2-(methylsulfamoylamino)pyridin-4-yl]methyl]-N-methylbenzamide

[Chemical Formula 55]

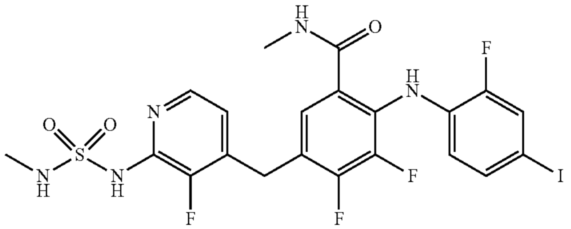

The title compound was synthesized from 5-[(2-amino-3-fluoropyridin-4-yl)methyl]-3,4-difluoro-2-(2-fluoro-4-iodoanilino)benzoic acid hydrochloride (compound a7) under the same conditions as the production examples for compound a10 and compound A-1. However, a 2 M methylamine THF solution was used instead of aminocyclopropane, which was used in the production example for compound a10.

LCMS m/z: 624 $[M+H]^+$

HPLC retention time: 1.62 min (analysis conditions B)

Compound a12:

5-((2-Amino-3-fluoropyridin-4-yl)methyl)-N-(tert-butoxy)-3,4-difluoro-2-((2-fluoro-4-iodophenyl)amino)benzamide

[Chemical Formula 56]

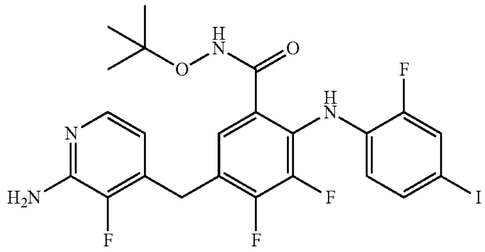

After dissolving 5-[(2-amino-3-fluoropyridin-4-yl)methyl]-3,4-difluoro-2-(2-fluoro-4-iodoanilino)benzoic acid hydrochloride (compound a7, 100 mg, 0.181 mmol) in anhydrous DMF (0.9 mL), HOOBt (58.9 mg, 0.361 mmol) and EDC HCl (69.2 mg, 0.361 mmol) were added and the mixture was stirred for 3.5 hours at room temperature. Next, tert-butoxyamine hydrochloride (68.1 mg, 0.542 mmol) and DIPEA (0.95 mL, 0.542 mmol) were added, and the mixture was stirred for 1.5 hours at room temperature. The reaction mixture was purified by reversed-phase column chromatography (0.1% formic acid aqueous solution/0.1% formic acid acetonitrile solution) to give the title compound (89 mg, 84%) as a colorless solid.

LCMS m/z: 589 $[M+H]^+$

HPLC retention time: 0.77 min (analysis conditions C)

Compound A-8:

3,4-Difluoro-2-(2-fluoro-4-iodoanilino)-5-[[3-fluoro-2-(methylsulfamoylamino)pyridin-4-yl]methyl]-N-[(2-methylpropan-2-yl)oxy]benzamide

[Chemical Formula 57]

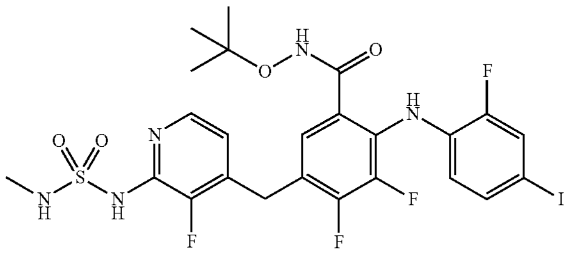

The title compound was synthesized from 5-((2-amino-3-fluoropyridin-4-yl)methyl)-N-(tert-butoxy)-3,4-difluoro-2-((2-fluoro-4-iodophenyl)amino)benzamide (compound a12) under the same conditions as the production example for compound A-1.

LCMS m/z: 682 $[M+H]^+$

HPLC retention time: 1.69 min (analysis conditions B)

Compound A-9:

3,4-Difluoro-2-(2-fluoro-4-iodoanilino)-5-[[3-fluoro-2-(2-methoxyethyl sulfamoylamino)pyridin-4-yl]methyl]-N-[(2-methylpropan-2-yl)oxy]benzamide

[Chemical Formula 58]

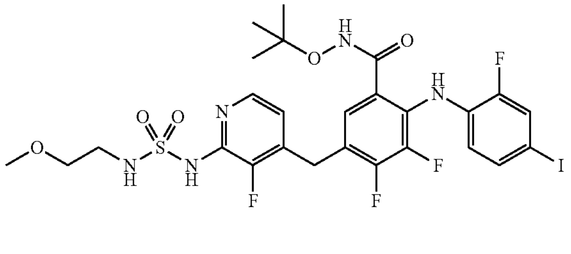

The title compound was synthesized from 5-((2-amino-3-fluoropyridin-4-yl)methyl)-N-(tert-butoxy)-3,4-difluoro-2-((2-fluoro-4-iodophenyl)amino)benzamide (compound a12) and the corresponding 4-nitrophenyl sulfamate under the same conditions as the production example for compound A-1.

LCMS m/z: 726 $[M+H]^+$

HPLC retention time: 1.71 min (analysis conditions B)

Compound A-10:

3,4-Difluoro-2-(2-fluoro-4-iodoanilino)-5-[[3-fluoro-2-(methylsulfamoylamino)pyridin-4-yl]methyl]-N-propan-2-yloxybenzamide

[Chemical Formula 59]

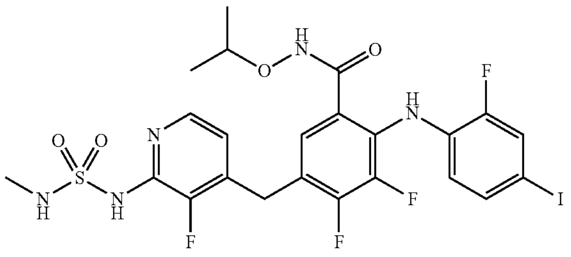

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1.

LCMS m/z: 668 $[M+H]^+$

HPLC retention time: 1.24 min (analysis conditions A)

Compound A-11:

3,4-Difluoro-2-(2-fluoro-4-iodoanilino)-5-[[3-fluoro-2-(2-methoxyethyl sulfamoylamino)pyridin-4-yl]methyl]-N-propan-2-yloxybenzamide

[Chemical Formula 60]

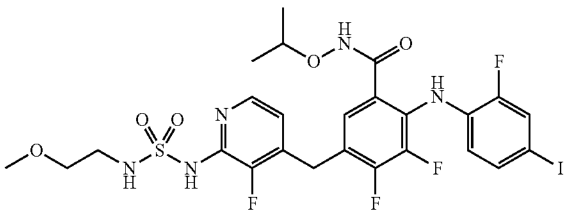

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 712 $[M+H]^+$

HPLC retention time: 1.26 min (analysis conditions A)

Compound A-12:

3,4-Difluoro-2-(2-fluoro-4-iodoanilino)-5-[[3-fluoro-2-[(1-methylcyclobutyl)sulfamoylamino]pyridin-4-yl]methyl]-N-propan-2-yloxybenzamide

[Chemical Formula 61]

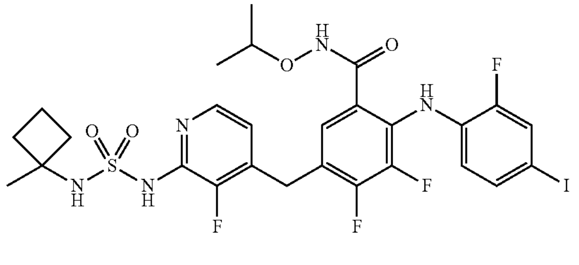

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 722 $[M+H]^+$

HPLC retention time: 1.81 min (analysis conditions B)

Compound A-13:

3,4-Difluoro-2-(2-fluoro-4-iodoanilino)-5-[[3-fluoro-2-(methylsulfamoylamino)pyridin-4-yl]methyl]-N-methoxybenzamide

[Chemical Formula 62]

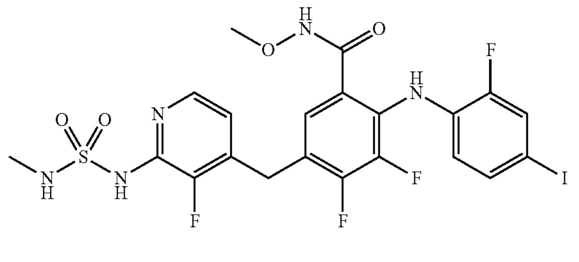

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1.

LCMS m/z: 640 $[M+H]^+$

HPLC retention time: 1.16 min (analysis conditions A)

Compound A-14:

3,4-Difluoro-2-(2-fluoro-4-iodoanilino)-5-[[3-fluoro-2-(2-methoxyethyl sulfamoylamino)pyridin-4-yl]methyl]-N-methoxybenzamide

[Chemical Formula 63]

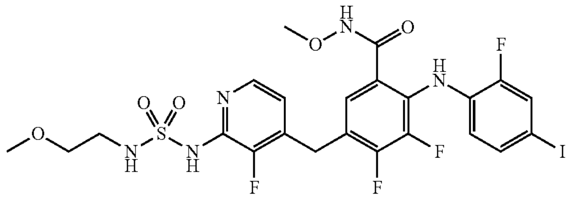

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 684 $[M+H]^+$

HPLC retention time: 1.18 min (analysis conditions A)

Compound A-15:

3,4-Difluoro-2-(2-fluoro-4-iodoanilino)-5-[[3-fluoro-2-[(1-methylcyclobutyl)sulfamoylamino]pyridin-4-yl]methyl]-N-methoxybenzamide

[Chemical Formula 64]

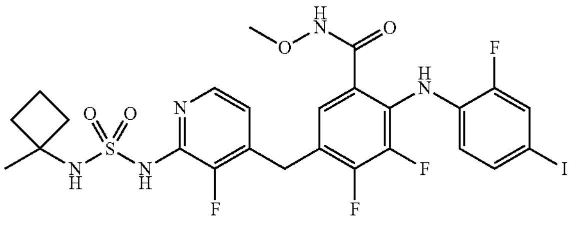

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 694 $[M+H]^+$

HPLC retention time: 1.72 min (analysis conditions B)

Compound A-16:

3,4-Difluoro-2-(2-fluoro-4-iodoanilino)-5-[[3-fluoro-2-[[1-(methoxymethyl)cyclopropyl]sulfamoylamino]pyridin-4-yl]methyl]benzamide

[Chemical Formula 65]

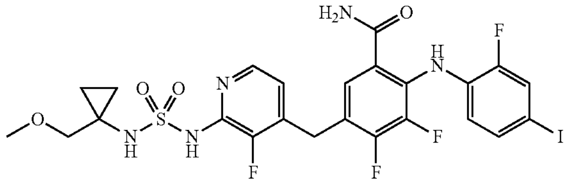

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 680 $[M+H]^+$

HPLC retention time: 1.20 min (analysis conditions A)

Compound a15:

5-[[2-[2-[tert-Butyl(dimethyl)silyl]oxypropylsulfamoylamino]-3-fluoropyridin-4-yl]methyl]-3,4-difluoro-2-(2-fluoro-4-iodoanilino)benzamide

[Chemical Formula 66]

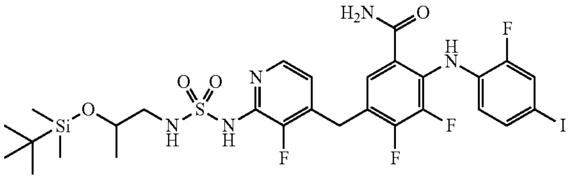

The title compound was synthesized from 5-[(2-amino-3-fluoropyridin-4-yl)methyl]-3,4-difluoro-2-(2-fluoro-4-iodoanilino)benzoic acid hydrochloride (compound a7) and the corresponding amine under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 768 $[M+H]^+$

HPLC retention time: 1.12 min (analysis conditions C)

Compound A-17:

(+/−)-3,4-Difluoro-5-[[3-fluoro-2-(2-hydroxypropylsulfamoylamino)pyridin-4-yl]methyl]-2-(2-fluoro-4-iodoanilino)benzamide (racemic)

[Chemical Formula 67]

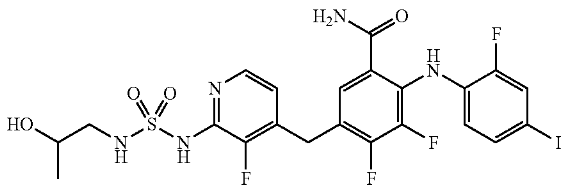

After dissolving 5-[[2-[2-[tert-butyl(dimethyl)silyl]oxypropylsulfamoylamino]-3-fluoropyridin-4-yl]methyl]-3,4-difluoro-2-(2-fluoro-4-iodoanilino)benzamide (compound a15, 60.0 mg, 0.78 mmol) in MeOH (0.4 mL), (−)-10-camphorsulfonic acid (27.2 mg, 0.117 mmol) was added and the mixture was stirred for 1 hour at room temperature. The reaction mixture was concentrated under reduced pressure, and the resulting residue was purified by reversed-phase column chromatography (0.1% formic acid aqueous solution/0.1% formic acid acetonitrile solution) to give the title compound (38 mg, 74%) as a colorless solid.

LCMS m/z: 654 $[M+H]^+$

HPLC retention time: 1.10 min (analysis conditions A)

Compound a16:

5-[(2-Amino-3-fluoropyridin-4-yl)methyl]-3,4-difluoro-2-(2-fluoro-4-methylsulfanylanilino)benzamide

[Chemical Formula 68]

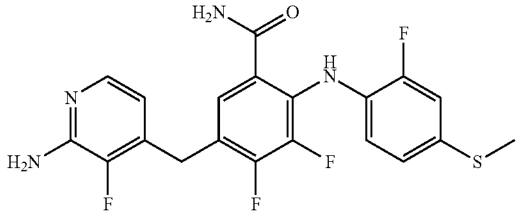

After dissolving 5-[(2-amino-3-fluoropyridin-4-yl)methyl]-3,4-difluoro-2-(2-fluoro-4-iodoanilino)benzamide (compound a8, 30.0 mg, 0.058 mmol) in anhydrous 1,4-dioxane (0.3 mL), methylmercaptan sodium (12.2 mg, 0.174 mmol), DIPEA (30.4 μL, 0.174 mmol) and [(4,5-bis(diphenylphosphino)-9,9-dimethylxanthene)-2-(2'-amino-1,1'-biphenyl)]palladium(II) methanesulfonate (11.2 mg, 0.012 mmol) were added, and the mixture was stirred for 30 minutes at room temperature under a nitrogen atmosphere. The reaction mixture was purified by reversed-phase column chromatography (0.1% formic acid aqueous solution/0.1% formic acid acetonitrile solution) to give the title compound (15 mg, 59%) as a colorless solid.

LCMS m/z: 437 $[M+H]^+$

HPLC retention time: 0.60 min (analysis conditions C)

Compound A-18:

3,4-Difluoro-5-[[3-fluoro-2-(methylsulfamoylamino)pyridin-4-yl]methyl]-2-(2-fluoro-4-methylsulfanylanilino)benzamide

[Chemical Formula 69]

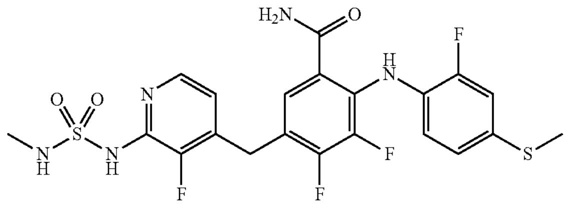

The title compound was synthesized from 5-[(2-amino-3-fluoropyridin-4-yl)methyl]-3,4-difluoro-2-(2-fluoro-4-methylsulfanylanilino)benzamide (compound a16) under the same conditions as the production example for compound A-1.

LCMS m/z: 530 $[M+H]^+$

HPLC retention time: 1.09 min (analysis conditions A)

Compound a17:

5-((2-Amino-3-fluoropyridin-4-yl)methyl)-3,4-difluoro-2-((2-fluoro-4-vinylphenyl)amino)benzamide

[Chemical Formula 70]

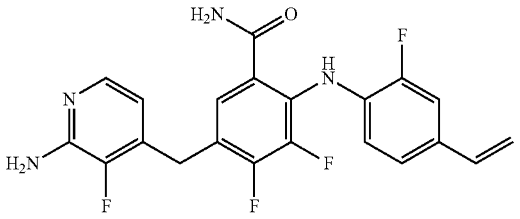

After dissolving 5-[(2-amino-3-fluoropyridin-4-yl)methyl]-3,4-difluoro-2-(2-fluoro-4-iodoanilino)benzamide (compound a8, 500 mg, 0.969 mmol) in degassed 2-propanol (12 mL) and anhydrous THF (2 mL), potassium vinyltrifluoroborate (143 mg, 1.07 mmol), triethylamine (0.405 mL, 2.91 mmol) and a [1,1'-bis(diphenylphosphino)ferrocene]palladium(II) dichloride-dichloromethane addition product (79.0 mg, 0.097 mmol) were added and the mixture was stirred for 2 hours at 80° C. under a nitrogen atmosphere. The reaction mixture was filtered with Celite and the solid portion was washed with ethyl acetate and MeOH. The filtrate was concentrated under reduced pressure, and the resulting residue was purified by reversed-phase column chromatography (0.1% formic acid aqueous solution/0.1% formic acid acetonitrile solution) to give the title compound (343 mg, 85%) as a colorless solid.

LCMS m/z: 417 $[M+H]^+$

HPLC retention time: 0.60 min (analysis conditions C)

Compound A-19:

2-(4-Ethenyl-2-fluoroanilino)-3,4-difluoro-5-[[3-fluoro-2-(methylsulfamoylamino)pyridin-4-yl]methyl]benzamide

[Chemical Formula 71]

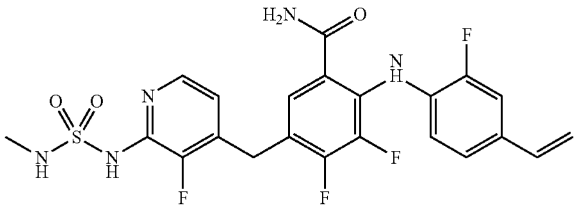

The title compound was synthesized from 5-((2-amino-3-fluoropyridin-4-yl)methyl)-3,4-difluoro-2-((2-fluoro-4-vinylphenyl)amino)benzamide (compound a17) under the same conditions as the production example for compound A-1.

LCMS m/z: 510 $[M+H]^+$

HPLC retention time: 1.11 min (analysis conditions A)

Compound a18:

5-[(2-Amino-3-fluoropyridin-4-yl)methyl]-3,4-difluoro-2-[2-fluoro-4-(2-trimethylsilylethynyl)anilino]benzamide

[Chemical Formula 72]

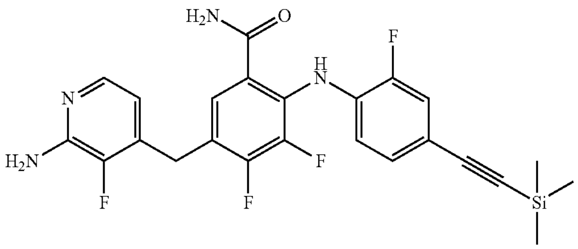

Triethylamine (31.7 mL, 228 mmol), trimethylsilylacetylene (1.43 mL, 10.3 mmol), bis(triphenylphosphine)palladium(II) dichloride (363 mg, 0.517 mmol) and copper(I) iodide (296 mg, 1.55 mmol) were added to an anhydrous THF solution (26 mL) of 5-[(2-amino-3-fluoropyridin-4-yl)methyl]-3,4-difluoro-2-(2-fluoro-4-iodoanilino)benzamide (compound a8, 2.67 g, 5.17 mmol), and the mixture was stirred for 3 hours at room temperature. The reaction mixture was concentrated under reduced pressure, and the resulting residue was purified by reversed-phase column chromatography (0.1% formic acid aqueous solution/0.1% formic acid acetonitrile solution) to give the title compound (2.57 g, 83%) as a colorless solid.

LCMS m/z: 487 $[M+H]^+$

HPLC retention time: 0.84 min (analysis conditions G)

Compound a19:

5-[(2-Amino-3-fluoropyridin-4-yl)methyl]-2-(4-ethynyl-2-fluoroanilino)-3,4-difluorobenzamide

[Chemical Formula 73]

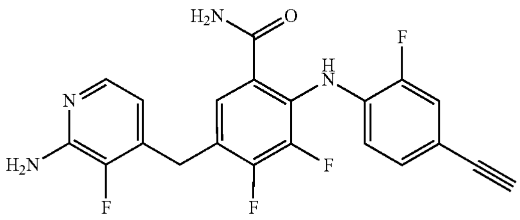

Potassium carbonate (17.0 mg, 0.123 mmol) was added to a MeOH solution (0.411 mL) of 5-[(2-amino-3-fluoropyridin-4-yl)methyl]-3,4-difluoro-2-[2-fluoro-4-(2-trimethylsilylethynyl)anilino]benzamide (compound a18, 20.0 mg, 0.041 mmol), and the mixture was stirred for 1.5 hours at room temperature. The reaction mixture was concentrated under reduced pressure, and the resulting residue was purified by reversed-phase column chromatography (0.1% formic acid aqueous solution/0.1% formic acid acetonitrile solution) to give the title compound (14 mg, 82%) as a colorless solid.

LCMS m/z: 415 $[M+H]^+$

HPLC retention time: 0.60 min (analysis conditions G)

Compound A-20:

2-(4-Ethynyl-2-fluoroanilino)-3,4-difluoro-5-[[3-fluoro-2-(propylsulfamoylamino)pyridin-4-yl]methyl]benzamide

[Chemical Formula 72]

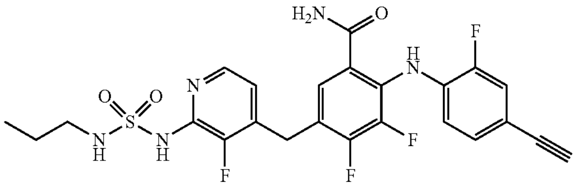

The title compound was synthesized from 5-[(2-amino-3-fluoropyridin-4-yl)methyl]-2-(4-ethynyl-2-fluoroanilino)-3,4-difluorobenzamide (compound a19) and the corresponding 4-nitrophenyl sulfamate under the same conditions as the production example for compound A-1.

LCMS m/z: 536 $[M+H]^+$

HPLC retention time: 1.18 min (analysis conditions A)

Compound A-21:

3,4-Difluoro-2-(2-fluoro-4-iodoanilino)-5-[[3-fluoro-2-(oxetan-3-ylmethylsulfamoylamino)pyridin-4-yl]methyl]benzamide

[Chemical Formula 75]

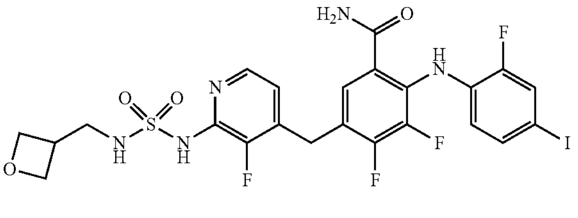

The title compound was synthesized from 5-[(2-amino-3-fluoropyridin-4-yl)methyl]-3,4-difluoro-2-(2-fluoro-4-iodoanilino)benzamide (compound a8) and the corresponding 4-nitrophenyl sulfamate under the same conditions as the production example for compound A-1, except that imidazole was used instead of pyridine.

LCMS m/z: 666 $[M+H]^+$

HPLC retention time: 1.11 min (analysis conditions A)

Compound A-22:

3,4-Difluoro-2-(2-fluoro-4-iodoanilino)-5-[[3-fluoro-2-(3-oxabicyclo[3.1.0]hexan-6-ylsulfamoylamino)pyridin-4-yl]methyl]benzamide

[Chemical Formula 76]

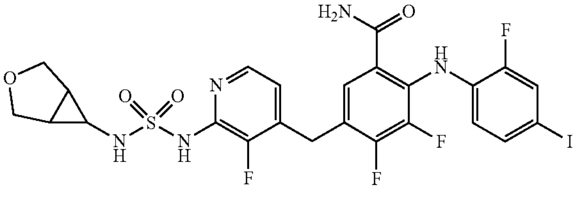

The title compound was synthesized from 5-[(2-amino-3-fluoropyridin-4-yl)methyl]-3,4-difluoro-2-(2-fluoro-4-iodoanilino)benzamide (compound a8) and the corresponding 4-nitrophenyl sulfamate under the same conditions as the production example for compound A-1, except that imidazole was used instead of pyridine.

LCMS m/z: 678 $[M+H]^+$

HPLC retention time: 1.16 min (analysis conditions A)

Compound A-23:

3,4-Difluoro-2-(2-fluoro-4-iodoanilino)-5-[[3-fluoro-2-[(1-methylcyclopropyl)sulfamoylamino]pyridin-4-yl]methyl]benzamide

[Chemical Formula 77]

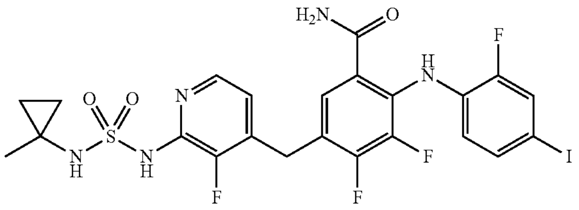

The title compound was synthesized from 5-[(2-amino-3-fluoropyridin-4-yl)methyl]-3,4-difluoro-2-(2-fluoro-4-iodoanilino)benzamide (compound a8) and the corresponding 4-nitrophenyl sulfamate under the same conditions as the production example for compound A-1, except that imidazole was used instead of pyridine and that anhydrous THF was used instead of anhydrous DMF.

LCMS m/z: 650 $[M+H]^+$

HPLC retention time: 1.25 min (analysis conditions A)

Compound A-24:

3,4-Difluoro-2-(2-fluoro-4-iodoanilino)-5-[[3-fluoro-2-[(I-methoxy-2-methylpropan-2-ylsulfamoylamino]pyridin-4-yl]methyl]benzamide

[Chemical Formula 78]

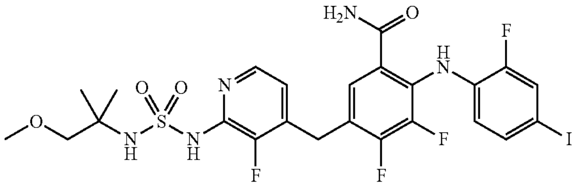

The title compound was synthesized from 5-[(2-amino-3-fluoropyridin-4-yl)methyl]-3,4-difluoro-2-(2-fluoro-4-iodoanilino)benzamide (compound a8) and the corresponding 4-nitrophenyl sulfamate under the same conditions as the production example for compound A-1, except that imidazole was used instead of pyridine and that anhydrous THF was used instead of anhydrous DMF.

LCMS m/z: 682 $[M+H]^+$

HPLC retention time: 1.27 min (analysis conditions A)

Compound A-25:

3,4-Difluoro-2-(2-fluoro-4-iodoanilino)-5-[[3-fluoro-2-(methylsulfamoylamino)pyridin-4-yl]methyl]benzamide

[Chemical Formula 79]

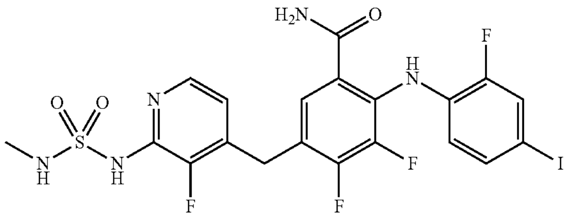

After dissolving 5-[(2-amino-3-fluoropyridin-4-yl)methyl]-3,4-difluoro-2-(2-fluoro-4-iodoanilino)benzamide (compound a8, 10.0 mg, 0.019 mmol) in anhydrous DMA (0.1 mL), pyridine (2.3 μL, 0.029 mmol) and methylsulfamoyl chloride (2.5 μL, 0.029 mmol) were added at 0° C., and the mixture was stirred for 1 hour at room temperature. The reaction mixture was purified by reversed-phase column chromatography (0.1% formic acid aqueous solution/0.1% formic acid acetonitrile solution) to give the title compound (10.2 mg, 86%) as a colorless solid.

LCMS m/z: 610 $[M+H]^+$

HPLC retention time: 1.15 min (analysis conditions A)

Compound s2:

N-(1-Bicyclo[1.1.1]pentanyl)sulfamoyl Chloride

[Chemical Formula 80]

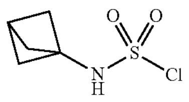

After dissolving sulfuryl chloride (0.102 mL, 1.25 mmol) in anhydrous acetonitrile (1.5 mL), bicyclo[1.1.1]pentane-1-amine hydrochloride (50.0 mg, 0.418 mmol) was added at 0° C. and the mixture was stirred for 16 hours at 80° C. under a nitrogen atmosphere. The reaction mixture was concentrated under reduced pressure to give a crude product of the title compound.

Compound s3:

N-(Oxan-4-yl)sulfamoyl Chloride

[Chemical Formula 81]

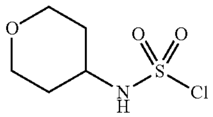

The title compound was synthesized from the corresponding amine under the same conditions as the production example for compound s2, except that triethylamine was also added.

Compound A-28:

5-[[2-(1-Bicyclo[1.1.1]pentanylsulfamoylamino)-3-fluoropyridin-4-yl]methyl]-3,4-difluoro-2-(2-fluoro-4-iodoanilino)benzamide

[Chemical Formula 82]

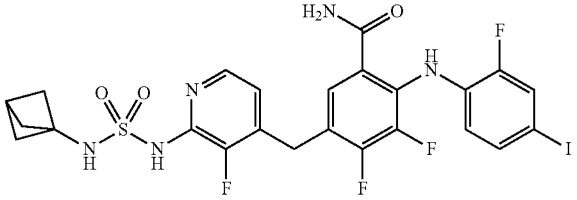

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 662 $[M+H]^+$

HPLC retention time: 1.27 min (analysis conditions A)

Compound A-29:

3,4-Difluoro-2-(2-fluoro-4-iodoanilino)-5-[[3-fluoro-2-(oxan-4-ylsulfamoylamino)pyridin-4-yl]methyl]benzamide

[Chemical Formula 83]

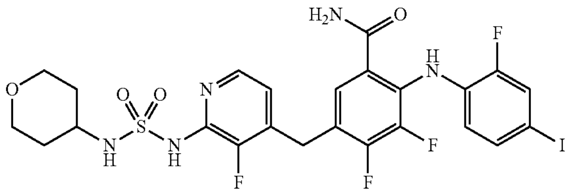

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 680 $[M+H]^+$

HPLC retention time: 1.16 min (analysis conditions A)

Compound A-30:

5-[[2-(Cyclopropylsulfamoylamino)-3-fluoropyridin-4-yl]methyl]-3,4-difluoro-2-(2-fluoro-4-iodoanilino)benzamide

[Chemical Formula 84]

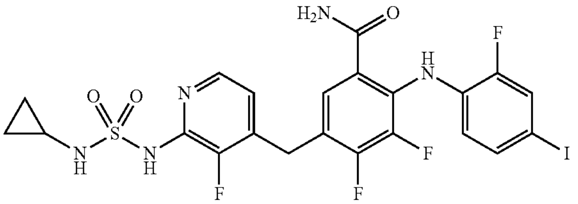

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 636 $[M+H]^+$

HPLC retention time: 1.21 min (analysis conditions A)

Compound A-31:

3,4-Difluoro-2-(2-fluoro-4-iodoanilino)-5-[[3-fluoro-2-(propan-2-ylsulfamoylamino)pyridin-4-yl]methyl]benzamide

[Chemical Formula 85]

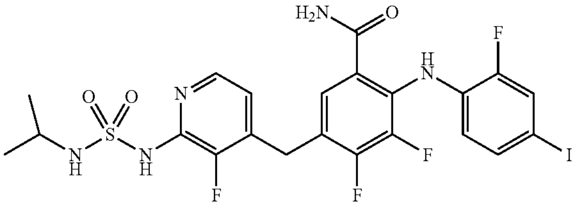

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 638 $[M+H]^+$

HPLC retention time: 1.24 min (analysis conditions A)

Compound A-32:

5-[[2-(Cyclobutylsulfamoylamino)-3-fluoropyridin-4-yl]methyl]-3,4-difluoro-2-(2-fluoro-4-iodoanilino)benzamide

[Chemical Formula 86]

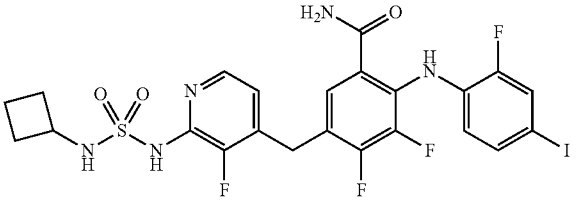

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 650 $[M+H]^+$

HPLC retention time: 1.26 min (analysis conditions A)

Compound A-33:

3,4-Difluoro-2-(2-fluoro-4-iodoanilino)-5-[[3-fluoro-2-(2-methoxyethylsulfamoylamino)pyridin-4-yl]methyl]benzamide

[Chemical Formula 87]

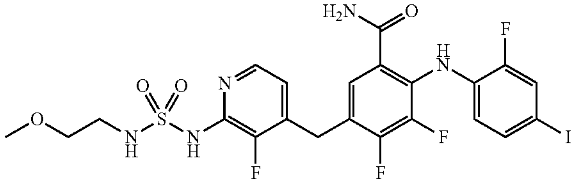

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 654 $[M+H]^+$

HPLC retention time: 1.17 min (analysis conditions A)

Compound A-34:

3,4-Difluoro-2-(2-fluoro-4-iodoanilino)-5-[[3-fluoro-2-(2-methylpropyl sulfamoylamino)pyridin-4-yl]methyl]benzamide

[Chemical Formula 88]

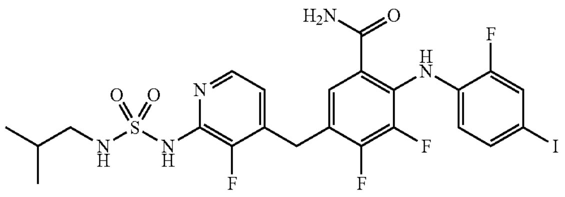

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 652 $[M+H]^+$

HPLC retention time: 1.31 min (analysis conditions A)

Compound A-35:

3,4-Difluoro-2-(2-fluoro-4-iodoanilino)-5-[[3-fluoro-2-[(1-methylcyclobutyl)sulfamoylamino]pyridin-4-yl]methyl]benzamide

[Chemical Formula 89]

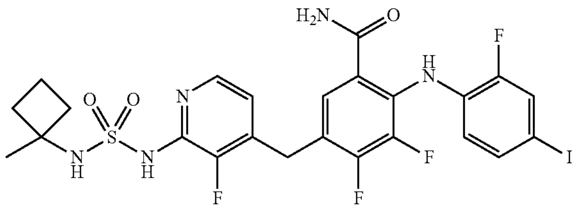

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25, except that the reaction was conducted at 0° C.

LCMS m/z: 664 $[M+H]^+$

HPLC retention time: 1.30 min (analysis conditions A)

Compound A-36:

5-[[2-(Cyclopropylmethylsulfamoylamino)-3-fluoropyridin-4-yl]methyl]-3,4-difluoro-2-(2-fluoro-4-iodoanilino)benzamide

[Chemical Formula 90]

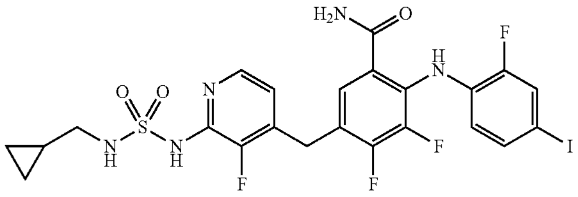

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25, except that the reaction was conducted at 0° C.

LCMS m/z: 650 $[M+H]^+$

HPLC retention time: 1.26 min (analysis conditions A)

Compound A-37:

5-[[2-(tert-Butylsulfamoylamino)-3-fluoropyridin-4-yl]methyl]-3,4-difluoro-2-(2-fluoro-4-iodoanilino)benzamide

[Chemical Formula 91]

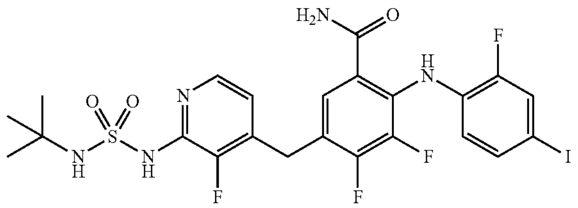

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25, except that the reaction was conducted at 0° C.

LCMS m/z: 652 $[M+H]^+$

HPLC retention time: 1.28 min (analysis conditions A)

Compound A-38:

5-[[2-(Ethylsulfonylamino)-3-fluoropyridin-4-yl]methyl]-3,4-difluoro-2-(2-fluoro-4-iodoanilino)benzamide

[Chemical Formula 92]

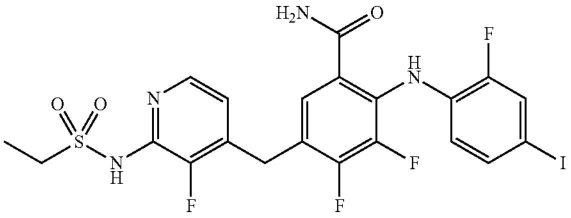

The title compound was synthesized from 5-[(2-amino-3-fluoropyridin-4-yl)methyl]-3,4-difluoro-2-(2-fluoro-4-iodoanilino)benzamide (compound a8) and the corresponding sulfonyl chloride under the same conditions as the production example for compound A-25, except that pyridine was used as the solvent.

LCMS m/z: 609 $[M+H]^+$

HPLC retention time: 1.20 min (analysis conditions A)

Compound A-39:

N-Cyclopropyl-5-[[2-(ethylsulfonylamino)-3-fluoropyridin-4-yl]methyl]-3,4-difluoro-2-(2-fluoro-4-iodoanilino)benzamide

[Chemical Formula 93]

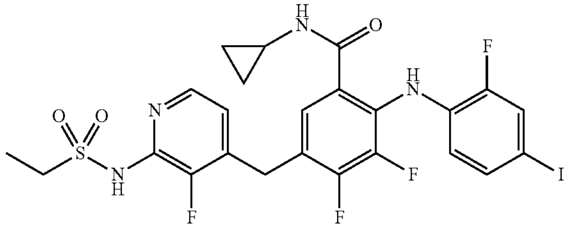

The title compound was synthesized from 5-[(2-amino-3-fluoropyridin-4-yl)methyl]-N-cyclopropyl-3,4-difluoro-2-(2-fluoro-4-iodoanilino)benzamide (compound a10) and the corresponding sulfonyl chloride under the same conditions as the production example for compound A-25, except that pyridine was used as the solvent.

LCMS m/z: 649 $[M+H]^+$

HPLC retention time: 1.68 min (analysis conditions B)

Compound A-40:

5-[[2-(Ethylsulfamoylamino)-3-fluoropyridin-4-yl]methyl]-3,4-difluoro-2-(2-fluoro-4-iodoanilino)benzamide

[Chemical Formula 94]

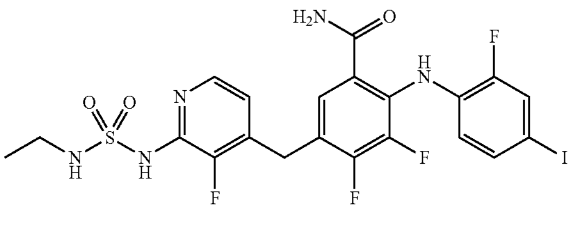

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 624 $[M+H]^+$

HPLC retention time: 1.20 min (analysis conditions A)

Compound A-41:

3,4-Difluoro-2-(2-fluoro-4-iodoanilino)-5-[[3-fluoro-2-(propylsulfamoylamino)pyridin-4-yl]methyl]benzamide

[Chemical Formula 95]

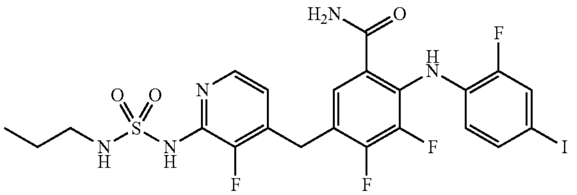

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 638 $[M+H]^+$

HPLC retention time: 1.25 min (analysis conditions A)

Compound A-42:

3,4-Difluoro-5-[[3-fluoro-2-(2-fluoroethylsulfamoylamino)pyridin-4-yl]methyl]-2-(2-fluoro-4-iodoanilino)benzamide

[Chemical Formula 96]

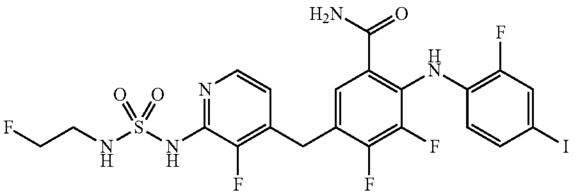

The title compound was synthesized from 5-[(2-amino-3-fluoropyridin-4-yl)methyl]-3,4-difluoro-2-(2-fluoro-4-iodoanilino)benzamide (compound a8) and the corresponding sulfamoyl chloride under the same conditions as the production example for compound A-25.

LCMS m/z: 642 $[M+H]^+$

HPLC retention time: 1.17 min (analysis conditions A)

Compound a20:

3,4-Difluoro-5-[[3-fluoro-2-(methylsulfamoylamino)pyridin-4-yl]methyl]-2-[2-fluoro-4-(2-trimethylsilylethynyl)anilino]benzamide

[Chemical Formula 97]

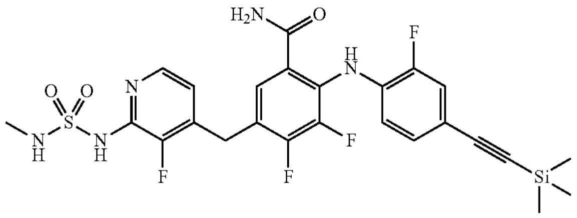

After dissolving 3,4-difluoro-2-(2-fluoro-4-iodoanilino)-5-[[3-fluoro-2-(methylsulfamoylamino)pyridin-4-yl]methyl]benzamide (compound A-25, 10.0 mg, 0.016 mmol) in anhydrous THE (0.1 mL), triethylamine (0.100 mL, 0.717 mmol), trimethylsilylacetylene (4.1 μL, 0.033 mmol), [1,1'-bis(diphenylphosphino)ferrocene]palladium(II) dichloride dichloromethane addition product (1.2 mg, 1.6 μmol) and copper(I) iodide (0.9 mg, 5 μmol) were added and the mixture was stirred for 24 hours at room temperature. The reaction mixture was purified by reversed-phase column chromatography (0.1% formic acid aqueous solution/0.1% formic acid acetonitrile solution) to give the title compound (12.4 mg) as an oil.

LCMS m/z: 580 $[M+H]^+$

HPLC retention time: 0.95 min (analysis conditions C)

Compound A-26:

2-(4-Ethynyl-2-fluoroanilino)-3,4-difluoro-5-[[3-fluoro-2-(methylsulfamoylamino)pyridin-4-yl]methyl]benzamide

[Chemical Formula 98]

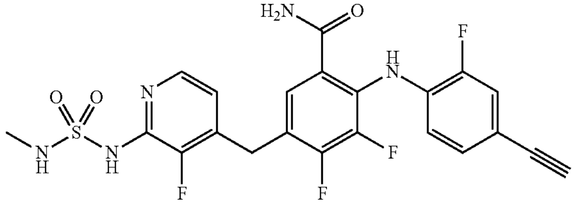

After dissolving 3,4-difluoro-5-[[3-fluoro-2-(methylsulfamoylamino)pyridin-4-yl]methyl]-2-[2-fluoro-4-(2-trimethylsilylethynyl)anilino]benzamide (compound a20, 11.0 mg, 0.019 mmol) in MeOH (0.2 mL), potassium carbonate (7.9 mg, 0.057 mmol) was added and the mixture was stirred for 1.5 hours at room temperature. The reaction mixture was purified by reversed-phase column chromatography (0.1% formic acid aqueous solution/0.1% formic acid acetonitrile solution) to give the title compound (5.0 mg, 52%) as a solid.

LCMS m/z: 508 $[M+H]^+$

HPLC retention time: 1.05 min (analysis conditions A)

Compound a21:

5-[(2-Amino-3-fluoropyridin-4-yl)methyl]-2-(4-bromo-2-fluoroanilino)-3,4-difluorobenzamide

[Chemical Formula 99]

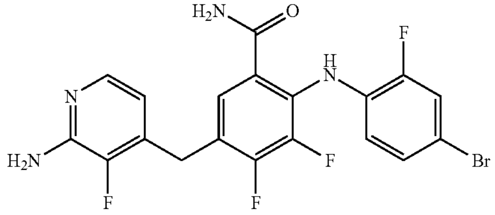

After dissolving 5-[(2-amino-3-fluoropyridin-4-yl)methyl]-3,4-difluoro-2-(2-fluoro-4-iodoanilino)benzamide (compound a8, 60.0 mg, 0.116 mmol) in anhydrous DMF (1.2 mL), copper(I) bromide (83.0 mg, 0.581 mmol) was added and the mixture was stirred for 24 hours at 100° C. The reaction mixture was purified by preparative HPLC (5 μm TSK-gel ODS 80TS, 20×250 mm column (TOSOH), 0.1% formic acid aqueous solution/0.1% formic acid acetonitrile solution) to give the title compound (35.6 mg) as a solid.

LCMS m/z: 469 $[M+H]^+$

HPLC retention time: 0.61 min (analysis conditions C)

Compound A-27:

2-(4-Bromo-2-fluoroanilino)-3,4-difluoro-5-[[3-fluoro-2-(methylsulfamoylamino)pyridin-4-yl]methyl]benzamide

[Chemical Formula 100]

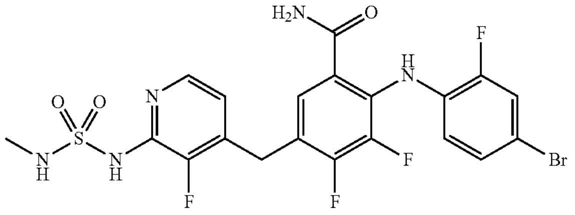

The title compound was synthesized from 5-[(2-amino-3-fluoropyridin-4-yl)methyl]-2-(4-bromo-2-fluoroanilino)-3,4-difluorobenzamide (compound a21) under the same conditions as the production example for compound A-25.

LCMS m/z: 562 $[M+H]^+$

HPLC retention time: 1.13 min (analysis conditions A)

Compound A-43:

3,4-Difluoro-2-(2-fluoro-4-iodoanilino)-5-[[3-fluoro-2-[[methyl-(methylamino)-oxo-λ6-sulfanylidene]amino]pyridin-4-yl]methyl]benzamide

[Chemical Formula 101]

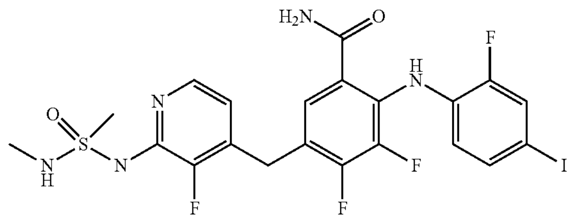

After dissolving 5-[(2-amino-3-fluoropyridin-4-yl)methyl]-3,4-difluoro-2-(2-fluoro-4-iodoanilino)benzamide (compound a8, 102 mg, 0.198 mmol) in anhydrous THF (2 mL), pyridine (0.160 mL, 1.98 mmol) and methanesulfinic acid chloride (0.100 mL, 0.717 mmol) were added at 0° C. under a nitrogen atmosphere. After adding tert-butyl hypochlorite (44.6 μL, 0.395 mmol) to the solution at 0° C. and stirring for 1 minute, tert-butyl hypochlorite (44.6 μL, 0.395 mmol) was further added. A 2 M methylamine THF solution (1.98 mL, 3.95 mmol) was then added, and the reaction mixture was stirred and purified by reversed-phase column chromatography (0.1% formic acid aqueous solution/0.1% formic acid acetonitrile solution) to give the title compound (45.9 mg, 38%) as a colorless solid.

LCMS m/z: 608 $[M+H]^+$

HPLC retention time: 1.00 min (analysis conditions A)

Compound a22:

5-[(2-Amino-3-fluoropyridin-4-yl)methyl]-3,4-difluoro-2-(2-fluoro-4-iodoanilino)benzoic acid trifluoroacetate

[Chemical Formula 102]

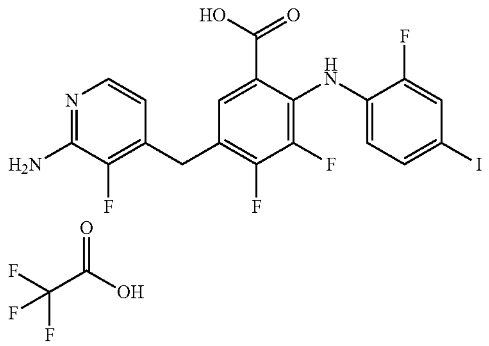

After dissolving methyl 5-[(2-amino-3-fluoropyridin-4-yl)methyl]-3,4-difluoro-2-(2-fluoro-4-iodoanilino)benzoate (compound a6, 1.05 g, 1.97 mmol) in THF (16.8 mL) and water (8.4 mL), lithium hydroxide monohydrate (415 mg, 9.88 mmol) was added at 0° C. and the mixture was stirred for 2 hours at room temperature. Trifluoroacetic acid (305 mL) was added to the reaction mixture, which was then concentrated under reduced pressure. The resulting residue was washed with water to give the title compound (1.06 g, 85%) as a colorless solid.

LCMS m/z: 518 $[M+H]^+$

HPLC retention time: 0.68 min (analysis conditions C)

Compound a23:

5-[(2-Amino-3-fluoropyridin-4-yl)methyl]-3,4-difluoro-2-(2-fluoro-4-iodoanilino)-N-(2-hydroxyethoxy)benzamide

[Chemical Formula 103]

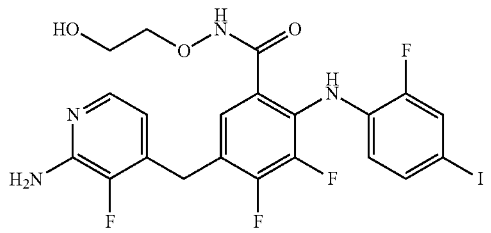

The title compound was synthesized from 5-[(2-amino-3-fluoropyridin-4-yl)methyl]-3,4-difluoro-2-(2-fluoro-4-iodoanilino)benzoic acid trifluoroacetate (compound a22) and the corresponding amine under the same conditions as the production example for compound A12.

LCMS m/z: 577 $[M+H]^+$

HPLC retention time: 0.58 min (analysis conditions C)

Compound a24:

5-[(2-Amino-3-fluoropyridin-4-yl)methyl]-N-[2-[tert-butyl(dimethyl)silyl]oxyethoxy]-3,4-difluoro-2-(2-fluoro-4-iodoanilino)benzamide

[Chemical Formula 104]

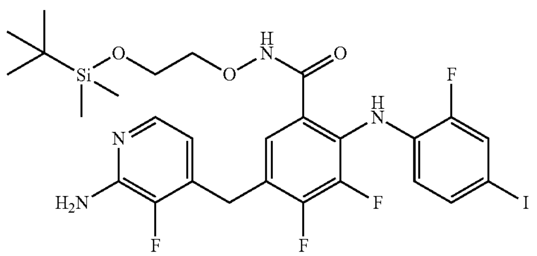

After dissolving 5-[(2-amino-3-fluoropyridin-4-yl)methyl]-3,4-difluoro-2-(2-fluoro-4-iodoanilino)-N-(2-hydroxyethoxy)benzamide (compound a23, 320 mg, 0.555 mmol) in anhydrous DMF (3 mL), triethylamine (0.116 mL, 0.833 mmol) and tert-butyldimethylchlorosilane (0.100 mL, 0.717 mmol) were added at 0° C. and the mixture was stirred at room temperature for 16 hours. Next, triethylamine (0.116 mL, 0.833 mmol) and tert-butyldimethylchlorosilane (0.100 mL, 0.717 mmol) were added, and stirring was continued for 7 hours. The reaction mixture was purified by reversed-phase column chromatography (10 mM ammonium acetate aqueous solution/methanol) to give the title compound (302 mg, 79%) as a yellow solid.

LCMS m/z: 691 $[M+H]^+$

HPLC retention time: 0.98 min (analysis conditions C)

Compound a25:

N-[2-[tert-Butyl(dimethyl)silyl]oxyethoxy]-5-[[2-(ethylsulfamoylamino)-3-fluoropyridin-4-yl]methyl]-3,4-difluoro-2-(2-fluoro-4-iodoanilino)benzamide

[Chemical Formula 105]

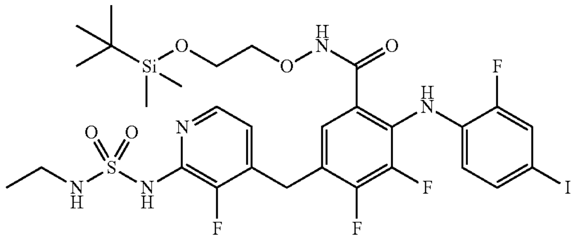

The title compound was synthesized from 5-[(2-amino-3-fluoropyridin-4-yl)methyl]-N-[2-[tert-butyl(dimethyl)silyl]oxyethoxy]-3,4-difluoro-2-(2-fluoro-4-iodoanilino)benzamide (compound a24) and the corresponding sulfamoyl chloride under the same conditions as the production example for compound A-25.

LCMS m/z: 798 $[M+H]^+$

HPLC retention time: 1.11 min (analysis conditions C)

Compound A-44:

5-[[2-(Ethylsulfamoylamino)-3-fluoropyridin-4-yl]methyl]-3,4-difluoro-2-(2-fluoro-4-iodoanilino)-N-(2-hydroxyethoxy)benzamide

[Chemical Formula 106]

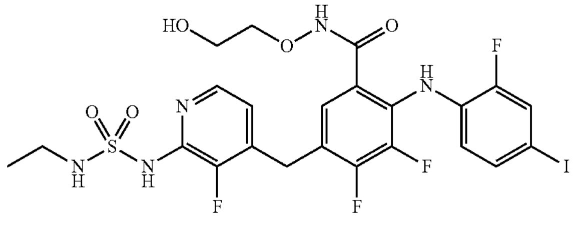

After dissolving N-[2-[tert-butyl(dimethyl)silyl]oxyethoxy]-5-[[2-(ethylsulfamoylamino)-3-fluoropyridin-4-yl]methyl]-3,4-difluoro-2-(2-fluoro-4-iodoanilino)benzamide (compound a25, 18 mg, 0.023 mmol) in anhydrous THF (0.2 mL), a 1 M tetrabutylammonium fluoride THF solution (27 μL, 0.27 mmol) was added at 0° C., and the mixture was stirred for 2 hours. The reaction mixture was purified by reversed-phase column chromatography (0.1% formic acid aqueous solution/0.1% formic acid acetonitrile solution) to give the title compound (14 mg, 91%) as a yellow solid.

LCMS m/z: 684 $[M+H]^+$

HPLC retention time: 0.79 min (analysis conditions C)

Compound A-45:

3,4-Difluoro-2-(2-fluoro-4-iodoanilino)-5-[[3-fluoro-2-(propylsulfamoylamino)pyridin-4-yl]methyl]-N-(2-hydroxyethoxy)benzamide

[Chemical Formula 107]

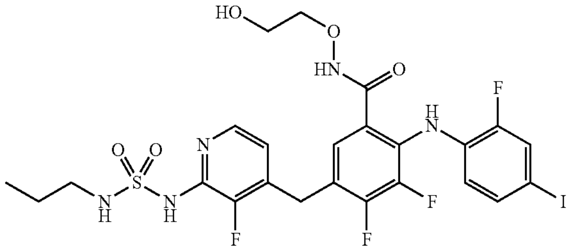

The title compound was synthesized from 5-[(2-amino-3-fluoropyridin-4-yl)methyl]-N-[2-[tert-butyl(dimethyl)silyl]oxyethoxy]-3,4-difluoro-2-(2-fluoro-4-iodoanilino)benzamide (compound a24) and the corresponding sulfamoyl chloride under the same conditions as the production example for compound A-25.

LCMS m/z: 698 $[M+H]^+$

HPLC retention time: 0.83 min (analysis conditions C)

Compound A-46:

2-(4-Cyclopropyl-2-fluoroanilino)-3,4-difluoro-5-[[3-fluoro-2-[(1-methylcyclobutyl)sulfamoylamino]pyridin-4-yl]methyl]benzamide

[Chemical Formula 108]

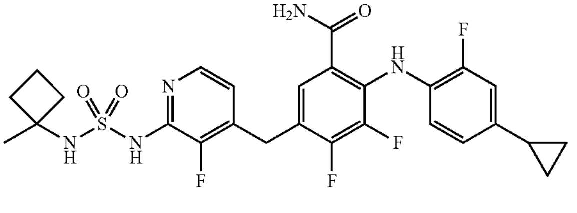

The title compound was synthesized from 5-[(2-amino-3-fluoropyridin-4-yl)methyl]-2-(4-cyclopropyl-2-fluoroanilino)-3,4-difluorobenzamide (compound a9) and the corresponding 4-nitrophenyl sulfamate under the same conditions as the production example for compound A-1.

LCMS m/z: 578 $[M+H]^+$

HPLC retention time: 0.89 min (analysis conditions C)

Compound A-47:

N-Cyclopropyl-3,4-difluoro-2-(2-fluoro-4-iodoanilino)-5-[[3-fluoro-2-[(1-methylcyclobutyl)sulfamoylamino]pyridin-4-yl]methyl]benzamide

[Chemical Formula 109]

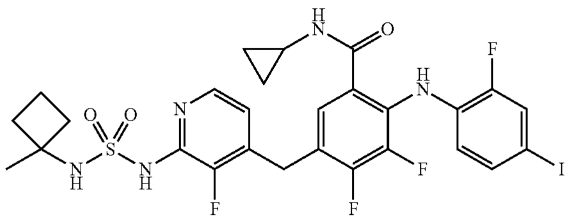

The title compound was synthesized from 5-[(2-amino-3-fluoropyridin-4-yl)methyl]-N-cyclopropyl-3,4-difluoro-2-(2-fluoro-4-iodoanilino)benzamide (compound a10) and the corresponding 4-nitrophenyl sulfamate under the same conditions as the production example for compound A-1.

LCMS m/z: 704 $[M+H]^+$

HPLC retention time: 0.97 min (analysis conditions C)

Compound a26:

5-Bromo-2,3,4-trifluorobenzoic acid

[Chemical Formula 110]

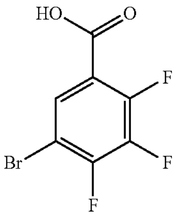

A reaction vessel in which water (81 mL) had been placed was cooled to an external temperature of 0° C., and concentrated sulfuric acid (162 mL) was added. Next, 2,3,4-trifluorobenzoic acid (27.0 g, 153 mmol) and potassium sulfate (401 mg, 2.30 mmol) were added, and the mixture was heated to an external temperature of 55° C. An aqueous solution prepared from sodium bromate (25.4 g, 169 mmoL) and water (108 mL) was added dropwise over a period of 2.5 hours, and the mixture was stirred for 2.5 hours. The reaction mixture was cooled to 0° C., and then an aqueous solution prepared from sodium sulfite (24.3 g, 161 mmol) and water (324 mL) was added. The crystals were filtered out, washed with water (162 mL) and dried by ventilation to give the title compound (27.9 g, 71%) as a colorless solid.

LCMS m/z: 253 $[M-H]^-$

HPLC retention time: 0.66 min (analysis conditions C)

Compound a27:

5-Bromo-2-(4-cyclopropyl-2-fluoroanilino)-3,4-difluorobenzoic acid

[Chemical Formula 111]

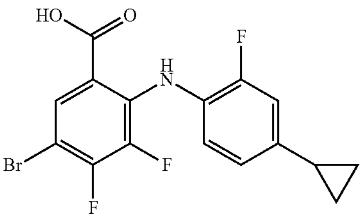

A reaction vessel in which a 1 M lithium bis(trimethylsilyl)amide THF solution (206 mL, 206 mmol) had been placed was cooled to an external temperature of −15° C., and a THF (30 mL) solution of 4-cyclopropyl-2-fluoroaniline (11.6 g, 76.5 mmol) was added dropwise. A THF (120 mL) solution of 5-bromo-2,3,4-trifluorobenzoic acid (compound a26, 15.0 g, 58.8 mmol) was added dropwise over 30 minutes, and the mixture was stirred for 30 minutes. After then adding 5 M hydrochloric acid (118 mL) to the reaction mixture, it was heated to room temperature and extraction was performed with isopropyl acetate (75 mL). The organic layer was washed twice with water (75 mL) and once with 15% sodium chloride aqueous solution (75 mL), and concentrated under reduced pressure. Acetone (120 mL) was added to the resulting concentrated residue, and after heating to dissolution, water (45 mL) and seed crystals (150 mg) were added to precipitate crystals. Water (45 mL) was added to the resulting slurry, and the crystals were filtered off. After washing with a liquid mixture of acetone/water (1/2), they were dried at an external temperature of 40° C. under reduced pressure to give the title compound (19.4 g, 85%).

LCMS m/z: 386 $[M+H]^+$

HPLC retention time: 0.62 min (analysis conditions C)

Compound a28:

5-Bromo-2-(4-cyclopropyl-2-fluoroanilino)-3,4-difluorobenzamide

[Chemical Formula 112]

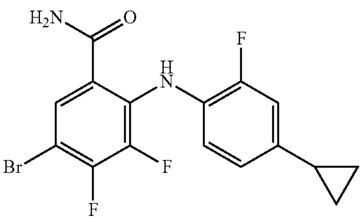

Acetonitrile (104 mL), THF (26 mL) and 1,1'-carbonyldiimidazole (8.2 g, 50.5 mmol) were added to a reaction vessel in which 5-bromo-2-(4-cyclopropyl-2-fluoroanilino)-3,4-difluorobenzoic acid (compound a27, 13.0 g, 33.7 mmol) had been placed, and the mixture was stirred at room temperature for 2 hours. After adding 28% ammonia water (13 mL) to the reaction mixture, it was stirred for 30 minutes at room temperature, and then water (117 mL) was added over a period of 1 hour. The crystals were filtered off and washed with water, and then dried at an external temperature of 40° C. under reduced pressure to give the title compound (12.0 g, 93%).

LCMS m/z: 385 $[M+H]^+$

HPLC retention time: 0.52 min (analysis conditions C)

Compound a30:

N-[3-Fluoro-4-(hydroxymethyl)pyridin-2-yl]acetamide methanesulfonate

[Chemical Formula 113]

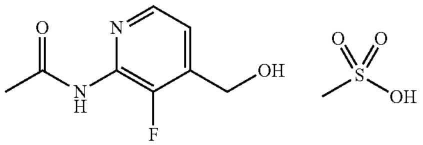

(1) Synthesis of N-[4-[[tert-butyl(dimethyl)silyl]oxymethyl]-3-fluoropyridin-2-yl]acetamide After adding tert-butyl-[(2-chloro-3-fluoropyridin-4-yl)methoxy]-dimethylsilane (180 g, 653 mmol), Xantphos (22.7 g, 39.2 mmol), potassium carbonate (135 g, 979 mmol), acetamide (77.1 g, 1.31 mol) and 2-methyl-2-butanol (540 mL) to a reaction vessel, it was vacuum deaerated and exchanged with nitrogen. After then adding tris(dibenzylideneacetone)dipalladium(0) (14.9 g, 16.3 mmol) and toluene (540 mL), vacuum deaeration and exchange with nitrogen were repeated. The mixture was heated to an external temperature of 120° C. under a nitrogen atmosphere and stirred for 7 hours. The external temperature was cooled to room temperature, and the reaction mixture was filtered and washed with toluene (450 mL). Active carbon (9.00 g, 749 mmol) was added to the filtrate and the mixture was stirred for 1 hour at room temperature. The reaction mixture was then filtered and washed twice with toluene (270 mL the first time and 180 mL the second time) to give a crude product of N-[4-[[tert-butyl(dimethyl)silyl]oxymethyl]-3-fluoropyridin-2-yl]acetamide as a toluene solution.

LCMS m/z: 299 $[M+H]^+$

HPLC retention time: 0.81 min (analysis conditions C)

(2) Synthesis of Compound a30

The obtained N-[4-[[tert-butyl(dimethyl)silyl]oxymethyl]-3-fluoropyridin-2-yl]acetamide toluene solution, toluene (175 mL) and methanol (195 mL) were added to a reaction vessel, and it was vacuum deaerated and exchanged with nitrogen. After then adding methanesulfonic acid (188 g, 1.96 mol) dropwise at an external temperature of 10° C., the mixture was stirred at room temperature for 2 hours. The reaction mixture was cooled to an external temperature of 0° C. and stirred for 3 hours. The precipitate was filtered off and washed with a cooled liquid mixture of toluene (312 mL) and methanol (78 mL). The filtered solid and a liquid mixture of toluene (1.1 L) and ethanol (492 mL) were added to the reaction vessel, and the mixture was stirred for 1 hours at an external temperature of 0° C. The solid was filtered off and washed with a liquid mixture of toluene (281 mL) and ethanol (117 mL), and then dried at an external temperature of 40° C. under reduced pressure to give compound a30 (149 g, 81%).

LCMS m/z: 185 $[M+H]^+$

HPLC retention time: 0.30 min (analysis conditions E)

Compound a31:

(2-Acetamide-3-fluoropyridin-4-yl)methyl Methylcarbonate

[Chemical Formula 114]

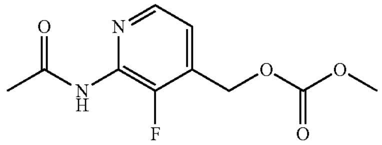

4-Dimethylaminopyridine (52.3 g, 428 mmol) was added at room temperature to a reaction vessel in which N-[3-fluoro-4-(hydroxymethyl)pyridin-2-yl]acetamide methanesulfonate (compound a30, 50.0 g, 178 mmol) and 2-methyltetrahydrofuran (750 mL) had been placed. The external temperature was cooled to 0° C., methyl chloroformate (21.9 g, 232 mmol) was added, and the mixture was heated to room temperature and stirred. The precipitated solid was filtered off and the filtrate was concentrated under reduced pressure at an external temperature of 40° C. Ethyl acetate (300 mL) was added to the concentrated residue to dissolve it at room temperature, and then DIPEA (31.2 mL, 178 mmol), heptane (150 mL) and seed crystals were added. After confirming precipitation of crystals, heptane (1 L) was added. The slurry was cooled to an external temperature of 0° C., and then the crystals were filtered off and washed with a liquid mixture of ethyl acetate/heptane (2/7). These were dried at an external temperature of 40° C. under reduced pressure to give the title compound (31.3 g, 72%) as a colorless solid.

LCMS m/z: 243 $[M+H]^+$

HPLC retention time: 0.37 min (analysis conditions C)

Compound a32:

5-[(2-Acetamide-3-fluoropyridin-4-yl)methyl]-2-(4-cyclopropyl-2-fluoroanilino)-3,4-difluorobenzamide

[Chemical Formula 115]

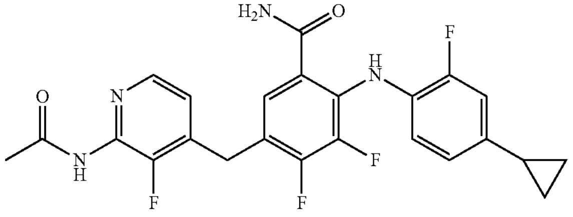

After adding 5-bromo-2-(4-cyclopropyl-2-fluoroanilino)-3,4-difluorobenzamide (compound a28, 10.0 g, 26.0 mmol), bis(pinacolato)diboron (7.3 g, 28.6 mmol), potassium acetate (7.6 g, 77.9 mmol) and 2-methyltetrahydrofuran (150 mL) to a reaction vessel, it was vacuum deaerated and exchanged with nitrogen. Next, (2-dicyclohexylphosphino-2',4',6'-triisopropyl-1,1'-biphenyl) [2-(2'-amino-1,1'-biphenyl)]palladium(II) methanesulfonate (440 mg, 0.52 mmol) was added and vacuum deaeration and exchange with nitrogen were repeated. The mixture was heated to an external temperature of 80° C. under a nitrogen atmosphere and stirred for 6 hours. The external temperature was cooled to room temperature, potassium carbonate (10.8 g, 77.9 mmol) was added, and the mixture was vacuum deaerated and exchanged with nitrogen. After then adding (2-dicyclohexylphosphino-2',4',6'-triisopropyl-1,1'-biphenyl) [2-(2'-amino-1,1'-biphenyl)]palladium(II) methanesulfonate (1.1 g, 1.3 mmol) and conducting further vacuum deaeration and exchange with nitrogen, a solution of (2-acetamide-3-fluoropyridin-4-yl)methyl methylcarbonate (compound a31, 12.6 g, 51.9 mmol) in 2-methyltetrahydrofuran (150 mL) was added. The mixture was heated to an external temperature of 70° C. under a nitrogen atmosphere, and after adding water (935 μL, 51.9 mmol) three times at 20 minute intervals, the mixture was stirred for 20 minutes. Water (7.0 mL) was further added dropwise, the mixture was stirred for 2 hours, a solution prepared from N-acetylcysteine (847 mg, 5.2 mmol) and water (150 mL) was added, and the mixture was stirred for 1 hour. After cooling to an external temperature of 40° C., the aqueous layer was discharged. The organic layer was washed with 15% sodium chloride aqueous solution (150 mL), the insoluble portion was filtered, and concentration was carried out under reduced pressure. Acetonitrile (500 mL) was added to the resulting concentrated residue, and the mixture was heated at an external temperature of 100° C. to dissolution and then cooled to room temperature. The crystals were filtered off and washed with acetonitrile (200 mL), and then dried at an external temperature of 40° C. under reduced pressure to give the title compound (8.34 g, 68%).

LCMS m/z: 471 $[M-H]^-$

HPLC retention time: 0.74 min (analysis conditions C)

Compound a9:

5-[(2-Amino-3-fluoropyridin-4-yl)methyl]-2-(4-cyclopropyl-2-fluoroanilino)-3,4-difluorobenzamide

[Chemical Formula 116]

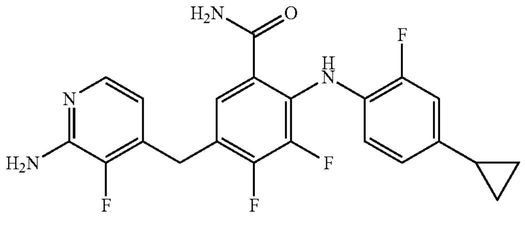

Production Example a9-2

Methanol (3 mL) and 5 M hydrochloric acid (0.42 mL, 2.1 mmol) were added to a reaction vessel in which 5-[(2-acetamide-3-fluoropyridin-4-yl)methyl]-2-(4-cyclopropyl-2-fluoro anilino)-3,4-difluorobenzamide (compound a32, 100 mg, 0.21 mmol) had been placed, and the mixture was stirred for 6 hours at an external temperature of 50° C. The reaction mixture was cooled to room temperature, and a 2 M sodium hydroxide aqueous solution (1.1 mL, 2.1 mmol) was added. Water (0.5 mL) was added to the resulting slurry, and the crystals were filtered off. After washing with a liquid mixture of methanol/water (3/2), they were dried at an external temperature of 40° C. under reduced pressure to give compound a9 (77.7 mg, 85%) as a colorless solid.

LCMS m/z: 431 $[M+H]^+$

HPLC retention time: 0.61 min (analysis conditions C)

Compound A-1:

2-(4-Cyclopropyl-2-fluoroanilino)-3,4-difluoro-5-[[3-fluoro-2-(methylsulfamoylamino)pyridin-4-yl]methyl]benzamide

[Chemical Formula 117]

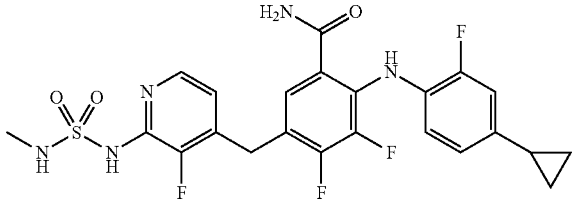

Production Example A-1-2

After dissolving 5-[(2-amino-3-fluoropyridin-4-yl)methyl]-2-(4-cyclopropyl-2-fluoroanilino)-3,4-difluorobenzamide (compound a9, 100 mg, 0.232 mmol) in anhydrous DMA (1 mL), pyridine (56.4 IL, 0.697 mmol) was added. After then cooling to 0° C., methylsulfamoyl chloride (30.2 μL, 0.349 mmol) was added and the mixture was stirred for 1 hour. Acetonitrile (0.6 mL), water (0.3 mL) and seed crystals (1 mg) were added to the reaction mixture, the temperature was increased to room temperature, and then water (0.7 mL) and acetonitrile (0.4 mL) were added and the mixture was stirred for 20 hours. The precipitate was filtered off and washed with a liquid mixture of acetonitrile/water (1/1) to give compound A-1 (93.1 mg, 77%) as a colorless solid.

LCMS m/z: 524 $[M+H]^+$

HPLC retention time: 1.13 min (analysis conditions A)

Sodium Salt of Compound A-1:

2-(4-Cyclopropyl-2-fluoroanilino)-3,4-difluoro-5-[[3-fluoro-2-(methylsulfamoylamino)pyridin-4-yl]methyl]benzamide sodium salt

[Chemical Formula 118]

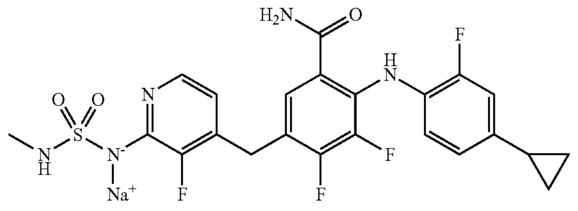

(1) Preparation of Sample A-1a (Form 1)

Acetone (10.6 mL) and DMSO (1.51 mL) were added to 2-(4-cyclopropyl-2-fluoroanilino)-3,4-difluoro-5-[[3-fluoro-2-(methylsulfamoylamino)pyridin-4-yl]methyl]benzamide (compound A-1, 3.03 g), dissolving it at room temperature. A 20% sodium ethoxide ethanol solution (3.03 mL) and seed crystals of a sodium salt of compound A-1 (sample A-1b mentioned below) were added to the solution and the mixture was stirred for 1 hour at room temperature, after which ethanol (15.1 mL) was added and the mixture was stirred at room temperature for 4 hours. Ethanol (15.1 mL) was then added, and the mixture was stirred for 4 hours at room temperature to give a sodium salt of compound A-1 (2.74 g) as powdered crystals (sample A-1a (Form I)).

(2) Preparation of Sample A-1b

A 20% sodium ethoxide ethanol solution (0.054 mL) and methyl isobutyl ketone (0.161 mL) were added to compound A-1 (53.6 mg), the mixture was stirred for 30 minutes at room temperature, and then methyl isobutyl ketone (0.161 mL) was added and stirring was continued for 4 days at 60° C. DMSO (0.054 mL) was then added, and the mixture was stirred for 5 hours at 60° C. to give a sodium salt of compound A-1 (25.6 mg) as powdered crystals (sample A-1b).

(3) Preparation of Sample A-1c

DMSO (4.26 mL) and a 2 M sodium hydroxide aqueous solution (1.07 mL) were added to compound A-1 (1.02 g). The solution was freeze-dried for 4 days at −20° C. and then dried under reduced pressure for 3 days at room temperature. After adding 1-pentanol (10.0 mL) to the obtained solid, the mixture was stirred for 10 minutes at 80° C. It was then stirred for 6 hours at room temperature to give a sodium salt of compound A-1 (0.966 g) as powdered crystals (sample A-1c).

(4) Powder X-Ray Diffraction Analysis

Sample A-1a (Form I), sample A-1b and sample A-1c were subjected to powder X-ray diffraction analysis under the following conditions.

Apparatus: SmartLab, D/Tex Ultra detector (Rigaku Corp.)
Anti-cathode: Cu
Tube voltage: 45 kV
Tube current: 200 mA
Sampling width: 0.020

Figure 2:
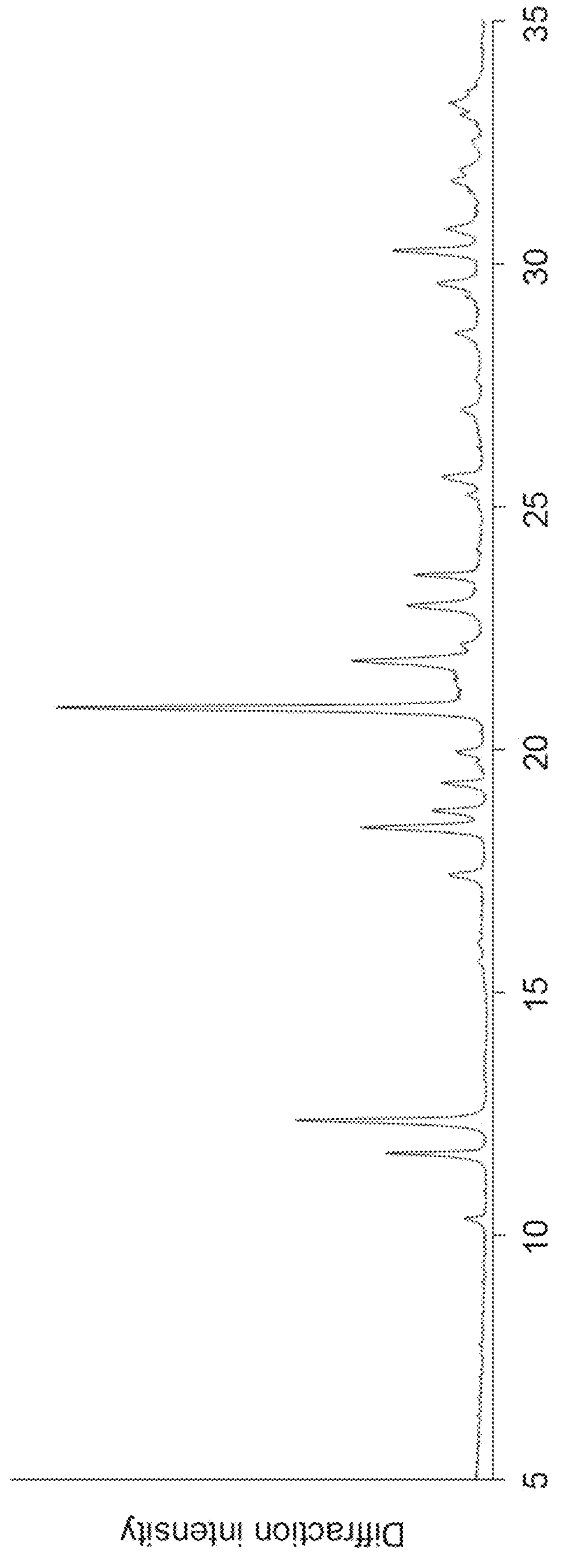
FIG. 2 shows a powder X-ray diffraction pattern of sample A-1b.
Figure 3:
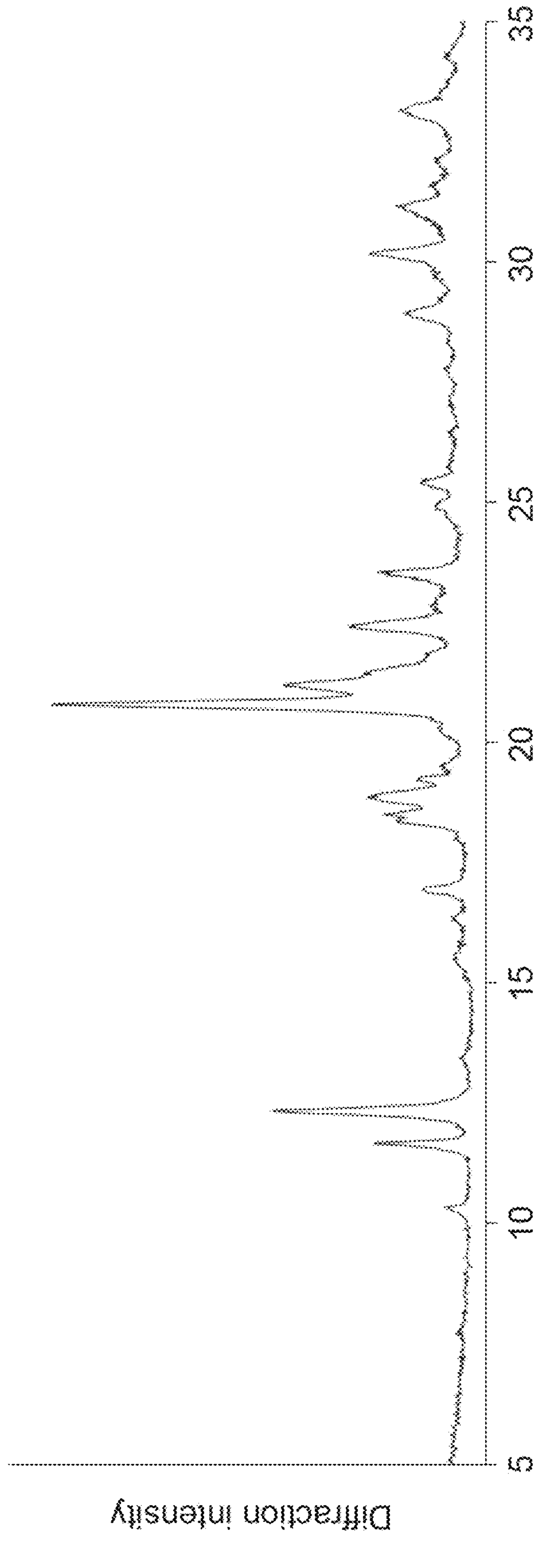
FIG. 3 shows a powder X-ray diffraction pattern of sample A-1c.
Figure 4:
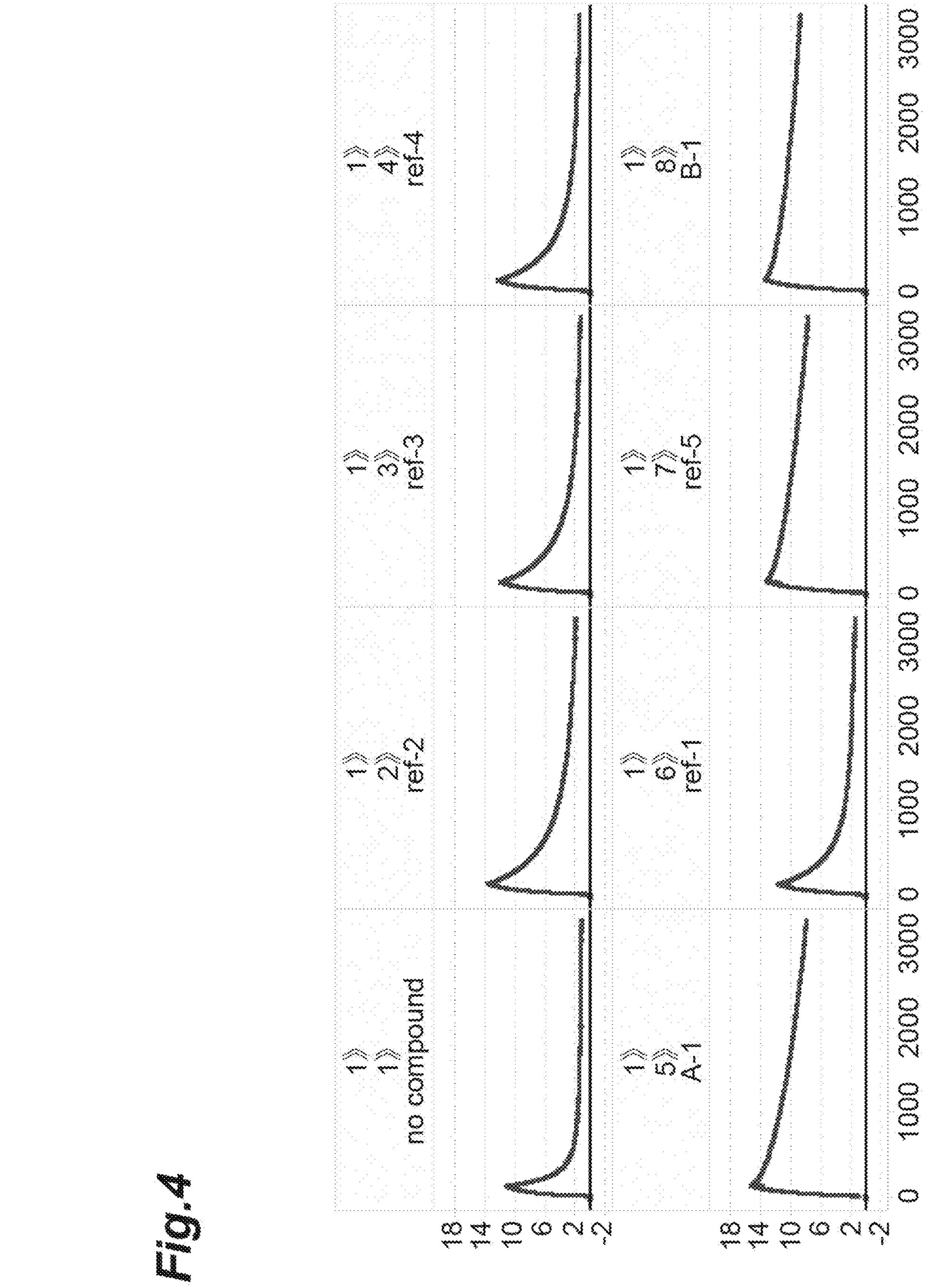
FIG. 4 is sensorgrams showing change over time in the amount of binding of MEK1 added onto a RAF1-immobilized sensor chip surface together with a test compound (ref-2, ref-3, ref-4, A-1, ref-1, ref-5 or B-1).
Figure 5:
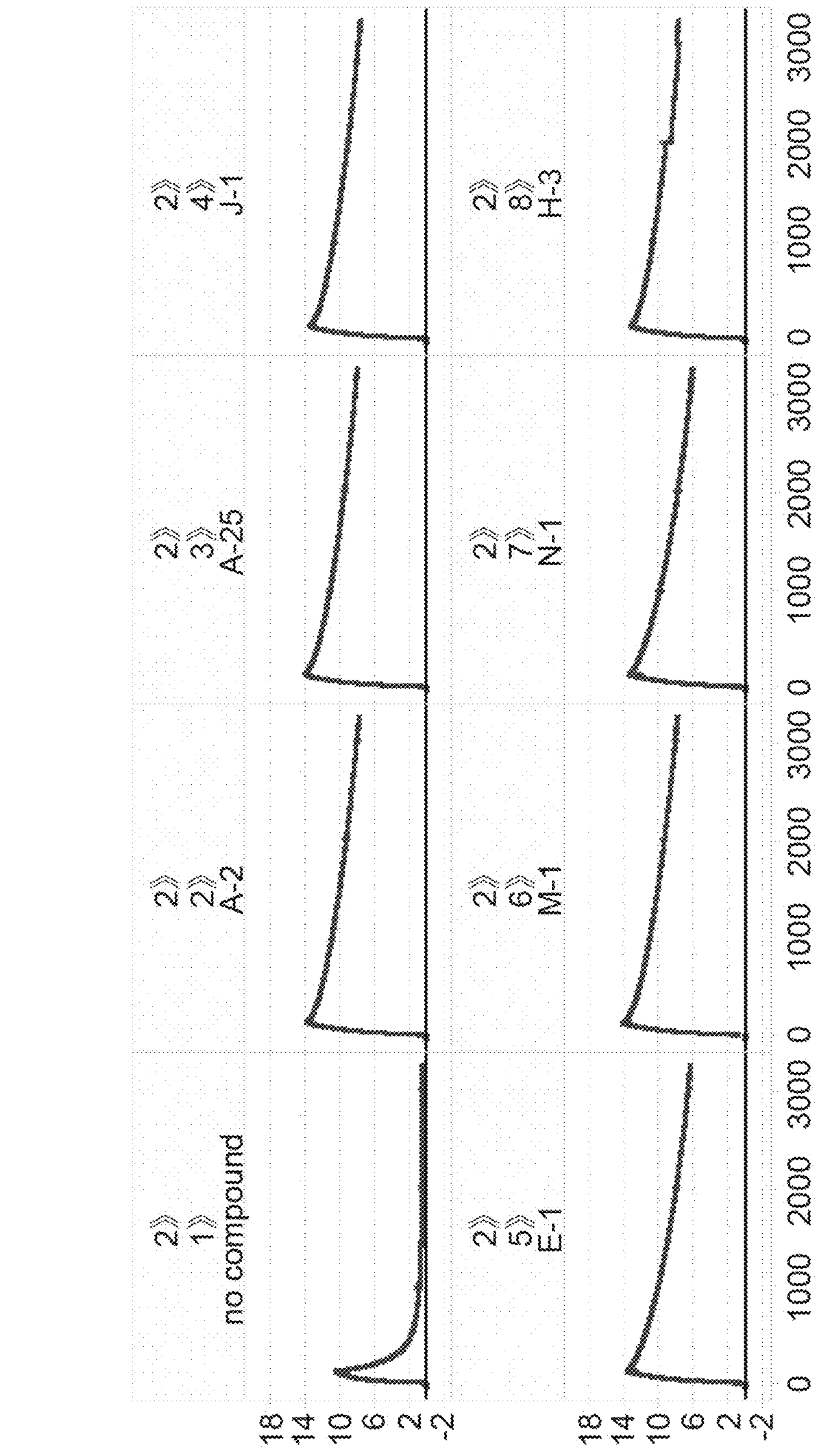
FIG. 5 is sensorgrams showing change over time in the amount of binding of MEK1 added onto a RAF1-immobilized sensor chip surface together with a test compound (A-2, A-25, J-1, E-1, M-1, N-1 or H-3).
Figure 6:
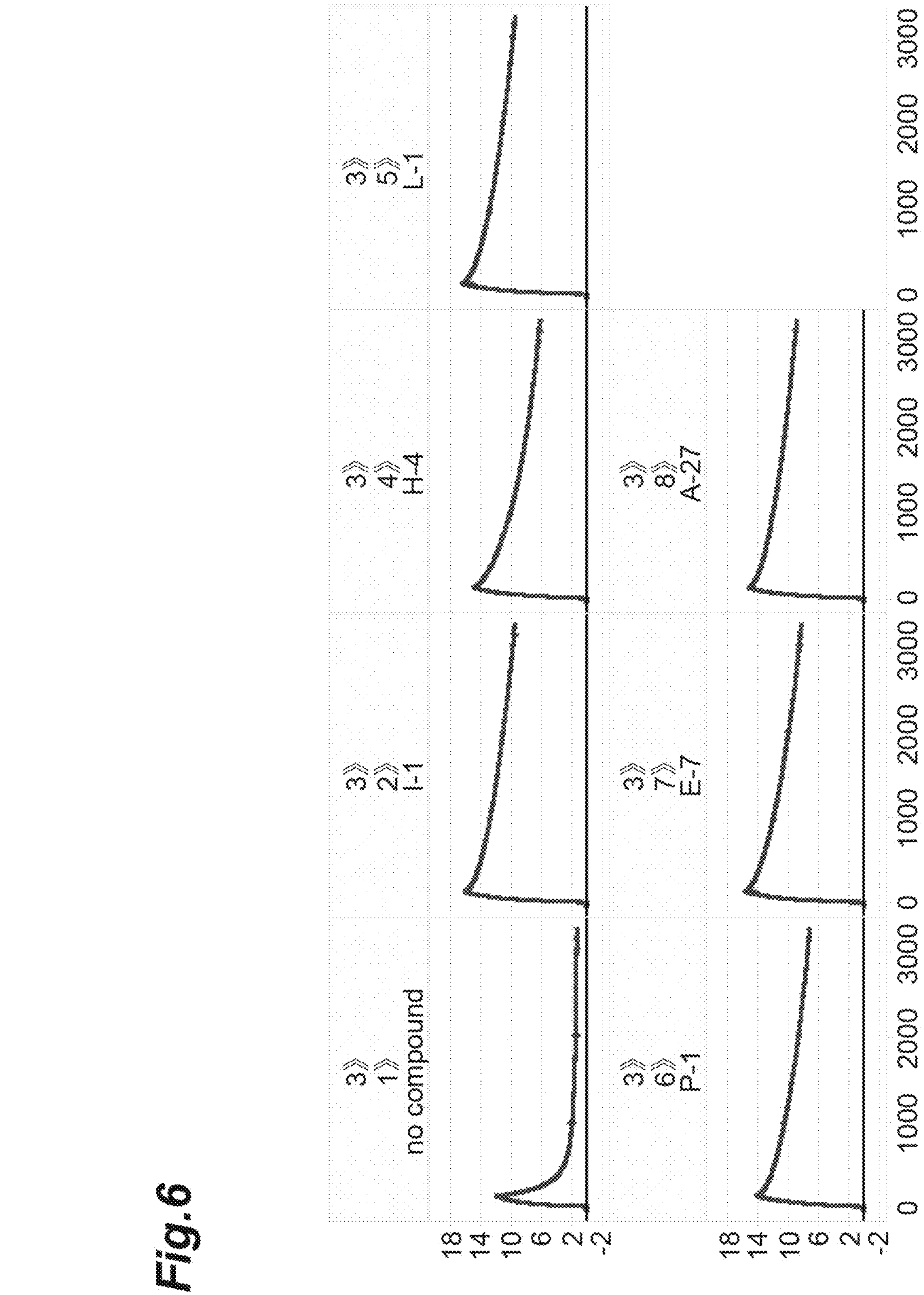
FIG. 6 is sensorgrams showing change over time in the amount of binding of MEK1 added onto a RAF1-immobilized sensor chip surface together with a test compound (I-1, H4, L-1, P-1, E-7 or A-27).
Figure 7:
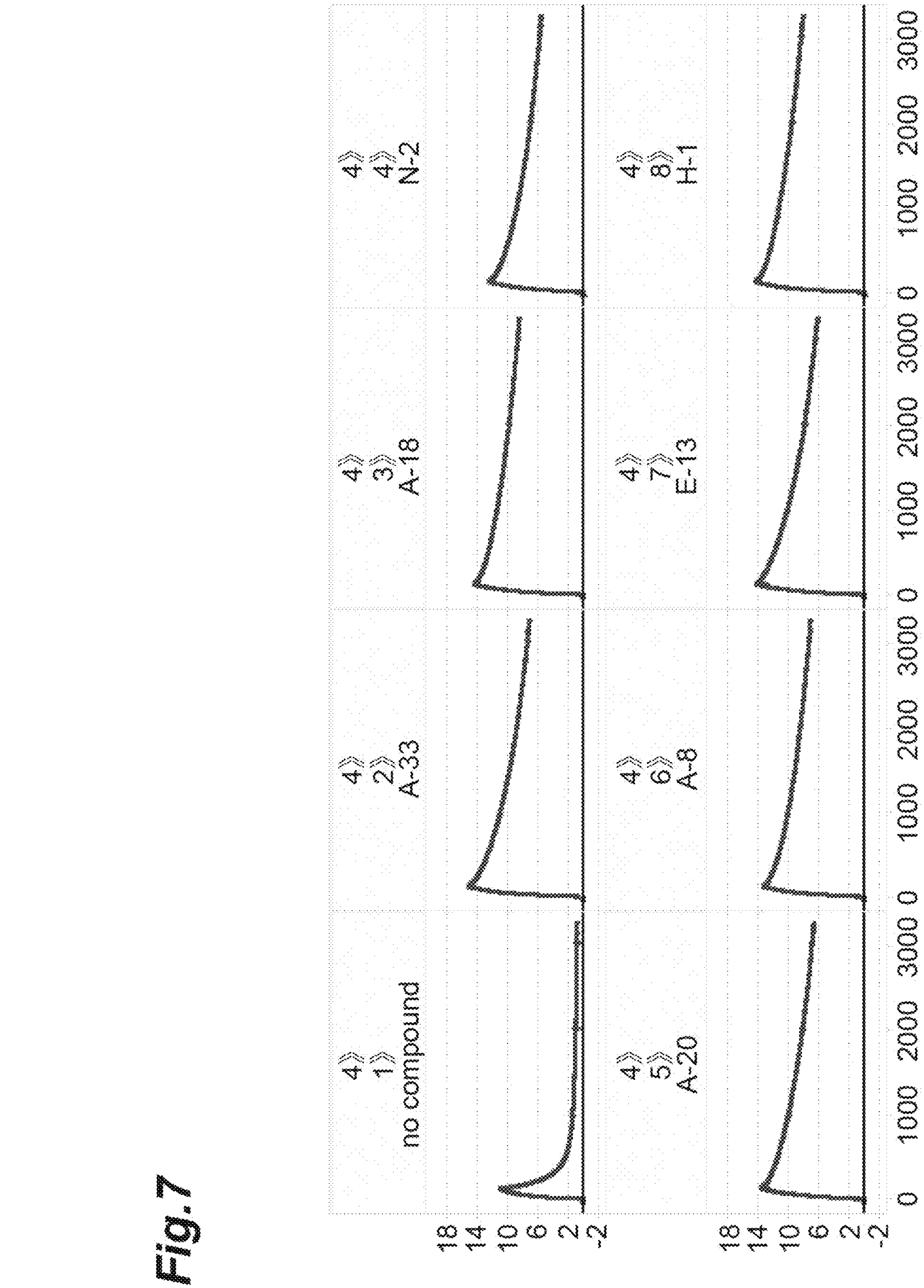
FIG. 7 is sensorgrams showing change over time in the amount of binding of MEK1 added onto a RAF1-immobilized sensor chip surface together with a test compound (A-33, A-18, N-2, A-20, A-8, E-13 or H-1).
Figure 8:
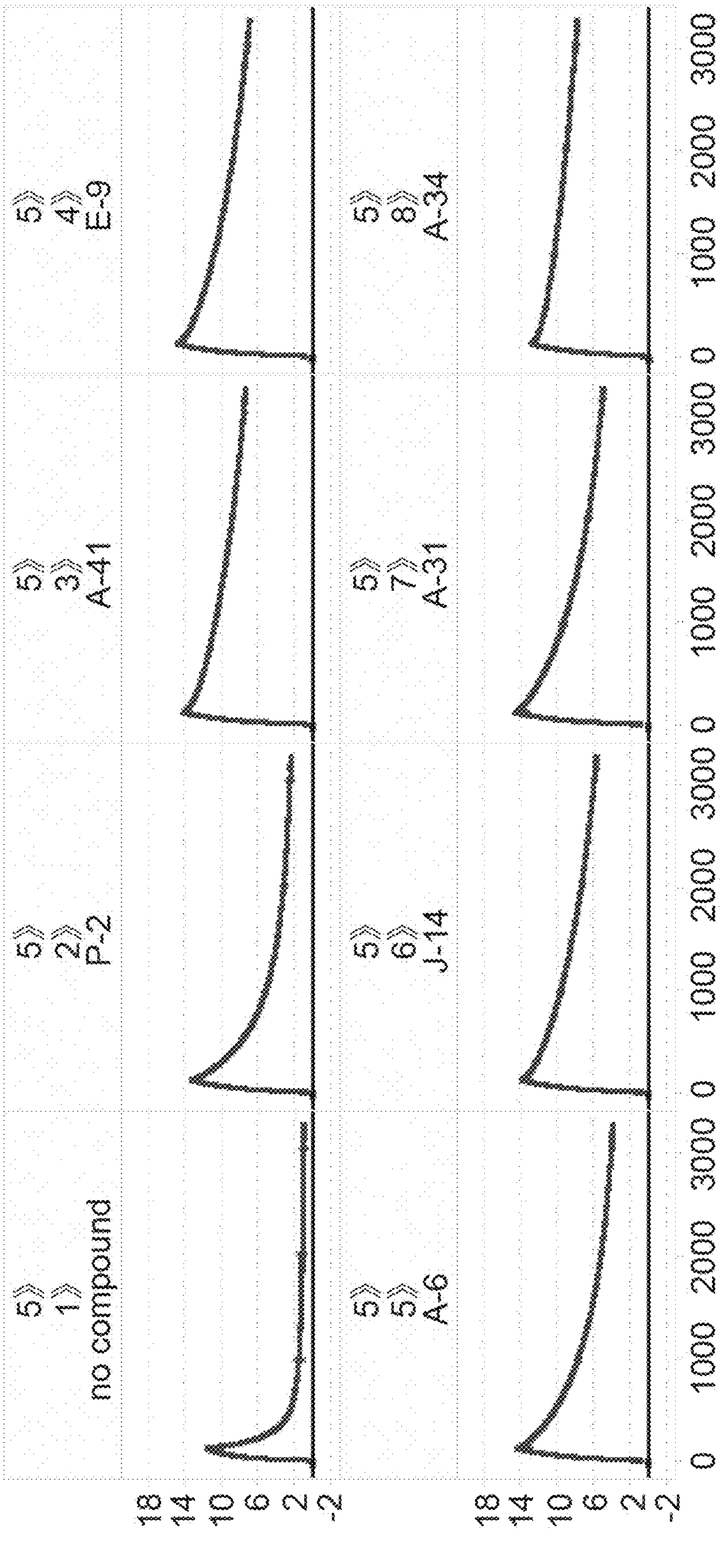
FIG. 8 is sensorgrams showing change over time in the amount of binding of MEK1 added onto a RAF1-immobilized sensor chip surface together with a test compound (P-2, A-41, E-9, A-6, J-14, A-31 or A-34).
Figure 9:
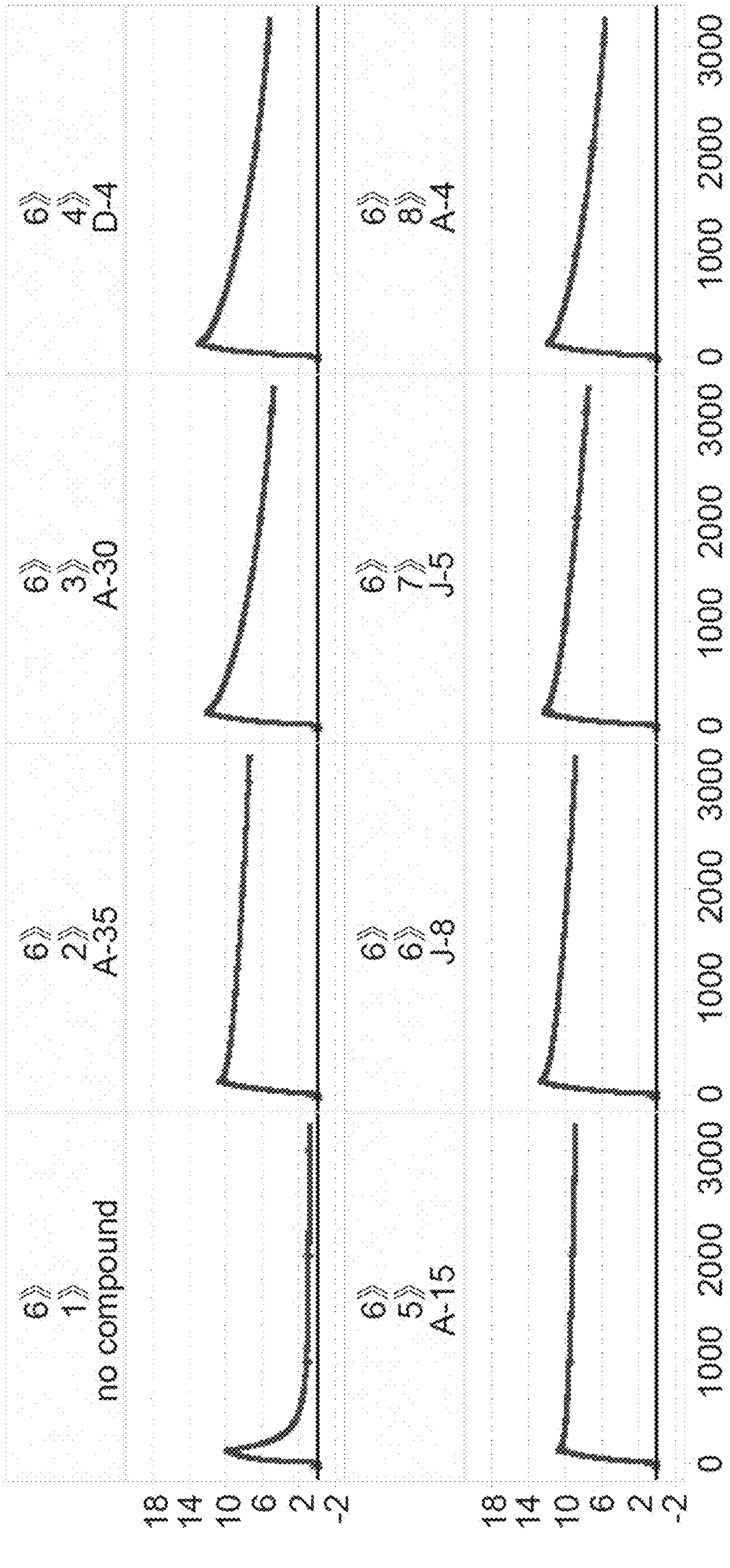
FIG. 9 is sensorgrams showing change over time in the amount of binding of MEK1 added onto a RAF1-immobilized sensor chip surface together with a test compound (A-35, A-30, D-4, A-15, J-8, J-5 or A-4).
Figure 10:
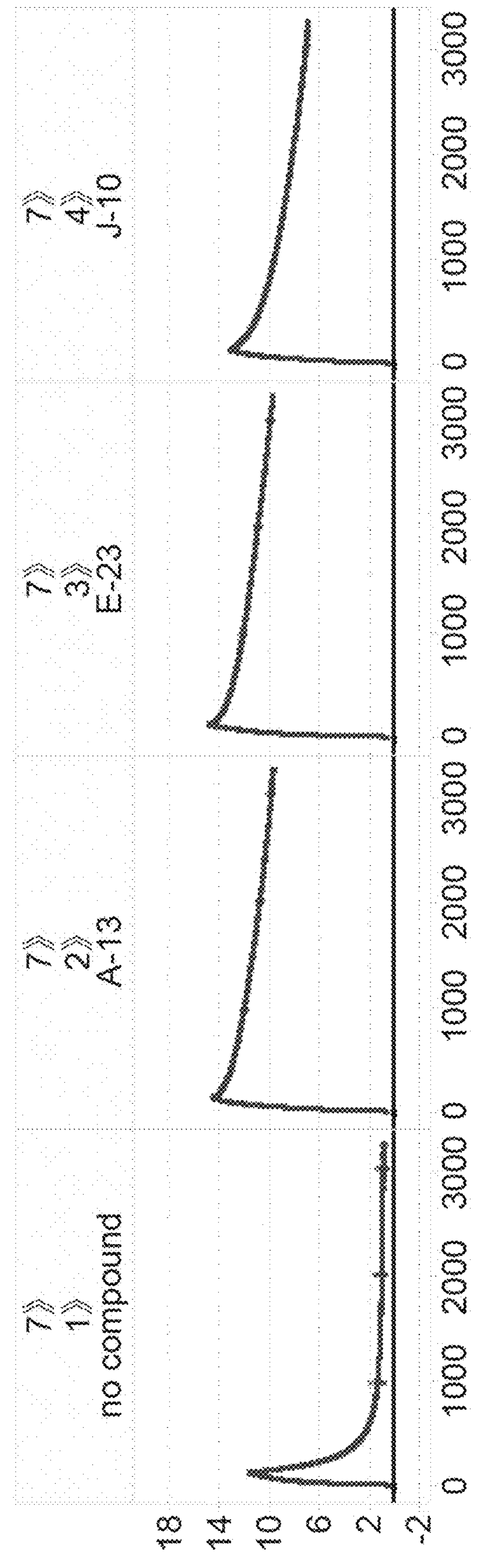
FIG. 10 is sensorgrams showing change over time in the amount of binding of MEK1 added onto a RAF1-immobilized sensor chip surface together with a test compound (A-13, E-23 or J-10).
Figure 11:
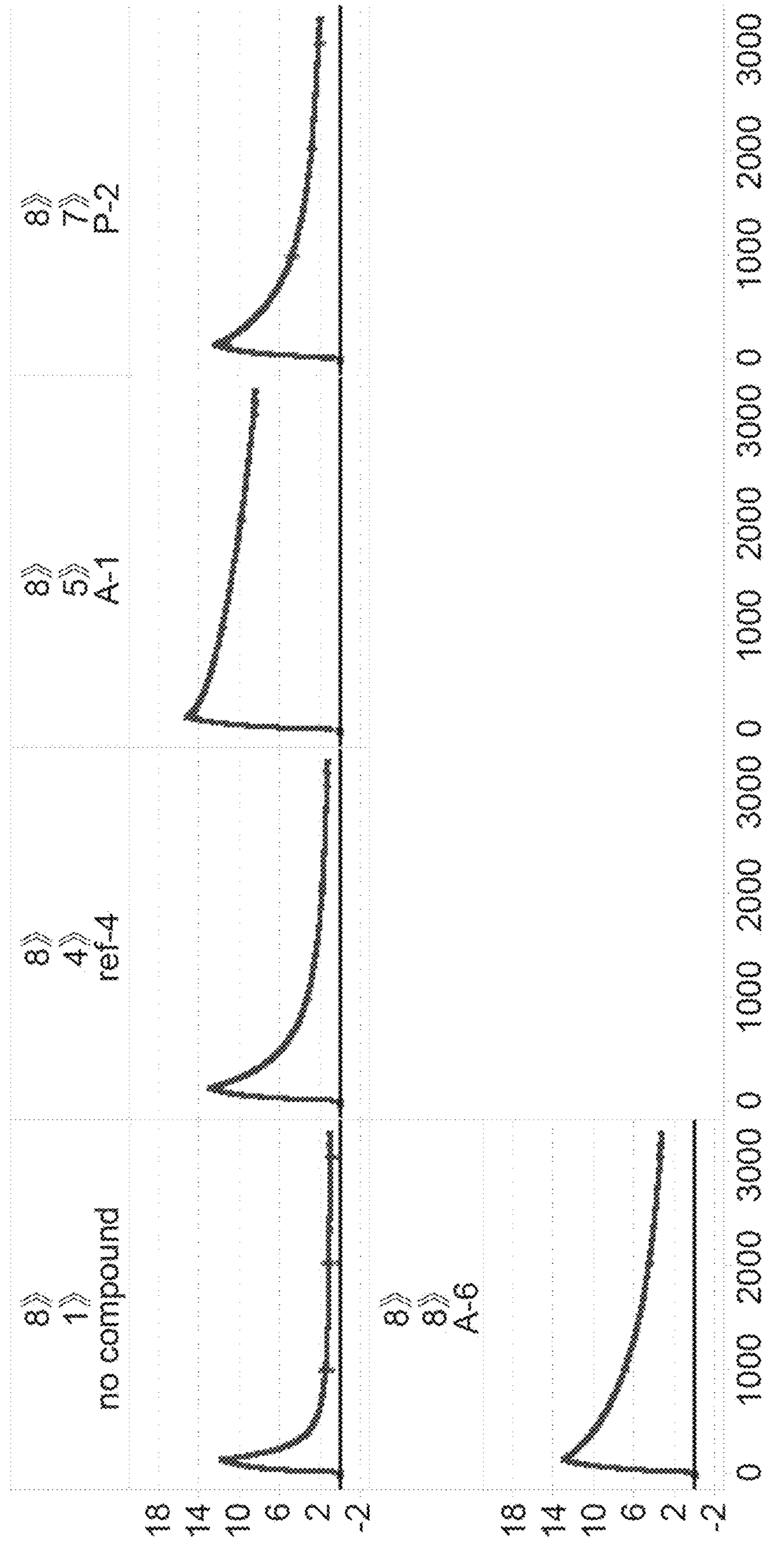
FIG. 11 is sensorgrams showing change over time in the amount of binding of MEK1 added onto a RAF1-immobilized sensor chip surface together with a test compound (ref-4, A-1, P-2 or A-6).

The results of powder X-ray diffraction analysis are shown in FIGS. 1 to 3. FIG. 1 shows a powder X-ray diffraction pattern of sample A-1a (Form I). FIG. 2 shows a powder X-ray diffraction pattern of sample A-1b. FIG. 3 shows a powder X-ray diffraction pattern of sample A-1c. In FIGS. 1 to 3, the horizontal axis (X-axis) represents the diffraction angle 2θ (°) and the vertical axis (Y-axis) represents the diffraction intensity.

(5) Ion Chromatography

When the proportion of sodium ion in the crystals was measured by ion chromatography for sample A-1a (Form I), the molar ratio of sodium ion to compound A-1 was found to be 0.99. This confirmed that sample A-1a is a monosodium salt. The ion chromatography was carried out under the following conditions.

Apparatus: Dionex ICS-1600, AS to AP (Thermo Fisher Scientific)
Column: Dionex IonPac CG16 (5×50 mm)/CS16 (5×250 mm) (Thermo Fisher Scientific)
Eluent: 30 mmol/L methanesulfonic acid solution
Suppressor: Dionex CERS-500 4 mm, 88 mA (Thermo Fisher Scientific)
Column temperature: 40° C.
Eluent flow rate: 1.00 m/min
Sample injection rate: 10 μL
Detector: Electric conductivity detector
Sample treatment: Sample A-1a was suspended in a 20 mmol/L methanesulfonic acid solution to a concentration of 0.5 mg/mL, and the suspension was shaken and stirred for 17 hours, the sodium ion was extracted, and the supernatant was measured.

Compound b1:

Methyl 3,4-difluoro-2-(2-fluoro-4-iodoanilino)-5-[[3-fluoro-2-(methylsulfamoylamino)pyridin-4-yl]methyl]benzoate

[Chemical Formula 119]

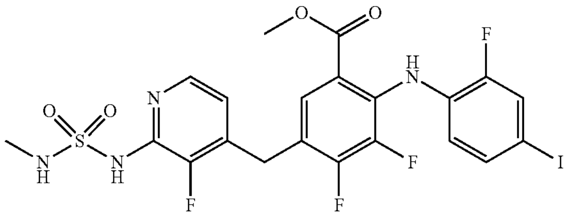

The title compound was synthesized from methyl 5-[(2-amino-3-fluoropyridin-4-yl)methyl]-3,4-difluoro-2-(2-fluoro-4-iodoanilino)benzoate (compound a6) under the same conditions as the production example for compound A-25, except that anhydrous NMP was used instead of anhydrous DMA.

LCMS m/z: 436 $[M+H]^+$

HPLC retention time: 1.00 min (analysis conditions D)

Compound b2:

3,4-Difluoro-2-(2-fluoro-4-iodoanilino)-5-[[3-fluoro-2-(methylsulfamoylamino)pyridin-4-yl]methyl]benzoic Acid

[Chemical Formula 120]

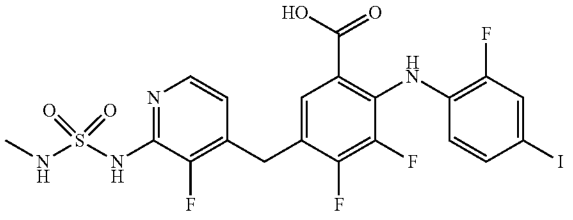

A mixed solution of methyl 3,4-difluoro-2-(2-fluoro-4-iodoanilino)-5-[[3-fluoro-2-(methylsulfamoylamino)pyridin-4-yl]methyl]benzoate (compound b1, 158 mg, 0.253 mmol) in THE (4.8 mL) and water (2.4 mL) was cooled to 0° C., lithium hydroxide monohydrate (60.6 mg, 2.53 mmol) was added, and the mixture was stirred at room temperature for 2 hours. After then adding 2 M hydrochloric acid to the reaction mixture, extraction was performed with ethyl acetate. The organic layer was washed with saturated brine and dried over anhydrous sodium sulfate. After filtering off the drying agent, it was concentrated under reduced pressure to give the title compound (161 mg) as a foam.

LCMS m/z: 611 $[M+H]^+$

HPLC retention time: 0.67 min (analysis conditions D)

Compound B-1:

3,4-Difluoro-2-(2-fluoro-4-iodoanilino)-5-[[3-fluoro-2-(methylsulfamoylamino)pyridin-4-yl]methyl]-N-(2-hydroxyethoxy)benzamide

[Chemical Formula 121]

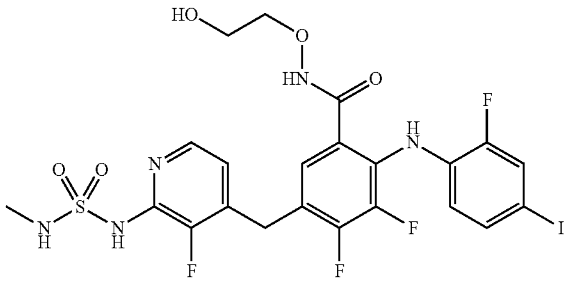

The title compound was synthesized from 3,4-difluoro-2-(2-fluoro-4-iodoanilino)-5-[[3-fluoro-2-(methylsulfamoylamino)pyridin-4-yl]methyl]benzoic acid (compound b2) and the corresponding amine under the same conditions as the production example for compound a8.

LCMS m/z: 670 $[M+H]^+$

HPLC retention time: 1.07 min (analysis conditions A)

Compound B-2:

3,4-Difluoro-2-(2-fluoro-4-iodoanilino)-5-[[3-fluoro-2-(methylsulfamoylamino)pyridin-4-yl]methyl]-N-(2-methoxyethoxy)benzamide

[Chemical Formula 122]

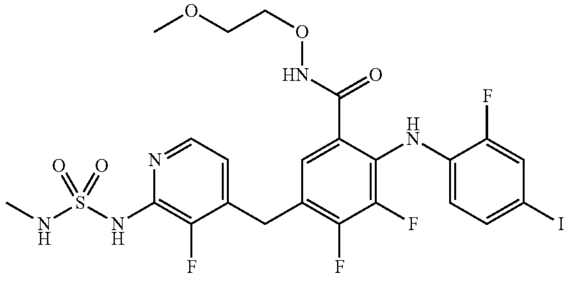

The title compound was synthesized from 3,4-difluoro-2-(2-fluoro-4-iodoanilino)-5-[[3-fluoro-2-(methylsulfamoylamino)pyridin-4-yl]methyl]benzoic acid (compound b2) and the corresponding amine under the same conditions as the production example for compound a8.

LCMS m/z: 684 $[M+H]^+$

HPLC retention time: 1.56 min (analysis conditions B)

Compound B-3:

3,4-Difluoro-2-(2-fluoro-4-iodoanilino)-5-[[3-fluoro-2-(methylsulfamoylamino)pyridin-4-yl]methyl]-N-(2-methylcyclopropyl)benzamide (mixture of 4 isomers)

[Chemical Formula 123]

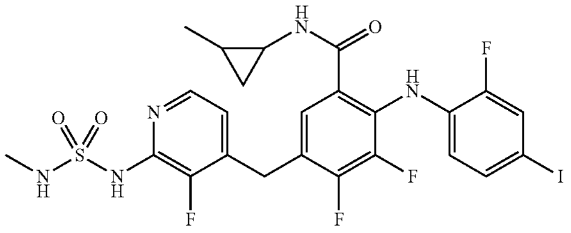

The title compound was synthesized from 3,4-difluoro-2-(2-fluoro-4-iodoanilino)-5-[[3-fluoro-2-(methylsulfamoylamino)pyridin-4-yl]methyl]benzoic acid (compound b2) and the corresponding amine under the same conditions as the production example for compound a8.

LCMS m/z: 664 $[M+H]^+$

HPLC retention time: 1.70 min and 1.72 min (analysis conditions B)

Compound B-6: (+/−)—N-(2,2-Difluorocyclopropyl)-3,4-difluoro-2-(2-fluoro-4-iodoanilino)-5-[[3-fluoro-2-(methylsulfamoylamino)pyridin-4-yl]methyl]benzamide (racemate)

[Chemical Formula 124]

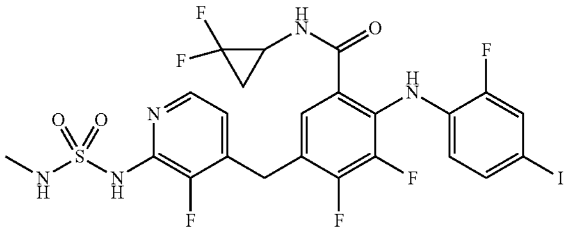

The title compound was synthesized from 3,4-difluoro-2-(2-fluoro-4-iodoanilino)-5-[[3-fluoro-2-(methylsulfamoylamino)pyridin-4-yl]methyl]benzoic acid (compound b2) and the corresponding amine under the same conditions as the production example for compound a12.

LCMS m/z: 686 $[M+H]^+$

HPLC retention time: 1.69 min (analysis conditions B)

Compound B4:

3,4-Difluoro-2-(2-fluoro-4-iodoanilino)-5-[[3-fluoro-2-(methylsulfamoylamino)pyridin-4-yl]methyl]-N-[(1S,2R)-(+/−)-2-methylcyclopropyl]benzamide (racemate)

[Chemical Formula 125]

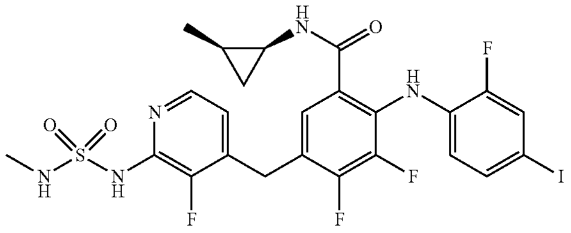

Compound B-5:

3,4-Difluoro-2-(2-fluoro-4-iodoanilino)-5-[[3-fluoro-2-(methylsulfamoylamino)pyridin-4-yl]methyl]-N-[(1R,2R)-(+/−)-2-methylcyclopropyl]benzamide (racemate)

[Chemical Formula 126]

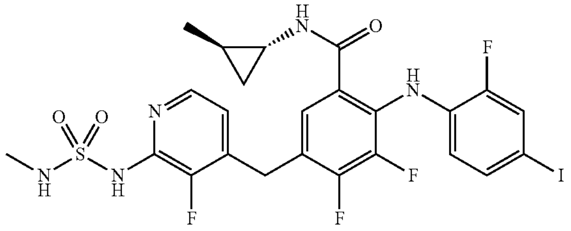

3,4-Difluoro-2-(2-fluoro-4-iodoanilino)-5-[[3-fluoro-2-(methylsulfamoylamino)pyridin-4-yl]methyl]-N-(2-methylcyclopropyl)benzamide (mixture of 4 isomers, compound B-3, 57 mg) was purified by preparative HPLC (5 μm YMC Triart C18 plus, 4.6×150 mm column, 0.1% TFA aqueous solution/0.1% TFA acetonitrile solution) to give compound B4 (14.7 mg) and compound B-5 (41 mg) as separate solids.

Compound B-4

LCMS m/z: 664 $[M+H]^+$

HPLC retention time: 1.70 min (analysis conditions B)

Compound B-5

LCMS m/z: 664 $[M+H]^+$

HPLC retention time: 1.72 min (analysis conditions B)

Compound B-8:

3,4-Difluoro-2-(2-fluoro-4-iodoanilino)-5-[[3-fluoro-2-(propylsulfonylamino)pyridin-4-yl]methyl]benzamide

[Chemical Formula 127]

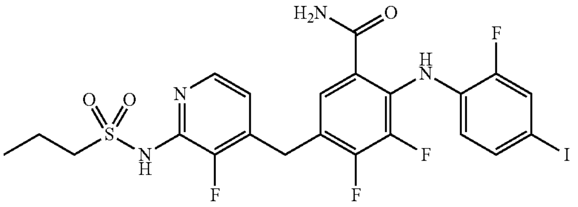

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfonyl chloride under the same conditions as the production examples for compound A-25, compound b2 and compound a8. However, triethylamine and anhydrous DCM were used instead of pyridine and anhydrous DMA respectively, which were used in the production example for compound A-25.

LCMS m/z: 623 $[M+H]^+$

HPLC retention time: 1.63 min (analysis conditions B)

Compound B-9:

3,4-Difluoro-5-[[3-fluoro-2-(2-hydroxyethylsulfamoylamino)pyridin-4-yl]methyl]-2-(2-fluoro-4-iodoanilino)benzamide

[Chemical Formula 128]

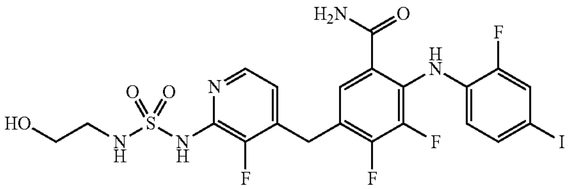

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfamoyl chloride under the same conditions as the production examples for compound A-25, compound b2 and compound a8. However, triethylamine and anhydrous DCM were used instead of pyridine and anhydrous DMA respectively, which were used in the production example for compound A-25.

LCMS m/z: 640 $[M+H]^+$

HPLC retention time: 1.06 min (analysis conditions A)

Compound b8:

3,4-Difluoro-2-(2-fluoro-4-iodoanilino)-5-[[3-fluoro-2-[(2-methylpropan-2-yl)oxycarbonylsulfamoylamino]pyridin-4-yl]methyl]benzoic acid

[Chemical Formula 129]

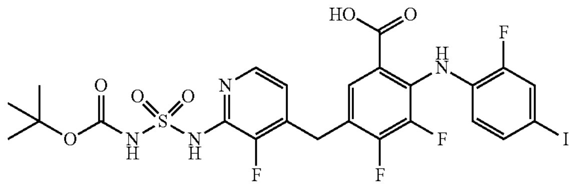

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfamoyl chloride under the same conditions as the production examples for compound A-25 and compound b2. However, anhydrous NMP was used instead of anhydrous DMA, which was used in the production example for compound A-25.

LCMS m/z: 697 $[M+H]^+$

HPLC retention time: 0.71 min (analysis conditions D)

Compound b9:

3,4-Difluoro-2-(2-fluoro-4-iodoanilino)-5-[[3-fluoro-2-(sulfamoylamino)pyridin-4-yl]methyl]benzoic Acid

[Chemical Formula 130]

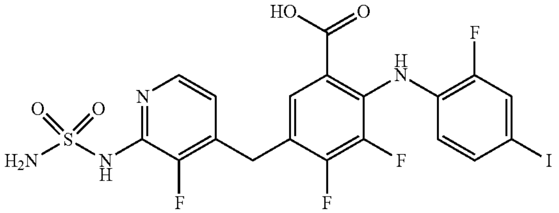

Chlorotrimethylsilane (71.5 μL, 0.564 mmol) was added to a 2,2,2-trifluoroethanol solution (2.6 mL) of 3,4-difluoro-2-(2-fluoro-4-iodoanilino)-5-[[3-fluoro-2-[(2-methylpropan-2-yl)oxycarbonylsulfamoylamino]pyridin-4-yl]methyl]benzoic acid (compound b8, 131 mg, 0.188 mmol), and the mixture was stirred for 1.5 hours at room temperature. The reaction mixture was purified by reversed-phase column chromatography (0.1% formic acid aqueous solution/0.1% formic acid acetonitrile solution) to give the title compound (75.0 mg, 67%) as a foam.

LCMS m/z: 597 $[M+H]^+$

HPLC retention time: 0.60 min (analysis conditions D)

Compound B-10:

3,4-Difluoro-2-(2-fluoro-4-iodoanilino)-5-[[3-fluoro-2-(sulfamoylamino)pyridin-4-yl]methyl]benzamide

[Chemical Formula 131]

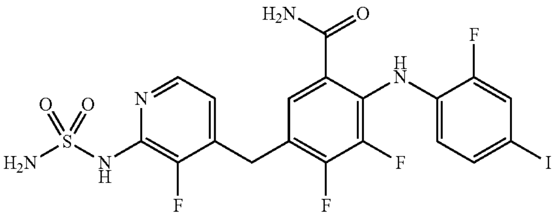

The title compound was synthesized from 3,4-difluoro-2-(2-fluoro-4-iodoanilino)-5-[[3-fluoro-2-(sulfamoylamino)pyridin-4-yl]methyl]benzoic acid (compound b9) and the corresponding amine under the same conditions as the production example for compound a12.

LCMS m/z: 596 $[M+H]^+$

HPLC retention time: 1.11 min (analysis conditions A)

Compound b10:

2-(2-Chloro-4-iodoanilino)-3,4-difluoro-5-formylbenzoic Acid

[Chemical Formula 132]

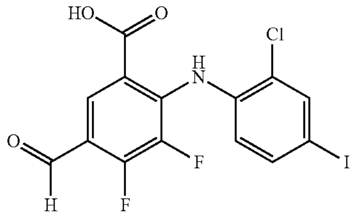

A 2 M LDA THF solution (6.53 mL, 13.1 mmol) was cooled to −78° C. and slowly added to a THF solution (6 mL) of 2,3,4-trifluorobenzoic acid (1.00 g, 5.68 mmol) under a nitrogen atmosphere. After stirring at −78° C. for 50 minutes, DMF (0.484 mL, 6.25 mmol) was slowly added and stirring was continued for 2 hours at −10° C. In a separate flask, a THF solution (15 mL) of 2-chloro-4-iodoaniline (1.44 g, 5.68 mmol) was cooled to −78° C., a 1 M lithium bis(trimethylsilyl)amide THF solution (13.6 mL, 13.6 mmol) was added dropwise, and the mixture was stirred for 30 minutes. After stirring, the previous reaction mixture was added and the resulting mixture was stirred at room temperature for 20 hours. After then adding water and 2 M hydrochloric acid to the reaction mixture, extraction was performed with ethyl acetate. The organic layer was dried over anhydrous magnesium sulfate and, after filtering off the drying agent, concentrated under reduced pressure to give a crude product of the title compound (1.2 g).

LCMS m/z: 438 $[M+H]^+$

HPLC retention time: 0.91 min (analysis conditions G)

Compound b12:

Methyl 2-(2-chloro-4-iodoanilino)-3,4-difluoro-5-[(E)-[(4-methylphenyl)sulfonylhydrazinylidene]methyl]benzoate

[Chemical Formula 133]

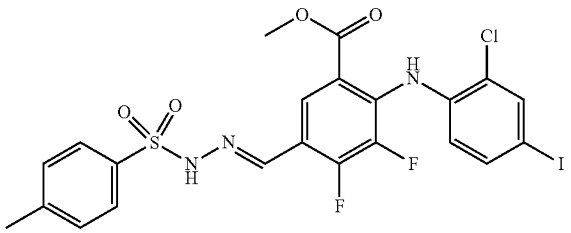

The title compound was synthesized from 2-(2-chloro-4-iodoanilino)-3,4-difluoro-5-formylbenzoic acid (compound b10) under the same conditions as the production examples for compound a1 and compound a2.

LCMS m/z: 620 $[M+H]^+$

HPLC retention time: 1.09 min (analysis conditions G)

Compound b114:

Methyl 5-[(2-amino-3-fluoropyridin-4-yl)methyl]-2-(2-chloro-4-iodoanilino)-3,4-difluorobenzoate

[Chemical Formula 134]

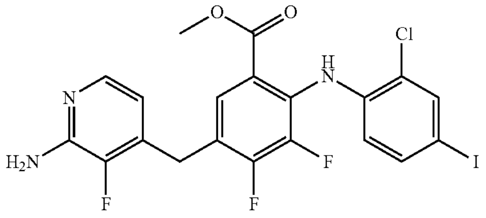

The title compound was synthesized from methyl 2-(2-chloro-4-iodoanilino)-3,4-difluoro-5-[(E)-[(4-methylphenyl)sulfonylhydrazinylidene]methyl]benzoate (compound b12) under the same conditions as the production examples for compound a5 and compound a6. However, DIPEA was used instead of potassium carbonate, which was used in the production example for compound a5.

LCMS m/z: 548 $[M+H]^+$

HPLC retention time: 0.89 min (analysis conditions C)

Compound B-11:

2-(2-Chloro-4-iodoanilino)-5-[[2-(cyclopropylsulfamoylamino)-3-fluoropyridin-4-yl]methyl]-3,4-difluorobenzamide

[Chemical Formula 135]

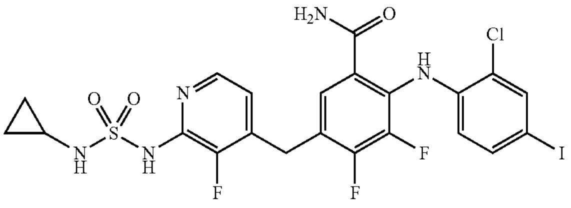

The title compound was synthesized from methyl 5-[(2-amino-3-fluoropyridin-4-yl)methyl]-2-(2-chloro-4-iodoanilino)-3,4-difluorobenzoate (compound b14) and the corresponding 4-nitrophenyl sulfamate under the same conditions as the production examples for compound A-1, compound b2 and compound a8.

LCMS m/z: 652 $[M+H]^+$

HPLC retention time: 1.67 min (analysis conditions B)

Compound B-12:

2-(2-Chloro-4-iodoanilino)-N-cyclopropyl-5-[[2-(cyclopropylsulfamoylamino)-3-fluoropyridin-4-yl]methyl]-3,4-difluorobenzamide

[Chemical Formula 136]

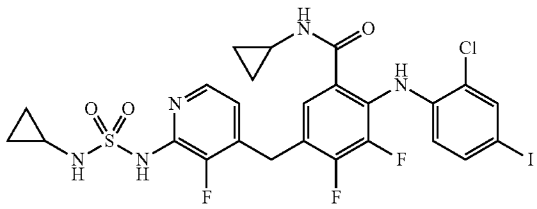

The title compound was synthesized from methyl 5-[(2-amino-3-fluoropyridin-4-yl)methyl]-2-(2-chloro-4-iodoanilino)-3,4-difluorobenzoate (compound b14) and the corresponding 4-nitrophenyl sulfamate under the same conditions as the production examples for compound A-1, compound b2 and compound a8. However, the corresponding amine was used instead of a 7 M ammonia MeOH solution, which was used in the production example for compound a8.

LCMS m/z: 692 $[M+H]^+$

HPLC retention time: 1.78 min (analysis conditions B)

Compound B-13:

2-(2-Chloro-4-iodoanilino)-5-[[2-(cyclopropylsulfamoylamino)-3-fluoropyridin-4-yl]methyl]-3,4-difluoro-N-[(2-methylpropan-2-yl)oxy]benzamide

[Chemical Formula 137]

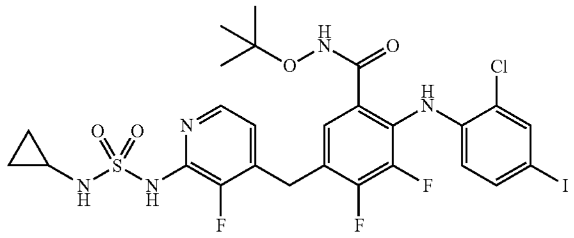

The title compound was synthesized from methyl 5-[(2-amino-3-fluoropyridin-4-yl)methyl]-2-(2-chloro-4-iodoanilino)-3,4-difluorobenzoate (compound b14) and the corresponding 4-nitrophenyl sulfamate under the same conditions as the production examples for compound A-1, compound b2 and compound a8. However, the corresponding amine was used instead of a 7 M ammonia MeOH solution, which was used in the production example for compound a8.

LCMS m/z: 724 $[M+H]^+$

HPLC retention time: 1.81 min (analysis conditions B)

Compound B-14:

N-Cyclopropyl-3,4-difluoro-2-(2-fluoro-4-iodoanilino)-5-[[3-fluoro-2-(methanesulfonamide)pyridin-4-yl]methyl]benzamide

[Chemical Formula 138]

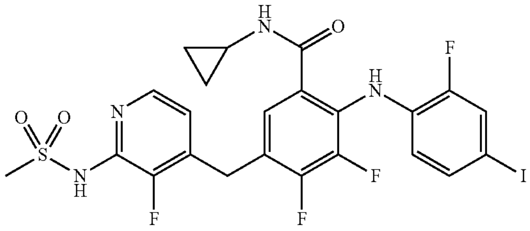

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfonyl chloride under the same conditions as the production examples for compound A-25, compound b2 and compound a12. However, triethylamine and anhydrous DCM were used instead of pyridine and anhydrous DMA respectively, which were used in the production example for compound A-25, a 1 M sodium hydroxide aqueous solution was used instead of lithium hydroxide monohydrate, which was used in the production example for compound b2, and the corresponding amine was used instead of tert-butoxyamine hydrochloride, which was used in the production example for compound a12.

LCMS m/z: 635 $[M+H]^+$

HPLC retention time: 0.87 min (analysis conditions C)

Compound B-15:

3,4-Difluoro-2-(2-fluoro-4-iodoanilino)-5-[[3-fluoro-2-(methanesulfonamide)pyridin-4-yl]methyl]-N-methoxybenzamide

[Chemical Formula 139]

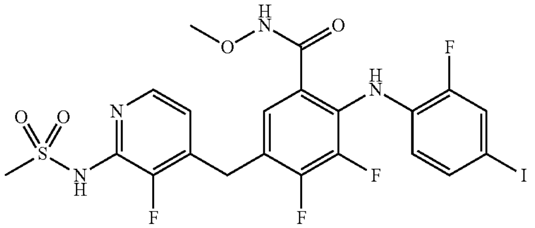

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfonyl chloride under the same conditions as the production examples for compound A-25, compound b2 and compound a12. However, triethylamine and anhydrous DCM were used instead of pyridine and anhydrous DMA respectively, which were used in the production example for compound A-25, a 1 M sodium hydroxide aqueous solution was used instead of lithium hydroxide monohydrate, which was used in the production example for compound b2, and the corresponding amine was used instead of tert-butoxyamine hydrochloride, which was used in the production example for compound a12.

LCMS m/z: 625 $[M+H]^+$

HPLC retention time: 0.80 min (analysis conditions C)

Compound B-16:

5-[[2-(Ethylsulfonylamino)-3-fluoropyridin-4-yl]methyl]-3,4-difluoro-2-(2-fluoro-4-iodoanilino)-N-methoxybenzamide

[Chemical Formula 140]

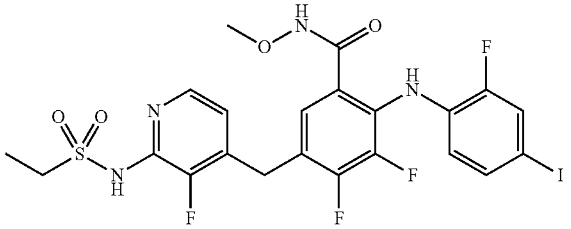

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfonyl chloride under the same conditions as the production examples for compound A-25, compound b2 and compound a12. However, triethylamine and anhydrous DCM were used instead of pyridine and anhydrous DMA respectively, which were used in the production example for compound A-25, a 1 M sodium hydroxide aqueous solution was used instead of lithium hydroxide monohydrate, which was used in the production example for compound b2, and the corresponding amine was used instead of tert-butoxyamine hydrochloride, which was used in the production example for compound a12.

LCMS m/z: 639 $[M+H]^+$

HPLC retention time: 0.83 min (analysis conditions C)

Compound c1:

3,4-Difluoro-2-(2-fluoro-4-iodoanilino)-5-[(E)-[(4-methylphenyl)sulfonylhydrazinylidene]methyl]benzamide

[Chemical Formula 141]

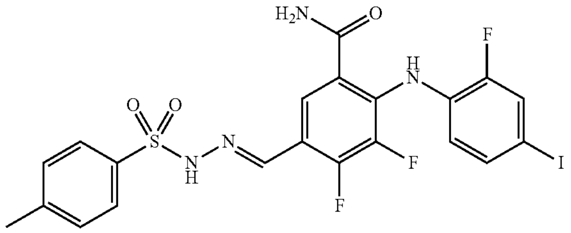

After adding 4-methylbenzenesulfonyl hydrazide (2.21 g, 11.9 mmol) to an anhydrous DMF solution (59 mL) of 3,4-difluoro-2-((2-fluoro-4-iodophenyl)amino)-5-formylbenzoic acid (5.00 g, 11.9 mmol), the mixture was stirred for 30 minutes at room temperature. Next, HOOBt (1.94 g, 11.9 mmol) and EDC·HCl (2.28 g, 11.9 mmol) were added and the mixture was stirred for 1.5 hours at room temperature. A 7 M ammonia MeOH solution (3.39 mL, 23.8 mmol) was added to the reaction mixture and stirring was continued for 30 minutes at room temperature, after which the solid was filtered out and washed with DMF (30 mL). Acetonitrile (90 mL) and 0.1 M hydrochloric acid (90 mL) were added to the filtrate, and the obtained solid was washed with a liquid mixture of acetonitrile/water to give the title compound (6.27 g, 90%) as a colorless solid.

LCMS m/z: 589 $[M+H]^+$

HPLC retention time: 0.90 min (analysis conditions C)

Compound c2:

[2-[(2,4-Dimethoxyphenyl)methylamino]pyridin-4-yl]boronic acid

[Chemical Formula 142]

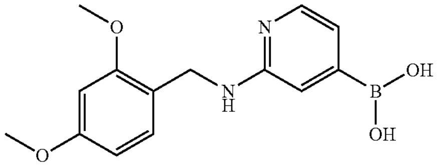

The title compound was synthesized from 4-bromo-2-fluoropyridine under the same conditions as the production examples for compound a3 and compound a4.

LCMS m/z: 289 $[M+H]^+$

HPLC retention time: 0.38 min (analysis conditions C)

Compound c4:

5-[(2-Aminopyridin-4-yl)methyl]-3,4-difluoro-2-(2-fluoro-4-iodoanilino)benzamide

[Chemical Formula 143]

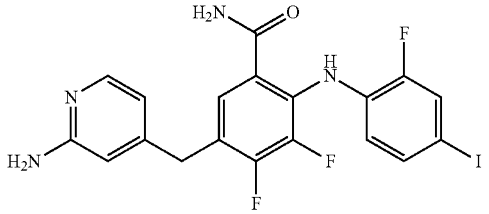

The title compound was synthesized from 3,4-difluoro-2-(2-fluoro-4-iodoanilino)-5-[(E)-[(4-methylphenyl)sulfonylhydrazinylidene]methyl]benzamide (compound c1) under the same conditions as the production examples for compound a5 and compound a6. However, [2-[(2,4-dimethoxyphenyl)methylamino]pyridin-4-yl]boronic acid (compound c2) was used instead of [2-[(2,4-dimethoxyphenyl)methylamino]-3-fluoropyridin-4-yl]boronic acid (compound a4), which was used in the production example for compound a5.

LCMS m/z: 649 $[M+H]^+$

HPLC retention time: 0.71 min (analysis conditions C)

Compound C-1:

3,4-Difluoro-2-(2-fluoro-4-iodoanilino)-5-[[2-(sulfamoylamino)pyridin-4-yl]methyl]benzamide

[Chemical Formula 144]

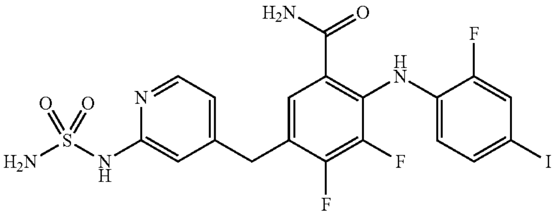

The title compound was synthesized from 5-[(2-aminopyridin-4-yl)methyl]-3,4-difluoro-2-(2-fluoro-4-iodoanilino)benzamide (compound c4) and the corresponding sulfamoyl chloride under the same conditions as the production example for compound A-1.

LCMS m/z: 578 $[M+H]^+$

HPLC retention time: 1.42 min (analysis conditions B)

Compound C-2:

3,4-Difluoro-2-(2-fluoro-4-iodoanilino)-5-[[2-(2-methoxyethylsulfamoylamino)pyridin-4-yl]methyl]benzamide

[Chemical Formula 145]

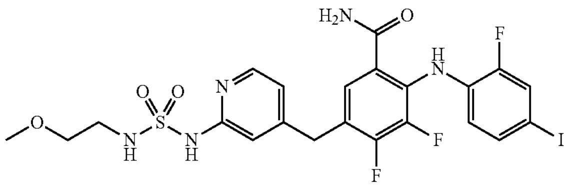

The title compound was synthesized from 5-[(2-amino-pyridin-4-yl)methyl]-3,4-difluoro-2-(2-fluoro-4-iodoanilino)benzamide (compound c4) and the corresponding sulfamoyl chloride under the same conditions as the production example for compound A-1, except that imidazole was used instead of pyridine.

LCMS m/z: 636 $[M+H]^+$

HPLC retention time: 1.10 min (analysis conditions A)

Compound C-3:

3,4-Difluoro-2-(2-fluoro-4-iodoanilino)-5-[[2-(methylsulfamoylamino)pyridin-4-yl]methyl]benzamide

[Chemical Formula 146]

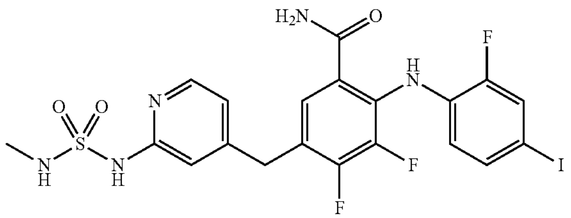

The title compound was synthesized from 5-[(2-amino-pyridin-4-yl)methyl]-3,4-difluoro-2-(2-fluoro-4-iodoanilino)benzamide (compound c4) and the corresponding sulfamoyl chloride under the same conditions as the production example for compound A-25.

LCMS m/z: 592 $[M+H]^+$

HPLC retention time: 1.08 min (analysis conditions A)

Compound C-4:

3,4-Difluoro-2-(2-fluoro-4-iodoanilino)-5-[[2-[[methyl-(methylamino)-oxo-λ6-sulfanylidene]amino]pyridin-4-yl]methyl]benzamide

[Chemical Formula 147]

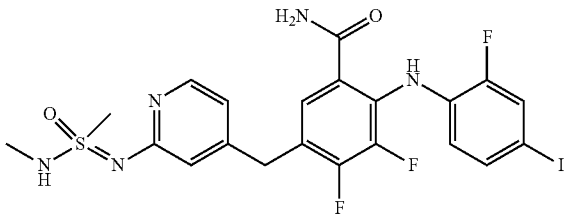

The title compound was synthesized from 5-[(2-amino-pyridin-4-yl)methyl]-3,4-difluoro-2-(2-fluoro-4-iodoanilino)benzamide (compound c4) and the corresponding sulfamoyl chloride under the same conditions as the production example for compound A-43.

LCMS m/z: 590 $[M+H]^+$

HPLC retention time: 0.92 min (analysis conditions A)

Compound c5:

5-Ethenyl-3,4-difluoro-2-(4-iodo-2-methylanilino)benzoic acid

[Chemical Formula 148]

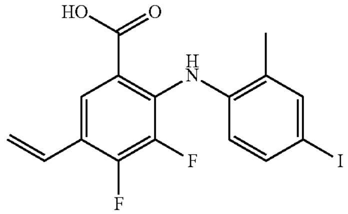

An anhydrous THF solution (1.8 ml) of 4-iodo-2-methylaniline 636 mg, 2.73 mmol was cooled to −78° C., and then a 1.3 M lithium bis(trimethylsilyl)amide THF solution (5.08 mL, 6.60 mmol) was added over a period of 1 hour and the mixture was stirred for 1 hour. An anhydrous THF solution (3.9 mL) of 2,3,4-trifluoro-5-vinylbenzoic acid (460 mg, 2.28 mmol) was then added, and the mixture was stirred for 2 hours at 0° C. Water and 2 M hydrochloric acid were added to the reaction mixture and extraction was performed twice with ethyl acetate. The organic layer was washed with saturated brine, dried over anhydrous sodium sulfate and, after filtering off the drying agent, concentrated under reduced pressure. The resulting residue was suspended and washed in DCM to give the title compound (631 mg, 67%) as a brown solid.

LCMS m/z: 416 $[M+H]^+$

HPLC retention time: 0.99 min (analysis conditions E)

Compound c6:

3,4-Difluoro-5-formyl-2-(4-iodo-2-methylanilino)benzoic acid

[Chemical Formula 149]

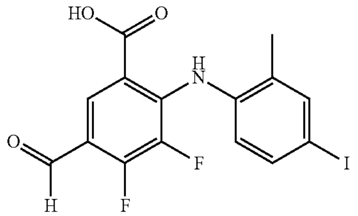

After adding a 1 M sodium hydrogen carbonate aqueous solution (3.02 mL, 3.02 mmol), sodium periodate (1.29 g, 6.03 mmol) and microcapsulated osmium(VIII) oxide (38.3 mg, 0.015 mmol) to an anhydrous THF solution (6.3 mL) of 5-ethenyl-3,4-difluoro-2-(4-iodo-2-methylanilino)benzoic acid (compound c5, 626 mg, 1.51 mmol), the mixture was stirred at room temperature for 6 hours. After then adding ethyl acetate to the reaction mixture, it was washed with 1 M hydrochloric acid and 0.2 M aqueous sodium thiosulfate solution. The organic layer was dried over anhydrous sodium sulfate and, after filtering off the drying agent, concentrated under reduced pressure. The resulting residue was suspended and washed in ethyl acetate/hexane (1/25, 42 mL), and the solid was filtered off. The obtained solid was washed with hexane to give the title compound (558 mg, 89%) as a colorless solid.

LCMS m/z: 418 $[M+H]^+$

HPLC retention time: 0.86 min (analysis conditions C)

Compound C-5:

3,4-Difluoro-5-[[3-fluoro-2-(methylsulfamoylamino) pyridin-4-yl]methyl]-2-(4-iodo-2-methylanilino) benzamide

[Chemical Formula 150]

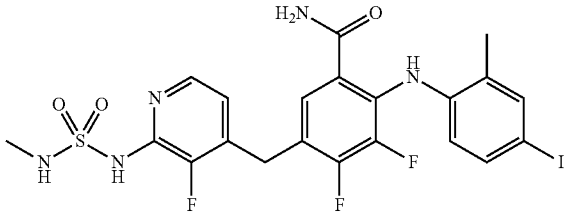

The title compound was synthesized from 3,4-difluoro-5-formyl-2-(4-iodo-2-methylanilino)benzoic acid (compound c6) under the same conditions as the production examples for compound c1, compound a5, compound a6 and compound A-1.

LCMS m/z: 606 $[M+H]^+$

HPLC retention time: 1.20 min (analysis conditions A)

Compound C-6:

N-Cyclopropyl-3,4-difluoro-2-(2-fluoro-4-iodoanilino)-5-[[3-(methylsulfamoylamino)phenyl] methyl]benzamide

[Chemical Formula 151]

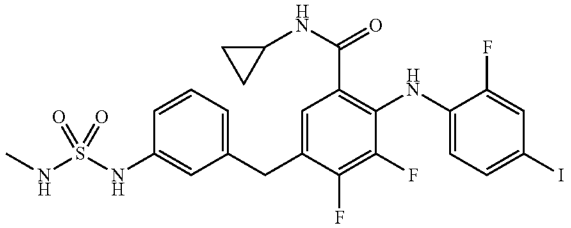

The title compound was synthesized from 3,4-difluoro-2-((2-fluoro-4-iodophenyl)amino)-5-formylbenzoic acid under the same conditions as the production examples for compound a2, compound a10, compound a5 and compound A-1.

LCMS m/z: 631 $[M+H]^+$

HPLC retention time: 1.70 min (analysis conditions B)

Compound d1:

Methyl 5-[(3-amino-2-fluorophenyl)methyl]-3,4-difluoro-2-(2-fluoro-4-iodoanilino)benzoate

[Chemical Formula 152]

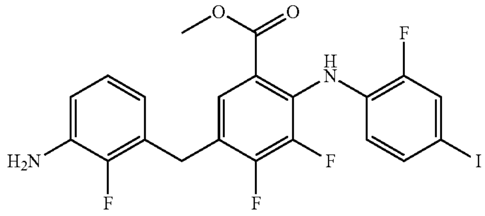

The title compound was synthesized from methyl 3,4-difluoro-2-(2-fluoro-4-iodoanilino)-5-[(E)-[(4-methylphenyl)sulfonylhydrazinylidene]methyl]benzoate (compound a2) under the same conditions as the production example for compound a5, except that (3-amino-2-fluorophenyl)boronic acid hydrochloride was used instead of [2-[(2,4-dimethoxyphenyl)methylamino]-3-fluoropyridin-4-yl]boronic acid (compound a4).

LCMS m/z: 531 $[M+H]^+$

HPLC retention time: 0.96 min (analysis conditions D)

Compound d2:

5-[(3-Amino-2-fluorophenyl)methyl]-3,4-difluoro-2-(2-fluoro-4-iodoanilino)benzoic acid

[Chemical Formula 153]

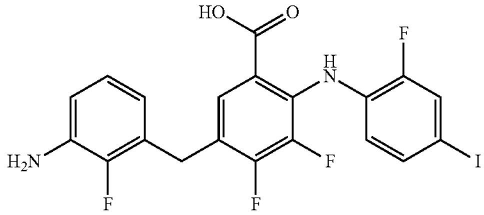

The title compound was synthesized from methyl 5-[(3-amino-2-fluorophenyl)methyl]-3,4-difluoro-2-(2-fluoro-4-iodoanilino)benzoate (compound d1) under the same conditions as the production example for compound a7.

LCMS m/z: 517 $[M+H]^+$

HPLC retention time: 0.95 min (analysis conditions C)

Compound D-1:

3,4-Difluoro-2-(2-fluoro-4-iodoanilino)-5-[[2-fluoro-3-(2-methoxyethylsulfamoylamino)phenyl]methyl]benzamide

[Chemical Formula 154]

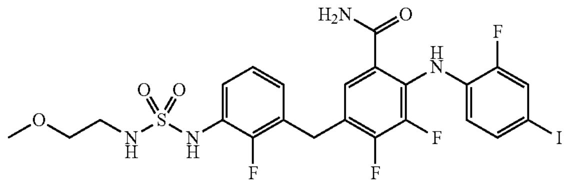

The title compound was synthesized from 5-[(3-amino-2-fluorophenyl)methyl]-3,4-difluoro-2-(2-fluoro-4-iodoanilino)benzoic acid (compound d2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 653 $[M+H]^+$

HPLC retention time: 1.24 min (analysis conditions A)

Compound D-2:

3,4-Difluoro-2-(2-fluoro-4-iodoanilino)-5-[[2-fluoro-3-[(1-methoxy-2-methylpropan-2-yl)sulfamoylamino]phenyl]methyl]benzamide

[Chemical Formula 155]

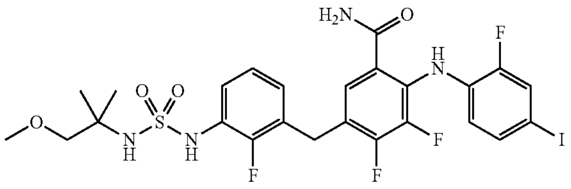

The title compound was synthesized from 5-[(3-amino-2-fluorophenyl)methyl]-3,4-difluoro-2-(2-fluoro-4-iodoanilino)benzoic acid (compound d2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 681 $[M+H]^+$

HPLC retention time: 1.35 min (analysis conditions A)

Compound D-3:

3,4-Difluoro-2-(2-fluoro-4-iodoanilino)-5-[[2-fluoro-3-[[(2R)-oxolan-2-yl]methylsulfamoylamino]phenyl]methyl]benzamide

[Chemical Formula 156]

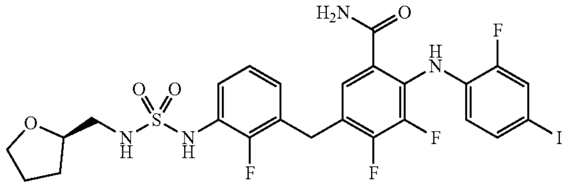

The title compound was synthesized from 5-[(3-amino-2-fluorophenyl)methyl]-3,4-difluoro-2-(2-fluoro-4-iodoanilino)benzoic acid (compound d2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 679 $[M+H]^+$

HPLC retention time: 1.27 min (analysis conditions A)

Compound D-4:

5-[[3-(Ethylsulfonylamino)-2-fluorophenyl]methyl]-3,4-difluoro-2-(2-fluoro-4-iodoanilino)benzamide

[Chemical Formula 157]

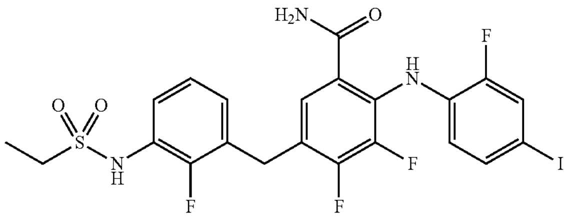

The title compound was synthesized from 5-[(3-amino-2-fluorophenyl)methyl]-3,4-difluoro-2-(2-fluoro-4-iodoanilino)benzoic acid (compound d2) under the same conditions as the production examples for compound a8 and compound A-25. However, the corresponding sulfonyl chloride was used instead of methylsulfamoyl chloride, which was used in the production example for compound A-25. Pyridine was used as the solvent in the sulfonamidation step.

LCMS m/z: 608 $[M+H]^+$

HPLC retention time: 1.26 min (analysis conditions A)

Compound D-5:

3,4-Difluoro-2-(2-fluoro-4-iodoanilino)-5-[[2-fluoro-3-(2-methoxyethyl sulfonylamino)phenyl]methyl]benzamide

[Chemical Formula 158]

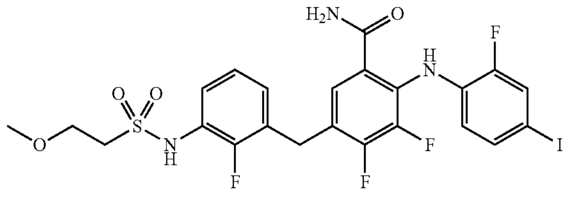

The title compound was synthesized from 5-[(3-amino-2-fluorophenyl)methyl]-3,4-difluoro-2-(2-fluoro-4-iodoanilino)benzoic acid (compound d2) under the same conditions as the production examples for compound a8 and compound A-25. However, the corresponding sulfonyl chloride was used instead of methylsulfamoyl chloride, which was used in the production example for compound A-25. Pyridine was used as the solvent in the sulfonamidation step.

LCMS m/z: 638 $[M+H]^+$

HPLC retention time: 1.67 min (analysis conditions B)

Compound D-6:

N-Cyclopropyl-3,4-difluoro-2-(2-fluoro-4-iodoanilino)-5-[[2-fluoro-3-(methylsulfamoylamino)phenyl]methyl]benzamide

[Chemical Formula 159]

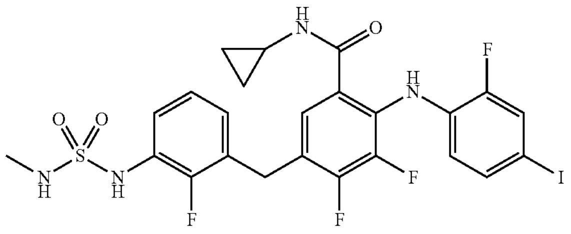

The title compound was synthesized from 5-[(3-amino-2-fluorophenyl)methyl]-3,4-difluoro-2-(2-fluoro-4-iodoanilino)benzoic acid (compound d2) and the corresponding amine under the same conditions as the production examples for compound a8 and compound A-1.

LCMS m/z: 649 $[M+H]^+$

HPLC retention time: 1.71 min (analysis conditions B)

Compound D-7:

N-Cyclopropyl-3,4-difluoro-2-(2-fluoro-4-iodoanilino)-5-[[2-fluoro-3-(sulfamoylamino)phenyl]methyl]benzamide

[Chemical Formula 160]

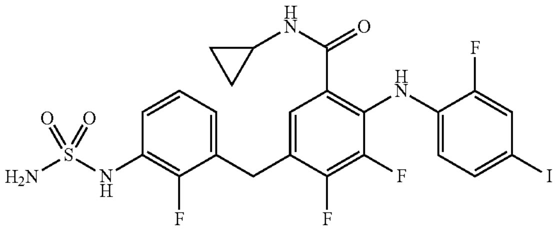

The title compound was synthesized from 5-[(3-amino-2-fluorophenyl)methyl]-3,4-difluoro-2-(2-fluoro-4-iodoanilino)benzoic acid (compound d2) and the corresponding amine under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 635 $[M+H]^+$

HPLC retention time: 1.65 min (analysis conditions B)

Compound D-8:

N-Cyclopropyl-5-[[3-(ethylsulfonylamino)-2-fluorophenyl]methyl]-3,4-difluoro-2-(2-fluoro-4-iodoanilino)benzamide

[Chemical Formula 161]

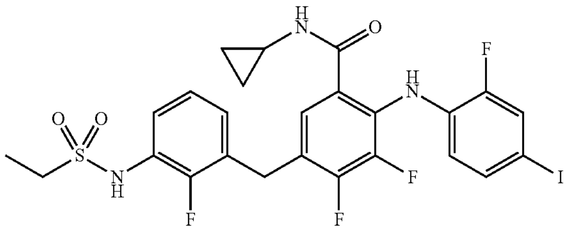

The title compound was synthesized from 5-[(3-amino-2-fluorophenyl)methyl]-3,4-difluoro-2-(2-fluoro-4-iodoanilino)benzoic acid (compound d2) and the corresponding amine under the same conditions as the production examples for compound a8 and compound A-25. However, the corresponding sulfonyl chloride was used instead of methylsulfamoyl chloride, which was used in the production example for compound A-25. Pyridine was used as the solvent in the sulfonamidation step.

LCMS m/z: 648 $[M+H]^+$

HPLC retention time: 1.77 min (analysis conditions B)

Compound D-9:

3,4-Difluoro-2-(2-fluoro-4-iodoanilino)-5-[[2-fluoro-3-[(1-methylcyclobutyl)sulfamoylamino]phenyl]methyl]benzamide

[Chemical Formula 162]

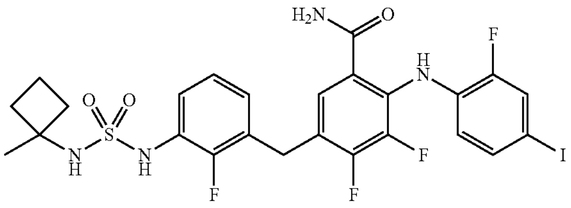

The title compound was synthesized from 5-[(3-amino-2-fluorophenyl)methyl]-3,4-difluoro-2-(2-fluoro-4-iodoanilino)benzoic acid (compound d2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 663 $[M+H]^+$

HPLC retention time: 0.95 min (analysis conditions C)

Compound D-10:

N-Cyclopropyl-3,4-difluoro-2-(2-fluoro-4-iodoanilino)-5-[[2-fluoro-3-[(1-methylcyclobutyl)sulfamoylamino]phenyl]methyl]benzamide

[Chemical Formula 163]

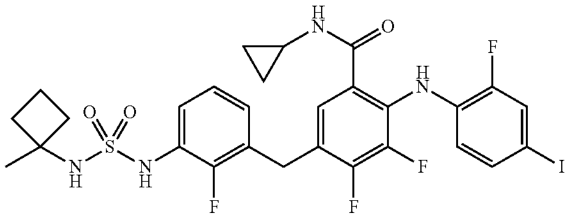

The title compound was synthesized from 5-[(3-amino-2-fluorophenyl)methyl]-3,4-difluoro-2-(2-fluoro-4-iodoanilino)benzoic acid (compound d2) and the corresponding amine under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 703 $[M+H]^+$

HPLC retention time: 1.01 min (analysis conditions C)

Compound D-11:

3,4-Difluoro-2-(2-fluoro-4-iodoanilino)-5-[[2-fluoro-3-(methylsulfamoylamino)phenyl]methyl]-N-methoxybenzamide

[Chemical Formula 164]

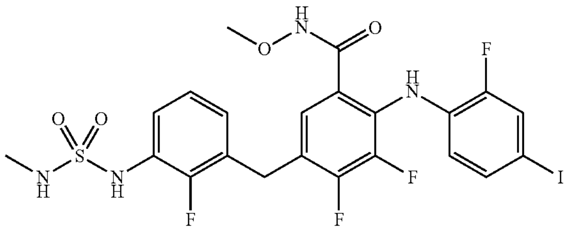

The title compound was synthesized from 5-[(3-amino-2-fluorophenyl)methyl]-3,4-difluoro-2-(2-fluoro-4-iodoanilino)benzoic acid (compound d2) and the corresponding amine under the same conditions as the production examples for compound a8 and compound A-1. However, triethylamine was used instead of DIPEA, which was used in the production example for compound a8.

LCMS m/z: 639 $[M+H]^+$

HPLC retention time: 1.62 min (analysis conditions B)

Compound D-12:

3,4-Difluoro-2-(2-fluoro-4-iodoanilino)-5-[[2-fluoro-3-(sulfamoylamino)phenyl]methyl]-N-methoxybenzamide

[Chemical Formula 165]

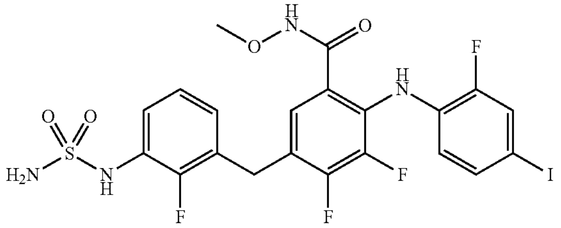

The title compound was synthesized from 5-[(3-amino-2-fluorophenyl)methyl]-3,4-difluoro-2-(2-fluoro-4-iodoanilino)benzoic acid (compound d2) and the corresponding amine under the same conditions as the production examples for compound a8 and compound A-1. However, triethylamine was used instead of DIPEA, which was used in the production example for compound a8, and the corresponding 4-nitrophenyl sulfamate was used instead of 4-nitrophenyl methylsulfamate, which was used in the production example for compound A-1.

LCMS m/z: 625 $[M+H]^+$

HPLC retention time: 0.81 min (analysis conditions C)

Compound D-13:

3,4-Difluoro-2-(2-fluoro-4-iodoanilino)-5-[[2-fluoro-3-[(1-methylcyclobutyl)sulfamoylamino]phenyl]methyl]-N-methoxybenzamide

[Chemical Formula 166]

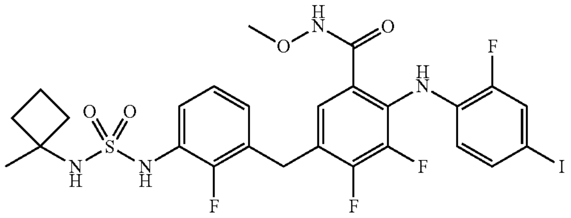

The title compound was synthesized from 5-[(3-amino-2-fluorophenyl)methyl]-3,4-difluoro-2-(2-fluoro-4-iodoanilino)benzoic acid (compound d2) and the corresponding amine under the same conditions as the production examples for compound a8 and compound A-1. However, triethylamine was used instead of DIPEA, which was used in the production example for compound a8, and the corresponding 4-nitrophenyl sulfamate was used instead of 4-nitrophenyl methylsulfamate, which was used in the production example for compound A-1.

LCMS m/z: 693 $[M+H]^+$

HPLC retention time: 0.95 min (analysis conditions C)

Compound D-14:

2-(4-Cyclopropyl-2-fluoroanilino)-3,4-difluoro-5-[[2-fluoro-3-(methylsulfamoylamino)phenyl]methyl]benzamide

[Chemical Formula 167]

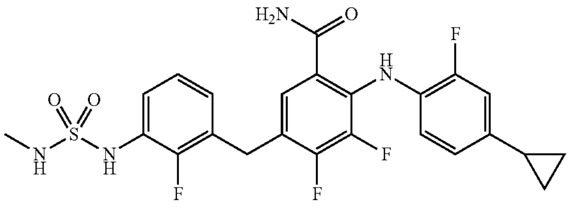

The title compound was synthesized from methyl 5-[(3-amino-2-fluorophenyl)methyl]-3,4-difluoro-2-(2-fluoro-4-iodoanilino)benzoate (compound d1) under the same conditions as the production examples for compound a9, compound a7, compound a8 and compound A-25. However, a 1 M sodium hydroxide aqueous solution was used instead of lithium hydroxide monohydrate, which was used in the production example for compound a7.

LCMS m/z: 523 $[M+H]^+$

HPLC retention time: 1.58 min (analysis conditions B)

Compound D-15:

N-Cyclopropyl-2-(4-cyclopropyl-2-fluoroanilino)-3,4-difluoro-5-[[2-fluoro-3-(methylsulfamoylamino)phenyl]methyl]benzamide

[Chemical Formula 168]

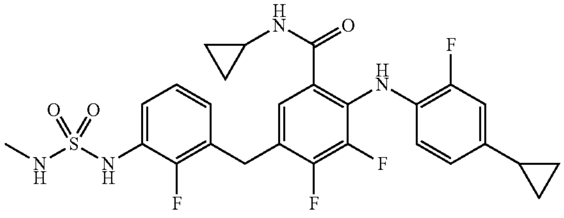

The title compound was synthesized from methyl 5-[(3-amino-2-fluorophenyl)methyl]-3,4-difluoro-2-(2-fluoro-4-iodoanilino)benzoate (compound d1) under the same conditions as the production examples for compound a9, compound a7, compound a8 and compound A-25. However, a 1 M sodium hydroxide aqueous solution was used instead of lithium hydroxide monohydrate, which was used in the production example for compound a7, and the corresponding amine was used instead of a 7 M ammonia MeOH solution, which was used in the production example for compound a8.

LCMS m/z: 563 $[M+H]^+$

HPLC retention time: 1.68 min (analysis conditions B)

Compound D-16:

2-(4-Cyclopropyl-2-fluoroanilino)-3,4-difluoro-5-[[2-fluoro-3-(methylsulfamoylamino)phenyl]methyl]-N-methoxybenzamide

[Chemical Formula 169]

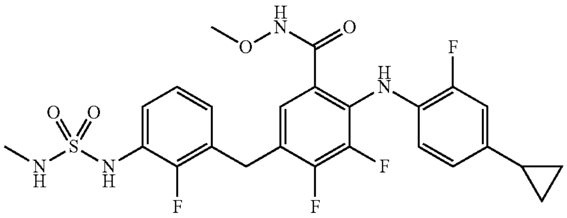

The title compound was synthesized from methyl 5-[(3-amino-2-fluorophenyl)methyl]-3,4-difluoro-2-(2-fluoro-4-iodoanilino)benzoate (compound d1) under the same conditions as the production examples for compound a9, compound a7, compound a8 and compound A-25. However, a 1 M sodium hydroxide aqueous solution was used instead of lithium hydroxide monohydrate, which was used in the production example for compound a7, and the corresponding amine was used instead of a 7 M ammonia MeOH solution, which was used in the production example for compound a8.

LCMS m/z: 551 $[M-H]^-$

HPLC retention time: 0.85 min (analysis conditions C)

Compound E-1:

5-[[3-(Ethylsulfonylamino)-2-fluorophenyl]methyl]-3,4-difluoro-2-(2-fluoro-4-iodoanilino)-N-methoxy-benzamide

[Chemical Formula 170]

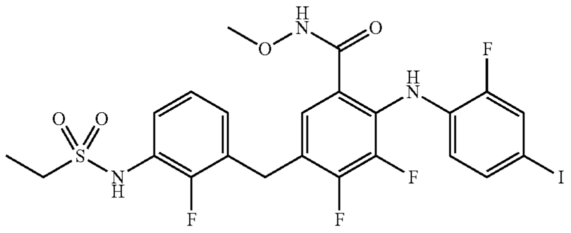

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25, compound b2 and compound a12. However, pyridine was used as the solvent in the sulfonamidation step. Also, the corresponding amine was used instead of tert-butoxyamine hydrochloride, which was used in the production example for compound a12.

LCMS m/z: 638 $[M+H]^+$

HPLC retention time: 1.68 min (analysis conditions B)

Compound E-2:

5-[[3-(Ethylsulfonylamino)-2-fluorophenyl]methyl]-3,4-difluoro-2-(2-fluoro-4-iodoanilino)-N-[(2-methylpropan-2-yl)oxy]benzamide

[Chemical Formula 171]

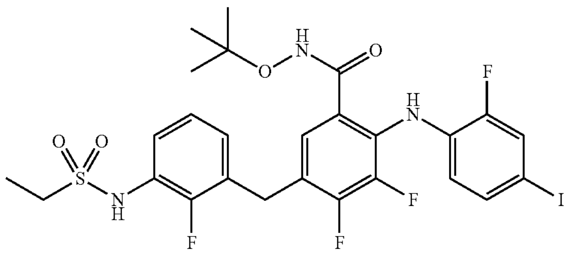

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25, compound b2 and compound a12. However, pyridine was used as the solvent in the sulfonamidation step.

LCMS m/z: 680 $[M+H]^+$

HPLC retention time: 1.80 min (analysis conditions B)

Compound E-3:

3,4-Difluoro-2-(2-fluoro-4-iodoanilino)-5-[[2-fluoro-3-[[1-(methoxymethyl)cyclopropyl]sulfonylamino]phenyl]methyl]-N-methoxybenzamide

[Chemical Formula 172]

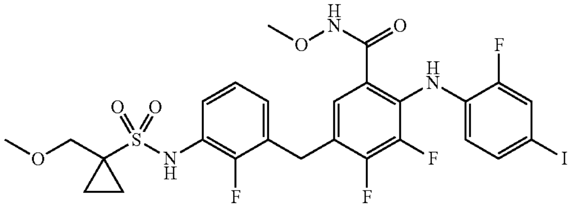

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25, compound b2 and compound a12. However, pyridine was used as the solvent in the sulfonamidation step. Also, the corresponding amine was used instead of tert-butoxyamine hydrochloride, which was used in the production example for compound a12.

LCMS m/z: 694 $[M+H]^+$

HPLC retention time: 1.74 min (analysis conditions B)

Compound E-4:

3,4-Difluoro-2-(2-fluoro-4-iodoanilino)-5-[[2-fluoro-3-[[1-(methoxymethyl)cyclopropyl]sulfonylamino]phenyl]methyl]-N-[(2-methylpropan-2-yl)oxy]benzamide

[Chemical Formula 173]

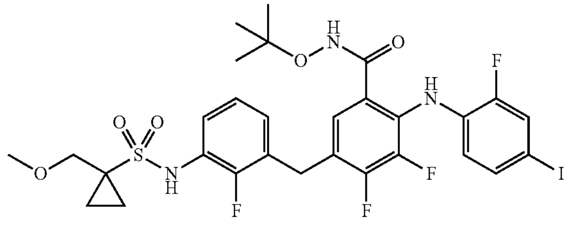

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25, compound b2 and compound a12. However, pyridine was used as the solvent in the sulfonamidation step.

LCMS m/z: 736 $[M+H]^+$

HPLC retention time: 1.87 min (analysis conditions B)

Compound E-5:

3,4-Difluoro-2-(2-fluoro-4-iodoanilino)-5-[[2-fluoro-3-[(1-methylcyclopropyl)sulfonylamino]phenyl]methyl]-N-methoxybenzamide

[Chemical Formula 174]

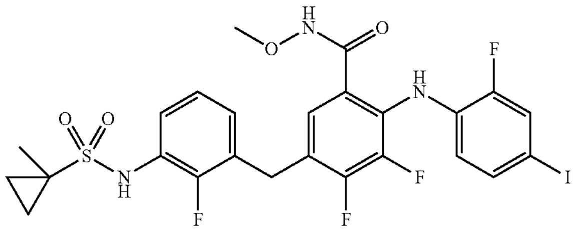

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25, compound b2 and compound a12. However, pyridine was used as the solvent in the sulfonamidation step. Also, the corresponding amine was used instead of tert-butoxyamine hydrochloride, which was used in the production example for compound a12.

LCMS m/z: 664 $[M+H]^+$

HPLC retention time: 1.73 min (analysis conditions B)

Compound E-6:

3,4-Difluoro-2-(2-fluoro-4-iodoanilino)-5-[[2-fluoro-3-[(1-methylcyclopropyl)sulfonylamino]phenyl]methyl]-N-[(2-methylpropan-2-yl)oxy]benzamide

[Chemical Formula 175]

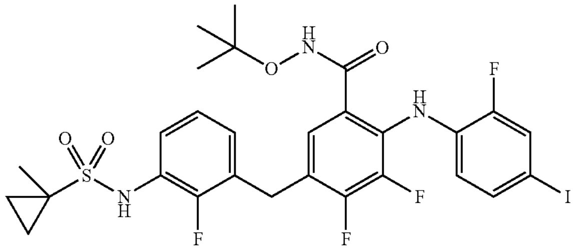

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25, compound b2 and compound a12. However, pyridine was used as the solvent in the sulfonamidation step.

LCMS m/z: 706 $[M+H]^+$

HPLC retention time: 1.86 min (analysis conditions B)

Compound E-7:

3,4-Difluoro-2-(2-fluoro-4-iodoanilino)-5-[[2-fluoro-3-(methylsulfamoylamino)phenyl]methyl]benzamide

[Chemical Formula 176]

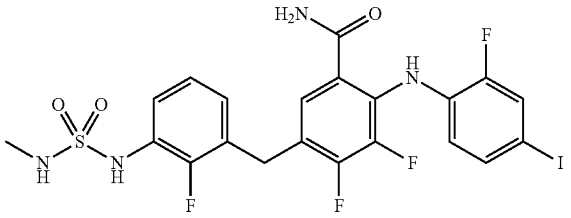

The title compound was synthesized from methyl 5-[(3-amino-2-fluorophenyl)methyl]-3,4-difluoro-2-(2-fluoro-4-iodoanilino)benzoate (compound d1) under the same conditions as the production examples for compound A-25, compound b2 and compound a12. However, pyridine was used as the solvent in the sulfamidation step. Also, the corresponding amine was used instead of tert-butoxyamine hydrochloride, which was used in the production example for compound a12.

LCMS m/z: 609 $[M+H]^+$

HPLC retention time: 1.23 min (analysis conditions A)

Compound e11:

Tert-Butyl N-[[3-[[5-carbamoyl-2,3-difluoro-4-(2-fluoro-4-iodoanilino)phenyl]methyl]-2-fluorophenyl]sulfamoyl]carbamate

[Chemical Formula 177]

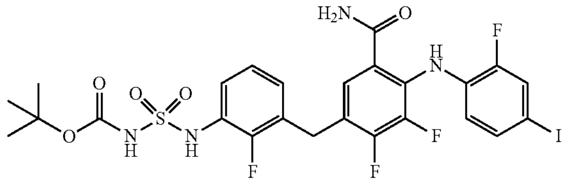

The title compound was synthesized from methyl 5-[(3-amino-2-fluorophenyl)methyl]-3,4-difluoro-2-(2-fluoro-4-iodoanilino)benzoate (compound d1) and the corresponding sulfamoyl chloride under the same conditions as the production examples for compound A-25, compound b2 and compound a12. However, pyridine was used as the solvent in the sulfamidation step. Also, the corresponding amine was used instead of tert-butoxyamine hydrochloride, which was used in the production example for compound a12.

LCMS m/z: 695 $[M+H]^+$

HPLC retention time: 0.74 min (analysis conditions D)

Compound E-8:

3,4-Difluoro-2-(2-fluoro-4-iodoanilino)-5-[[2-fluoro-3-(sulfamoylamino)phenyl]methyl]benzamide

[Chemical Formula 178]

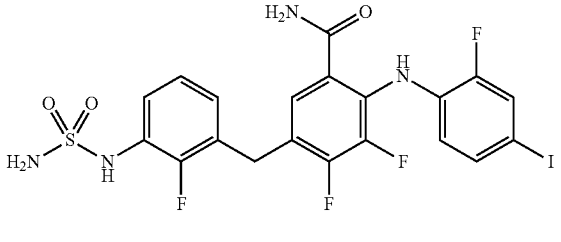

The title compound was synthesized from tert-butyl N-[[3-[[5-carbamoyl-2,3-difluoro-4-(2-fluoro-4-iodoanilino)phenyl]methyl]-2-fluorophenyl]sulfamoyl]carbamate (compound e11) under the same conditions as the production example for compound b9.

LCMS m/z: 595 $[M+H]^+$

HPLC retention time: 1.17 min (analysis conditions A)

Compound E-9:

2-(2-Chloro-4-iodoanilino)-5-[[3-(ethylsulfonylamino)-2-fluorophenyl]methyl]-3,4-difluoro-N-methoxybenzamide

[Chemical Formula 179]

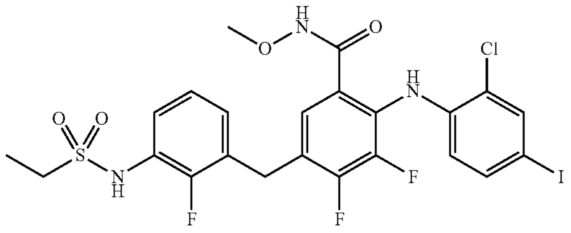

The title compound was synthesized from methyl 5-[(2-amino-3-fluoropyridin-4-yl)methyl]-2-(2-chloro-4-iodoanilino)-3,4-difluorobenzoate (compound b14) and the corresponding sulfonyl chloride under the same conditions as the production examples for compound A-25, compound b2 and compound a12. However, pyridine was used as the solvent in the sulfonamidation step. Also, the corresponding amine was used instead of tert-butoxyamine hydrochloride, which was used in the production example for compound a12.

LCMS m/z: 654 $[M+H]^+$

HPLC retention time: 1.75 min (analysis conditions B)

Compound E-10:

2-(2-Chloro-4-iodoanilino)-5-[[3-(ethylsulfonylamino)-2-fluorophenyl]methyl]-3,4-difluoro-N-[(2-methylpropan-2-yl)oxy]benzamide

[Chemical Formula 180]

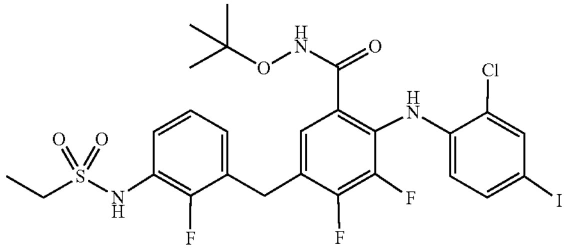

The title compound was synthesized from methyl 5-[(2-amino-3-fluoropyridin-4-yl)methyl]-2-(2-chloro-4-iodoanilino)-3,4-difluorobenzoate (compound b14) and the corresponding sulfonyl chloride under the same conditions as the production examples for compound A-25, compound b2 and compound a12. However, pyridine was used as the solvent in the sulfonamidation step. Also, the corresponding amine was used instead of tert-butoxyamine hydrochloride, which was used in the production example for compound a12.

LCMS m/z: 696 $[M+H]^+$

HPLC retention time: 1.87 min (analysis conditions B)

Compound E-11:

2-(2-Chloro-4-iodoanilino)-5-[[3-(ethylsulfonylamino)-2-fluorophenyl]methyl]-3,4-difluorobenzamide

[Chemical Formula 181]

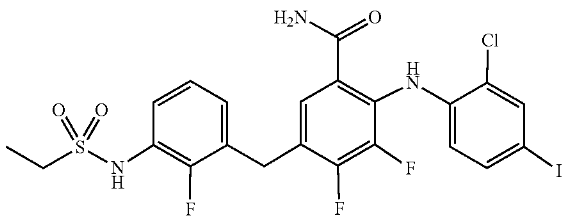

The title compound was synthesized from methyl 5-[(2-amino-3-fluoropyridin-4-yl)methyl]-2-(2-chloro-4-iodoanilino)-3,4-difluorobenzoate (compound b14) and the corresponding sulfonyl chloride under the same conditions as the production examples for compound A-25, compound b2 and compound a12. However, pyridine was used as the solvent in the sulfonamidation step. Also, the corresponding amine was used instead of tert-butoxyamine hydrochloride, which was used in the production example for compound a12.

LCMS m/z: 624 $[M+H]^+$

HPLC retention time: 1.73 min (analysis conditions B)

Compound e17:

Methyl 5-[(3-amino-2-fluorophenyl)methyl]-2-(2-chloro-4-iodoanilino)-3,4-difluorobenzoate

[Chemical Formula 182]

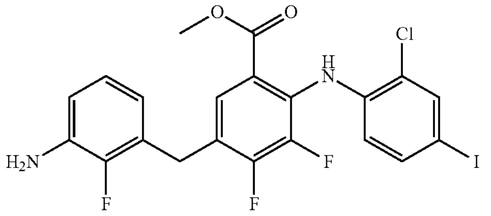

The title compound was synthesized from methyl 2-(2-chloro-4-iodoanilino)-3,4-difluoro-5-[(E)-[(4-methylphenyl)sulfonylhydrazinylidene]methyl]benzoate (compound b12) under the same conditions as the production example for compound a5, except that (3-amino-2-fluorophenyl) boronic acid hydrochloride was used instead of [2-[(2,4-dimethoxyphenyl)methylamino]-3-fluoropyridin-4-yl]boronic acid (compound a4) and that DIPEA was used instead of potassium carbonate.

LCMS m/z: 547 $[M+H]^+$

HPLC retention time: 1.13 min (analysis conditions C)

Compound E-12:

2-(2-Chloro-4-iodoanilino)-5-[[3-(cyclopropylsulfamoylamino)-2-fluorophenyl]methyl]-3,4-difluoro-N-[(2-methylpropan-2-yl)oxy]benzamide

[Chemical Formula 183]

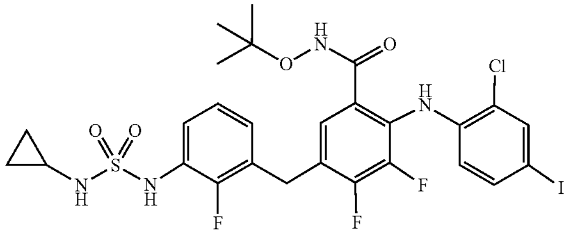

The title compound was synthesized from methyl 5-[(3-amino-2-fluorophenyl)methyl]-2-(2-chloro-4-iodoanilino)-3,4-difluorobenzoate (compound e17) and the corresponding 4-nitrophenyl sulfamate under the same conditions as the production examples for compound A-1, compound b2 and compound a12.

LCMS m/z: 723 $[M+H]^+$

HPLC retention time: 1.87 min (analysis conditions B)

Compound e20:

Methyl 3,4-difluoro-2-(2-fluoro-4-iodoanilino)-5-[[2-fluoro-3-(methanesulfonamide)phenyl]methyl] benzoate

[Chemical Formula 184]

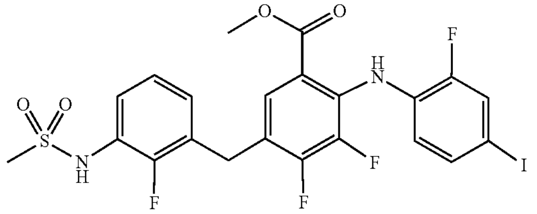

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production example for compound A-25, except that pyridine was used as the solvent.

LCMS m/z: 609 $[M+H]^+$

HPLC retention time: 1.01 min (analysis conditions C)

Compound E-13:

3,4-Difluoro-2-(2-fluoro-4-iodoanilino)-5-[[2-fluoro-3-(methanesulfonamide)phenyl]methyl]benzamide

[Chemical Formula 185]

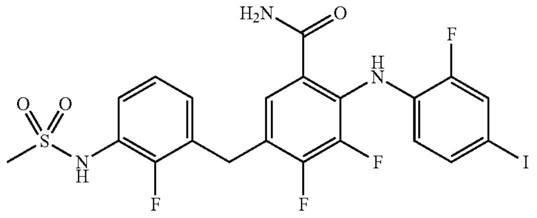

Lithium hydroxide monohydrate (7.9 mg, 0.19 mmol) was added to a mixed solution of methyl 3,4-difluoro-2-(2-fluoro-4-iodoanilino)-5-[[2-fluoro-3-(methanesulfonamide) phenyl]methyl]benzoate (compound e20, 23.0 mg, 0.038 mmol) in THF (0.7 mL) and water (0.3 mL), and the mixture was stirred at room temperature for 2 hours. The reaction mixture was concentrated under reduced pressure, and then 1 M hydrochloric acid (0.76 mL) was added and the mixture was further concentrated under reduced pressure. After then adding HOOBt (9.3 mg, 0.057 mmol) and EDC HCl (10.9 mg, 0.057 mmol) to an anhydrous DMF solution (0.3 mL) of the obtained mixture, the resulting mixture was stirred at room temperature for 3 hours. After then adding a 7 M ammonia MeOH solution (22 μL, 0.15 mmol) at 0° C., stirring was continued for 30 minutes. A 10% trifluoroacetic acid aqueous solution (1 mL) was added to the reaction mixture, which was then purified by reversed-phase column chromatography (0.1% formic acid aqueous solution/0.1% formic acid acetonitrile solution) to give the title compound (19.7 mg, 97%) as a colorless solid.

LCMS m/z: 594 $[M+H]^+$

HPLC retention time: 1.61 min (analysis conditions B)

Compound E-14:

5-[[3-(Cyclopropylmethylsulfonylamino)-2-fluorophenyl]methyl]-3,4-difluoro-2-(2-fluoro-4-iodoanilino)benzamide

[Chemical Formula 186]

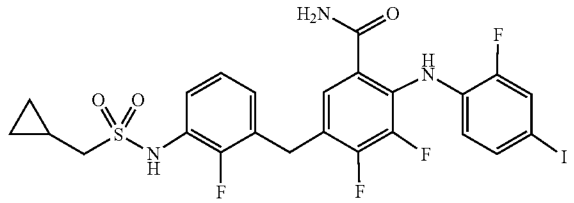

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 634 $[M+H]^+$

HPLC retention time: 1.72 min (analysis conditions B)

Compound E-15:

3,4-Difluoro-5-[[2-fluoro-3-(3-fluoropropylsulfonylamino)phenyl]methyl]-2-(2-fluoro-4-iodoanilino) benzamide

[Chemical Formula 187]

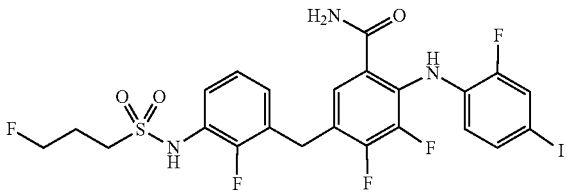

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, anhydrous DCM was used instead of anhydrous DMA, which was used in the production example for compound A-25.

LCMS m/z: 640 $[M+H]^+$

HPLC retention time: 1.67 min (analysis conditions B)

Compound E-16:

3,4-Difluoro-2-(2-fluoro-4-iodoanilino)-5-[[2-fluoro-3-[1-methylcyclopropyl)sulfonylamino]phenyl] methyl]benzamide

[Chemical Formula 188]

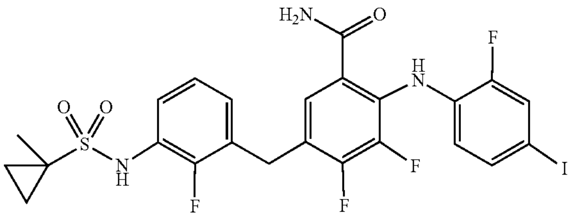

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 634 $[M+H]^+$

HPLC retention time: 1.72 min (analysis conditions B)

Compound E-17:

3,4-Difluoro-2-(2-fluoro-4-iodoanilino)-5-[[2-fluoro-3-(2-methylpropyl sulfonylamino)phenyl]methyl] benzamide

[Chemical Formula 189]

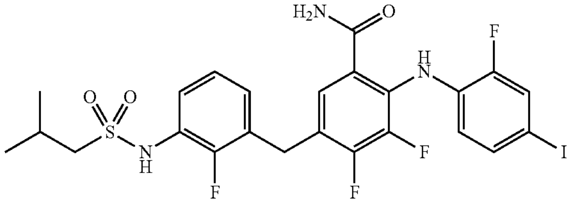

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 636 $[M+H]^+$

HPLC retention time: 1.77 min (analysis conditions B)

Compound E-18:

3,4-Difluoro-2-(2-fluoro-4-iodoanilino)-5-[[2-fluoro-3-(propylsulfonylamino)phenyl]methyl]benzamide

[Chemical Formula 190]

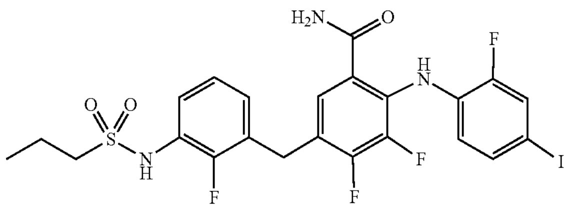

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 622 $[M+H]^+$

HPLC retention time: 1.72 min (analysis conditions B)

Compound E-19:

3,4-Difluoro-2-(2-fluoro-4-iodoanilino)-5-[[2-fluoro-3-[[1-(methoxymethyl)cyclopropyl]sulfonylamino]phenyl]methyl]benzamide

[Chemical Formula 191]

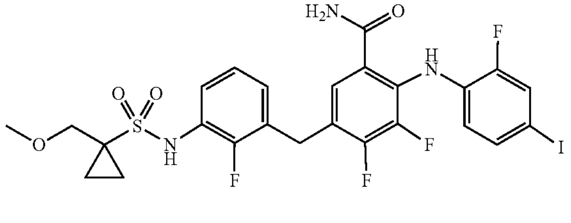

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 664 $[M+H]^+$

HPLC retention time: 1.73 min (analysis conditions B)

Compound E-20:

5-[[3-(Cyclobutylsulfonylamino)-2-fluorophenyl]methyl]-3,4-difluoro-2-(2-fluoro-4-iodoanilino)benzamide

[Chemical Formula 192]

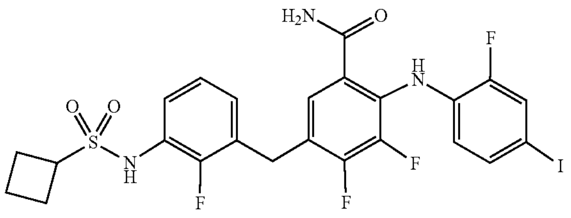

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 634 $[M+H]^+$

HPLC retention time: 1.73 min (analysis conditions B)

Compound E-21:

3,4-Difluoro-2-(2-fluoro-4-iodoanilino)-5-[[2-fluoro-3-(oxetan-3-ylsulfonylamino)phenyl]methyl]benzamide

[Chemical Formula 193]

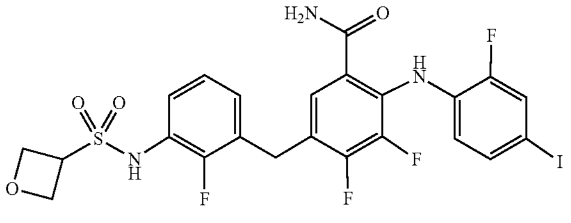

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 636 $[M+H]^+$

HPLC retention time: 1.61 min (analysis conditions B)

Compound E-22:

5-[[3-(Cyclopropylsulfonylamino)-2-fluorophenyl]methyl]-3,4-difluoro-2-(2-fluoro-4-iodoanilino)benzamide

[Chemical Formula 194]

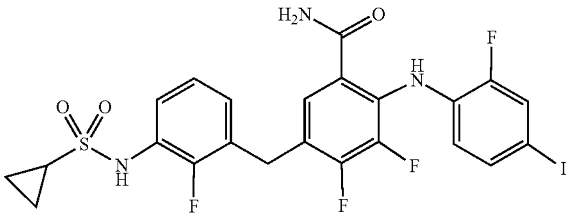

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 620 $[M+H]^+$

HPLC retention time: 1.68 min (analysis conditions B)

Compound E-23:

3,4-Difluoro-2-(2-fluoro-4-iodoanilino)-5-[[2-fluoro-3-(oxan-4-ylsulfonylamino)phenyl]methyl]benzamide

[Chemical Formula 195]

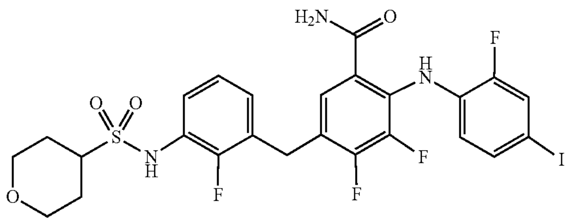

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, triethylamine and anhydrous DCM were used instead of pyridine and anhydrous DMA respectively, which were used in the production example for compound A-25.

LCMS m/z: 664 $[M+H]^+$

HPLC retention time: 1.65 min (analysis conditions B)

Compound E-24:

3,4-Difluoro-2-(2-fluoro-4-iodoanilino)-5-[[2-fluoro-3-(propan-2-ylsulfonylamino)phenyl]methyl]benzamide

[Chemical Formula 196]

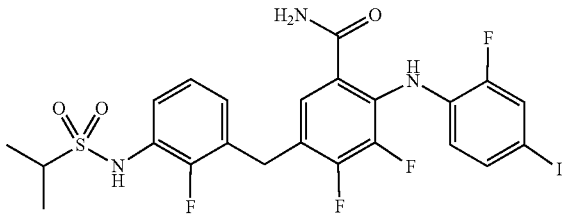

The title compound was synthesized from methyl 5-[(3-amino-2-fluorophenyl)methyl]-3,4-difluoro-2-(2-fluoro-4-iodoanilino)benzoate (compound d1) and the corresponding sulfonyl chloride under the same conditions as the production examples for compound A-25 and compound E-13. However, pyridine was used as the solvent in the sulfonamidation step.

LCMS m/z: 622 $[M+H]^+$

HPLC retention time: 1.71 min (analysis conditions B)

Compound E-25:

N-Cyclopropyl-3,4-difluoro-2-(2-fluoro-4-iodoanilino)-5-[[2-fluoro-3-(methanesulfonamide)phenyl]methyl]benzamide

[Chemical Formula 197]

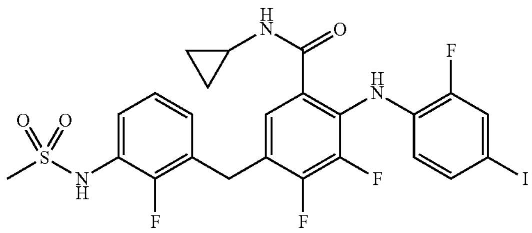

The title compound was synthesized from methyl 3,4-difluoro-2-(2-fluoro-4-iodoanilino)-5-[[2-fluoro-3-(methanesulfonamide)phenyl]methyl]benzoate (compound e20) under the same conditions as the production examples for compound b2 and compound a12. However, the corresponding amine was used instead of tert-butoxyamine hydrochloride, which was used in the production example for compound a12.

LCMS m/z: 634 $[M+H]^+$

HPLC retention time: 0.92 min (analysis conditions C)

Compound E-26:

3,4-Difluoro-2-(2-fluoro-4-iodoanilino)-5-[[2-fluoro-3-(methanesulfonamide)phenyl]methyl]-N-methoxy-benzamide

[Chemical Formula 198]

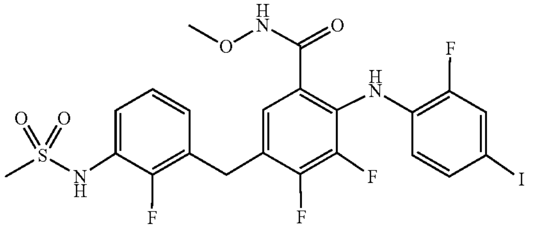

The title compound was synthesized from methyl 3,4-difluoro-2-(2-fluoro-4-iodoanilino)-5-[[2-fluoro-3-(methanesulfonamide)phenyl]methyl]benzoate (compound e20) under the same conditions as the production examples for compound b2 and compound a12. However, the corresponding amine was used instead of tert-butoxyamine hydrochloride, which was used in the production example for compound a12.

LCMS m/z: 624 $[M+H]^+$

HPLC retention time: 0.86 min (analysis conditions C)

Compound F-1:

3,4-Difluoro-2-(2-fluoro-4-iodoanilino)-5-[[3-(methylsulfamoylamino)phenyl]methyl]benzamide

[Chemical Formula 199]

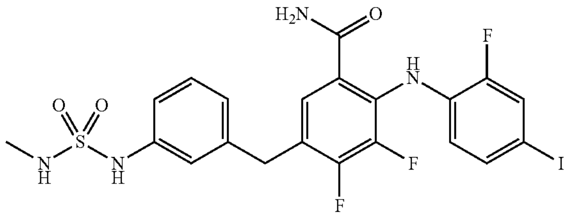

The title compound was synthesized from 3,4-difluoro-2-(2-fluoro-4-iodoanilino)-5-[(E)-[(4-methylphenyl)sulfonylhydrazinylidene]methyl]benzamide (compound c1) under the same conditions as the production examples for compound a5 and compound A-25. However, 3-aminophenylboronic acid was used instead of [2-[(2,4-dimethoxyphenyl)methylamino]-3-fluoropyridin-4-yl]boronic acid (compound a4), which was used in the production example for compound a5.

LCMS m/z: 591 $[M+H]^+$

HPLC retention time: 0.84 min (analysis conditions C)

Compound F-2:

5-[[3-(Ethylsulfonylamino)phenyl]methyl]-3,4-difluoro-2-(2-fluoro-4-iodoanilino)benzamide

[Chemical Formula 200]

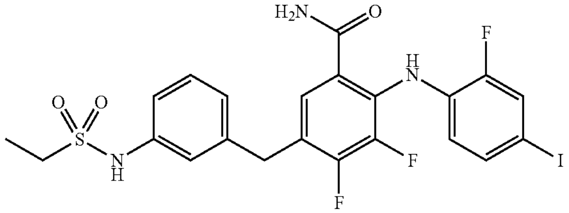

The title compound was synthesized from 3,4-difluoro-2-(2-fluoro-4-iodoanilino)-5-[(E)-[(4-methylphenyl)sulfonylhydrazinylidene]methyl]benzamide (compound c1) and the corresponding sulfonyl chloride under the same conditions as the production examples for compound a5 and compound A-25. However, 3-aminophenylboronic acid was used instead of [2-[(2,4-dimethoxyphenyl)methylamino]-3-fluoropyridin-4-yl]boronic acid (compound a4), which was used in the production example for compound a5. Pyridine was used as the solvent in the sulfonamidation step.

LCMS m/z: 590 $[M+H]^+$

HPLC retention time: 1.26 min (analysis conditions A)

Compound F-3:

3,4-Difluoro-2-(2-fluoro-4-iodoanilino)-5-[[3-(2-methoxyethylsulfonylamino)phenyl]methyl]benzamide

[Chemical Formula 201]

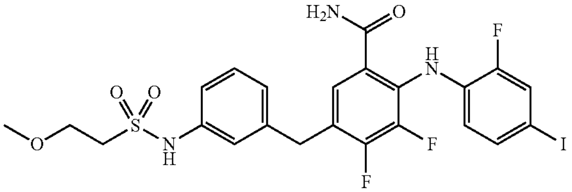

The title compound was synthesized from 3,4-difluoro-2-(2-fluoro-4-iodoanilino)-5-[(E)-[(4-methylphenyl)sulfon ylhydrazinylidene]methyl]benzamide (compound c1) and the corresponding sulfonyl chloride under the same conditions as the production examples for compound a5 and compound A-25. However, 3-aminophenylboronic acid was used instead of [2-[(2,4-dimethoxyphenyl)methylamino]-3-fluoropyridin-4-yl]boronic acid (compound a4), which was used in the production example for compound a5. Pyridine was used as the solvent in the sulfonamidation step.

LCMS m/z: 620 $[M+H]^+$

HPLC retention time: 1.65 min (analysis conditions B)

Compound g2:

2-(4-Cyclopropyl-2-fluoroanilino)-3,4-difluoro-5-[[3-fluoro-2-(methylsulfamoylamino)pyridin-4-yl]methyl]benzoic Acid

[Chemical Formula 202]

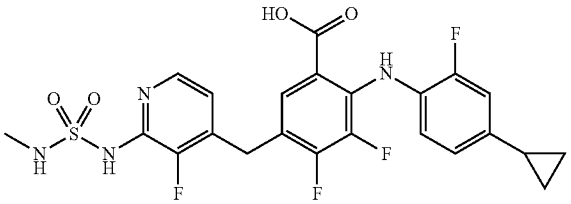

The title compound was synthesized from 5-[(2-amino-3-fluoropyridin-4-yl)methyl]-3,4-difluoro-2-(2-fluoro-4-iodoanilino)benzoic acid hydrochloride (compound a7) under the same conditions as the production examples for compound a9 and compound A-1.

LCMS m/z: 525 $[M+H]^+$

HPLC retention time: 0.83 min (analysis conditions C)

Compound G-1:

N-Cyclopropyl-2-(4-cyclopropyl-2-fluoroanilino)-3,4-difluoro-5-[[3-fluoro-2-(methylsulfamoylamino)pyridin-4-yl]methyl]benzamide

[Chemical Formula 203]

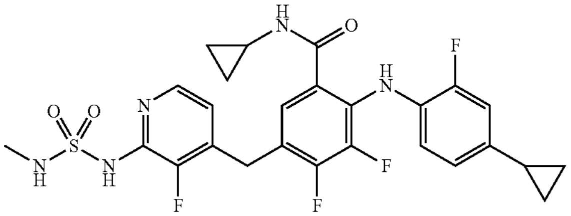

The title compound was synthesized from 2-(4-cyclopropyl-2-fluoroanilino)-3,4-difluoro-5-[[3-fluoro-2-(methylsulfamoylamino)pyridin-4-yl]methyl]benzoic acid (compound g2) under the same conditions as the production example for compound a10.

LCMS m/z: 564 $[M+H]^+$

HPLC retention time: 1.61 min (analysis conditions B)

Compound G-2:

2-(4-Cyclopropyl-2-fluoroanilino)-3,4-difluoro-5-[[3-fluoro-2-(methylsulfamoylamino)pyridin-4-yl]methyl]-N-methoxybenzamide

[Chemical Formula 204]

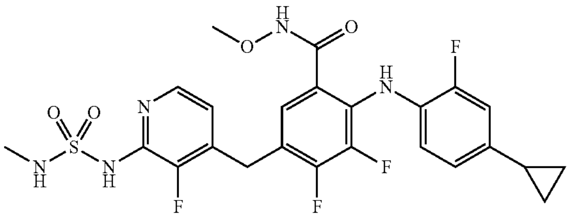

After adding O-methylhydroxyamine hydrochloride (6.4 mg, 0.076 mmol), propylphosphonic anhydride (cyclic trimer) (56 μL, 0.095 mmol) and triethylamine (27 μL, 0.19 mmol) to an anhydrous DMF solution (0.2 mL) of 2-(4-cyclopropyl-2-fluoroanilino)-3,4-difluoro-5-[[3-fluoro-2-(methylsulfamoylamino)pyridin-4-yl]methyl]benzoic acid (compound g2, 20 mg, 0.038 mmol), the mixture was stirred at room temperature for 16 hours. The reaction mixture was purified by reversed-phase column chromatography (0.1% formic acid aqueous solution/0.1% formic acid acetonitrile solution) to give the title compound (14 mg, 66%) as a colorless solid.

LCMS m/z: 554 $[M+H]^+$

HPLC retention time: 1.53 min (analysis conditions B)

Compound G-3:

2-(4-Bromo-2-fluoroanilino)-3,4-difluoro-5-[[3-fluoro-2-(methylsulfamoylamino)pyridin-4-yl]methyl]-N-methoxybenzamide

[Chemical Formula 205]

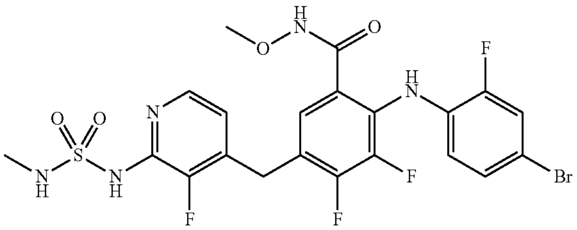

The title compound was synthesized from 5-[(2-amino-3-fluoropyridin-4-yl)methyl]-3,4-difluoro-2-(2-fluoro-4-iodoanilino)benzoic acid hydrochloride (compound a7) under the same conditions as the production examples for compound a21, compound A-1 and compound G-2.

LCMS m/z: 592 $[M+H]^+$

HPLC retention time: 1.52 min (analysis conditions B)

Compound G-4:

2-(4-Chloro-2-fluoroanilino)-3,4-difluoro-5-[[3-fluoro-2-(methylsulfamoylamino)pyridin-4-yl]methyl]-N-methoxybenzamide

[Chemical Formula 206]

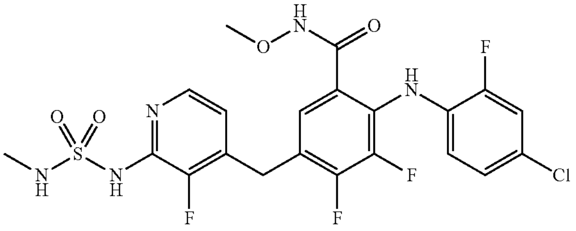

The title compound was synthesized from 5-[(2-amino-3-fluoropyridin-4-yl)methyl]-3,4-difluoro-2-(2-fluoro-4-iodoanilino)benzoic acid hydrochloride (compound a7) under the same conditions as the production examples for compound a21, compound A-1 and compound G-2. However, copper(I) chloride was used instead of copper(I) bromide, which was used in the production example for compound a21.

LCMS m/z: 548 $[M+H]^+$

HPLC retention time: 1.50 min (analysis conditions B)

Compound G-5:

N-Cyclopropyl-2-(4-cyclopropyl-2-fluoroanilino)-3,4-difluoro-5-[[3-fluoro-2-[(1-methylcyclobutyl)sulfamoylamino]pyridin-4-yl]methyl]benzamide

[Chemical Formula 207]

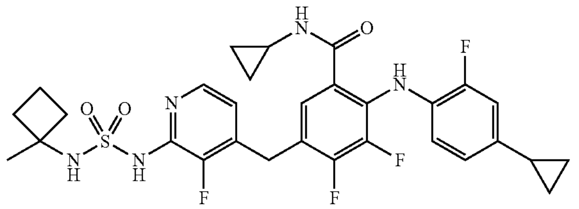

The title compound was synthesized from methyl 5-[(2-amino-3-fluoropyridin-4-yl)methyl]-3,4-difluoro-2-(2-fluoro-4-iodoanilino)benzoate (compound a6) under the same conditions as the production examples for compound a9, compound a7, compound a12 and compound A-1. However, a 1 M sodium hydroxide aqueous solution was used instead of lithium hydroxide monohydrate, which was used in the production example for compound a7, and triethylamine was used instead of DIPEA, which was used in the production example for compound a12. Also, the corresponding amine was used instead of tert-butoxyamine hydrochloride, which was used in the production example for compound a12, and the corresponding 4-nitrophenyl sulfamate was used instead of 4-nitrophenyl methylsulfamate, which was used in the production example for compound A-1.

LCMS m/z: 618 $[M+H]^+$

HPLC retention time: 0.95 min (analysis conditions C)

Compound G-6:

2-(4-Cyclopropyl-2-fluoroanilino)-3,4-difluoro-5-[[3-fluoro-2-[(1-methylcyclobutyl)sulfamoylamino]pyridin-4-yl]methyl]-N-methoxybenzamide

[Chemical Formula 208]

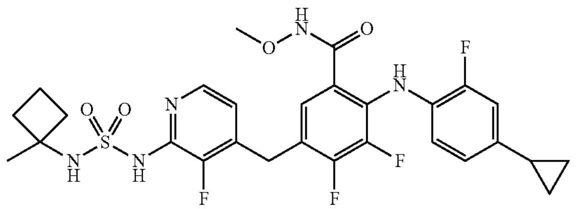

The title compound was synthesized from methyl 5-[(2-amino-3-fluoropyridin-4-yl)methyl]-3,4-difluoro-2-(2-fluoro-4-iodoanilino)benzoate (compound a6) under the same conditions as the production examples for compound a9, compound a7, compound a12 and compound A-1. However, a 1 M sodium hydroxide aqueous solution was used instead of lithium hydroxide monohydrate, which was used in the production example for compound a7, and triethylamine was used instead of DIPEA, which was used in the production example for compound a12. Also, the corresponding amine was used instead of tert-butoxyamine hydrochloride, which was used in the production example for compound a12, and the corresponding 4-nitrophenyl sulfamate was used instead of 4-nitrophenyl methylsulfamate, which was used in the production example for compound A-1.

LCMS m/z: 608 $[M+H]^+$

HPLC retention time: 0.90 min (analysis conditions C)

Compound G-7:

N-Cyclopropyl-2-(4-cyclopropyl-2-fluoroanilino)-5-[[2-(ethylsulfonylamino)-3-fluoropyridin-4-yl]methyl]-3,4-difluorobenzamide

[Chemical Formula 209]

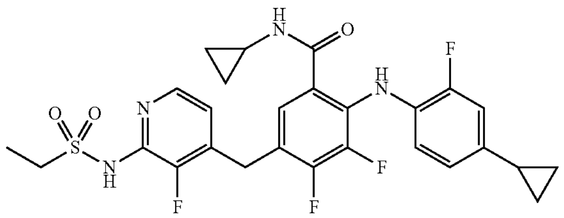

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfonyl chloride under the same conditions as the production examples for compound A-25, compound a9, compound a7 and compound a12. However, triethylamine and anhydrous DCM were used instead of pyridine and anhydrous DMA respectively, which were used in the production example for compound A-25, and a 1 M sodium hydroxide aqueous solution was used instead of lithium hydroxide monohydrate, which was used in the production example for compound a7. Also, the corresponding amine was used instead of tert-butoxyamine hydrochloride, which was used in the production example for compound a12.

LCMS m/z: 563 $[M+H]^+$

HPLC retention time: 0.88 min (analysis conditions C)

Compound G-8:

2-(4-Cyclopropyl-2-fluoroanilino)-5-[[2-(ethylsulfonylamino)-3-fluoropyridin-4-yl]methyl]-3,4-difluoro-N-methoxybenzamide

[Chemical Formula 210]

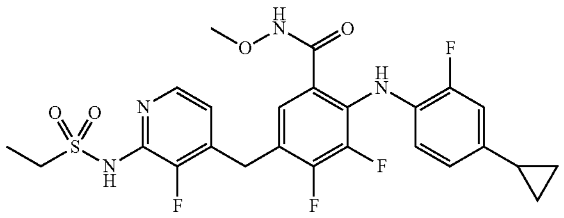

The title compound was synthesized from methyl 5-[(2-amino-3-fluoropyridin-4-yl)methyl]-3,4-difluoro-2-(2- fluoro-4-iodoanilino)benzoate (compound a6) and the corresponding sulfonyl chloride under the same conditions as the production examples for compound A-25, compound a9, compound a7 and compound a12. However, triethylamine and anhydrous DCM were used instead of pyridine and anhydrous DMA respectively, which were used in the production example for compound A-25, and a 1 M sodium hydroxide aqueous solution was used instead of lithium hydroxide monohydrate, which was used in the production example for compound a7. Also, the corresponding amine was used instead of tert-butoxyamine hydrochloride, which was used in the production example for compound a12.

LCMS m/z: 553 $[M+H]^+$

HPLC retention time: 0.82 min (analysis conditions C)

example for compound a7. Also, the corresponding amine was used instead of tert-butoxyamine hydrochloride, which was used in the production example for compound a12.

LCMS m/z: 539 $[M+H]^+$

HPLC retention time: 0.79 min (analysis conditions C)

Compound h1:

Methyl

5-[(2-amino-3-fluoropyridin-4-yl)methyl]-2-[4-[3-(2-ethylhexoxy)-3-oxopropyl]sulfanyl-2-fluoroanilino]-3,4-difluorobenzoate

[Chemical Formula 212]

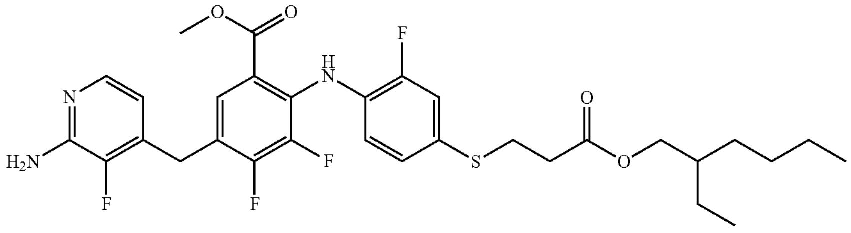

Compound G-9:

2-(4-Cyclopropyl-2-fluoroanilino)-3,4-difluoro-5-[[3-fluoro-2-(methane sulfonamide)pyridin-4-yl]methyl]-N-methoxybenzamide

[Chemical Formula 211]

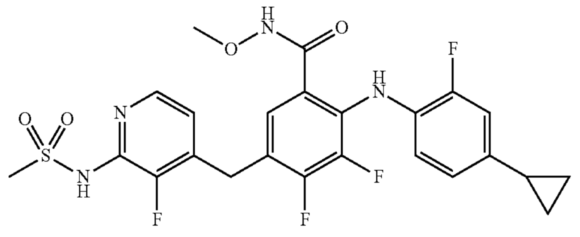

The title compound was synthesized from methyl 5-[(2-amino-3-fluoropyridin-4-yl)methyl]-3,4-difluoro-2-(2-fluoro-4-iodoanilino)benzoate (compound a6) and the corresponding sulfonyl chloride under the same conditions as the production examples for compound A-25, compound a9, compound a7 and compound a12. However, triethylamine and anhydrous DCM were used instead of pyridine and anhydrous DMA respectively, which were used in the production example for compound A-25, and a 1 M sodium hydroxide aqueous solution was used instead of lithium hydroxide monohydrate, which was used in the production A suspension of methyl 5-((2-amino-3-fluoropyridin-4-yl)methyl)-3,4-difluoro-2-((2-fluoro-4-iodophenyl)amino)benzoate (compound a6, 500 mg, 0.941 mmol), 2-ethylhexyl 3-mercaptopropionate (226 mg, 1.04 mmol), Xantphos (109 mg, 0.188 mmol), tris(dibenzylideneacetone)dipalladium(0) (86 mg, 0.094 mmol) and DIPEA (0.492 mL, 2.82 mmol) in 1,4-dioxane (17 mL) was stirred for 1 hour at 110° C. After adding acetonitrile to the reaction mixture it was filtered with Celite and the filtrate was concentrated under reduced pressure. The resulting residue was purified by reversed-phase column chromatography (0.1% formic acid aqueous solution/0.1% formic acid acetonitrile solution) to give the title compound (584 mg, quant.) as a yellow viscous oil.

LCMS m/z: 622 $[M+H]^+$

HPLC retention time: 1.14 min (analysis conditions G)

Compound h2:

Methyl

5-[(2-amino-3-fluoropyridin-4-yl)methyl]-2-[4-(difluoromethylsulfanyl)-2-fluoroanilino]-3,4-difluorobenzoate

[Chemical Formula 213]

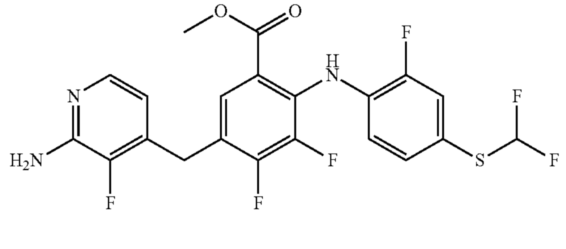

A methanol solution (9 mL) of methyl 5-[(2-amino-3-fluoropyridin-4-yl)methyl]-2-[4-[3-(2-ethylhexoxy)-3-oxopropyl]sulfanyl-2-fluoroanilino]-3,4-difluorobenzoate (compound h1, 584 mg, 0.939 mmol) was cooled to 0° C., and then a 25% sodium methoxide methanol solution (1.29 mL, 5.64 mmol) was added and the mixture was stirred for 3 hours at room temperature. Diethyl (bromodifluoromethyl)phosphonate (1.00 g, 3.76 mmol) was then added at 0° C., and the mixture was stirred for 10 minutes at room temperature. The reaction mixture was cooled to 0° C., a 25% sodium methoxide methanol solution (1.29 mL, 5.64 mmol) and diethyl (bromodifluoromethyl)phosphonate (1.51 g, 5.64 mmol) were added, and the mixture was stirred for 20 minutes at room temperature. The reaction mixture was cooled to 0° C., formic acid (0.213 mL, 5.64 mmol) was added, and the mixture was concentrated under reduced pressure. The resulting residue was purified by reversed-phase column chromatography (0.1% formic acid aqueous solution/0.1% formic acid acetonitrile solution) to give the title compound (195 mg, 43%) as a colorless solid.

LCMS m/z: 488 $[M+H]^+$

HPLC retention time: 0.81 min (analysis conditions G)

Compound h3:

5-[(2-Amino-3-fluoropyridin-4-yl)methyl]-2-[4-(difluoromethylsulfanyl)-2-fluoroanilino]-3,4-difluorobenzamide

[Chemical Formula 214]

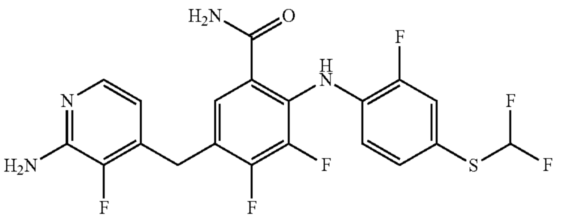

A mixture of methyl 5-[(2-amino-3-fluoropyridin-4-yl)methyl]-2-[4-(difluoromethylsulfanyl)-2-fluoroanilino]-3,4-difluorobenzoate (compound h2, 60.0 mg, 0.123 mmol) and a 7 M ammonia MeOH solution (1.80 mL, 12.6 mmol) was stirred for 6 hours at 85° C. in a sealed tube using a microwave reactor. The reaction mixture was concentrated under reduced pressure, and the resulting residue was purified by reversed-phase column chromatography (0.05% trifluoroacetic acid aqueous solution/0.05% trifluoroacetic acid acetonitrile solution) to give the title compound (53.2 g, 91%) as a yellow oil.

LCMS m/z: 473 $[M+H]^+$

HPLC retention time: 0.63 min (analysis conditions C)

Compound H-1:

2-[4-(Difluoromethylsulfanyl)-2-fluoroanilino]-3,4-difluoro-5-[[3-fluoro-2-(methylsulfamoylamino)pyridin-4-yl]methyl]benzamide

[Chemical Formula 215]

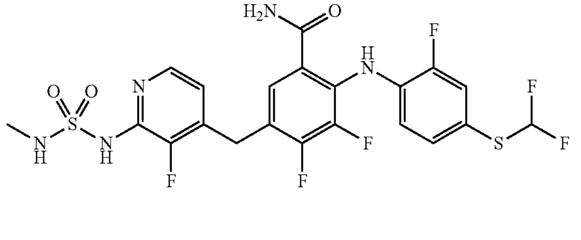

The title compound was synthesized from 5-[(2-amino-3-fluoropyridin-4-yl)methyl]-2-[4-(difluoromethylsulfanyl)-2-fluoroanilino]-3,4-difluorobenzamide (compound h3) under the same conditions as the production example for compound A-1.

LCMS m/z: 566 $[M+H]^+$

HPLC retention time: 1.49 min (analysis conditions B)

Compound h4:

2-(1-Benzothiophen-5-ylamino)-3,4-difluoro-5-formylbenzoic acid

[Chemical Formula 216]

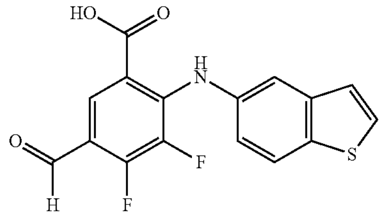

An anhydrous THF solution (30 mL) of 2,2,6,6-tetramethylpiperidine (2.53 g, 17.9 mmol) was cooled to −78° C., a 1.6 M n-butyllithium hexane solution (11.2 mL, 17.9 mmol) was added under a nitrogen atmosphere, and the mixture was stirred for 5 minutes. The reaction mixture was added to a THF solution (9.0 mL) of 2,3,4-trifluorobenzoic acid (1.50 g, 8.52 mmol) at −78° C. and the mixture was stirred for 10 minutes, and then anhydrous DMF (0.759 mL, 9.80 mmol) was added and stirring was continued for 2 hours at 0° C. In a separate flask, a THF solution (30 mL) of benzo[b]thiophenone-5-amine (1.65 g, 11.1 mmol) was cooled to −78° C., and then a 1.3 M lithium bis(trimethylsilyl)amide THF solution (15.1 mL, 19.6 mmol) and the previous reaction mixture were added and the resulting mixture was stirred for 24 hours at room temperature. After adding 2 M hydrochloric acid to the reaction mixture and stirring for 24 hours, water and 2 M hydrochloric acid were added and extraction was performed with ethyl acetate. The organic layer was washed with saturated brine, dried over anhydrous sodium sulfate and, after filtering off the drying agent, concentrated under reduced pressure. The resulting residue was purified by reversed-phase column chromatography (0.1% formic acid aqueous solution/0.1% formic acid acetonitrile solution) to give the title compound (609 mg, 21%) as a gray solid.

LCMS m/z: 334 $[M+H]^+$

HPLC retention time: 0.80 min (analysis conditions C)

Compound h5:

2-(1-Benzothiophen-5-ylamino)-3,4-difluoro-5-[(E)-[(4-methylphenyl)sulfonylhydrazinylidene]methyl]benzamide

[Chemical Formula 217]

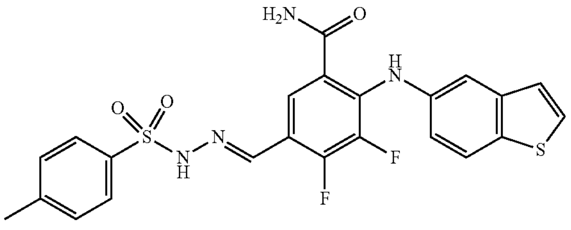

After adding HOOBt (595 mg, 3.65 mmol) and EDC·HCl (699 mg, 3.65 mmol) to an anhydrous DMF suspension (9.1 mL) of 2-(1-benzothiophen-5-ylamino)-3,4-difluoro-5-formylbenzoic acid (compound h4, 608 mg, 1.82 mmol), the mixture was stirred for 1.5 hours at room temperature. A 7 M ammonia MeOH solution (0.912 mL, 6.38 mmol) was then added at 0° C. and stirring was continued for 30 minutes, 4-methylbenzenesulfonyl hydrazide (340 mg, 1.82 mmol) was further added at 0° C., and stirring was continued for 16 hours at room temperature. After filtering the reaction mixture, acetonitrile (14 mL) and 0.1 M hydrochloric acid (100 mL) were added to the filtrate. The solid was filtered and then washed with water to give the title compound (412 mg, 45%) as a light brown solid.

LCMS m/z: 501 $[M+H]^+$

HPLC retention time: 0.83 min (analysis conditions C)

Compound h7:

5-[(2-Amino-3-fluoropyridin-4-yl)methyl]-2-(1-benzothiophen-5-ylamino)-3,4-difluorobenzamide

[Chemical Formula 218]

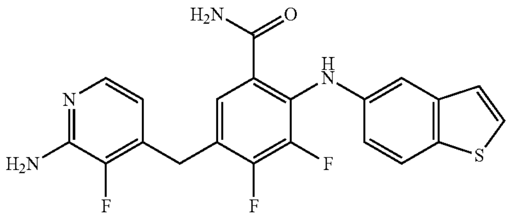

The title compound was synthesized from 2-(1-benzothiophen-5-ylamino)-3,4-difluoro-5-[(E)-[(4-methylphenyl)sulfonylhydrazinylidene]methyl]benzamide (compound h5) under the same conditions as the production examples for compound a5 and compound a6.

LCMS m/z: 429 $[M+H]^+$

HPLC retention time: 0.57 min (analysis conditions C)

Compound H-2:

2-(1-Benzothiophen-5-ylamino)-3,4-difluoro-5-[[3-fluoro-2-(methylsulfamoylamino)pyridin-4-yl]methyl]benzamide

[Chemical Formula 219]

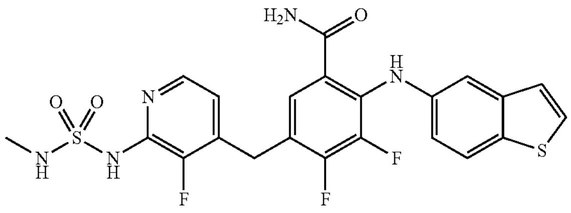

The title compound was synthesized from 5-[(2-amino-3-fluoropyridin-4-yl)methyl]-2-(1-benzothiophen-5-ylamino)-3,4-difluorobenzamide (compound h7) under the same conditions as the production example for compound A-1.

LCMS m/z: 522 $[M+H]^+$

HPLC retention time: 1.06 min (analysis conditions A)

Compound h8:

5-[(2-Amino-3-fluoropyridin-4-yl)methyl]-3,4-difluoro-2-[(4-fluoro-1-benzothiophen-5-yl)amino]benzamide

[Chemical Formula 220]

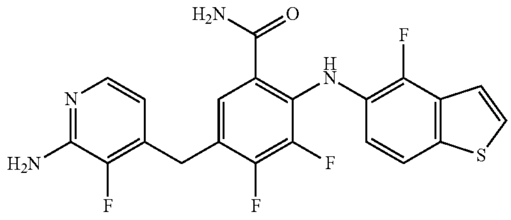

An anhydrous acetonitrile solution (0.3 mL) of 5-[(2-amino-3-fluoropyridin-4-yl)methyl]-2-(1-benzothiophen-5-ylamino)-3,4-difluorobenzamide (compound h7, 22 mg, 0.051 mmol) was cooled to 0° C., and then N-fluoro-N'-(chloromethyl)triethylenediamine bis(tetrafluoroborate) (9.5 mg, 0.027 mmol) was added and the mixture was stirred for 2.5 hours. Next, N-fluoro-N'-(chloromethyl)triethylenediamine bis(tetrafluoroborate) (8.0 mg, 0.023 mmol) was added and the mixture was stirred for 1 hours. The reaction mixture was concentrated under reduced pressure, and the resulting residue was purified by reversed-phase column chromatography (0.05% trifluoroacetic acid aqueous solution/0.05% trifluoroacetic acid acetonitrile solution) to give the title compound (8.0 mg, 35%) as a brown solid.

LCMS m/z: 447 $[M+H]^+$

HPLC retention time: 0.61 min (analysis conditions C)

Compound H-3:

3,4-Difluoro-2-[(4-fluoro-1-benzothiophen-5-yl) amino]-5-[[3-fluoro-2-(methylsulfamoylamino)pyridin-4-yl]methyl]benzamide

[Chemical Formula 221]

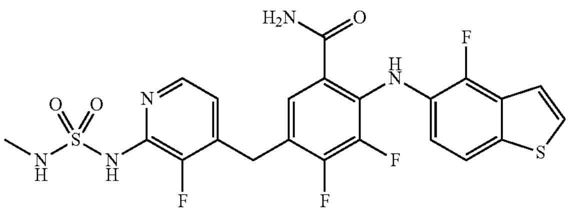

The title compound was synthesized from 5-[(2-amino-3-fluoropyridin-4-yl)methyl]-3,4-difluoro-2-[(4-fluoro-1-benzothiophen-5-yl)amino]benzamide (compound h8) under the same conditions as the production example for compound A-1.

LCMS m/z: 540 $[M+H]^+$

HPLC retention time: 1.10 min (analysis conditions A)

Compound h9:

1,2,3-Trifluoro-4-[(4-methoxyphenyl)methoxy]benzene

[Chemical Formula 222]

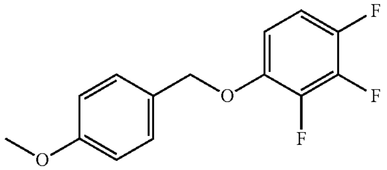

Potassium carbonate (9.90 g, 71.6 mmol) and 4-methoxybenzyl chloride (5.55 mL, 40.9 mmol) were added to an anhydrous acetone solution (101 mL) of 2,3,4-trifluorophenol (5.05 g, 34.1 mmol), and the mixture was stirred for 8 hours at 70° C. Water (150 mL) was added to the reaction mixture, and extraction was performed with ethyl acetate. The organic layer was dried over anhydrous sodium sulfate and, after filtering off the drying agent, concentrated under reduced pressure. DMSO (15 mL) and water (100 mL) were added to the resulting residue, and the obtained solid was washed to give the title compound (8.72 g, 95%) as a gray solid.

LCMS m/z: 267 $[M-H]^-$

HPLC retention time: 0.92 min (analysis conditions C)

Compound h0:

2,3,4-Trifluoro-5-[(4-methoxyphenyl)methoxy]benzoic Acid

[Chemical Formula 223]

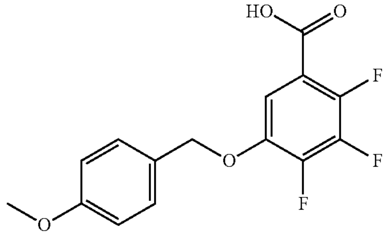

An anhydrous THF solution (15 mL) of 2,2,6,6-tetramethylpiperidine (4.15 mL, 24.6 mmol) was cooled to −78° C., and then a 1.6 M lithium bis(trimethylsilyl)amide hexane solution (15.4 mL, 24.6 mmol) was added under a nitrogen atmosphere and the mixture was stirred for 10 minutes. The reaction mixture was added to an anhydrous THF solution (15 mL) of 1,2,3-trifluoro-4-[(4-methoxyphenyl)methoxy] benzene (compound h9, 3.00 g, 11.2 mmol) at −78° C., and then the mixture was stirred for 3 hours and further stirred for another 30 minutes while injecting carbon dioxide gas. After then adding 1 M hydrochloric acid (60 mL) to the reaction mixture, extraction was performed with ethyl acetate. The organic layer was washed with water, dried over anhydrous sodium sulfate and, after filtering off the drying agent, concentrated under reduced pressure. The resulting residue was purified by reversed-phase column chromatography (0.1% formic acid aqueous solution/0.1% formic acid acetonitrile solution) to give the title compound (1.32 g, 34%) as a gray solid.

LCMS m/z: 311 $[M-H]^-$

HPLC retention time: 0.80 min (analysis conditions C)

Compound h13:

3,4-Difluoro-2-(2-fluoro-4-iodoanilino)-5-methyl Hydroxybenzoate

[Chemical Formula 224]

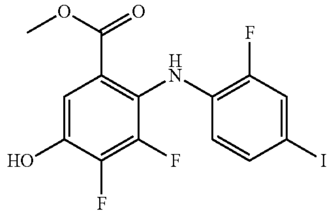

The title compound was synthesized from 2,3,4-trifluoro-5-[(4-methoxyphenyl)methoxy]benzoic acid (compound h10) under the same conditions as the production examples for compound c5, compound a1 and compound a6. However, 2-fluoro-4-iodoaniline was used instead of 4-iodo-2-methylaniline, which was used in the production example for compound c5, and anhydrous THF was used instead of toluene, which was used in the production example for compound a1.

LCMS m/z: 424 $[M+H]^+$

HPLC retention time: 0.91 min (analysis conditions C)

Compound h14:

Methyl 5-[2-[(2,4-dimethoxyphenyl)methylamino]-3-fluoropyridin-4-yl]oxy-3,4-difluoro-2-(2-fluoro-4-iodoanilino)benzoate

[Chemical Formula 225]

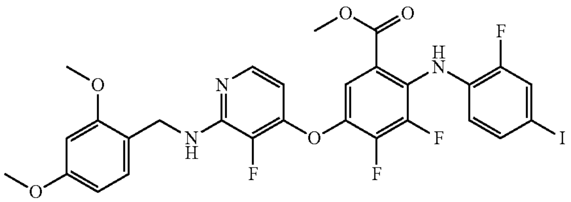

After adding [2-[(2,4-dimethoxyphenyl)methylamino]-3-fluoropyridin-4-yl]boronic acid (compound a4, 814 mg, 2.66 mmol), molecular sieves 4A (375 mg), tetrakis(acetonitrile) copper(I) hexafluorophosphate (495 mg, 1.33 mmol) and pyridine (0.287 mL, 3.55 mmol) to a DCM solution (15 mL) of 3,4-difluoro-2-(2-fluoro-4-iodoanilino)-5-methyl hydroxybenzoate (compound h13, 375 mg, 0.886 mmol), the mixture was stirred for 2.5 hours at room temperature. Next, [2-[(2,4-dimethoxyphenyl)methylamino]-3-fluoropyridin-4-yl]boronic acid (compound a4, 231 mg, 0.753 mmol) was added and the mixture was stirred for 4 hours. After then adding N-acetylcysteine (434 mg, 2.66 mmol) to the reaction mixture, stirring was continued for 3 hours. The solid portion was filtered off and washed with DCM (10 mL), and the filtrate was concentrated under reduced pressure. The resulting residue was purified by reversed-phase column chromatography (0.1% formic acid aqueous solution/0.1% formic acid acetonitrile solution) to give the title compound (168 mg, 28%) as a foam.

LCMS m/z: 684 $[M+H]^+$

HPLC retention time: 1.07 min (analysis conditions C)

Compound H-4:

3,4-Difluoro-2-(2-fluoro-4-iodoanilino)-5-[3-fluoro-2-(methylsulfamoylamino)pyridin-4-yl]oxybenzamide

[Chemical Formula 226]

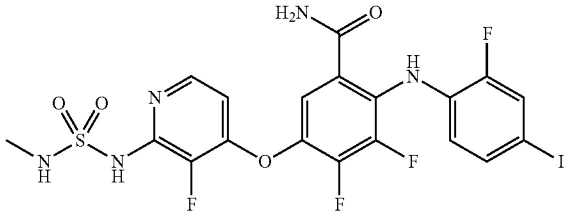

The title compound was synthesized from methyl 5-[2-[(2,4-dimethoxyphenyl)methylamino]-3-fluoropyridin-4-yl]oxy-3,4-difluoro-2-(2-fluoro-4-iodoanilino)benzoate (compound h14) under the same conditions as the production examples for compound a6, compound E-13 and compound A-1.

LCMS m/z: 612 $[M+H]^+$

HPLC retention time: 1.55 min (analysis conditions B)

Compound h17:

5-[[6-[bis[(4-Methoxyphenyl)methyl]amino]pyridin-2-yl]-hydroxymethyl]-3,4-difluoro-2-(2-fluoro-4-iodoanilino)benzoic Acid

[Chemical Formula 227]

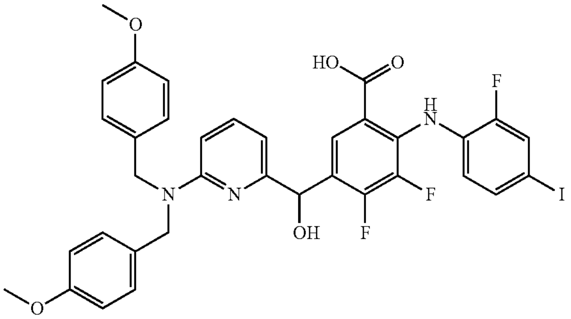

An anhydrous THE solution (12 mL) of 6-bromo-N,N-bis(4-methoxybenzyl)pyridine-2-amine (1.22 g, 2.95 mmol) was cooled to −40° C., and then a 1.6 M lithium bis(trimethylsilyl)amide THE solution (1.85 mL, 2.95 mmol) was added under a nitrogen atmosphere and the mixture was stirred for 30 minutes. The reaction mixture was added to an anhydrous THF solution (2.4 mL) of 3,4-difluoro-2-((2-fluoro-4-iodophenyl)amino)-5-formylbenzoic acid (414 mg, 0.984 mmol) at −78° C., and stirring was continued for 20 minutes. After then adding 1 M hydrochloric acid (2 mL) to the reaction mixture, it was concentrated under reduced pressure. The resulting residue was purified by reversed-phase column chromatography (10 mM ammonium acetate aqueous solution/methanol) to give the title compound (192 mg, 26%) as a yellow solid.

LCMS m/z: 756 $[M+H]^+$

HPLC retention time: 1.06 min (analysis conditions E)

Compound h18:

5-[(6-Aminopyridin-2-yl)methyl]-3,4-difluoro-2-(2-fluoro-4-iodoanilino)benzoic acid

[Chemical Formula 228]

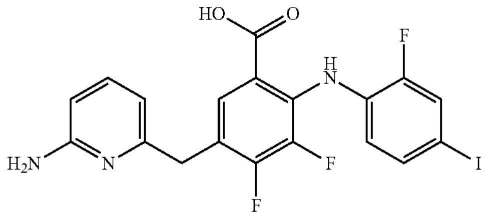

Triethylsilane (0.129 mL, 0.810 mmol), trifluoroacetic acid (0.520 mL, 6.75 mmol) and trifluoromethanesulfonic acid (14 μL, 0.162 mmol) were added to a DCM solution (0.8 mL) of 5-[[6-[bis[(4-methoxyphenyl)methyl]amino]

pyridin-2-yl]-hydroxymethyl]-3,4-difluoro-2-(2-fluoro-4-iodoanilino)benzoic acid (compound h17, 130 mg, 0.162 mmol), and the mixture was stirred for 1 hour at room temperature. Triethylsilane (0.129 mL, 0.810 mmol) and trifluoromethanesulfonic acid (14 μL, 0.162 mmol) were then added and stirring was continued for 5 hours at room temperature. The reaction mixture was purified by reversed-phase column chromatography (0.1% formic acid aqueous solution/0.1% formic acid acetonitrile solution) to give the title compound (72.7 mg, 90%) as a pink solid.

LCMS m/z: 500 $[M+H]^+$

HPLC retention time: 0.61 min (analysis conditions C)

Compound H-5:

3,4-Difluoro-2-(2-fluoro-4-iodoanilino)-5-[[6-(methylsulfamoylamino)pyridin-2-yl]methyl]benzamide

[Chemical Formula 229]

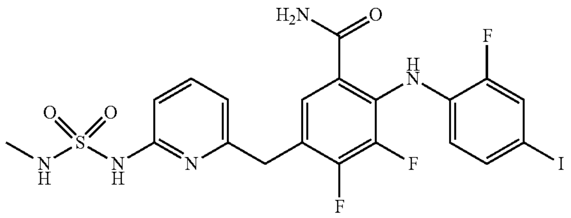

The title compound was synthesized from 5-[(6-aminopyridin-2-yl)methyl]-3,4-difluoro-2-(2-fluoro-4-iodoanilino)benzoic acid (compound h18) under the same conditions as the production examples for compound a8 and compound A-1.

LCMS m/z: 592 $[M+H]^+$

HPLC retention time: 1.19 min (analysis conditions A)

Compound 1-1:

4-Fluoro-2-(2-fluoro-4-iodoanilino)-5-[[3-fluoro-2-(methylsulfamoylamino)pyridin-4-yl]methyl]benzamide

[Chemical Formula 230]

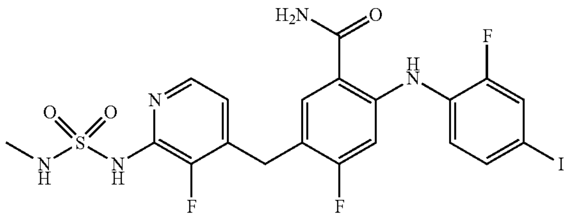

The title compound was synthesized from 2,4-difluoro-5-vinylbenzoic acid under the same conditions as the production examples for compound c5, compound c6, compound c1, compound a5, compound a6 and compound A-1. However, 2-fluoro-4-iodoaniline was used instead of 4-iodo-2-methylaniline, which was used in the production example for compound c5.

LCMS m/z: 592 $[M+H]^+$

HPLC retention time: 1.17 min (analysis conditions A)

Compound I-2:

5-[[2-(Ethylsulfamoylamino)-3-fluoropyridin-4-yl]methyl]-4-fluoro-2-(2-fluoro-4-iodoanilino)benzamide

[Chemical Formula 231]

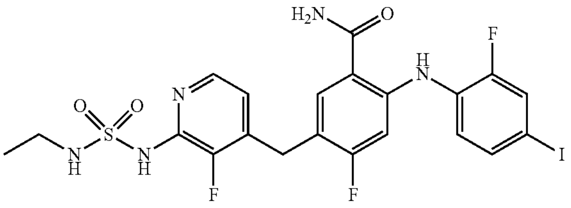

The title compound was synthesized from 2,4-difluoro-5-vinylbenzoic acid under the same conditions as the production examples for compound c5, compound c6, compound c1, compound a5, compound a6 and compound A-1. However, 2-fluoro-4-iodoaniline was used instead of 4-iodo-2-methylaniline, which was used in the production example for compound c5, and the corresponding 4-nitrophenyl sulfamate was used instead of 4-nitrophenyl methylsulfamate, which was used in the production example for compound A-1.

LCMS m/z: 606 $[M+H]^+$

HPLC retention time: 1.62 min (analysis conditions B)

Compound I-3:

5-[[2-(Cyclopropylsulfamoylamino)-3-fluoropyridin-4-yl]methyl]-4-fluoro-2-(2-fluoro-4-iodoanilino)benzamide

[Chemical Formula 232]

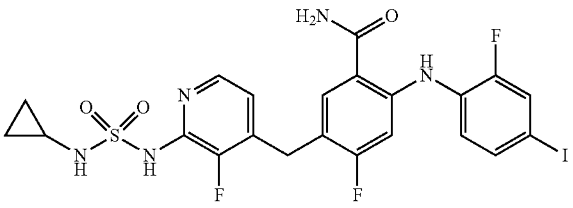

The title compound was synthesized from 2,4-difluoro-5-vinylbenzoic acid under the same conditions as the production examples for compound c5, compound c6, compound c1, compound a5, compound a6 and compound A-1. However, 2-fluoro-4-iodoaniline was used instead of 4-iodo-2-methylaniline, which was used in the production example for compound c5, and the corresponding 4-nitrophenyl sulfamate was used instead of 4-nitrophenyl methylsulfamate, which was used in the production example for compound A-1.

LCMS m/z: 618 $[M+H]^+$

HPLC retention time: 1.64 min (analysis conditions B)

Compound I-4:

4-Fluoro-2-(2-fluoro-4-iodoanilino)-5-[[3-fluoro-2-(2-methoxyethylsulfamoylamino)pyridin-4-yl] methyl]benzamide

[Chemical Formula 233]

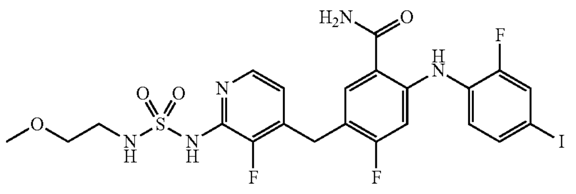

The title compound was synthesized from 2,4-difluoro-5-vinylbenzoic acid under the same conditions as the production examples for compound c5, compound c6, compound c1, compound a5, compound a6 and compound A-1. However, 2-fluoro-4-iodoaniline was used instead of 4-iodo-2-methylaniline, which was used in the production example for compound c5, and the corresponding 4-nitrophenyl sulfamate was used instead of 4-nitrophenyl methylsulfamate, which was used in the production example for compound A-1.

LCMS m/z: 636 $[M+H]^+$

HPLC retention time: 1.19 min (analysis conditions A)

Compound j1:

Methyl 5-[(2-amino-3-fluoropyridin-4-yl)methyl]-2-(2-fluoro-4-iodoanilino)-1-methyl-6-oxopyridine-3-carboxylate

[Chemical Formula 234]

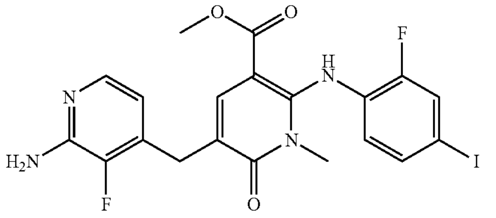

Thionyl chloride (10.6 mL, 145 mmol) was added to a DCM suspension (91 mL) of (2-amino-3-fluoropyridin-4-yl)methanol (10.3 g, 72.7 mmol) over a period of 10 minutes, and the mixture was stirred for 65 minutes at room temperature. After filtering the reaction mixture, the obtained solid was dissolved in ethyl acetate and washed with sodium hydrogen carbonate aqueous solution. The organic layer was dried over anhydrous magnesium sulfate and, after filtering off the drying agent, concentrated under reduced pressure to give a crude product of 2-amino-4-(chloromethyl)-3-fluoropyridine (10.3 g).

The crude product of 2-amino-4-(chloromethyl)-3-fluoropyridine (3.47 g) and tripotassium phosphate (5.00 g, 23.6 mmol) were added to a 1,3-dimethyl-2-imidazolidinone solution (39 mL) of methyl 2-((2-fluoro-4-iodophenyl) amino)-1-methyl-6-oxo-1,6-dihydropyridine-3-carboxylate (7.90 g, 19.7 mmol) and tetrabutylammonium iodide (0.726 g, 1.97 mmol), and the mixture was stirred for 4 hours at 50° C. Water was added to the reaction mixture and the obtained solid was filtered off and washed with a liquid mixture of acetonitrile/water to give the title compound (10.3 g, 60%).

LCMS m/z: 527 $[M+H]^+$

HPLC retention time: 0.63 min (analysis conditions C)

Compound j2:

5-[(2-Amino-3-fluoropyridin-4-yl)methyl]-2-(2-fluoro-4-iodoanilino)-1-methyl-6-oxopyridine-3-carboxylic Acid Hydrochloride

[Chemical Formula 235]

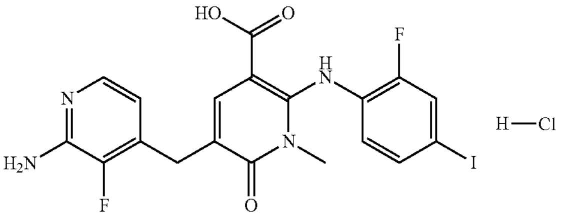

The title compound was synthesized from methyl 5-[(2-amino-3-fluoropyridin-4-yl)methyl]-2-(2-fluoro-4-iodoanilino)-1-methyl-6-oxopyridine-3-carboxylate (compound j1) under the same conditions as the production example for compound a7.

LCMS m/z: 513 $[M+H]^+$

HPLC retention time: 0.76 min (analysis conditions E)

Compound j3:

5-[(2-Amino-3-fluoropyridin-4-yl)methyl]-2-(2-fluoro-4-iodoanilino)-1-methyl-6-oxopyridine-3-carboxamide

[Chemical Formula 236]

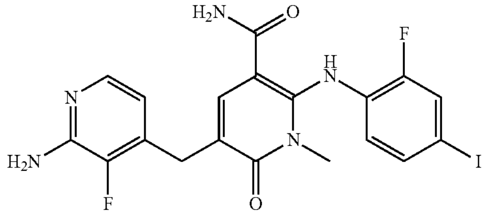

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) under the same conditions as the production example for compound a8.

LCMS m/z: 512 $[M+H]^+$

HPLC retention time: 0.84 min (analysis conditions E)

Compound J-1:

2-(2-Fluoro-4-iodoanilino)-5-[[3-fluoro-2-(methylsulfamoylamino)pyridin-4-yl]methyl]-1-methyl-6-oxopyridine-3-carboxamide

[Chemical Formula 237]

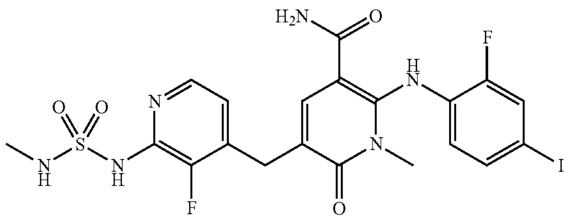

The title compound was synthesized from methyl 5-[(2-amino-3-fluoropyridin-4-yl)methyl]-2-(2-fluoro-4-iodoanilino)-1-methyl-6-oxopyridine-3-carboxamide (compound j3) under the same conditions as the production example for compound A-25.

LCMS m/z: 605 $[M+H]^+$

HPLC retention time: 0.95 min (analysis conditions A)

Compound J-2:

2-(2-Fluoro-4-iodoanilino)-5-[[3-fluoro-2-(2-methoxyethylsulfamoylamino)pyridin-4-yl]methyl]-1-methyl-6-oxopyridine-3-carboxamide

[Chemical Formula 238]

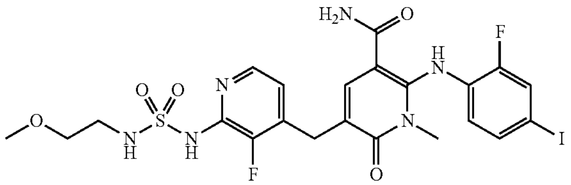

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 649 $[M+H]^+$

HPLC retention time: 0.97 min (analysis conditions A)

Compound J-5:

N-Cyclopropyl-2-(2-fluoro-4-iodoanilino)-5-[[3-fluoro-2-(methylsulfamoylamino)pyridin-4-yl]methyl]-1-methyl-6-oxopyridine-3-carboxamide

[Chemical Formula 239]

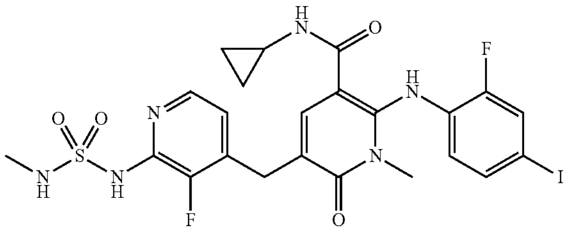

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) and the corresponding amine under the same conditions as the production examples for compound a8 and compound A-1.

LCMS m/z: 645 $[M+H]^+$

HPLC retention time: 1.40 min (analysis conditions B)

Compound J-6:

N-Cyclopropyl-5-[[2-(cyclopropylsulfamoylamino)-3-fluoropyridin-4-yl]methyl]-2-(2-fluoro-4-iodoanilino)-1-methyl-6-oxopyridine-3-carboxamide

[Chemical Formula 240]

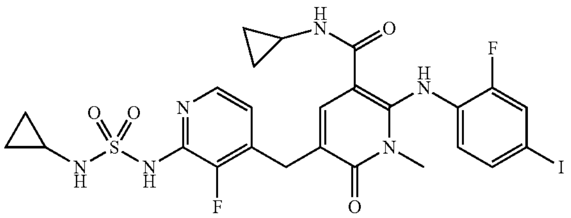

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) and the corresponding amine under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 671 $[M+H]^+$

HPLC retention time: 1.47 min (analysis conditions B)

Compound J-7:

N-Cyclopropyl-2-(2-fluoro-4-iodoanilino)-5-[[3-fluoro-2-(2-methoxyethylsulfamoylamino)pyridin-4-yl]methyl]-1-methyl-6-oxopyridine-3-carboxamide

[Chemical Formula 241]

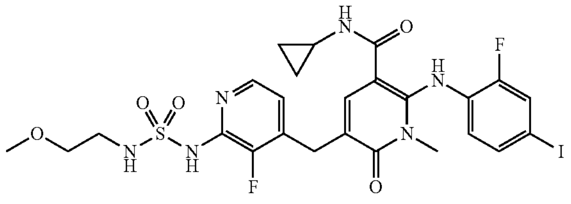

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) and the corresponding amine under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 689 $[M+H]^+$

HPLC retention time: 1.43 min (analysis conditions B)

Compound J-8:

2-(2-Fluoro-4-iodoanilino)-5-[[3-fluoro-2-(methylsulfamoylamino)pyridin-4-yl]methyl]-N-methoxy-1-methyl-6-oxopyridine-3-carboxamide

[Chemical Formula 242]

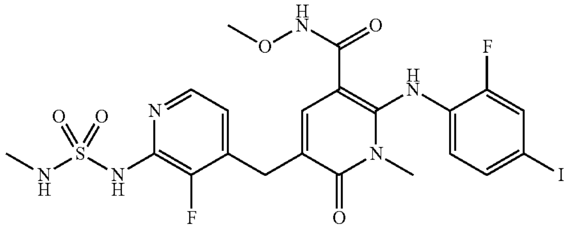

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) and the corresponding amine under the same conditions as the production examples for compound a12 and compound A-1.

LCMS m/z: 635 $[M+H]^+$

HPLC retention time: 1.29 min (analysis conditions B)

Compound J-9:

2-(2-Fluoro-4-iodoanilino)-5-[[3-fluoro-2-(2-methoxyethylsulfamoylamino)pyridin-4-yl]methyl]-N-methoxy-1-methyl-6-oxopyridine-3-carboxamide

[Chemical Formula 243]

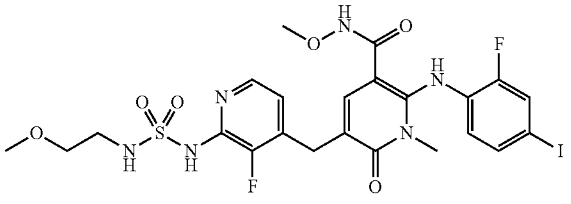

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) and the corresponding amine under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 679 $[M+H]^+$

HPLC retention time: 1.31 min (analysis conditions B)

Compound J-10:

2-(2-Fluoro-4-iodoanilino)-5-[[3-fluoro-2-(methylsulfamoylamino)pyridin-4-yl]methyl]-1-methyl-N-[(2-methylpropan-2-yl)oxy]-6-oxopyridin e-3-carboxamide

[Chemical Formula 244]

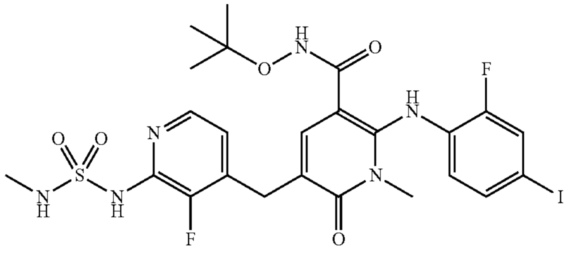

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) under the same conditions as the production examples for compound a12 and compound A-1.

LCMS m/z: 677 $[M+H]^+$

HPLC retention time: 1.46 min (analysis conditions B)

Compound J-11:

5-[[2-(Cyclopropylsulfamoylamino)-3-fluoropyridin-4-yl]methyl]-2-(2-fluoro-4-iodoanilino)-1-methyl-N-[(2-methylpropan-2-yl)oxy]-6-oxopyridine-3-carboxamide

[Chemical Formula 245]

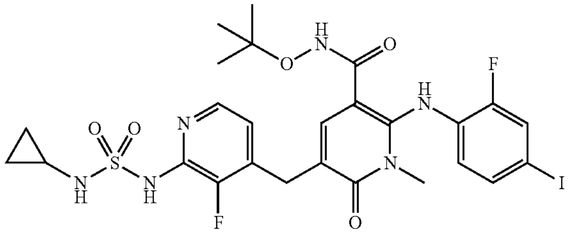

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) under the same conditions as the production examples for compound a12 and compound A-1. However, the corresponding 4-nitrophenyl sulfamate was used instead of 4-nitrophenyl methylsulfamate, which was used in the production example for compound A-1.

LCMS m/z: 703 [M+H]+

HPLC retention time: 1.52 min (analysis conditions B)

Compound J-13:

5-[[2-(Cyclopropylsulfamoylamino)-3-fluoropyridin-4-yl]methyl]-2-(2-fluoro-4-iodoanilino)-1-methyl-6-oxopyridine-3-carboxamide

[Chemical Formula 246]

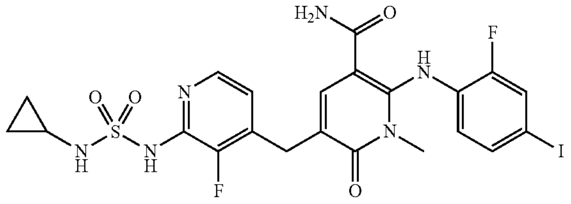

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 631 [M+H]+

HPLC retention time: 1.37 min (analysis conditions B)

Compound J-14:

5-[[2-(Ethylsulfamoylamino)-3-fluoropyridin-4-yl]methyl]-2-(2-fluoro-4-iodoanilino)-1-methyl-6-oxopyridine-3-carboxamide

[Chemical Formula 247]

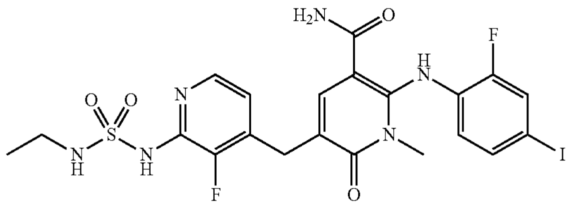

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 619 [M+H]+

HPLC retention time: 1.35 min (analysis conditions B)

Compound J-15:

2-(2-Fluoro-4-iodoanilino)-5-[[3-fluoro-2-[(1-methylcyclobutyl)sulfamoylamino]pyridin-4-yl]methyl]-1-methyl-6-oxopyridine-3-carboxamide

[Chemical Formula 248]

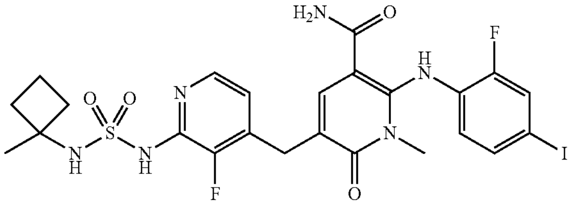

The title compound was synthesized from 5-[(2-amino-3-fluoropyridin-4-yl)methyl]-2-(2-fluoro-4-iodoanilino)-1-methyl-6-oxopyridine-3-carboxylic acid hydrochloride (compound j2) under the same conditions as the production examples for compound a8 and compound A-1. However, the corresponding 4-nitrophenyl sulfamate was used instead of 4-nitrophenyl methylsulfamate, which was used in the production example for compound A-1.

LCMS m/z: 659 [M+H]+

HPLC retention time: 0.77 min (analysis conditions C)

Compound J-3:

2-(4-Cyclopropyl-2-fluoroanilino)-5-[[3-fluoro-2-(methylsulfamoylamino)pyridin-4-yl]methyl]-1-methyl-6-oxopyridine-3-carboxamide

[Chemical Formula 249]

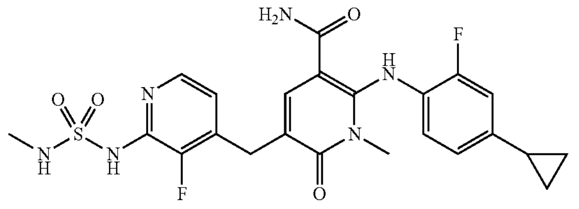

The title compound was synthesized from methyl 5-[(2-amino-3-fluoropyridin-4-yl)methyl]-2-(2-fluoro-4-iodoanilino)-1-methyl-6-oxopyridine-3-carboxamide (compound j3) under the same conditions as the production examples for compound a9 and compound A-1.

LCMS m/z: 519 $[M+H]^+$

HPLC retention time: 1.31 min (analysis conditions B)

Compound J-4:

2-(4-Cyclopropyl-2-fluoroanilino)-5-[[2-(cyclopropylsulfamoylamino)-3-fluoropyridin-4-yl]methyl]-1-methyl-6-oxopyridine-3-carboxamide

[Chemical Formula 250]

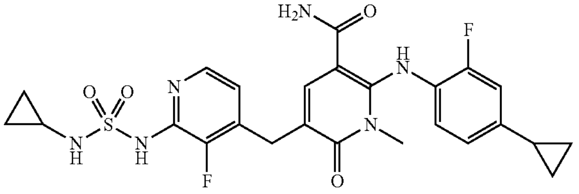

The title compound was synthesized from methyl 5-[(2-amino-3-fluoropyridin-4-yl)methyl]-2-(2-fluoro-4-iodoanilino)-1-methyl-6-oxopyridine-3-carboxamide (compound j3) under the same conditions as the production examples for compound a9 and compound A-1. However, the corresponding 4-nitrophenyl sulfamate was used instead of 4-nitrophenyl methylsulfamate, which was used in the production example for compound A-1.

LCMS m/z: 545 $[M+H]^+$

HPLC retention time: 1.37 min (analysis conditions B)

Compound j12:

5-[[2-(Ethylsulfonylamino)pyridin-4-yl]methyl]-2-(2-fluoro-4-iodoanilino)-1-methyl-6-oxopyridine-3-carboxylic Acid

[Chemical Formula 251]

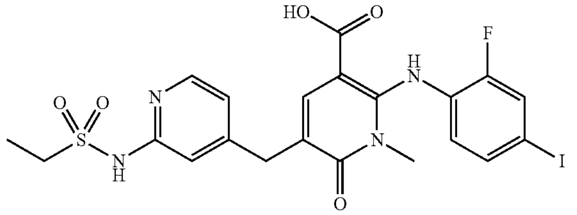

The title compound was synthesized from 2-amino-4-(hydroxymethyl)pyridine under the same conditions as the production examples for compound j1, compound A-25 and compound a7. However, the corresponding sulfonyl chloride was used instead of methylsulfamoyl chloride, which was used in the production example for compound A-25. Pyridine was used as the solvent in the sulfonamidation step.

LCMS m/z: 587 $[M+H]^+$

HPLC retention time: 0.64 min (analysis conditions C)

Compound J-12:

5-[[2-(Ethylsulfonylamino)pyridin-4-yl]methyl]-2-(2-fluoro-4-iodoanilino)-1-methyl-6-oxopyridine-3-carboxamide

[Chemical Formula 252]

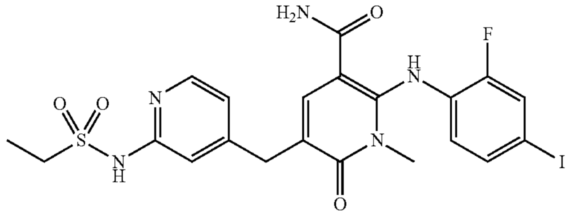

A DMF solution (85 μL) of 5-[[2-(ethylsulfonylamino)pyridin-4-yl]methyl]-2-(2-fluoro-4-iodoanilino)-1-methyl-6-oxopyridine-3-carboxylic acid (compound j12, 10 mg, 0.017 mmol) and ammonium chloride (2.74 mg, 0.051 mmol) was cooled to 0° C., and then HATU (13.0 mg, 0.034 mmol) and DIPEA (17.9 μL, 0.102 mmol) were added and the mixture was stirred overnight at room temperature. The reaction mixture was purified by reversed-phase column chromatography (0.1% formic acid aqueous solution/0.1% formic acid acetonitrile solution) to give the title compound (7.2 mg, 29%) as a colorless solid.

LCMS m/z: 586 $[M+H]^+$

HPLC retention time: 1.24 min (analysis conditions B)

Compound k1:

Methyl 2-(2-fluoro-4-iodoanilino)-5-formyl-1-methyl-6-oxopyridine-3-carboxylate

[Chemical Formula 253]

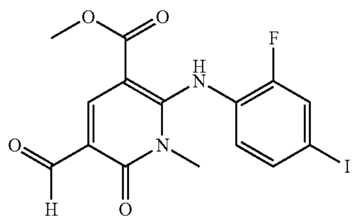

After adding (chloromethylene)dimethyliminium chloride (168 mg, 1.31 mmol) to an acetonitrile solution (2.7 mL) of methyl 2-((2-fluoro-4-iodophenyl)amino)-1-methyl-6-oxo-1,6-dihydropyridine-3-carboxylate (132 mg, 0.328 mmol), the mixture was stirred for 1.5 hours at room temperature. Water was added to the reaction mixture, stirring was continued for 30 minutes, and then the solid was filtered off to give the title compound (108 mg, 76%).

LCMS m/z: 431 $[M+H]^+$

HPLC retention time: 0.80 min (analysis conditions C)

Compound k4:

Methyl 5-[(3-amino-2-fluorophenyl)methyl]-2-(2-fluoro-4-iodoanilino)-1-methyl-6-oxopyridine-3-carboxylate

[Chemical Formula 254]

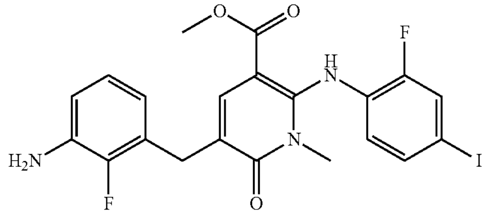

The title compound was synthesized from methyl 2-(2-fluoro-4-iodoanilino)-5-formyl-1-methyl-6-oxopyridine-3-carboxylate (compound k1) under the same conditions as the production examples for compound a2, compound a5 and compound a6. However, 2-nitrobenzene-1-sulfonohydrazide was used instead of 4-methylbenzenesulfonyl hydrazide, which was used in the production example for compound a2. Also, [2-fluoro-3-[(2-methylpropan-2-yl)oxycarbonylamino]phenyl]boronic acid and DIPEA were used instead of [2-[(2,4-dimethoxyphenyl)methylamino]-3-fluoropyridin-4-yl]boronic acid (compound a4) and potassium carbonate respectively, which were used in the production example for compound a5.

LCMS m/z: 526 $[M+H]^+$

HPLC retention time: 0.90 min (analysis conditions C)

Compound K-1:

2-(2-Fluoro-4-iodoanilino)-5-[[2-fluoro-3-(methylsulfamoylamino)phenyl]methyl]-1-methyl-6-oxopyridine-3-carboxamide

[Chemical Formula 255]

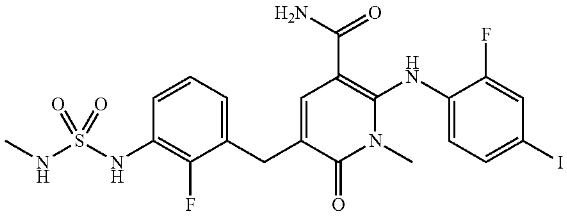

The title compound was synthesized from methyl 5-[(3-amino-2-fluorophenyl)methyl]-2-(2-fluoro-4-iodoanilino)-1-methyl-6-oxopyridine-3-carboxylate (compound k4) under the same conditions as the production examples for compound b2, compound a8 and compound A-1.

LCMS m/z: 604 $[M+H]^+$

HPLC retention time: 1.37 min (analysis conditions B)

Compound K-2:

5-[[3-(Ethylsulfamoylamino)-2-fluorophenyl]methyl]-2-(2-fluoro-4-iodoanilino)-1-methyl-6-oxopyridine-3-carboxamide

[Chemical Formula 256]

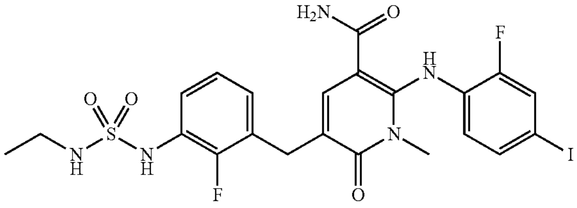

The title compound was synthesized from methyl 5-[(3-amino-2-fluorophenyl)methyl]-2-(2-fluoro-4-iodoanilino)-1-methyl-6-oxopyridine-3-carboxylate (compound k4) under the same conditions as the production examples for compound b2, compound a8 and compound A-1. However, the corresponding 4-nitrophenyl sulfamate was used instead of 4-nitrophenyl methylsulfamate, which was used in the production example for compound A-1.

LCMS m/z: 618 $[M+H]^+$

HPLC retention time: 1.41 min (analysis conditions B)

Compound K-3:

5-[[3-(Cyclopropylsulfamoylamino)-2-fluorophenyl]methyl]-2-(2-fluoro-4-iodoanilino)-1-methyl-6-oxopyridine-3-carboxamide

[Chemical Formula 257]

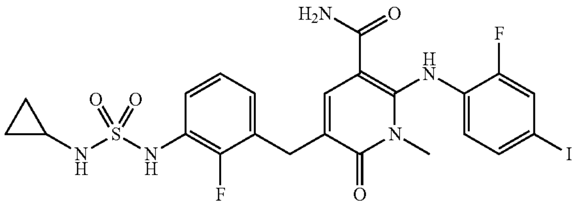

The title compound was synthesized from methyl 5-[(3-amino-2-fluorophenyl)methyl]-2-(2-fluoro-4-iodoanilino)-1-methyl-6-oxopyridine-3-carboxylate (compound k4) under the same conditions as the production examples for compound b2, compound a8 and compound A-1. However, the corresponding 4-nitrophenyl sulfamate was used instead of 4-nitrophenyl methylsulfamate, which was used in the production example for compound A-1.

LCMS m/z: 630 $[M+H]^+$

HPLC retention time: 1.43 min (analysis conditions B)

Compound K-4:

N-Cyclopropyl-2-(2-fluoro-4-iodoanilino)-5-[[2-fluoro-3-(methylsulfamoylamino)phenyl]methyl]-1-methyl-6-oxopyridine-3-carboxamide

[Chemical Formula 258]

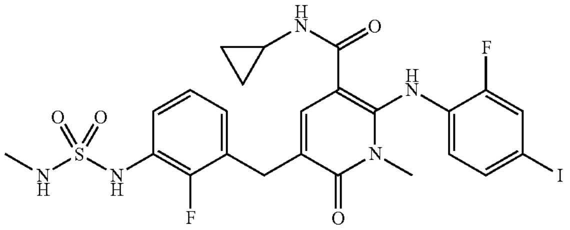

The title compound was synthesized from methyl 5-[(3-amino-2-fluorophenyl)methyl]-2-(2-fluoro-4-iodoanilino)-1-methyl-6-oxopyridine-3-carboxylate (compound k4) under the same conditions as the production examples for compound b2, compound a10 and compound A-1.

LCMS m/z: 644 $[M+H]^+$

HPLC retention time: 1.48 min (analysis conditions B)

Compound K-5:

N-Cyclopropyl-5-[[3-(cyclopropylsulfamoylamino)-2-fluorophenyl]methyl]-2-(2-fluoro-4-iodoanilino)-1-methyl-6-oxopyridine-3-carboxamide

[Chemical Formula 259]

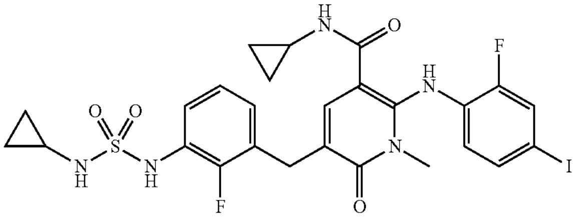

The title compound was synthesized from methyl 5-[(3-amino-2-fluorophenyl)methyl]-2-(2-fluoro-4-iodoanilino)-1-methyl-6-oxopyridine-3-carboxylate (compound k4) under the same conditions as the production examples for compound b2, compound a10 and compound A-1. However, the corresponding 4-nitrophenyl sulfamate was used instead of 4-nitrophenyl methylsulfamate, which was used in the production example for compound A-1.

LCMS m/z: 670 $[M+H]^+$

HPLC retention time: 1.53 min (analysis conditions B)

Compound K-13:

N-Cyclopropyl-5-[[3-(ethylsulfamoylamino)-2-fluorophenyl]methyl]-2-(2-fluoro-4-iodoanilino)-1-methyl-6-oxopyridine-3-carboxamide

[Chemical Formula 260]

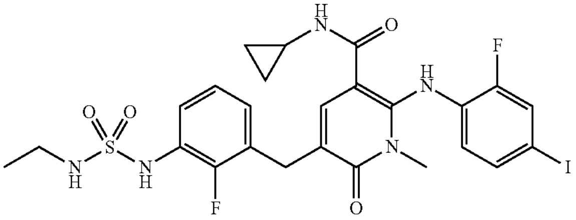

The title compound was synthesized from methyl 5-[(3-amino-2-fluorophenyl)methyl]-2-(2-fluoro-4-iodoanilino)-1-methyl-6-oxopyridine-3-carboxylate (compound k4) under the same conditions as the production examples for compound b2, compound a10 and compound A-1. However, the corresponding 4-nitrophenyl sulfamate was used instead of 4-nitrophenyl methylsulfamate, which was used in the production example for compound A-1.

LCMS m/z: 658 $[M+H]^+$

HPLC retention time: 1.52 min (analysis conditions B)

Compound K-6:

2-(2-Fluoro-4-iodoanilino)-5-[[2-fluoro-3-[(1-methylcyclopropyl)sulfonylamino]phenyl]methyl]-1-methyl-6-oxopyridine-3-carboxamide

[Chemical Formula 261]

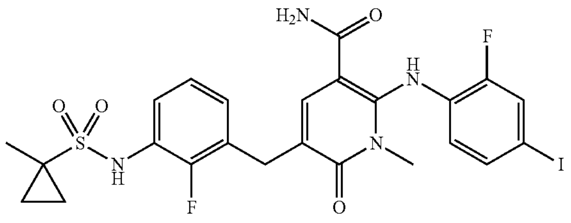

The title compound was synthesized from methyl 5-[(3-amino-2-fluorophenyl)methyl]-2-(2-fluoro-4-iodoanilino)-1-methyl-6-oxopyridine-3-carboxylate (compound k4) and the corresponding sulfonyl chloride under the same conditions as the production examples for compound A-25, compound b2 and compound a8. However, pyridine was used as the solvent in the sulfonamidation step.

LCMS m/z: 629 $[M+H]^+$

HPLC retention time: 1.48 min (analysis conditions B)

Compound K-7:

2-(2-Fluoro-4-iodoanilino)-5-[[2-fluoro-3-[(1-methylcyclopropyl)sulfonylamino]phenyl]methyl]-N-methoxy-1-methyl-6-oxopyridine-3-carboxamide

[Chemical Formula 262]

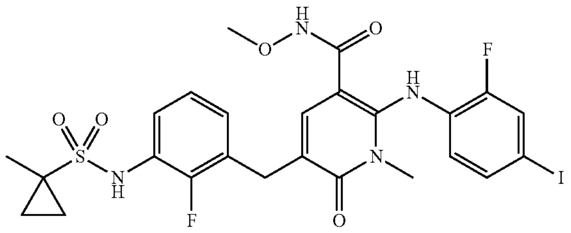

The title compound was synthesized from methyl 5-[(3-amino-2-fluorophenyl)methyl]-2-(2-fluoro-4-iodoanilino)-1-methyl-6-oxopyridine-3-carboxylate (compound k4) and the corresponding sulfonyl chloride under the same conditions as the production examples for compound A-25, compound b2 and compound a12. However, pyridine was used as the solvent in the sulfonamidation step. Also, the corresponding amine was used instead of tert-butoxyamine hydrochloride, which was used in the production example for compound a12.

LCMS m/z: 659 $[M+H]^+$

HPLC retention time: 1.47 min (analysis conditions B)

Compound K-11:

N-Cyclopropyl-2-(2-fluoro-4-iodoanilino)-5-[[2-fluoro-3-[(1-methylcyclopropyl)sulfonylamino]phenyl]methyl]-1-methyl-6-oxopyridine-3-carboxamide

[Chemical Formula 263]

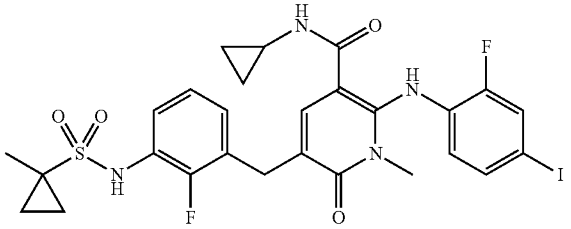

The title compound was synthesized from methyl 5-[(3-amino-2-fluorophenyl)methyl]-2-(2-fluoro-4-iodoanilino)-1-methyl-6-oxopyridine-3-carboxylate (compound k4) and the corresponding sulfonyl chloride under the same conditions as the production examples for compound A-25, compound b2 and compound a8. However, pyridine was used as the solvent in the sulfonamidation step. The corresponding amine was used instead of a 7 M ammonia MeOH solution, which was used in the production example for compound a8.

LCMS m/z: 669 $[M+H]^+$

HPLC retention time: 1.59 min (analysis conditions B)

Compound K-12:

2-(2-Fluoro-4-iodoanilino)-5-[[2-fluoro-3-[(1-methylcyclopropyl)sulfonylamino]phenyl]methyl]-1-methyl-N-[(2-methylpropan-2-yl)oxy]-6-oxopyridine-3-carboxamide

[Chemical Formula 264]

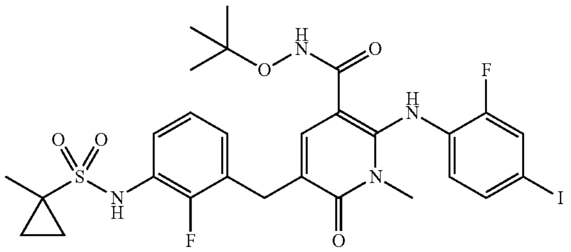

The title compound was synthesized from methyl 5-[(3-amino-2-fluorophenyl)methyl]-2-(2-fluoro-4-iodoanilino)-1-methyl-6-oxopyridine-3-carboxylate (compound k4) and the corresponding sulfonyl chloride under the same conditions as the production examples for compound A-25, compound b2 and compound a12. However, pyridine was used as the solvent in the sulfonamidation step.

LCMS m/z: 701 $[M+H]^+$

HPLC retention time: 1.62 min (analysis conditions B)

Compound k11:

5-[[3-(Ethylsulfonylamino)-2-fluorophenyl]methyl]-2-(2-fluoro-4-iodoanilino)-1-methyl-6-oxopyridine-3-carboxylic Acid

[Chemical Formula 265]

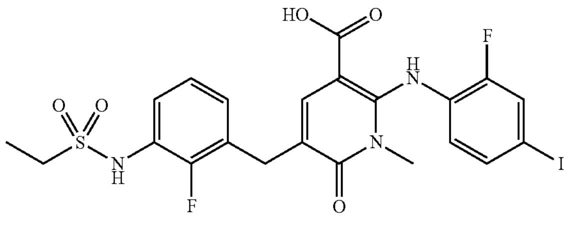

The title compound was synthesized from methyl 5-[(3-amino-2-fluorophenyl)methyl]-2-(2-fluoro-4-iodoanilino)-1-methyl-6-oxopyridine-3-carboxylate (compound k4) and the corresponding sulfonyl chloride under the same conditions as the production examples for compound A-25 and compound b2. However, pyridine was used as the solvent in the sulfonamidation step.

LCMS m/z: 604 $[M+H]^+$

HPLC retention time: 0.77 min (analysis conditions C)

Compound K-8:

N-Cyclopropyl-5-[[3-(ethylsulfonylamino)-2-fluorophenyl]methyl]-2-(2-fluoro-4-iodoanilino)-1-methyl-6-oxopyridine-3-carboxamide

[Chemical Formula 266]

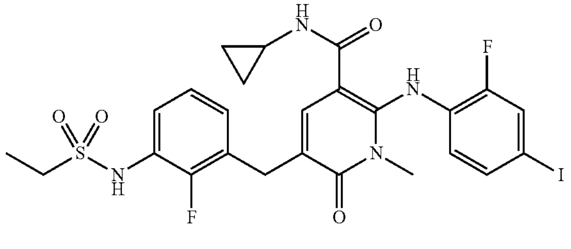

The title compound was synthesized from 5-[[3-(ethylsulfonylamino)-2-fluorophenyl]methyl]-2-(2-fluoro-4-iodoanilino)-1-methyl-6-oxopyridine-3-carboxylic acid (compound k1) under the same conditions as the production example for compound a10.

LCMS m/z: 643 $[M+H]^+$

HPLC retention time: 1.53 min (analysis conditions B)

Compound K-9:

5-[[3-(Ethylsulfonylamino)-2-fluorophenyl]methyl]-2-(2-fluoro-4-iodoanilino)-1-methyl-N-[(2-methylpropan-2-yl]oxy-6-oxopyridine-3-carboxamide

[Chemical Formula 267]

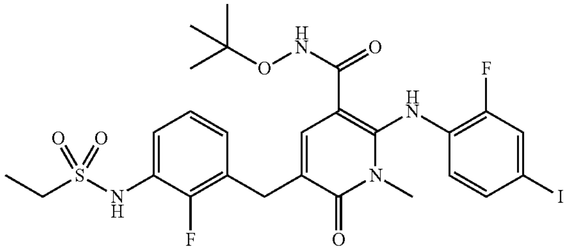

The title compound was synthesized from 5-[[3-(ethylsulfonylamino)-2-fluorophenyl]methyl]-2-(2-fluoro-4-iodoanilino)-1-methyl-6-oxopyridine-3-carboxylic acid (compound k11) under the same conditions as the production example for compound a12.

LCMS m/z: 675 $[M+H]^+$

HPLC retention time: 1.57 min (analysis conditions B)

Compound K-10:

5-[[3-(Ethylsulfonylamino)-2-fluorophenyl]methyl]-2-(2-fluoro-4-iodoanilino)-1-methyl-6-oxopyridine-3-carboxamide

[Chemical Formula 268]

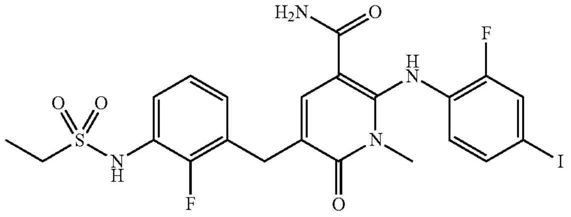

After adding HOOBt (8.92 mg, 0.055 mmol) and EDC·HCl (10.5 mg, 0.055 mmol) to an anhydrous DMF solution (0.264 mL) of 5-[[3-(ethylsulfonylamino)-2-fluorophenyl]methyl]-2-(2-fluoro-4-iodoanilino)-1-methyl-6-oxopyridine-3-carboxylic acid (compound k11, 22.0 mg, 0.036 mmol), the mixture was stirred for 3 hours at room temperature. After then adding a 7 M ammonia MeOH solution (20.8 μL, 0.146 mmol) at 0° C., stirring was continued for 1 hour. The reaction mixture was purified by reversed-phase column chromatography (0.1% formic acid aqueous solution/0.1% formic acid acetonitrile solution) to give the title compound (15.8 mg, 72%) as a colorless solid.

LCMS m/z: 603 $[M+H]^+$

HPLC retention time: 1.42 min (analysis conditions B)

Compound 12:

Methyl 2-bromo-5-(2-fluoro-4-trimethylsilylaniline) pyridine-4-carboxylate

[Chemical Formula 269]

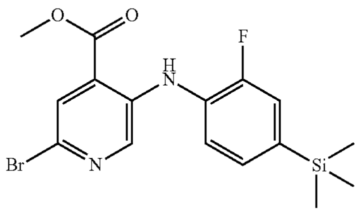

The title compound was synthesized from 2-bromo-5-fluoropyridine-4-carboxylic acid under the same conditions as the production examples for compound c5 and compound a1. However, 2-fluoro-4-trimethylsilylaniline was used instead of 4-iodo-2-methylaniline, which was used in the production example for compound c5.

LCMS m/z: 397 $[M+H]^+$

HPLC retention time: 1.17 min (analysis conditions G)

Compound 13a:

Methyl 5-(2-fluoro-4-trimethylsilylaniline)-2-formylpyridine-4-carboxylate

[Chemical Formula 270]

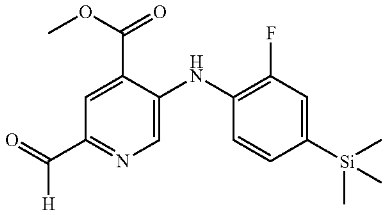

Compound 13b:

5-(2-Fluoro-4-trimethylsilylaniline)-4-methoxycarbonylpyridine-2-carb oxylic acid

[Chemical Formula 271]

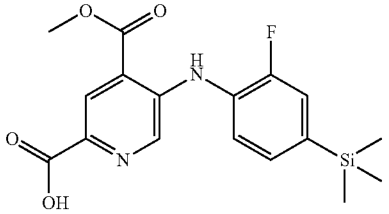

After adding an anhydrous DMF solution (63 mL) of triethylsilane (2.01 mL, 12.6 mmol) to an anhydrous DMF suspension (63 mL) of methyl 2-bromo-5-(2-fluoro-4-trimethylsilylaniline)pyridine-4-carboxylate (compound 12, 2.5 g, 6.29 mmol), 1,1,3-trioxo-1,2-benzothiazole-2-carbaldehyde (2.66 g, 612.6 mmol), Xantphos (728 mg, 1.26 mmol), palladium acetate (141 mg, 0.629 mmol) and sodium carbonate (1.67 g, 15.7 mmol), the mixture was stirred for 10 minutes at room temperature and then for 2.5 hours at 75° C. The reaction mixture was purified by reversed-phase column chromatography (0.1% formic acid aqueous solution/0.1% formic acid acetonitrile solution) to give compound 13a (0.4 g, 18%) and compound 13b (1.4 g, 61%), each as a yellow solid.

Compound 13a

LCMS m/z: 347 $[M+H]^+$

HPLC retention time: 1.06 min (analysis conditions G)

Compound 13b

LCMS m/z: 363 $[M+H]^+$

HPLC retention time: 0.92 min (analysis conditions G)

Compound 14:

Methyl 5-(2-fluoro-4-trimethylsilylaniline)-2-(hydroxymethyl)pyridine-4-carboxylate

[Chemical Formula 272]

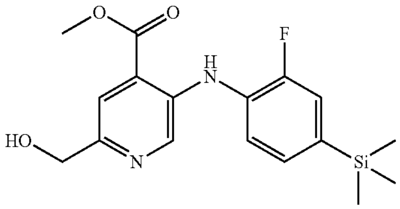

After adding a 1 M borane-tetrahydrofuran complex THE solution (4.33 mL, 4.33 mmol) to an anhydrous THF solution (14 mL) of methyl 5-(2-fluoro-4-trimethylsilylaniline)-2-formylpyridine-4-carboxylate (compound 13a, 500 mg, 1.44 mmol), the mixture was stirred for 1 hour at room temperature. Acetic acid (0.496 mL, 8.66 mmol) was added to the reaction mixture, which was then concentrated under reduced pressure. The resulting residue was purified by reversed-phase column chromatography (0.1% formic acid aqueous solution/0.1% formic acid acetonitrile solution) to give the title compound (360 mg, 72%) as a light yellow solid.

LCMS m/z: 349 $[M+H]^+$

HPLC retention time: 0.91 min (analysis conditions G)

Compound 14:

Methyl 5-(2-fluoro-4-trimethylsilylaniline)-2-(hydroxymethyl)pyridine-4-carboxylate

[Chemical Formula 273]

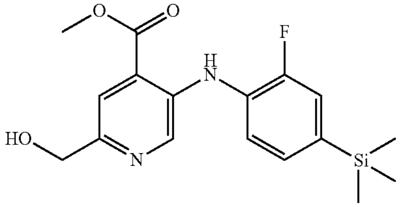

After adding a borane-dimethyl sulfide complex (0.747 mL, 7.86 mmol) to an anhydrous THF solution (16 mL) of 5-(2-fluoro-4-trimethylsilylaniline)-4-methoxycarbonylpyridine-2-carboxylic acid (compound 13b, 570 mg, 1.57 mmol), the mixture was stirred for 2 hours at room temperature. Acetic acid (1.58 mL, 27.6 mmol) was added to the reaction mixture, which was then concentrated under reduced pressure. The resulting residue was purified by reversed-phase column chromatography (0.1% formic acid aqueous solution/0.1% formic acid acetonitrile solution) to give the title compound (350 mg, 64%) as a light yellow solid.

LCMS m/z: 349 $[M+H]^+$

HPLC retention time: 0.91 min (analysis conditions G)

Compound 15:

Methyl 2-(chloromethyl)-5-(2-fluoro-4-trimethylsilylaniline)pyridine-4-carboxylate

[Chemical Formula 274]

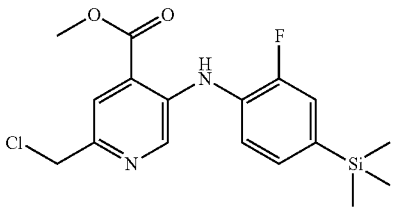

After adding thionyl chloride (0.168 mL, 2.30 mmol) to a DCM solution (12 mL) of methyl 5-(2-fluoro-4-trimethylsilylaniline)-2-(hydroxymethyl)pyridine-4-carboxylate (compound 14, 400 mg, 1.15 mmol), the mixture was stirred for 50 minutes at room temperature. The reaction mixture was concentrated under reduced pressure to give a crude product of the title compound (400 mg).

LCMS m/z: 367 $[M+H]^+$

HPLC retention time: 1.11 min (analysis conditions G)

Compound 16:

Methyl 2-[[2-[(2,4-dimethoxyphenyl)methylamino]-3-fluoropyridin-4-yl]methyl]-5-(2-fluoro-4-trimethylsilylaniline)pyridine-4-carboxylate

[Chemical Formula 275]

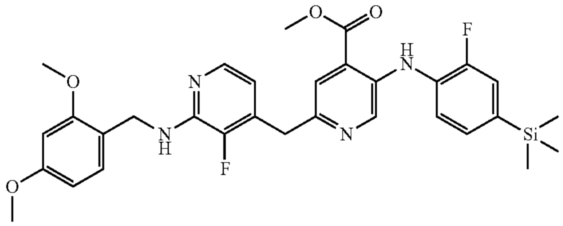

A 1,4-dioxane suspension (17 mL) of methyl 2-(chloromethyl)-5-(2-fluoro-4-trimethylsilylaniline)pyridine-4-carboxy late (compound 15, 584 mg, 1.59 mmol), [2-[(2,4-dimethoxyphenyl)methylamino]-3-fluoropyridin-4-yl] boronic acid (compound a4, 731 mg, 2.39 mmol), tetrakistriphenylphosphine palladium (184 mg, 0.159 mmol) and potassium carbonate (660 mg, 4.78 mmol) was stirred for 2 hours at 110° C. Water was added to the reaction mixture, and extraction was performed with ethyl acetate.

The organic layer was washed with saturated brine, dried over anhydrous sodium sulfate and, after filtering off the drying agent, concentrated under reduced pressure. The resulting residue was purified by column chromatography (hexane/ethyl acetate) to give the title compound (583 mg, 62%) as a yellow solid.

LCMS m/z: 593 $[M+H]^+$

HPLC retention time: 1.13 min (analysis conditions G)

Compound 17:

Methyl 2-[(2-amino-3-fluoropyridin-4-yl)methyl]-5-(2-fluoro-4-trimethylsilylaniline)pyridine-4-carboxylate

[Chemical Formula 276]

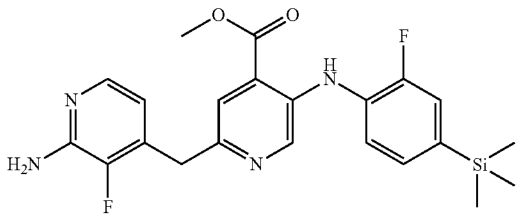

The title compound was synthesized from methyl 2-[[2-[(2,4-dimethoxyphenyl)methylamino]-3-fluoropyridin-4-yl]methyl]-5-(2-fluoro-4-trimethylsilylaniline)pyridine-4-carboxylate (compound 16) under the same conditions as the production example for compound a6.

LCMS m/z: 443 $[M+H]^+$

HPLC retention time: 0.83 min (analysis conditions G)

Compound 18:

Methyl 2-[(2-amino-3-fluoropyridin-4-yl)methyl]-5-(2-fluoro-4-iodoanilino)pyridine-4-carboxylate

[Chemical Formula 277]

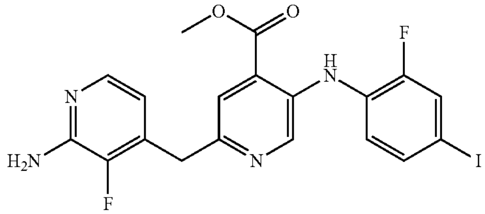

An anhydrous DCM solution (14 mL) of methyl 2-[(2-amino-3-fluoropyridin-4-yl)methyl]-5-(2-fluoro-4-trimethylsilylaniline)pyridine-4-carboxylate (compound 17, 300 mg, 0.678 mmol) was cooled to 0° C., iodine monochloride (220 mg, 1.36 mmol) was added, and the mixture was stirred for 30 minutes at 0° C. and then for 3 hours at room temperature. The reaction mixture was concentrated under reduced pressure, and the resulting residue was purified by reversed-phase column chromatography to give the title compound (320 mg, 95%) as a yellow solid.

LCMS m/z: 497 $[M+H]^+$

HPLC retention time: 0.69 min (analysis conditions G)

Compound L-1:

5-(2-Fluoro-4-iodoanilino)-2-[[3-fluoro-2-(methylsulfamoylamino)pyridin-4-yl]methyl]pyridine-4-carboxamide

[Chemical Formula 278]

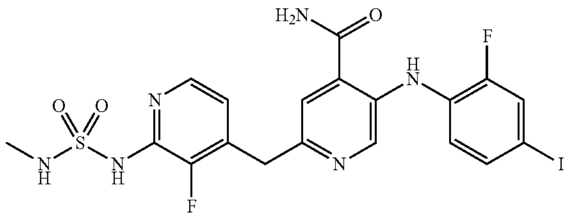

The title compound was synthesized from methyl 2-[(2-amino-3-fluoropyridin-4-yl)methyl]-5-(2-fluoro-4-iodoanilino)pyridine-4-carboxylate (compound 18) under the same conditions as the production examples for compound a7, compound K-10 and compound A-1.

LCMS m/z: 575 $[M+H]^+$

HPLC retention time: 1.36 min (analysis conditions B)

Compound m1:

Methyl 2-amino-6-(aminomethyl)pyridine-3-carboxylate Diacetate

[Chemical Formula 279]

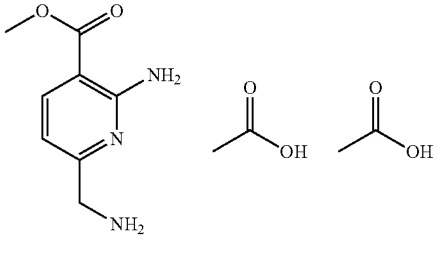

After adding a palladium on activated carbon powder catalyst (10% palladium) (933 mg, 0.877 mmol) to a mixed solution of methyl 2-amino-6-cyanopyridine-3-carboxylate (9.14 g, 51.6 mmol) in acetic acid (100 mL) and methanol (100 mL), the mixture was stirred for 4 hours at room temperature under a hydrogen atmosphere. The reaction mixture was filtered with Celite, and the filtrate was concentrated under reduced pressure to give a crude product of the title compound (15.3 g).

LCMS m/z: 182 $[M+H]^+$

HPLC retention time: 0.26 min (analysis conditions G)

Compound m2:

Methyl 2-amino-6-(formamidomethyl)pyridine-3-carboxylate

[Chemical Formula 280]

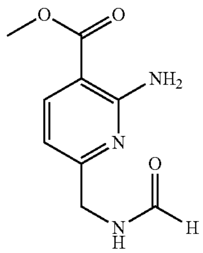

Acetic anhydride (115 mL, 1.22 mol) was added to a formic acid solution (230 mL) of methyl 2-amino-6-(aminomethyl)pyridine-3-carboxylate diacetate (compound m1, 14.7 g, 48.8 mmol) over a period of 30 minutes, and the mixture was stirred overnight at 70° C. The reaction mixture was concentrated under reduced pressure, a saturated sodium hydrogen carbonate aqueous solution was added to the resulting residue, and extraction was performed with ethyl acetate. The organic layer was washed with saturated brine, dried over anhydrous magnesium sulfate and, after filtering off the drying agent, concentrated under reduced pressure. The resulting residue was purified by amino-silica gel column chromatography (hexane/DCM) to give the title compound (8.16 g, 80%) as a yellow solid.

LCMS m/z: 210 $[M+H]^+$

HPLC retention time: 0.29 min (analysis conditions G)

Compound m3:

Methyl 2-amino-5-bromo-6-(formamidomethyl) pyridine-3-carboxylate

[Chemical Formula 281]

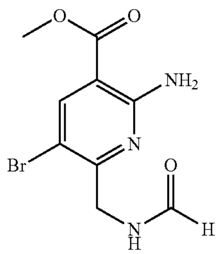

After adding N-bromosuccinimide (7.87 g, 44.2 mmol) to an anhydrous acetonitrile solution (400 mL) of methyl 2-amino-6-(formamidomethyl)pyridine-3-carboxylate (compound m2, 9.25 g, 44.2 mmol) in several portions, the mixture was stirred for 1 hour at room temperature. The reaction mixture was concentrated under reduced pressure and water was added to the resulting residue. The obtained solid was washed with water to give the title compound (12.0 g, 94%) as a yellow solid.

LCMS m/z: 288 $[M+H]^+$

HPLC retention time: 0.52 min (analysis conditions G)

Compound m4:

Methyl 5-amino-8-bromoimidazo[1,5-a]pyridine-6-carboxylate

[Chemical Formula 282]

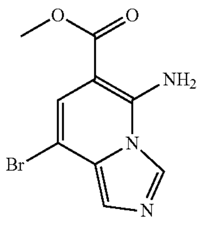

After adding phosphoryl chloride (17.5 mL, 187 mmol) to an anhydrous toluene suspension (200 mL) of methyl 2-amino-5-bromo-6-(formamidomethyl)pyridine-3-carboxylate (compound m3, 12.0 g, 41.7 mmol), the mixture was stirred for 1 hour at 95° C. The reaction mixture was concentrated under reduced pressure, and a saturated sodium hydrogen carbonate aqueous solution and water were added to the resulting residue. The obtained solid was washed with water and dissolved in DCM, and then dried over anhydrous magnesium sulfate. After filtering off the drying agent, the filtrate was concentrated under reduced pressure to give the title compound (10.5 g, 93%) as a light brown solid.

LCMS m/z: 270 $[M+H]^+$

HPLC retention time: 0.65 min (analysis conditions G)

Compound m5:

Methyl 5-[bis[(2-methylpropan-2-yl)oxycarbonyl]amino]-8-bromoimidazo[1,5-a]pyridine-6-carboxylate

[Chemical Formula 283]

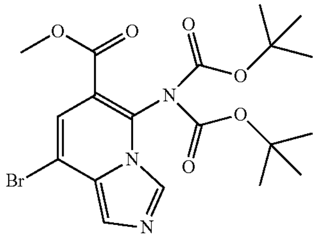

After adding 4-dimethylaminopyridine (143 mg, 1.17 mmol) to an anhydrous DCM solution (50 mL) of methyl 5-amino-8-bromoimidazo[1,5-a]pyridine-6-carboxylate (compound m4, 1.58 g, 5.85 mmol) and di-tert-butyl dicarbonate (3.19 g, 14.6 mmol), the mixture was stirred for 2 hours at room temperature. The reaction mixture was concentrated under reduced pressure, and the resulting residue was purified by silica gel column chromatography to give the title compound (2.5 g, 91%) as a yellow solid.

LCMS m/z: 470 $[M+H]^+$

HPLC retention time: 0.95 min (analysis conditions G)

Compound m6:

Methyl 5-[bis[(2-methylpropan-2-yl)oxycarbonyl]amino]-8-ethenylimidazo[1,5-a]pyridine-6-carboxylate

[Chemical Formula 284]

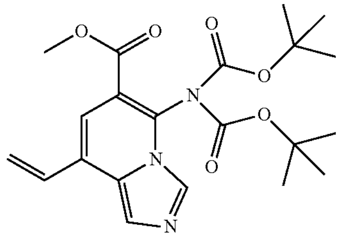

A mixed suspension of methyl 5-[bis[(2-methylpropan-2-yl)oxycarbonyl]amino]-8-bromoimidazo[1,5-a]pyridine-6-carboxylate (compound m5, 2.5 g, 5.32 mmol), potassium vinyl trifluoroborane (1.07 g, 7.97 mmol), tetrakistriphenylphosphine palladium (614 mg, 0.532 mmol) and cesium carbonate (5.20 g, 16.0 mmol) in 1,4-dioxane (40 mL) and water (10 mL) was stirred for 2 hours at 100° C. The reaction mixture was extracted with ethyl acetate and the organic layer was washed with saturated brine and dried over anhydrous magnesium sulfate. After filtering off the drying agent, the mixture was concentrated under reduced pressure and the resulting residue was purified by silica gel column chromatography to give the title compound (1.68 g, 76%) as a yellow solid.

LCMS m/z: 418 $[M+H]^+$

HPLC retention time: 0.89 min (analysis conditions G)

Compound m8:

Methyl 5-amino-8-formylimidazo[1,5-a]pyridine-6-carboxylate trifluoroacetate

[Chemical Formula 285]

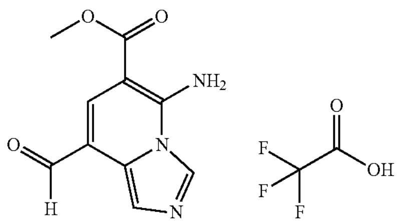

The title compound was synthesized from methyl 5-[bis[(2-methylpropan-2-yl)oxycarbonyl]amino]-8-ethenylimidazo[1,5-a]pyridine-6-carboxylate (compound m6) under the same conditions as the production examples for compound c6 and compound a6.

LCMS m/z: 220 $[M+H]^+$

HPLC retention time: 0.48 min (analysis conditions G)

Compound m9:

Methyl 5-amino-8-(5,5-dimethyl-1,3-dioxan-2-yl) imidazo[1,5-a]pyridine-6-carboxylate

[Chemical Formula 286]

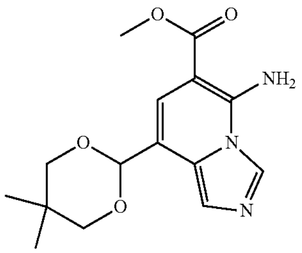

A toluene suspension (30 mL) of methyl 5-amino-8-formylimidazo[1,5-a]pyridine-6-carboxylate trifluoroacetate (compound m8, 475 mg, 1.43 mmol), p-toluenesulfonic acid monohydrate (54.2 mg, 0.285 mmol) and 2,2-dimethyl-1,3-propanediol (742 mg, 7.13 mmol) was stirred overnight at 110° C. DIPEA (1 mL) was added to the reaction mixture, which was then concentrated under reduced pressure. The resulting residue was purified by reversed-phase column chromatography to give the title compound (340 mg, 78%) as a red solid.

LCMS m/z: 306 $[M+H]^+$

HPLC retention time: 0.66 min (analysis conditions G)

Compound m10:

Methyl 5-chloro-8-(5,5-dimethyl-1,3-dioxan-2-yl) imidazo[1,5-a]pyridine-6-carboxylate

[Chemical Formula 287]

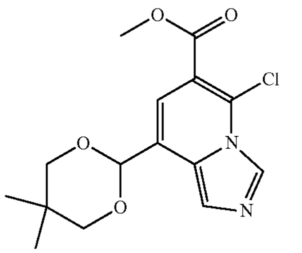

An acetonitrile suspension (15 mL) of methyl 5-amino-8-(5,5-dimethyl-1,3-dioxan-2-yl)imidazo[1,5-a]pyridine-6-carboxylate (compound m9, 340 mg, 1.11 mmol) was cooled to 0° C., and then copper(I) chloride (165 mg, 1.67 mmol) and copper(II) chloride (225 mg, 1.67 mmol) were added. After then adding tert-butyl nitrite (172 mg, 1.67 mmol), the mixture was stirred for 30 minutes at room temperature. The reaction mixture was concentrated under reduced pressure, and the resulting residue was purified by reversed-phase column chromatography to give the title compound (237 mg, 66%) as a red solid.

LCMS m/z: 325 $[M+H]^+$

HPLC retention time: 0.77 min (analysis conditions G)

Compound m11:

Methyl 8-(5,5-dimethyl-1,3-dioxan-2-yl)-5-(2-fluoro-4-iodoanilino)imidazo[1,5-a]pyridine-6-carboxylate

[Chemical Formula 288]

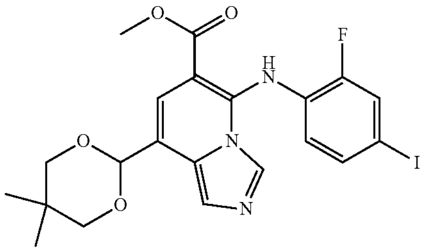

A DMA suspension (4 mL) of methyl 5-chloro-8-(5,5-dimethyl-1,3-dioxan-2-yl)imidazo[1,5-a]pyridine-6-carboxylate (compound m10, 237 mg, 0.730 mmol), cesium carbonate (713 mg, 2.19 mmol) and 2-fluoro-4-iodoaniline (346 mg, 1.46 mmol) was stirred overnight at 50° C. Water was added to the reaction mixture, and extraction was performed with ethyl acetate. The organic layer was washed with saturated brine, dried over anhydrous magnesium sulfate and, after filtering off the drying agent, concentrated under reduced pressure. The resulting residue was purified by reversed-phase column chromatography to give the title compound (210 mg, 55%) as a yellow solid.

LCMS m/z: 526 $[M+H]^+$

HPLC retention time: 1.02 min (analysis conditions G)

Compound m12:

Methyl 5-(2-fluoro-4-iodoanilino)-8-formylimidazo [1,5-a]pyridine-6-carboxylate

[Chemical Formula 289]

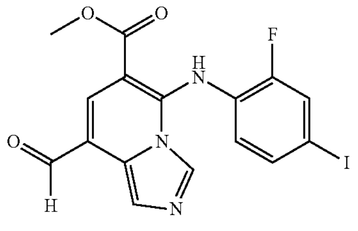

A mixed suspension of methyl 8-(5,5-dimethyl-1,3-dioxan-2-yl)-5-(2-fluoro-4-iodoanilino)imidazo[1,5-a]pyridine-6-carboxylate (compound m11, 210 mg, 0.400 mmol) in water (2 mL) and TFA (2 mL) was stirred for 1 hour at room temperature. The reaction mixture was concentrated under reduced pressure, and the resulting residue was purified by reversed-phase column chromatography (0.1% formic acid aqueous solution/0.1% formic acid acetonitrile solution) to give the title compound (168 mg, 96%) as a yellow solid.

LCMS m/z: 440 $[M+H]^+$

HPLC retention time: 0.84 min (analysis conditions G)

Compound m15:

Methyl 8-[(2-amino-3-fluoropyridin-4-yl)methyl]-5-(2-fluoro-4-iodoanilino)imidazo[1,5-a]pyridine-6-carboxylate Trifluoroacetate

[Chemical Formula 290]

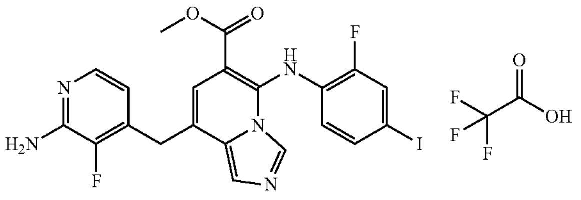

The title compound was synthesized from methyl 5-(2-fluoro-4-iodoanilino)-8-formylimidazo[1,5-a]pyridine-6-carboxylate (compound m12) under the same conditions as the production examples for compound a2, compound a5 and compound a6. However, MeOH was used instead of EtOH, which was used in the production example for compound a2.

LCMS m/z: 536 $[M+H]^+$

HPLC retention time: 0.54 min (analysis conditions F)

Compound m16:

8-[(2-Amino-3-fluoropyridin-4-yl)methyl]-5-(2-fluoro-4-iodoanilino)imidazo[1,5-a]pyridine-6-carboxylic Acid Trifluoroacetate

[Chemical Formula 291]

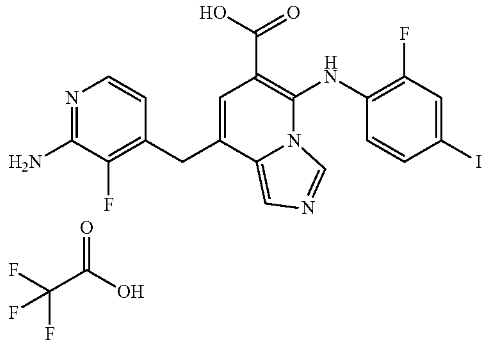

A mixed suspension of methyl 8-[(2-amino-3-fluoropyridin-4-yl)methyl]-5-(2-fluoro-4-iodoanilino)imidazo[1,5-a]pyridine-6-carboxylate trifluoroacetate (compound m15, 60 mg, 0.092 mmol) and lithium hydroxide monohydrate (78 mg, 1.85 mmol) in THF (3 mL) and water (2 mL) was stirred overnight at 50° C. The reaction mixture was acidified by addition of formic acid, and concentrated under reduced pressure. The resulting residue was purified by reversed-phase column chromatography (0.1% TFA aqueous solution/0.1% TFA acetonitrile solution) to give the title compound (42 mg, 72%) as a yellow solid.

LCMS m/z: 522 $[M+H]^+$

HPLC retention time: 0.45 min (analysis conditions F)

Compound m17:

8-[(2-Amino-3-fluoropyridin-4-yl)methyl]-5-(2-fluoro-4-iodoanilino)imidazo[1,5-a]pyridine-6-carboxamide Trifluoroacetate

[Chemical Formula 292]

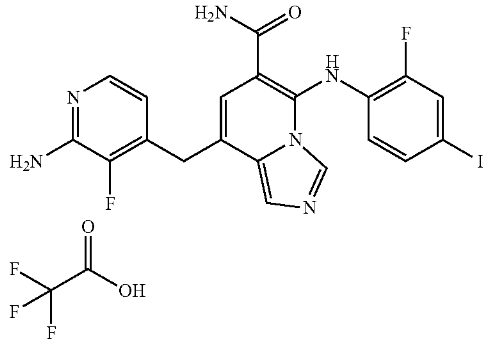

A DMF solution (1.6 mL) of 8-[(2-amino-3-fluoropyridin-4-yl)methyl]-5-(2-fluoro-4-iodoanilino)imidazo[1,5-a]pyridine-6-carboxylic acid trifluoroacetate (compound m16, 42 mg, 0.066 mmol) was cooled to 0° C., and then HATU (390 mg, 1.03 mmol), ammonium chloride (67.2 mg, 1.26 mmol) and DIPEA (0.253 mL, 1.45 mmol) were added and the mixture was stirred for 5 hours at room temperature. The reaction mixture was concentrated under reduced pressure, and the resulting residue was purified by reversed-phase column chromatography (0.1% TFA aqueous solution/0.1% TFA acetonitrile solution) to give the title compound (25 mg, 60%) as a yellow solid.

LCMS m/z: 521 $[M+H]^+$

HPLC retention time: 0.41 min (analysis conditions F)

Compound M-1:

5-(2-Fluoro-4-iodoanilino)-8-[[3-fluoro-2-(methylsulfamoylamino)pyridin-4-yl]methyl]imidazo[1,5-a]pyridine-6-carboxamide

[Chemical Formula 293]

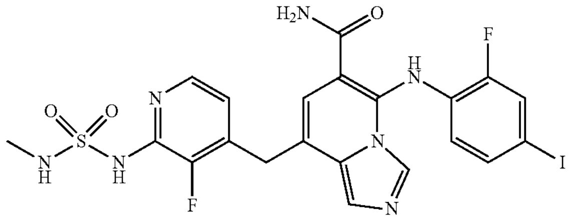

The title compound was synthesized from 8-[(2-amino-3-fluoropyridin-4-yl)methyl]-5-(2-fluoro-4-iodoanilino)imidazo[1,5-a]pyridine-6-carboxamide trifluoroacetate (compound m17) under the same conditions as the production example for compound A-1.

LCMS m/z: 614 $[M+H]^+$

HPLC retention time: 1.18 min (analysis conditions B)

Compound n1:

6-Chloro-5-fluoro-4-(2-fluoro-4-iodoanilino)pyridine-3-carboxylic Acid

[Chemical Formula 294]

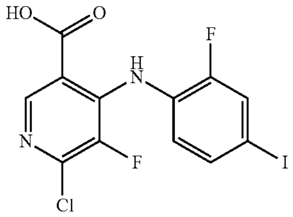

An anhydrous THF solution (8 ml) of 2-fluoro-4-iodoaniline (2.26 g, 9.52 mmol) was cooled to −78° C., and then a 2 M LDA THF/heptane/ethylbenzene solution (7.14 mL, 14.3 mmol) was added and the mixture was stirred for 30 minutes. An anhydrous THF solution (8 mL) of 4,6-dichloro-5-fluoropyridine-3-carboxylic acid (1.00 g, 4.76 mmol) was added, and the mixture was stirred for 30 minutes at −78° C. Water and 6 M hydrochloric acid were then added to the reaction mixture to adjust the pH to between 1 and 2, and extraction was performed with ethyl acetate. The organic layer was dried over anhydrous sodium sulfate and, after filtering off the drying agent, concentrated under reduced pressure. Recrystallization (DCM) was carried out from the resulting residue to give the title compound (850 mg, 44%) as a light brown solid.

LCMS m/z: 411 $[M+H]^+$

HPLC retention time: 0.85 min (analysis conditions G)

Compound n2:

Methyl 6-chloro-5-fluoro-4-(2-fluoro-4-iodoanilino) pyridine-3-carboxylate

[Chemical Formula 295]

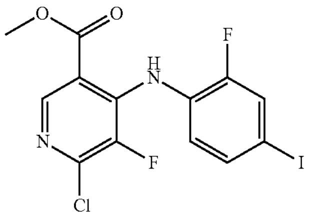

The title compound was synthesized from 6-chloro-5-fluoro-4-(2-fluoro-4-iodoanilino)pyridine-3-carboxylic acid (compound n1) under the same conditions as the production example for compound a1.

LCMS m/z: 425 $[M+H]^+$

HPLC retention time: 1.04 min (analysis conditions G)

Compound n3:

Methyl 5-fluoro-4-(2-fluoro-4-iodoanilino)-6-hydroxypyridine-3-carboxylate

[Chemical Formula 296]

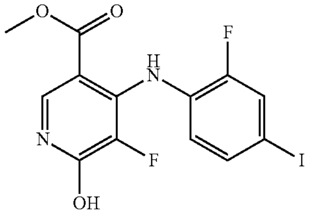

Potassium carbonate (570 mg, 4.12 mmol) and N-hydroxyacetamide (186 mg, 2.47 mmol) were added to a DMSO solution (2.75 mL) of methyl 6-chloro-5-fluoro-4-(2-fluoro-4-iodoanilino)pyridine-3-carboxylate (compound n2, 350 mg, 0.824 mmol), and the mixture was stirred for 1 hour at 100° C. Water was added to the reaction mixture, and the obtained solid was washed with water and DCM to give the title compound (281 mg, 84%) as a light brown solid.

LCMS m/z: 407 $[M+H]^+$

HPLC retention time: 0.72 min (analysis conditions G)

Compound n4:

N-[4-(Bromomethyl)-3-fluoropyridin-2-yl]-1,1-diphenylmethanimine

[Chemical Formula 297]

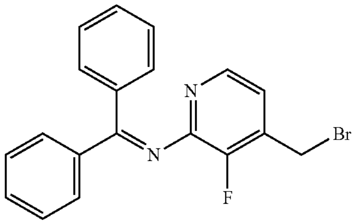

DIPEA (3.93 mL, 22.5 mmol) and methanesulfonic anhydride (2.07 g, 11.3 mmol) were added to an anhydrous DCM solution (37.5 mL) of [2-(benzhydrylideneamino)-3-fluoropyridin-4-yl]methanol (2.30 g, 7.51 mmol), and the mixture was stirred for 30 minutes at room temperature. An anhydrous THF solution (0.5 mL) of lithium bromide (3.26 g, 37.5 mmol) was then added, and the mixture was stirred for 2 hours at room temperature. Water was added to the reaction mixture and extraction was performed with DCM. The organic layer was dried over anhydrous sodium sulfate and, after filtering off the drying agent, concentrated under reduced pressure. The resulting residue was purified by reversed-phase column chromatography to give the title compound (990 mg, 34%) as a yellow semi-solid.

LCMS m/z: 369 $[M+H]^+$

HPLC retention time: 0.94 min (analysis conditions G)

Compound n5:

Methyl 1-[[2-(benzhydrylideneamino)-3-fluoropyridin-4-yl]methyl]-5-fluoro-4-(2-fluoro-4-iodoanilino)-6-oxopyridine-3-carboxylate

[Chemical Formula 298]

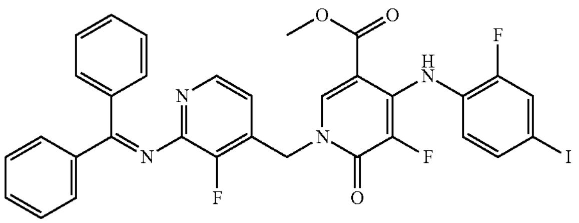

Lithium hydride (1.85 mg, 0.222 mmol) was added to an anhydrous DMF solution (0.739 mL) of methyl 5-fluoro-4-(2-fluoro-4-iodoanilino)-6-hydroxypyridine-3-carboxylate (compound n3, 30 mg, 0.074 mmol), and the mixture was stirred for 30 minutes at room temperature. An anhydrous THF solution (0.5 mL) of N-[4-(bromomethyl)-3-fluoropyridin-2-yl]-1,1-diphenylmethanimine (compound n4, 82 mg, 0.222 mmol) was then added and the resulting mixture was stirred for 1 hour at room temperature. An anhydrous THF solution (0.5 mL) of lithium hydride (1 mg, 0.126 mmol) and compound n4 (25 mg, 0.068 mmol) was then further added, and stirring was continued for 1 hour at room temperature. The reaction mixture was cooled to 0° C., acetic acid (21.1 μL) and water were added, and extraction was performed with ethyl acetate. The organic layer was dried over anhydrous sodium sulfate and, after filtering off the drying agent, concentrated under reduced pressure. The resulting residue was purified by silica gel column chromatography (hexane/ethyl acetate) to give the title compound (19 mg, 37%) as a colorless solid.

LCMS m/z: 695 $[M+H]^+$

HPLC retention time: 1.05 min (analysis conditions G)

Compound n8:

1-[(2-Amino-3-fluoropyridin-4-yl)methyl]-5-fluoro-4-(2-fluoro-4-iodoanilino)-6-oxopyridine-3-carboxamide

[Chemical Formula 299]

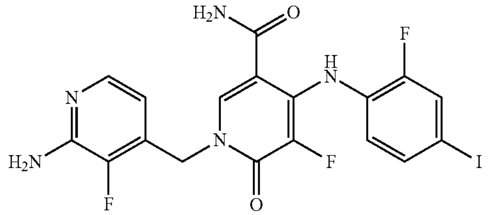

The title compound was synthesized from methyl 1-[[2-(benzhydrylideneamino)-3-fluoropyridin-4-yl]methyl]-5-fluoro-4-(2-fluoro-4-iodoanilino)-6-oxopyridine-3-carboxylate (compound n5) under the same conditions as the production examples for compound a6, compound a7 and compound K-10. However, 4 M hydrochloric acid was added during the initial step in which the reaction was carried out under the same conditions as the production example for compound a6.

LCMS m/z: 516 $[M+H]^+$

HPLC retention time: 0.52 min (analysis conditions C)

Compound N-1:

5-Fluoro-4-(2-fluoro-4-iodoanilino)-1-[[3-fluoro-2-(methylsulfamoylamino)pyridin-4-yl]methyl]-6-oxopyridine-3-carboxamide

[Chemical Formula 300]

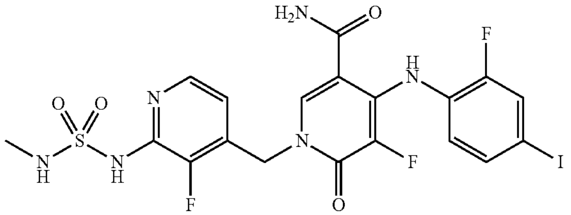

The title compound was synthesized from 1-[(2-amino-3-fluoropyridin-4-yl)methyl]-5-fluoro-4-(2-fluoro-4-iodoanilino)-6-oxopyridine-3-carboxamide (compound n8) under the same conditions as the production example for compound A-1.

LCMS m/z: 609 $[M+H]^+$

HPLC retention time: 0.94 min (analysis conditions A)

Compound N-2:

5-Fluoro-4-(2-fluoro-4-iodoanilino)-1-[[3-fluoro-2-(propylsulfamoylamino)pyridin-4-yl]methyl]-6-oxopyridine-3-carboxamide

[Chemical Formula 301]

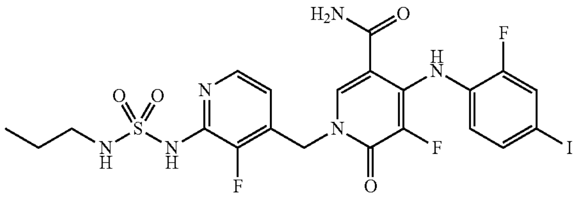

The title compound was synthesized from 1-[(2-amino-3-fluoropyridin-4-yl)methyl]-5-fluoro-4-(2-fluoro-4-iodoanilino)-6-oxopyridine-3-carboxamide (compound n8) and the corresponding 4-nitrophenyl sulfamate under the same conditions as the production example for compound A-1.

LCMS m/z: 637 $[M+H]^+$

HPLC retention time: 1.04 min (analysis conditions A)

Compound N-3:

5-Fluoro-1-[[3-fluoro-2-(methylsulfamoylamino) pyridin-4-yl]methyl]-4-(2-fluoro-4-methylsulfanylanilino)-6-oxopyridine-3-carboxamide

[Chemical Formula 302]

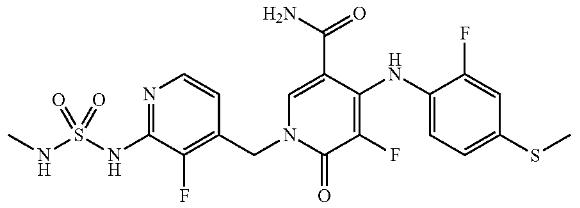

The title compound was synthesized from 1-[(2-amino-3-fluoropyridin-4-yl)methyl]-5-fluoro-4-(2-fluoro-4-iodoanilino)-6-oxopyridine-3-carboxamide (compound n8) under the same conditions as the production examples for compound a16 and compound A-1.

LCMS m/z: 529 $[M+H]^+$

HPLC retention time: 0.88 min (analysis conditions A)

Compound p3:

Methyl 4-(2-fluoro-4-iodoanilino)-6-hydroxy-5-methylpyridine-3-carboxylate

[Chemical Formula 303]

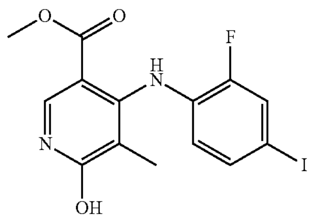

The title compound was synthesized from 4,6-dichloro-5-methylpyridine-3-carboxylic acid under the same conditions as the production examples for compound c5, compound a1 and compound n3. However, 2-fluoro-4-iodoaniline was used instead of 4-iodo-2-methylaniline, which was used in the production example for compound c5.

LCMS m/z: 403 $[M+H]^+$

HPLC retention time: 0.76 min (analysis conditions G)

Compound P-1:

4-(2-Fluoro-4-iodoanilino)-1-[[3-fluoro-2-(methylsulfamoylamino)pyridin-4-yl]methyl]-5-methyl-6-oxopyridine-3-carboxamide

[Chemical Formula 304]

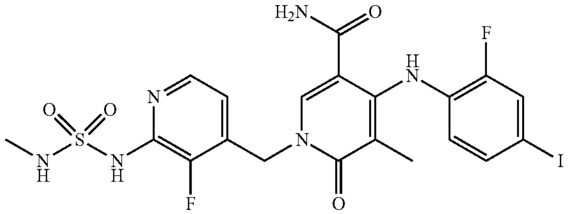

The title compound was synthesized from methyl 4-(2-fluoro-4-iodoanilino)-6-hydroxy-5-methylpyridine-3-carboxylate (compound p3) under the same conditions as the production examples for compound n4, compound b2, compound m17, compound a6 and compound A-1. However, a 2 M sodium hydroxide aqueous solution was used instead of lithium hydroxide monohydrate, which was used in the production example for compound b2, and a 4 M hydrochloric acid 1,4-dioxane solution was used instead of trifluoroacetic acid, which was used in the production example for compound a6.

LCMS m/z: 605 $[M+H]^+$

HPLC retention time: 0.66 min (analysis conditions C)

Compound P-3:

4-(2-Fluoro-4-iodoanilino)-1-[[3-fluoro-2-[(1-methylcyclobutyl)sulfamoylamino]pyridin-4-yl]methyl]-5-methyl-6-oxopyridine-3-carboxamide

[Chemical Formula 305]

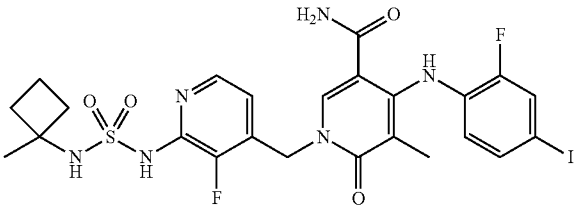

The title compound was synthesized from methyl 4-(2-fluoro-4-iodoanilino)-6-hydroxy-5-methylpyridine-3-carboxylate (compound p3) under the same conditions as the production examples for compound n4, compound b2, compound m17, compound a6 and compound A-1. However, a 2 M sodium hydroxide aqueous solution was used instead of lithium hydroxide monohydrate, which was used in the production example for compound b2, a 4 M hydrochloric acid 1,4-dioxane solution was used instead of trifluoroacetic acid, which was used in the production example for compound a6, and the corresponding 4-nitrophenyl sulfamate was used instead of 4-nitrophenyl methylsulfamate, which was used in the production example for compound A-1.

LCMS m/z: 659 $[M+H]^+$

HPLC retention time: 0.76 min (analysis conditions C)

Compound p9:

Methyl 4-(2-fluoro-4-iodoanilino)-6-hydroxy-5-methylpyridine-3-carboxylate

[Chemical Formula 306]

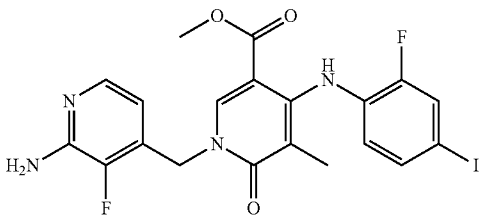

The title compound was synthesized from methyl 4-(2-fluoro-4-iodoanilino)-6-hydroxy-5-methylpyridine-3-carboxylate (compound p3) under the same conditions as the production examples for compound n4 and compound a6. However, di-tert-butyl 2-[4-(bromomethyl)-3-fluoropyridin-2-yl]iminopropanedioate was used instead of N-[4-(bromomethyl)-3-fluoropyridin-2-yl]-1,1-diphenylmethanimine, which was used in the production example for compound n4, and a 4 M hydrochloric acid 1,4-dioxane solution was used instead of trifluoroacetic acid, which was used in the production example for compound a6.

LCMS m/z: 527 $[M+H]^+$

HPLC retention time: 0.72 min (analysis conditions G)

Compound p10:

Methyl 1-[[2-(ethylsulfonylamino)-3-fluoropyridin-4-yl]methyl]-4-(2-fluoro-4-iodoanilino)-5-methyl-6-oxopyridine-3-carboxylate

[Chemical Formula 307]

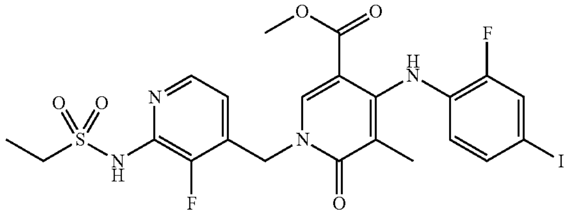

The title compound was synthesized from methyl 4-(2-fluoro-4-iodoanilino)-6-hydroxy-5-methylpyridine-3-carboxylate (compound p9) and ethylsulfonyl chloride under the same conditions as the production example for compound A-25, except that DIPEA was used instead of pyridine and that anhydrous DCM was used instead of anhydrous DMA.

LCMS m/z: 619 $[M+H]^+$

HPLC retention time: 0.87 min (analysis conditions G)

Compound P-2:

1-[[2-(Ethylsulfonylamino)-3-fluoropyridin-4-yl]methyl]-4-(2-fluoro-4-iodoanilino)-5-methyl-6-oxopyridine-3-carboxamide

[Chemical Formula 308]

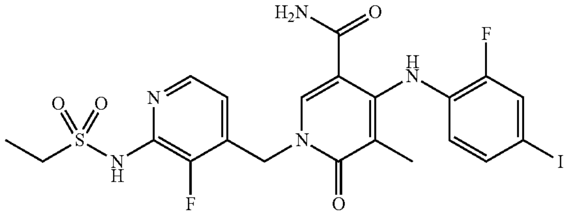

The title compound was synthesized from methyl 1-[[2-(ethylsulfonylamino)-3-fluoropyridin-4-yl]methyl]-4-(2-fluoro-4-iodoanilino)-5-methyl-6-oxopyridine-3-carboxylate (compound p10) under the same conditions as the production examples for compound b2 and compound K-10. However, a 1 M sodium hydroxide aqueous solution was used instead of lithium hydroxide monohydrate, which was used in the production example for compound b2.

LCMS m/z: 604 $[M+H]^+$

HPLC retention time: 0.67 min (analysis conditions C)

Compound P4:

N-Cyclopropyl-1-[[2-(ethylsulfonylamino)-3-fluoropyridin-4-yl]methyl]-4-(2-fluoro-4-iodoanilino)-5-methyl-6-oxopyridine-3-carboxamide

[Chemical Formula 309]

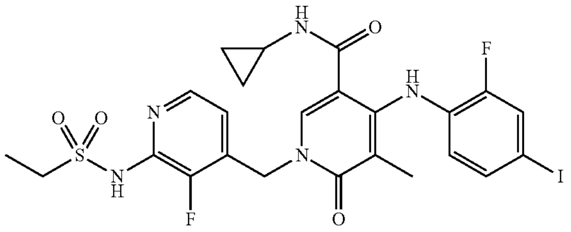

The title compound was synthesized from methyl 1-[[2-(ethylsulfonylamino)-3-fluoropyridin-4-yl]methyl]-4-(2-fluoro-4-iodoanilino)-5-methyl-6-oxopyridine-3-carboxylate (compound p10) under the same conditions as the production examples for compound b2 and compound K-10. However, a 1 M sodium hydroxide aqueous solution was used instead of lithium hydroxide monohydrate, which was used in the production example for compound b2, and the corresponding amine was used instead of a 7 M ammonia MeOH solution, which was used in the production example for compound K-10.

LCMS m/z: 644 $[M+H]^+$

HPLC retention time: 0.74 min (analysis conditions C)

Compound P-5:

1-[[2-(Ethylsulfonylamino)-3-fluoropyridin-4-yl]methyl]-4-(2-fluoro-4-iodoanilino)-N-methoxy-5-methyl-6-oxopyridine-3-carboxamide

[Chemical Formula 310]

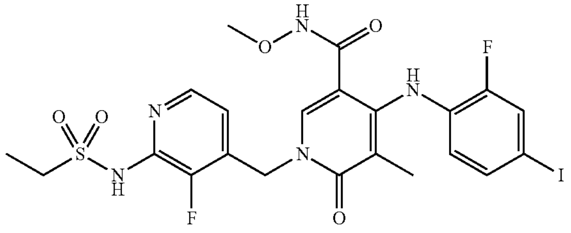

The title compound was synthesized from methyl 1-[[2-(ethylsulfonylamino)-3-fluoropyridin-4-yl]methyl]-4-(2-fluoro-4-iodoanilino)-5-methyl-6-oxopyridine-3-carboxylate (compound p10) under the same conditions as the production examples for compound b2 and compound K-10. However, a 1 M sodium hydroxide aqueous solution was used instead of lithium hydroxide monohydrate, which was used in the production example for compound b2, and the corresponding amine was used instead of a 7 M ammonia MeOH solution, which was used in the production example for compound K-10.

LCMS m/z: 634 $[M+H]^+$

HPLC retention time: 0.67 min (analysis conditions C)

Compound P-6:

N-Cyclopropyl-4-(2-fluoro-4-iodoanilino)-1-[[3-fluoro-2-(methylsulfamoylamino)pyridin-4-yl]methyl]-5-methyl-6-oxopyridine-3-carboxamide

[Chemical Formula 311]

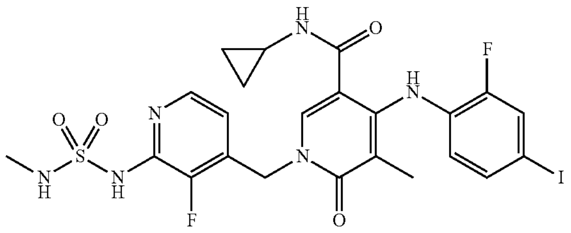

The title compound was synthesized from methyl 1-[(2-amino-3-fluoropyridin-4-yl)methyl]-4-(2-fluoro-4-iodoanilino)-5-methyl-6-oxopyridine-3-carboxylate (compound p9) under the same conditions as the production examples for compound b2, compound a12 and compound A-25. However, the corresponding amine was used instead of tert-butoxyamine hydrochloride, which was used in the production example for compound a12.

LCMS m/z: 645 $[M+H]^+$

HPLC retention time: 0.73 min (analysis conditions C)

Compound P-7:

4-(2-Fluoro-4-iodoanilino)-1-[[3-fluoro-2-(methylsulfamoylamino)pyridin-4-yl]methyl]-N-methoxy-5-methyl-6-oxopyridine-3-carboxamide

[Chemical Formula 312]

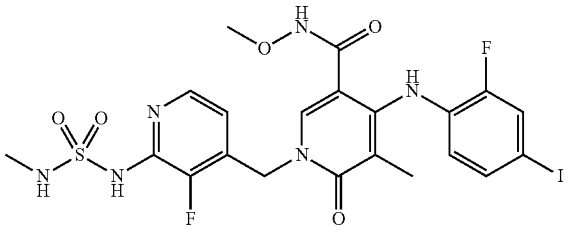

The title compound was synthesized from methyl 1-[(2-amino-3-fluoropyridin-4-yl)methyl]-4-(2-fluoro-4-iodoanilino)-5-methyl-6-oxopyridine-3-carboxylate (compound p9) under the same conditions as the production examples for compound b2, compound a12 and compound A-25. However, the corresponding amine was used instead of tert-butoxyamine hydrochloride, which was used in the production example for compound a12.

LCMS m/z: 635 $[M+H]^+$

HPLC retention time: 0.65 min (analysis conditions C)

Compound aa01:

3,4-Difluoro-2-(2-fluoro-4-iodoanilino)-5-[(E)-methoxyiminomethyl]benzoic acid

[Chemical Formula 313]

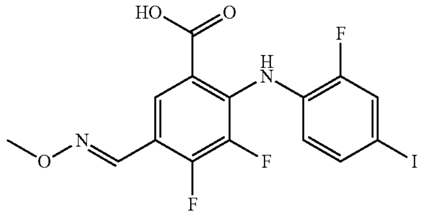

After suspending 3,4-difluoro-2-((2-fluoro-4-iodophenyl)amino)-5-formylbenzoic acid (20.0 g, 47.5 mmol) in toluene (200 mL), methylhydroxylamine hydrochloride (4.73 g, 56.6 mmol) and triethylamine (5.75 g, 56.8 mmol) were added, and the mixture was stirred for 4 hours at 100° C. Water (200 mL) was added to the reaction mixture, which was then adjusted to pH 5 with 1 M hydrochloric acid and extracted twice with ethyl acetate. The organic layer was washed with brine and dried over anhydrous sodium sulfate. After filtering off the drying agent, the filtrate was concentrated under reduced pressure to give the title compound (20 g, 94%) as a green solid.

Compound aa02:

Methyl 3,4-difluoro-2-(2-fluoro-4-iodoanilino)-5-[(E)-methoxyiminomethyl]benzoate

[Chemical Formula 314]

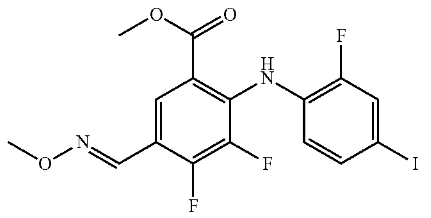

A mixed suspension of 3,4-difluoro-2-(2-fluoro-4-iodoanilino)-5-[(E)-methoxyiminomethyl]benzoic acid (compound aa01, 6.00 g, 13.3 mmol) in THE (100 mL) a MeOH (50 mL) was cooled to 0° C., and then a 2 M diazomethyltrimethylsilane hexane solution (10 mL, 20 mmol) was added and the mixture was stirred for 2 hours at room temperature. Water was added to the reaction mixture, which was then extracted twice with ethyl acetate. The organic layer was washed twice with saturated brine and dried over anhydrous sodium sulfate. After filtering off the drying agent, the filtrate was concentrated under reduced pressure to give the title compound (5.10 g, 82%) as a grayish white solid.

Compound aa03:

Methyl 3,4-difluoro-2-(2-fluoro-4-iodoanilino)-5-[(methoxyamino)methyl]benzoate

[Chemical Formula 315]

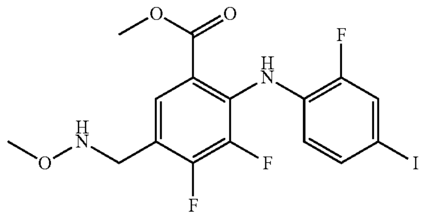

A solution of methyl 3,4-difluoro-2-(2-fluoro-4-iodoanilino)-5-[(E)-methoxyiminomethyl]benzoate (compound aa02, 5.00 g, 10.8 mmol) in dichloromethane (200 mL) was cooled to 0° C., and then dichloroacetic acid (11.0 g, 86.2 mmol) and a borane-pyridine complex (7.93 g, 86.2 mmol) were added and the mixture was stirred for 16 hours at room temperature. A sodium hydrogen carbonate aqueous solution was added to the reaction mixture, which was then extracted twice with dichloromethane. The organic layer was washed twice with saturated brine and dried over anhydrous sodium sulfate. After filtering off the drying agent, the mixture was concentrated under reduced pressure and the resulting residue was purified by silica gel column chromatography (ethyl acetate/petroleum ether) to give the title compound (3.00 g, 60%) as a white solid.

Compound aa04:

Methyl 5-[[(2-acetyloxyacetyl)-methoxyamino]methyl]-3,4-difluoro-2-(2-fluoro-4-iodoanilino)benzoate

[Chemical Formula 316]

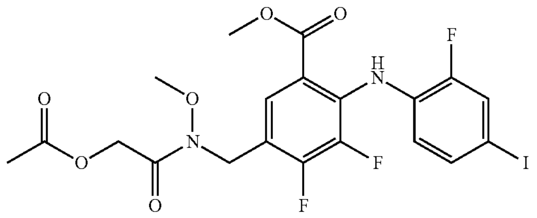

Methyl 3,4-difluoro-2-(2-fluoro-4-iodoanilino)-5-[(methoxyamino)methyl]benzoate (compound aa03, 3.00 g, 6.44 mmol) was dissolved in dichloromethane (100 mL), and then triethylamine (975 mg, 9.65 mmol) was added. After further adding 2-chloro-2-(hydroxyamino)ethyl acetate (923 mg, 6.76 mmol) dropwise at −10° C., the mixture was stirred for 20 minutes at the same temperature. Water was added to the reaction mixture, which was then extracted twice with dichloromethane. The organic layer was washed twice with saturated brine and dried over anhydrous sodium sulfate. After filtering off the drying agent, the filtrate was concentrated under reduced pressure to give the title compound (1.1 g, 70%) as a white solid.

Compound aa05:

Methyl 3,4-difluoro-2-(2-fluoro-4-iodoanilino)-5-[[(2-hydroxyacetyl)-methoxyamino]methyl]benzoate

[Chemical Formula 317]

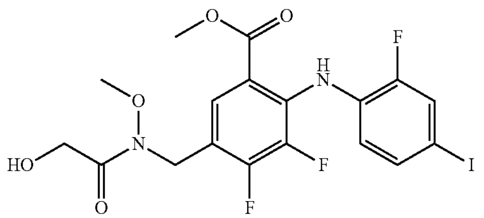

After dissolving methyl 5-[[(2-acetyloxyacetyl)-methoxyamino]methyl]-3,4-difluoro-2-(2-fluoro-4-iodoanilino)benzoate (compound aa04, 2.20 g, 3.89 mmol) in methanol (100 mL), potassium carbonate (536 mg, 3.88 mmol) was added at 0° C. and the mixture was stirred for 20 minutes at the same temperature. An ammonium chloride aqueous solution was added to the reaction mixture, which was then extracted twice with dichloromethane. The organic layer was washed twice with saturated brine and dried over anhydrous sodium sulfate. After filtering off the drying agent, the filtrate was concentrated under reduced pressure to give the title compound (1.80 g, 88%) as a white solid.

Compound aa06:

tert-Butyl N-(methylsulfamoyl)carbamate

[Chemical Formula 318]

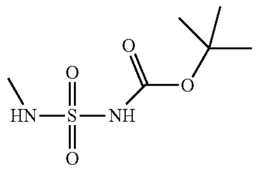

After dissolving 2-methyl-propan-2-ol (4.3 g, 58.1 mmol) in dichloromethane (100 mL), chlorosulfonyl isocyanate (8.15 g, 58.5 mmol) was added at −5° C. and the mixture was stirred for 30 minutes at the same temperature. Triethylamine (17.4 g, 172 mmol) and a 2 M methylamine dichloromethane solution (30 mL) were further added, and the mixture was stirred for 3 hours at room temperature. The reaction mixture was washed with 1 M hydrochloric acid and saturated brine, and the organic layer was dried over anhydrous sodium sulfate. After filtering off the drying agent, the filtrate was concentrated under reduced pressure to give the title compound (4.0 g, 33%) as a white solid.

Compound aa07:

Methyl 3,4-difluoro-2-(2-fluoro-4-iodoanilino)-5-[[methoxy-[2-[(2-methylpropan-2-yl)oxycarbonyl-(methylsulfamoyl)amino]acetyl]amino]methyl]benzoate

[Chemical Formula 319]

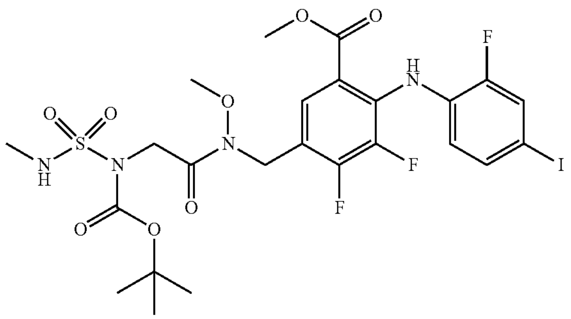

After dissolving methyl 3,4-difluoro-2-(2-fluoro-4-iodoanilino)-5-[[(2-hydroxyacetyl)-methoxyamino]methyl]benzoate (compound aa05, 1.80 g, 3.43 mmol) in anhydrous THF (50 mL), triphenylphosphine (1.35 g, 5.15 mmol) and tert-butyl N-(methylsulfamoyl)carbamate (compound aa06, 865 mg, 4.11 mmol) were added. Diisopropyl azodicarboxylate (1.04 g, 5.15 mmol) was also added at 0° C., and the mixture was stirred for 2 hours at room temperature. Water was added to the reaction mixture, which was then extracted three times with ethyl acetate. The organic layer was washed three times with saturated brine and dried over anhydrous sodium sulfate. After filtering off the drying agent, the mixture was concentrated under reduced pressure and the resulting residue was purified by silica gel column chromatography (petroleum ether/ethyl acetate) to give the title compound (1.50 g, 61%) as a white solid.

Compound aa08:

3,4-Difluoro-2-(2-fluoro-4-iodoanilino)-5-[[methoxy-[2-[(2-methylpropan-2-yl)oxycarbonyl-(methylsulfamoyl)amino]acetyl]amino]methyl]benzoic acid

[Chemical Formula 320]

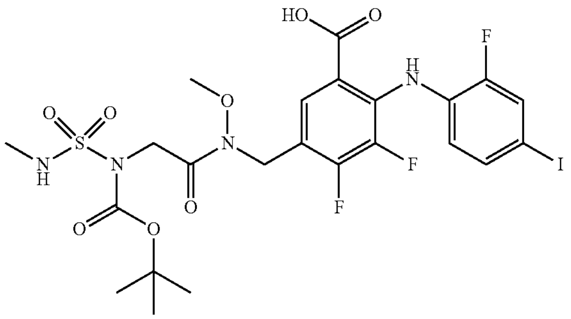

A solution of methyl 3,4-difluoro-2-(2-fluoro-4-iodoanilino)-5-[[methoxy-[2-[(2-methylpropan-2-yl)oxycarbonyl-(methylsulfamoyl)amino]acetyl]amino]methyl]benz oate (compound aa07, 1.50 g, 2.09 mmol) in THF (50 mL) was cooled to 0° C., and then a 1 M lithium hydroxide aqueous solution (20.9 mL, 20.9 mmol) was added and the mixture was stirred for 16 hours at room temperature. After adding 1 M hydrochloric acid to the reaction mixture to adjust it to pH 4, it was extracted twice with ethyl acetate. The organic layer was washed twice with saturated brine and dried over anhydrous sodium sulfate. After filtering off the drying agent, the filtrate was concentrated under reduced pressure, and the resulting residue was purified by reversed-phase column chromatography (0.5% trifluoroacetic acid aqueous solution/0.5% trifluoroacetic acid acetonitrile solution) to give the title compound (0.80 g, 54%) as a white solid.

Compound aa09:

tert-Butyl N-[2-[[2,3-difluoro-4-(2-fluoro-4-iodoanilino)-5-(2-hydroxyethoxycarbamoyl)phenyl]methyl-methoxyamino]-2-oxoethyl]-N-(methylsulfamoyl)carbamate

[Chemical Formula 321]

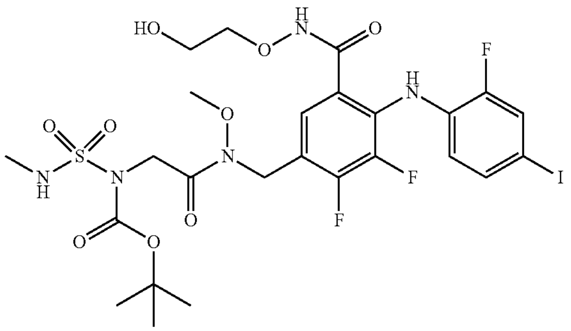

After adding EDC·HCl (33 mg), 3,4-dihydro-3-hydroxy-4-oxo-1,2,3-benzotriazine (28 mg), 2-aminooxyethanol (25

μL) and DIPEA (0.10 mL) to an anhydrous DMF solution (0.6 mL) of 3,4-difluoro-2-(2-fluoro-4-iodoanilino)-5-[[methoxy-[2-[(2-methylpropa n-2-yl)oxycarbonyl-(methylsulfamoyl)amino]acetyl]amino]methyl]benzoic acid (compound aa08, 80 mg, 0.114 mmol), the mixture was stirred for 3 hours at room temperature. The reaction mixture was purified by reversed-phase column chromatography (0.1% formic acid aqueous solution/0.1% formic acid acetonitrile solution) to give the title compound (49 mg, 56%) as a colorless liquid.

LCMS m/z: 762 $[M+H]^+$

HPLC retention time: 0.89 min (analysis conditions C)

Compound AA-1:

3,4-Difluoro-2-(2-fluoro-4-iodoanilino)-N-(2-hydroxyethoxy)-5-[[methoxy-[2-(methylsulfamoylamino)acetyl]amino]methyl]benzamide

[Chemical Formula 322]

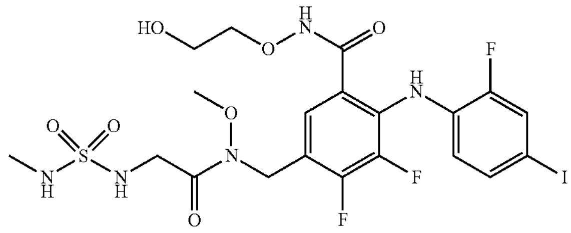

After dissolving tert-butyl N-[2-[[2,3-difluoro-4-(2-fluoro-4-iodoanilino)-5-(2-hydroxyethoxycarbamoyl)phenyl]methyl-methoxyamino]-2-oxoethyl]-N-(methylsulfamoyl)carbamate (compound aa09, 84.9 mg, 1.11 mmol) in a 4 M hydrochloric acid 1,4-dioxane solution (1.7 mL), the solution was stirred at room temperature. After concentrating the reaction mixture, it was purified by reversed-phase column chromatography (0.1% formic acid aqueous solution/0.1% formic acid acetonitrile solution) to give the title compound (49 mg, 66%) as a white solid.

LCMS m/z: 662 $[M+H]^+$

HPLC retention time: 1.00 min (analysis conditions A)

Compound aa19:

2-[3-[(2-Fluoro-3-nitrophenyl)methyl]-2-oxo-7-pyrimidin-2-yloxychromen-4-yl]acetic Acid

[Chemical Formula 323]

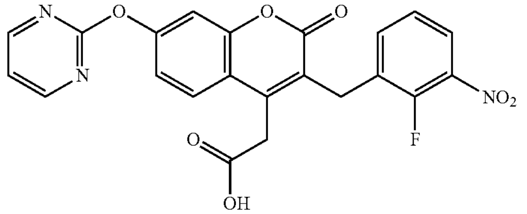

After adding a THF solution (61.4 mL) of 1 M lithium bis(trimethylsilyl)amide to a solution of 3-[(2-fluoro-3-nitrophenyl)methyl]-4-methyl-7-pyrimidin-2-yloxychromen-2-one (2.50 g, 5.84 mmol) in anhydrous THE (80 mL) at −78° C. under a nitrogen atmosphere, the mixture was stirred for 3 hours at 0° C. Carbon dioxide was added into the reaction vessel, and the reaction mixture was further stirred for 60 minutes at −20° C. to 0° C. under a carbon dioxide atmosphere. Water was added to the reaction mixture, extraction was performed with ethyl acetate, and the organic layer was dried over anhydrous sodium sulfate. After filtering off the drying agent, the filtrate was concentrated under reduced pressure and the resulting residue was purified by silica gel column chromatography (dichloromethane/methanol) to give the title compound (2.0 g, 74%) as a yellow solid.

Compound aa20:

2-[3-[(2-Fluoro-3-nitrophenyl)methyl]-2-oxo-7-pyrimidin-2-yloxychromen-4-yl]-N-(2-hydroxyethoxy)acetamide

[Chemical Formula 324]

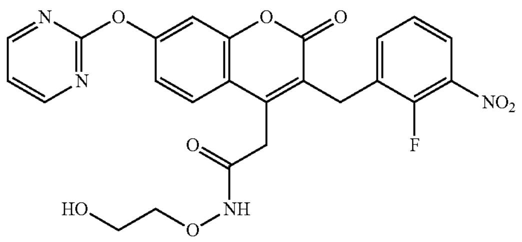

After dissolving 2-[3-[(2-fluoro-3-nitrophenyl)methyl]-2-oxo-7-pyrimidin-2-yloxychromen-4-yl]acetic acid (compound aa19, 100 mg, 0.21 mmol) in dichloromethane (10 mL) and anhydrous DMF (1 mL), HATU (91.2 mg, 0.24 mmol) and DIPEA (56.8 mg, 0.44 mmol) were added and the mixture was stirred for 10 minutes at room temperature. A dichloromethane solution of 2-aminooxyethanol was added to the reaction mixture, which was further stirred for 2 hours. After adding water to the reaction mixture, it was extracted three times with dichloromethane and the organic layer was dried over anhydrous sodium sulfate. After filtering off the drying agent, the filtrate was concentrated under reduced pressure and the resulting residue was purified by silica gel column chromatography (dichloromethane/methanol) to give the title compound (70 mg, 59%) as a yellow solid.

Compound aa21:

2-[3-[(3-Amino-2-fluorophenyl)methyl]-2-oxo-7-pyrimidin-2-yloxychromen-4-yl]-N-(2-hydroxyethoxy)acetamide

[Chemical Formula 325]

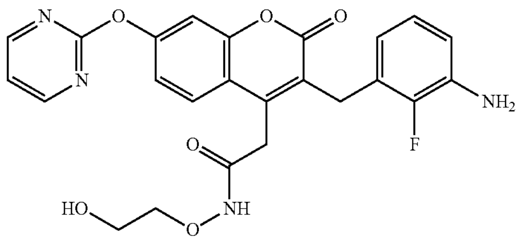

After dissolving 2-[3-[(2-fluoro-3-nitrophenyl)methyl]-2-oxo-7-pyrimidin-2-yloxychromen-4-yl]-N-(2-hydroxyethoxy)acetamide (compound aa20, 20 mg, 0.04 mmol) in 2,2,2-trifluoroethanol (5 mL), palladium/carbon (5 mg) was added and the mixture was stirred for 16 hours under a hydrogen atmosphere. The reaction mixture was filtered and the filtrate was concentrated to give the title compound as a solid.

Compound AA-2:

2-[3-[[2-Fluoro-3-(methylsulfamoylamino)phenyl]methyl]-2-oxo-7-pyrimidin-2-yloxychromen-4-yl]-N-(2-hydroxyethoxy)acetamide

[Chemical Formula 326]

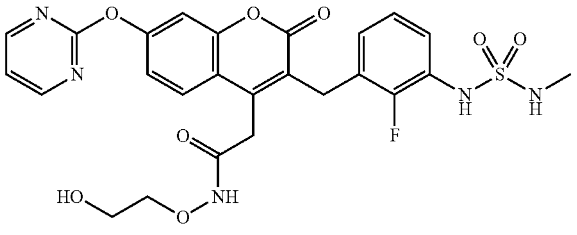

After dissolving 2-[3-[(3-amino-2-fluorophenyl)methyl]-2-oxo-7-pyrimidin-2-yloxychromen-4-yl]-N-(2-hydroxyethoxy)acetamide (compound aa12, 95 mg, 0.20 mmol) in anhydrous DMF (10 mL), pyridine (32 mg, 0.40 mmol) and 4-dimethylaminopyridine (2.4 mg, 0.02 mmol) were added. A solution of methylsulfamoyl chloride (52 mg, 0.32 mmol) in anhydrous DMF (5 mL) was further added over a period of 10 minutes at −40° C., and the mixture was stirred for 4 hours at 0° C. After then adding 1 M hydrochloric acid to the reaction mixture, extraction was performed with ethyl acetate. The organic layer was washed with sodium hydrogen carbonate aqueous solution and brine, and then dried over anhydrous sodium sulfate. After filtering off the drying agent, the mixture was concentrated under reduced pressure and the resulting residue was purified by thin-layer chromatography to give the title compound (10 mg, 9%) as a white solid.

LCMS m/z: 574 $[M+H]^+$

HPLC retention time: 1.06 min (analysis conditions A)

TEST EXAMPLES

The compounds in the following test examples that were referred in the production examples are represented by the same compound numbers as in the production examples. The compound denoted as “ref-1” is the compound represented by formula (A) below, which is compound 34 in Bioorg. Med. Chem. Lett. 2008, vol. 18, no. 24, p. 6501-6504. The compound denoted as “ref-2” is the compound represented by formula (B) below, which is compound 27 in Bioorg. Med. Chem. Lett. 2013, vol. 23, no. 8, p. 2384-2390. The compounds denoted as “ref-3” and “ref-4” are the compounds represented by formulas (C) and (D) below respectively, which are compound 9 and compound 10 in Chem. Med. Chem. 2015, vol. 10, no. 12, p. 2004-2013. The compound denoted as “ref-5” is the compound represented by formula (E) below, which is compound 1 in ACS Medchem. Lett. 2014, vol. 5, no. 4, p. 309-314.

Ref-1:

N-[(2R)-2,3-Dihydroxypropoxy]-3,4-difluoro-2-(2-fluoro-4-iodoanilino)benzamide (PD0325901)

[Chemical Formula 327]

(A)

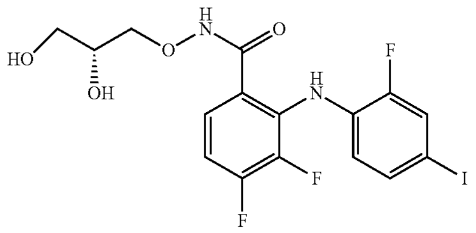

Ref-2:

4-Fluoro-2-(2-fluoro-4-iodoanilino)-6-[3-(methylsulfamoylamino)phenoxy]benzamide

[Chemical Formula 328]

(B)

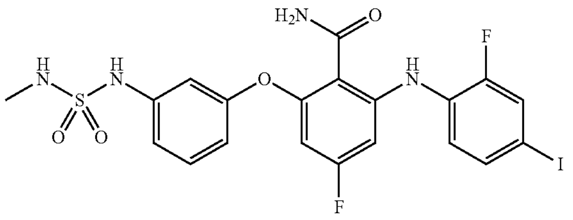

Ref-3:

3-(2-Fluoro-4-iodoanilino)-5-[3-(propan-2-ylsulfonylamino)phenoxy]pyridine-4-carboxamide

[Chemical Formula 327]

(C)

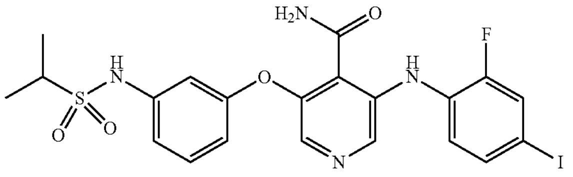

Ref-4:

3-[3-(Cyclopropylsulfonylamino)phenoxy]-5-(2-fluoro-4-iodoanilino)pyridine-4-carboxamide

[Chemical Formula 327]

(D)

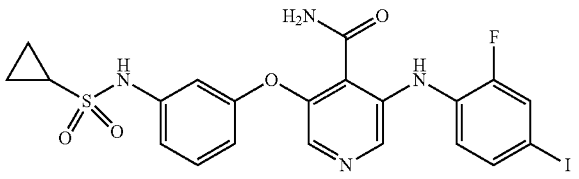

Ref-5:

3-[[3-Fluoro-2-(methylsulfamoylamino)pyridin-4-yl]methyl]-4-methyl-7-pyrimidin-2-yloxychromen-2-one (CH5126766)

[Chemical Formula 331]

(E)

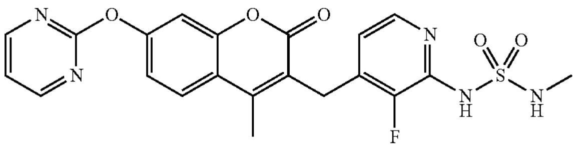

Test Example 1

Effect on Interaction Between RAF1 and MEK1

The effects of the compounds of FIGS. 4 to 11 on interaction between RAF1 and MEK1 were investigated as described below using a Biacore 8K (GE Healthcare).

GST tag-fused RAF1 (Carna Biosciences) was immobilized on the surface of a Sensor Chip CM5 (GE Healthcare) using Anti-GST Antibody (GE Healthcare). Next, a running buffer (blank), a 40 nM MEK1 solution, or a mixed solution of 40 nM MEK1 and 3 μM test compound was flowed over the surface of the sensor chip for 120 seconds, and the running buffer was then flowed over it. The MEK1 used was MEK1 Recombinant Human protein, Inactive (Thermo Fisher Scientific). The running buffer used was PBS (Sigma-Aldrich) with the addition of 1 mM DTT (Wako), 10 mM $MgCl_2$ (Wako), 500 μM ATP (Wako), 0.01% Tween 20 (Junsei-Kagaku) and 1% DMSO (Sigma-Aldrich), and this running buffer was also used for preparation of the sample solution. The measurement was carried out at 15° C. Both RAF1 and MEK1 were subjected to dephosphorylation treatment with Lambda Protein Phosphatase (New England Biolabs) before use, and MEK1 was purified by size exclusion chromatography.

The obtained sensorgrams (graphs representing change over time in the amount of MEK1 bound to immobilized RAF1) were double-referenced with Biacore Insight Evaluation Software, and normalization of the sensorgrams by the amount of immobilized RAF1 was performed using TIBCO Spotfire. The normalized sensorgrams are shown in FIGS. 4 to 11. The experiment ID, the channel No. in the Biacore, and the compound No. are listed in order on each sensorgram (with "no compound" meaning that no test compound is present). For each sensorgram, the horizontal axis (X-axis) represents the time (sec) after the start of addition of the sample solution and the vertical axis (Y-axis) represents the normalized amount of binding of MEK1.

Test Example 2

Effect on Phosphorylation of MEK and ERK

Figure 12:
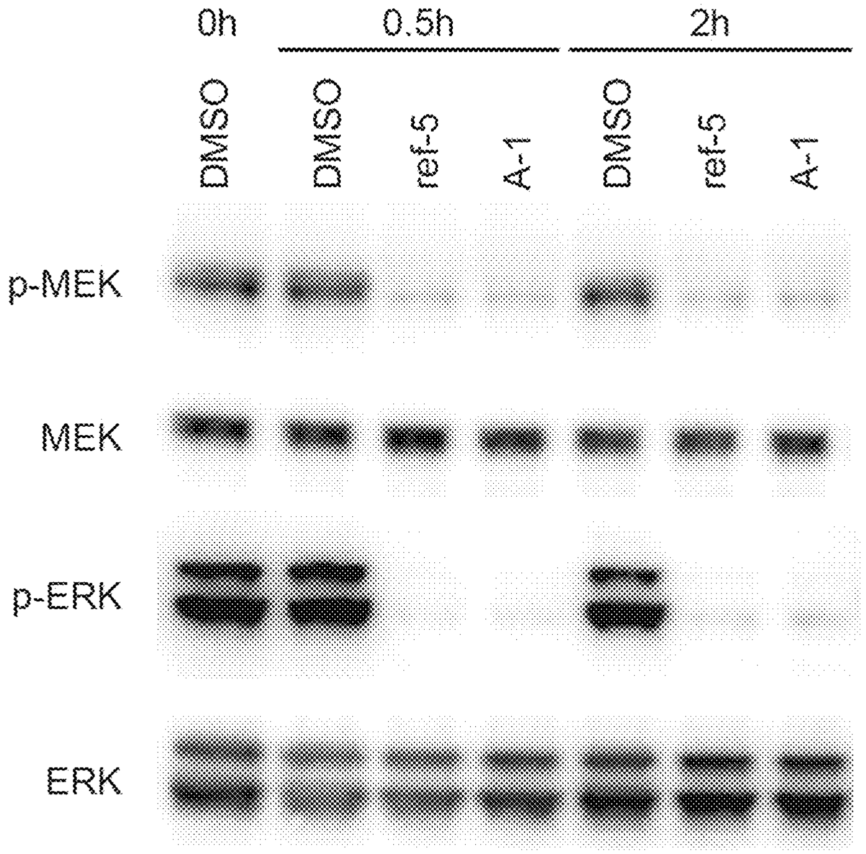
FIG. 12 is electrophoresis images showing the results of Western blotting of proteins (p-MEK, MEK, p-ERK, and ERK) extracted from A549 cells cultured in the presence of a test compound (ref-5 or compound A-1).

The effects of the compounds listed in FIG. 12 (ref-5 and compound A-1) on intracellular phosphorylation of MEK and ERK were investigated by Western blotting as described below.

A549 cells were seeded in a 12-well plate at 400,000 cells per well and cultured in a 5% carbon dioxide gas incubator at 37° C. using Dulbecco's Modified Eagle's Medium with the addition of 10% fetal bovine serum (Sigma). On the following day, the test compound (0.3 μM ref-5 or 0.05 μM compound A-1) or DMSO was added to the culture medium and cultured for 30 minutes or 2 hours, and the cells were harvested with a cell scraper and solubilized. The extracted protein was separated by SDS-PAGE and transferred to a PVDF membrane. After blocking, the PVDF membrane was treated with Phospho-MEK1/2 (Ser217/221) antibody, MEK1/2 antibody, Phospho-ERK1/2 (Thr202/Tyr204) antibody, or ERK1/2 antibody (all by Cell Signaling Technology, Inc.). After washing the primary antibody, it was treated with HRP-labeled secondary antibody (Cell Signaling Technology, Inc.), and after washing, the signal was detected by chemiluminescence using a Chemi-Lumi One Super (Nacalai Tesque Inc.). FIG. 12 is electrophoresis images showing the results of the Western blotting. In FIG. 12, "p-MEK" and "p-ERK" represent phosphorylated MEK and phosphorylated ERK, respectively.

Test Example 3

MEK1-Inhibiting Activity

The MEK1-inhibiting activity of the compounds listed in Table 2 below were evaluated by the fluorescent polarization method as described below.

The test compound, CRAF (Thermo Fisher Scientific Inc.), MEK1 (Thermo Fisher Scientific Inc.) and ERK2 (Carna Biosciences, Inc.) were mixed in ATP-containing buffer and reacted for 60 minutes at 30° C. FAM-labeled ERKtide (Molecular Devices Corp.) was then added and reaction was continued for 45 minutes at 30° C. IMAP (registered trademark) Progressive Binding Reagent (Molecular Devices Corp.) was further added, and reaction was continued for 15 minutes at room temperature. Following the reaction, the fluorescent polarization was measured with a fluorescent plate reader and the 50% inhibition concentration ($IC_{50}$) was calculated based on the percent inhibition relative to a test compound-free control. The results are shown in Table 2.

Test Example 4

BRAF-Inhibiting Activity

The BRAF-inhibiting activity of the compounds listed in Table 2 below was evaluated by the time-resolved fluorescence-fluorescence resonance energy transfer assay as described below.

The test compound, BRAF (Eurofins Genomics KK.) and MEK1 (Thermo Fisher Scientific Inc.) were mixed in ATP-containing buffer and reacted for 90 minutes at 30° C. LANCE (registered trademark) Eu-Phospho-MEK1/2 (Ser217/221) antibody (Perkin-Elmer) was then added, and reaction was continued for 60 minutes at room temperature. Following the reaction, the fluorescence resonance energy transfer was measured with a fluorescent plate reader and the 50% inhibition concentration ($IC_{50}$) was calculated based on the percent inhibition relative to a test compound-free control. The results are shown in Table 2.

Test Example 5

Cell Proliferation-Inhibiting Activity

The cell proliferation-inhibiting activity of the compounds listed in Table 2 below was evaluated by measuring the amount of ATP in viable cells as described below.

The test compound was serially diluted with DMSO and then diluted 25-fold with $Ca^{2+}$, $Mg^{2+}$-free phosphate-buffered saline, and was then dispensed into a 96-well plate at 5 μL per well. A cell suspension containing the below indicated concentration of A549, Calu-6 or NCI-H2122 human lung cancer cells (all obtained from ATCC) was prepared using the below indicated medium with the addition of 10% fetal bovine serum (Sigma). The cell suspension was dispensed into the test compound-added plate at 95 μL per well and cultured in a 5% carbon dioxide gas incubator at 37° C. After 4 days, 80 μL of CellTiter-Glo (registered trademark) (Promega Corp.) was added to each well and the bioluminescence was measured with a fluorescent plate reader. The 50% inhibition concentration ($IC_{50}$) was calculated based on the percent inhibition relative to a test compound-free control. The results are shown in Table 2.

A549: Dulbecco's Modified Eagle's Medium (Sigma); 2000 cells/95 μL

Calu-6: Eagle's Minimum Essential Medium (Sigma); 4000 cells/95 μL

NCI-H2122: RPMI-1640 culture medium (Sigma); 2000 cells/95 μL

Test Example 6

Human Liver Microsome Stability

The compounds listed in Table 2 below were tested for metabolic stability in human liver microsomes as described below using a Biomek3000 (Beckman Coulter).

There were dispensed 400 ILL of 1 mg/mL human liver microsomes (XENOTECH)/0.1 M potassium phosphate buffer (pH 7.4) into each well of a 96-well plate. A DMSO solution (4 μL) of 200 μM test compound was then added, and incubation was conducted until reaching 37° C. To this reaction mixture (200 IL) there was added a solution (200 μL) containing 2 mM NADPH (ORIENTAL YEAST)/0.1 M potassium phosphate buffer (pH 7.4) that had been incubated at 37° C. At 0 min, 5 min, 15 min or 30 min after addition, the reaction mixture (50 μL) was added to acetonitrile (100 μL) to stop the metabolic reaction. After the metabolic reaction was stopped, a 1 μM warfarin aqueous solution (50 μL) was added to each reaction mixture as an internal standard. The reaction mixture was filtered and analyzed by LC/MS/MS (LC: NEXERA by Shimadzu; MS: 4000Q trap by ABSciex; column: Ascentis Express C18 HPLC column (5 cm×2.1 mm, 2.7 μm); ionization method: electrospray ionization). The percent remaining relative to the amount of test compound at 0 min was calculated from the obtained peak area ratio of the test compound to internal standard. The elimination rate constant (ke) was calculated from the incubation time and percent remaining using the primary elimination rate equation, and the hepatic intrinsic clearance (CLint) was calculated using the formula shown below. The results are shown in Table 2.

$$CLint(\mu L/min/mg)=ke(min^{-1})/\text{human liver microsome concentration (mg protein}/\mu L)$$

TABLE 2

| Compound No. | MEK1 $IC_{50}$ (nM) | BRAF $IC_{50}$ (nM) | A549 $IC_{50}$ (nM) | Calu-6 $IC_{50}$ (nM) | NCI-H2122 $IC_{50}$ (nM) | CLint (μL/min/mg) |
|---|---|---|---|---|---|---|
| A-1 | 17 | 1 | 26 | 64 | 5 | 1 |
| A-2 | 5 | 3 | 1 | 2 | 0.1 | 25 |
| A-3 | 31 | 5 | 25 | 28 | 13 | 10 |
| A-4 | 17 | 2 | 5 | 7 | 1 | 21 |
| A-5 | 10 | 5 | 5 | 12 | 1 | 36 |
| A-6 | 12 | 10 | 17 | 19 | 3 | 20 |
| A-7 | 18 | 5 | 2 | 18 | 1 | 28 |
| A-8 | 3 | 4 | 0.4 | 2 | 0.1 | 33 |
| A-9 | 4 | 4 | 2 | 7 | 0.4 | 56 |
| A-10 | 5 | 7 | 0.1 | ND | 0.2 | 89 |
| A-11 | 7 | 9 | 1 | ND | 1 | 128 |
| A-12 | 13 | 6 | 6 | 18 | 5 | 121 |
| A-13 | 1 | 3 | 1 | 3 | 0.3 | 31 |
| A-14 | 2 | 3 | 11 | 27 | 1 | 39 |
| A-15 | 8 | 4 | 2 | 5 | 1 | 57 |
| A-16 | 8 | 3 | 14 | ND | 3 | 47 |
| A-17 | 6 | 4 | 53 | ND | 15 | 6 |
| A-18 | 8 | 4 | 5 | 7 | 2 | 53 |
| A-19 | 30 | 3 | 6 | ND | 5 | 35 |
| A-20 | 23 | 2 | 7 | ND | 6 | 14 |
| A-21 | 5 | 4 | 3 | ND | 14 | 4 |
| A-22 | 6 | 2 | 31 | ND | 10 | 47 |
| A-23 | 35 | 5 | 5 | ND | 1 | <1 |
| A-24 | 129 | 3 | 11 | 51 | 4 | 48 |
| A-25 | 5 | 2 | 0.5 | 2 | 0.2 | 7 |
| A-26 | 5 | 9 | 7 | ND | 2 | 13 |
| A-27 | 32 | 7 | 24 | ND | 10 | 4 |
| A-28 | 13 | 9 | 5 | ND | 2 | 11 |
| A-29 | 14 | 1 | 28 | ND | 6 | 18 |
| A-30 | 9 | 8 | 3 | 8 | 1 | 10 |
| A-31 | 49 | 6 | 20 | 31 | 7 | 9 |
| A-32 | 25 | 6 | 7 | ND | 5 | 19 |
| A-33 | 10 | 2 | 27 | 68 | 8 | 6 |
| A-34 | 81 | 3 | 27 | 79 | 12 | 17 |
| A-35 | 66 | 28 | 2 | 34 | 4 | 15 |
| A-36 | 74 | 5 | 26 | 61 | 17 | 18 |
| A-37 | 50 | 7 | 21 | 26 | 7 | 10 |
| A-38 | 16 | 3 | 66 | 122 | 15 | 17 |
| A-39 | 41 | 14 | 30 | 79 | 7 | ND |
| A-40 | 19 | 2 | 4 | 12 | 2 | 2 |
| A-41 | 29 | 7 | 12 | 8 | 2 | 5 |
| A-42 | 18 | 6 | 9 | 68 | 7 | 6 |
| A-43 | 41 | 10 | 2 | ND | 13 | 37 |
| A-44 | 2 | 9 | ND | ND | 1 | ND |
| A-45 | 2 | 6 | 5 | ND | 1 | ND |
| A-46 | 811 | 30 | ND | 367 | 31 | 23 |
| A-47 | 39 | 21 | ND | 104 | 17 | 38 |
| B-1 | 2 | 5 | 6 | 11 | 2 | 15 |
| B-2 | 4 | 3 | 1 | 7 | 1 | 53 |
| B-3 | 82 | 4 | 2 | 14 | 1 | 22 |
| B-4 | 19 | 5 | 2 | 6 | 1 | 28 |
| B-5 | 93 | 6 | 7 | 29 | 5 | 22 |
| B-6 | 97 | 15 | 2 | 16 | 1 | 20 |
| B-8 | 47 | 7 | 95 | 233 | 14 | 24 |
| B-9 | 2 | 4 | 10 | ND | 7 | 11 |
| B-10 | 22 | 11 | 72 | 33 | 8 | 3 |
| B-11 | 19 | 3 | 18 | 43 | 16 | 26 |
| B-12 | 61 | 8 | 14 | 30 | 8 | 39 |
| B-13 | 13 | 10 | 26 | 34 | 14 | 66 |
| B-14 | 104 | 13 | ND | 74 | 11 | 4 |
| B-15 | 8 | 4 | ND | 60 | 6 | 13 |
| B-16 | 4 | 12 | ND | 9 | 1 | 10 |
| C-1 | 72 | 4 | 7 | 16 | 4 | 10 |
| C-2 | 104 | 2 | 16 | ND | 7 | 17 |
| C-3 | 12 | 3 | 1 | ND | 0.4 | 9 |
| C-4 | 224 | 23 | 7 | ND | 43 | 40 |
| C-5 | 56 | 3 | 22 | ND | 4 | 29 |

TABLE 2-continued

| Compound No. | MEK1 $IC_{50}$ (nM) | BRAF $IC_{50}$ (nM) | A549 $IC_{50}$ (nM) | Calu-6 $IC_{50}$ (nM) | NCI-H2122 $IC_{50}$ (nM) | CLint (μL/min/mg) |
|---|---|---|---|---|---|---|
| C-6 | 268 | 9 | 6 | 31 | 4 | 74 |
| D-1 | 96 | 1 | 9 | ND | 5 | 25 |
| D-2 | 242 | 3 | 9 | ND | 5 | 103 |
| D-3 | 130 | 1 | 26 | ND | 12 | 68 |
| D-4 | 196 | 3 | 16 | 67 | 5 | 9 |
| D-5 | 169 | 7 | 10 | 71 | 5 | 28 |
| D-6 | 55 | 8 | 8 | 24 | 2 | 34 |
| D-7 | 282 | 4 | 3 | 9 | 2 | 11 |
| D-8 | 161 | 21 | 66 | 112 | 8 | 20 |
| D-9 | 252 | 24 | ND | 28 | 3 | 53 |
| D-10 | 261 | 34 | ND | 307 | 28 | 107 |
| D-11 | 6 | 3 | ND | 2 | 0.3 | 24 |
| D-12 | 15 | 14 | ND | 6 | 0.4 | 18 |
| D-13 | 29 | 18 | ND | 6 | 1 | 88 |
| D-14 | 1596 | 7 | ND | 117 | 10 | 15 |
| D-15 | 1242 | 17 | ND | 118 | 11 | 91 |
| D-16 | 48 | 6 | ND | 17 | 1 | 51 |
| E-1 | 40 | 12 | 2 | 6 | 0.4 | 17 |
| E-2 | 86 | 22 | 6 | 19 | 2 | 42 |
| E-3 | 33 | 5 | 4 | 7 | 2 | 149 |
| E-4 | 131 | 11 | 6 | 26 | 5 | 168 |
| E-5 | 19 | 8 | 5 | 17 | 3 | 78 |
| E-6 | 34 | 17 | 8 | 28 | 6 | 105 |
| E-7 | 334 | 6 | 1 | 8 | 0.4 | 5 |
| E-8 | 137 | 2 | 3 | ND | 2 | 1 |
| E-9 | 95 | 11 | 7 | 57 | 6 | 13 |
| E-10 | 84 | 23 | 4 | 27 | 3 | 51 |
| E-11 | 454 | 5 | 6 | 73 | 6 | 11 |
| E-12 | 260 | 17 | 3 | 8 | 2 | 160 |
| E-13 | 290 | 1 | 30 | 84 | 6 | 25 |
| E-14 | 343 | 17 | 13 | 71 | 7 | 22 |
| E-15 | 287 | 4 | 20 | 152 | 7 | 21 |
| E-16 | 352 | 12 | 33 | 87 | 7 | <1 |
| E-17 | 199 | 6 | 31 | 110 | 7 | 24 |
| E-18 | 366 | 5 | 7 | 122 | 8 | 29 |
| E-19 | 332 | 34 | 9 | 87 | 9 | 115 |
| E-20 | 467 | 13 | 37 | 103 | 11 | 18 |
| E-21 | 189 | 24 | 30 | 109 | 14 | 13 |
| E-22 | 302 | 4 | 6 | 87 | 3 | 18 |
| E-23 | 61 | 6 | 31 | 47 | 4 | 98 |
| E-24 | 189 | 20 | 26 | 63 | 5 | 10 |
| E-25 | 284 | 11 | ND | 28 | 7 | 8 |
| E-26 | 13 | 6 | ND | 5 | 0.6 | 13 |
| F-1 | 246 | 5 | 7 | ND | 3 | 10 |
| F-2 | 383 | 5 | 8 | 66 | 8 | 15 |
| F-3 | 380 | 5 | 8 | 118 | 24 | 28 |
| G-1 | 222 | 12 | 21 | 65 | 6 | 32 |
| G-2 | 6 | 3 | 2 | 13 | 0.4 | 31 |
| G-3 | 15 | 5 | 7 | 47 | 2 | 29 |
| G-4 | 53 | 4 | 28 | 259 | 12 | 26 |
| G-5 | 751 | 78 | ND | 374 | 57 | 86 |
| G-6 | 32 | 15 | ND | 23 | 2 | 57 |
| G-7 | 2468 | 46 | ND | 443 | 75 | 21 |
| G-8 | 53 | 7 | ND | 232 | 25 | 26 |
| G-9 | 230 | 13 | ND | 444 | 67 | 22 |
| H-1 | 7 | 2 | 9 | 21 | 5 | 39 |
| H-2 | 49 | 2 | 31 | ND | 16 | 77 |
| H-3 | 2 | 4 | 5 | ND | 1 | 149 |
| H-4 | 8 | 12 | 9 | 6 | 1 | 11 |
| H-5 | 115 | 2 | 6 | ND | 4 | 26 |
| I-1 | 25 | 3 | 5 | 15 | 3 | 19 |
| I-2 | 47 | 3 | 25 | 103 | 11 | 12 |
| I-3 | 55 | 2 | 32 | 120 | 21 | 16 |
| I-4 | 275 | 4 | 444 | ND | 83 | 25 |
| J-1 | 58 | 4 | 38 | 29 | 8 | 11 |
| 1-2 | 495 | 11 | 351 | ND | 130 | 16 |
| J-3 | 308 | 11 | 854 | 972 | 123 | 23 |
| J-4 | 877 | 14 | >2000 | >2000 | 1061 | 67 |
| J-5 | 117 | 8 | 7 | 29 | 4 | 20 |
| J-6 | 86 | 7 | 14 | 27 | 7 | 45 |
| J-7 | 627 | 12 | 101 | 380 | 29 | 30 |
| J-8 | 15 | 2 | 24 | 77 | 5 | 3 |
| J-9 | 64 | 3 | 167 | 232 | 17 | 23 |
| J-10 | 42 | 10 | 8 | 13 | 2 | 28 |
| J-11 | 48 | 17 | 13 | 27 | 6 | 47 |
| J-12 | 2287 | ND | 226 | 471 | 180 | 19 |
| J-13 | 29 | 4 | 196 | 281 | 80 | 39 |
| J-14 | 22 | 3 | 121 | 123 | 37 | 34 |
| J-15 | 56 | 12 | ND | 284 | 46 | 225 |
| K-1 | 55 | 3 | 3 | 14 | 4 | 97 |
| K-2 | 73 | 4 | 6 | 27 | 6 | 234 |
| K-3 | 84 | 5 | 9 | 31 | 10 | 247 |
| K-4 | 106 | 11 | 6 | 25 | 5 | 129 |
| K-5 | 139 | 9 | 25 | 110 | 23 | 245 |
| K-6 | 227 | 15 | 25 | 83 | 21 | 499 |
| K-7 | 31 | 14 | 9 | 27 | 7 | 357 |
| K-8 | 209 | 14 | 68 | 122 | 29 | 103 |
| K-9 | 23 | 8 | 17 | 34 | 8 | 185 |
| K-10 | 128 | 8 | 25 | 81 | 16 | 69 |
| K-11 | 278 | 15 | 93 | 230 | 85 | 437 |
| K-12 | 10 | 14 | 7 | 27 | 6 | 546 |
| K-13 | 115 | 9 | 18 | 53 | 13 | 321 |
| L-1 | 6 | 2 | 21 | 41 | 17 | 10 |
| M-1 | 5 | 4 | 27 | 28 | 13 | 59 |
| N-1 | 1 | 2 | 20 | ND | 28 | 8 |
| N-2 | 1 | 1 | 193 | ND | 60 | 11 |
| N-3 | 4 | 5 | 475 | ND | 311 | 19 |
| P-1 | 2 | ND | ND | 22 | 6 | 15 |
| P-2 | 8 | ND | ND | 337 | 109 | 3 |
| P-3 | 3 | 10 | ND | 223 | 96 | 37 |
| P-4 | 34 | 16 | ND | 45 | 24 | 1 |
| P-5 | 11 | 11 | ND | 447 | 31 | 2 |
| P-6 | 13 | 9 | ND | 8 | 4 | 4 |
| P-7 | 7 | 7 | ND | 72 | 7 | 12 |
| ref-1 | 7 | 17 | 7 | 91 | 7 | 20 |
| ref-2 | 364 | 12 | 8 | 35 | 3 | 12 |
| ref-3 | 5 | 12 | 2 | 10 | 1 | 11 |
| ref-4 | 11 | 9 | 2 | 18 | 2 | 32 |
| ref-5 | 292 | 11 | 113 | 418 | 27 | <1 |

ND: Not determined

Test Example 7

In Vivo Antitumor Effect

The effect of compound A-1 against KRAS-mutant cancer cells was evaluated as described below using tumor-bearing mice.

Calu-6 KRAS-mutant human lung cancer cells were transplanted into nude mice (CAnN.Cg-Foxn1nu/CrlCrlj, female, 5-week-old, Charles River) by subcutaneous injection of a cell suspension into the lateral abdomen using a 26G needle. The mice were divided into 5 groups (8 mice per group) according to the dosage of the test compound and administration of the test compound was initiated at 17 days post transplantation, when the tumor volume reached approximately 200 $mm^3$. The mice in 4 groups (A-1 treatment groups) were orally administered 0.0625 mg/kg, 0.25 mg/kg, 1 mg/kg or 4 mg/kg of compound A-1 each time using 10% DMSO/10% Cremophor EL/15% PEG400/15% HPCD as the solvent (vehicle). The mice in the remaining group (vehicle control) were orally administered the solvent alone. Administration of the test compound or solvent was carried out once per day for 10 days.

The tumor volumes were measured at 20 days, 24 days and 27 days post transplantation. The tumor volumes were calculated by the formula shown below after measuring the tumor long diameters and short diameters using a caliper.

Figure 13:
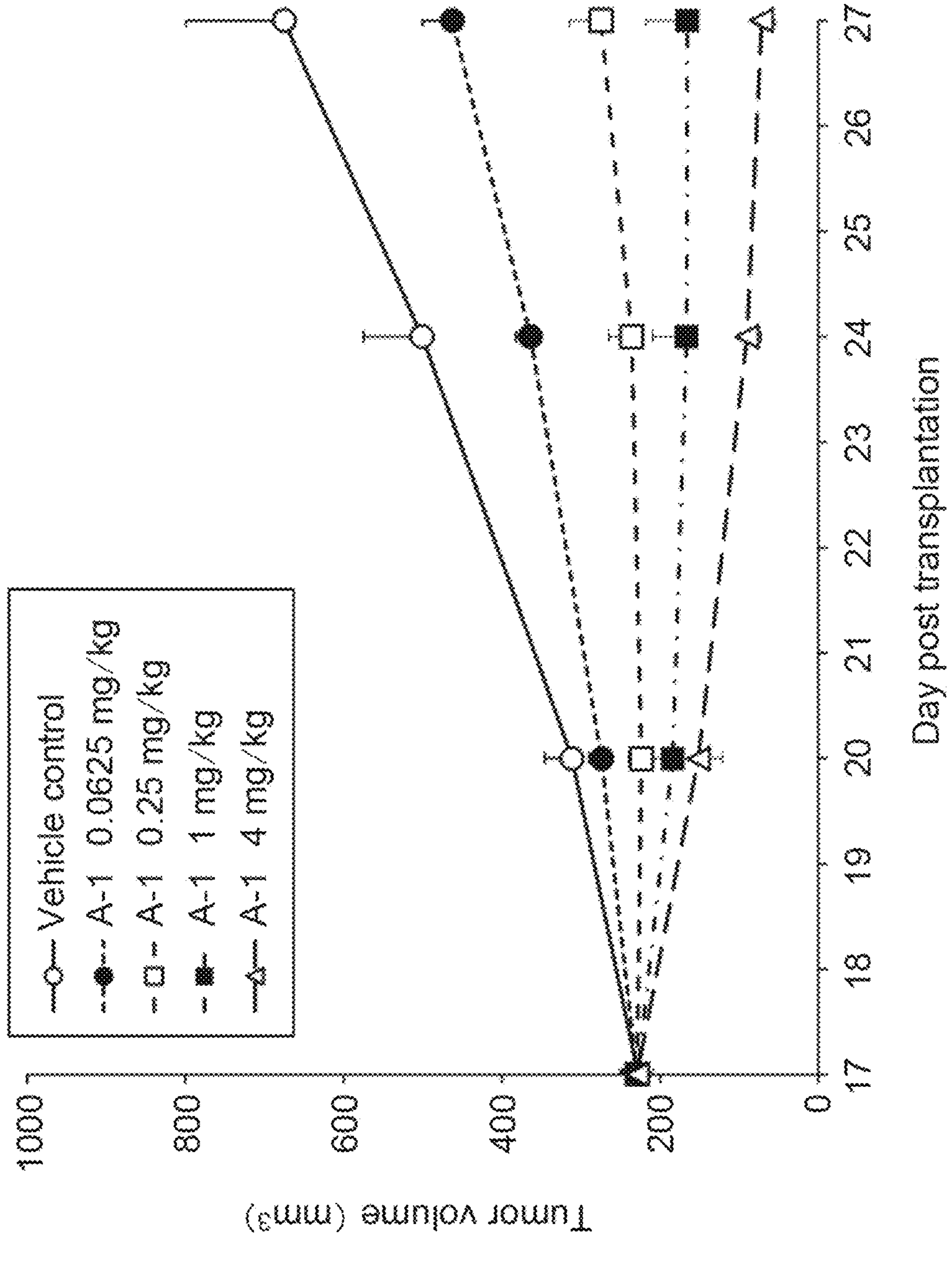
FIG. 13 is a graph showing change over time in tumor volume (mean±SD) in nude mice subcutaneously transplanted with Calu-6 human lung cancer cells.

The results are shown in FIG. 13. FIG. 13 is a graph showing change over time in tumor volume (mean±SD). The horizontal axis (X-axis) represents the days post transplantation and the vertical axis (Y-axis) represents the tumor volume.

Tumor volume ($mm^3$)=½×long diameter (mm)×short diameter (mm)×short diameter (mm)

Test Example 8

Effect of a Dispersant on the Dissolution of an Aryl Amide Derivative

The compositions described in Table 3 below (samples 1 to 9) were investigated as described below for the dissolution of the sodium salt of compound A-1 into FaSSIF after treatment with Japanese Pharmacopoeia 1st fluid for dissolution test. Table 3 shows the ingredients of each composition and their amounts (mg).

TABLE 3

| | Sample 1 | Sample 2 | Sample 3 | Sample 4 | Sample 5 |
|---|---|---|---|---|---|
| Sodium salt of compound A-1 | 5 | 5 | 5 | 5 | 5 |
| Lactose hydrate | 45 | — | — | — | — |
| Methylcellulose | — | 50 | — | — | — |
| Polyvinyl alcohol | — | — | 50 | — | — |
| Hydroxypropyl-cellulose | — | — | — | 50 | — |
| Copolyvidone | — | — | — | — | 50 |
| Hydroxypropyl-methylcellulose | — | — | — | — | — |
| Methacrylic acid copolymer | — | — | — | — | — |
| Polyvinylpyrrolidone | — | — | — | — | — |
| Hypromellose acetate succinate | — | — | — | — | — |
| Total | 50 | 55 | 55 | 55 | 55 |

| | Sample 6 | Sample 7 | Sample 8 | Sample 9 |
|---|---|---|---|---|
| Sodium salt of compound A-1 | 5 | 5 | 5 | 5 |
| Lactose hydrate | — | — | — | — |
| Methylcellulose | — | — | — | — |
| Polyvinyl alcohol | — | — | — | — |
| Hydroxypropylcellulose | — | — | — | — |
| Copolyvidone | — | — | — | — |
| Hydroxypropyl-methylcellulose | 50 | — | — | — |
| Methacrylic acid copolymer | — | 50 | — | — |
| Polyvinylpyrrolidone | — | — | 50 | — |
| Hypromellose acetate succinate | — | — | — | 50 |
| Total | 55 | 55 | 55 | 55 |

The ingredients shown in Table 3 were mixed in a mortar, and the mixture was added to 25 mL of Japanese Pharmacopoeia 1 st fluid for dissolution test and stirred for 1 hour. Next, 25 mL of a double concentration of FaSSIF was added and stirring was continued. After a predetermined time from the addition of FaSSIF, the concentration of compound A-1 in the solution was measured using high-performance liquid chromatography (HPLC). HPLC was carried out using the analysis conditions H shown in Table 29 below.

Figure 14:
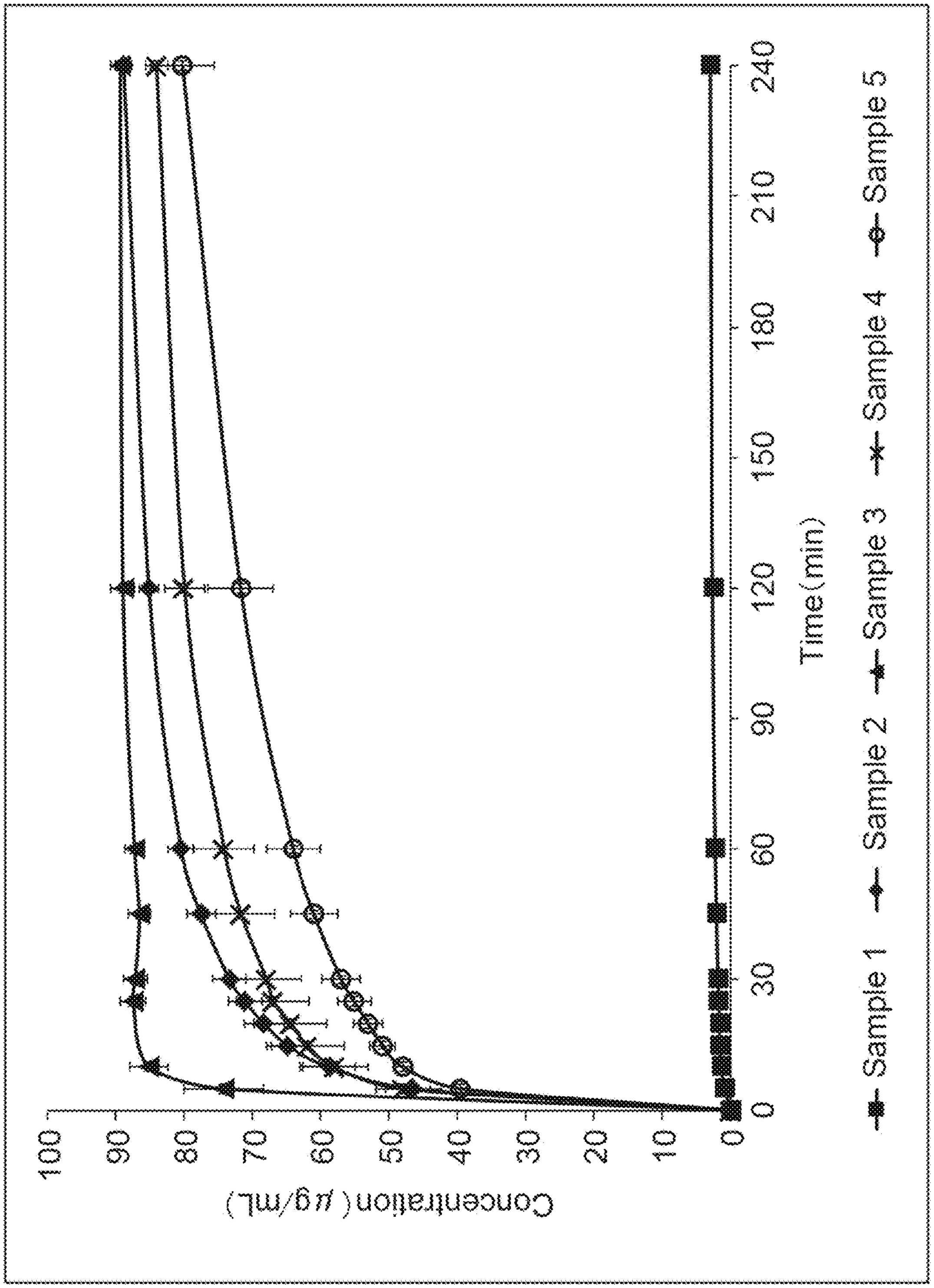
FIG. 14 is a graph showing change over time in concentration (mean±SD) of compound A-1 in a solution obtained by: treating a composition containing a sodium salt of compound A-1 (sample 1, 2, 3, 4 or 5) with Japanese Pharmacopoeia 1st fluid for dissolution test; and thereafter adding FaSSIF thereto, followed by stirring.
Figure 15:
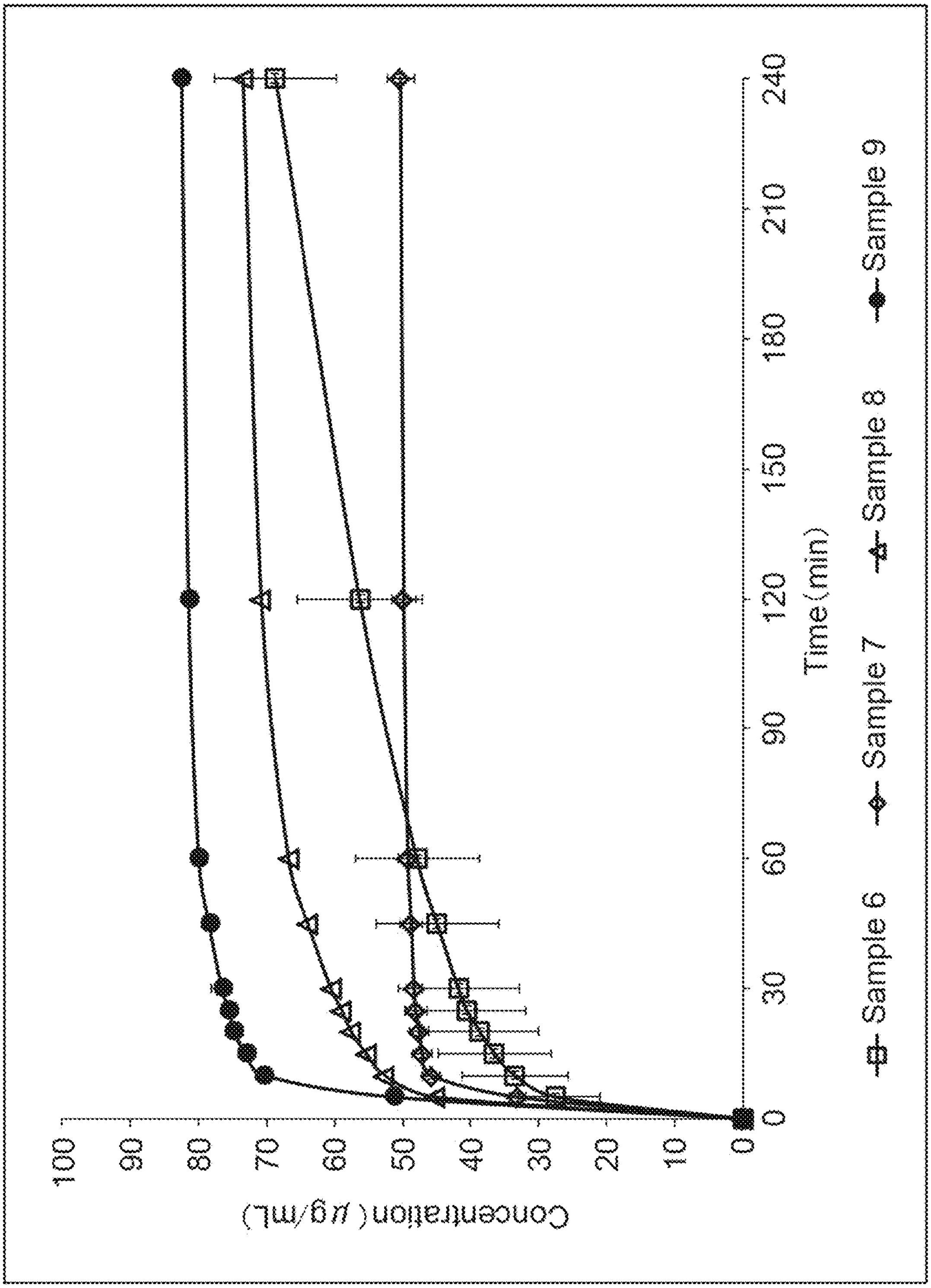
FIG. 15 is a graph showing change over time in concentration (mean±SD) of compound A-1 in a solution obtained by: treating a composition containing a sodium salt of compound A-1 (sample 6, 7, 8 or 9) with Japanese Pharmacopoeia 1st fluid for dissolution test; and thereafter adding FaSSIF thereto, followed by stirring.

The results are shown in FIGS. 14 and 15. In the graphs of FIGS. 14 and 15, the horizontal axis (X axis) represents the time (minutes) after the addition of FaSSIF and the vertical axis (Y axis) represents the concentration (μg/mL) of compound A-1 in the solution.

As is clear from FIGS. 14 and 15, samples 2 to 9 exhibited remarkably high performance with respect to the dissolution of the sodium salt of compound A-1 into FaSSIF compared with sample 1.

Test Example 9

Effect of a Dispersant on the Dissolution of an Aryl Amide Derivative

The compositions described in Table 4 below (samples 10 to 15) were investigated for the dissolution of the sodium salt of compound A-1 into FaSSIF after treatment with Japanese Pharmacopoeia 1st fluid for dissolution test in the same manner as in Test Example 8. Table 4 shows the ingredients of each composition and their amounts (mg).

TABLE 4

| | Sample 10 | Sample 11 | Sample 12 |
|---|---|---|---|
| Sodium salt of compound A-1 | 5 | 5 | 5 |
| Methylcellulose | 5 | 25 | — |
| Polyvinyl alcohol | — | — | 5 |
| Hydroxypropylmethylcellulose | — | — | — |
| Total | 10 | 30 | 10 |

| | Sample 13 | Sample 14 | Sample 15 |
|---|---|---|---|
| Sodium salt of compound A-1 | 5 | 5 | 5 |
| Methylcellulose | — | — | — |
| Polyvinyl alcohol | 25 | — | — |
| Hydroxypropylmethylcellulose | — | 5 | 25 |
| Total | 30 | 10 | 30 |

Figure 16:
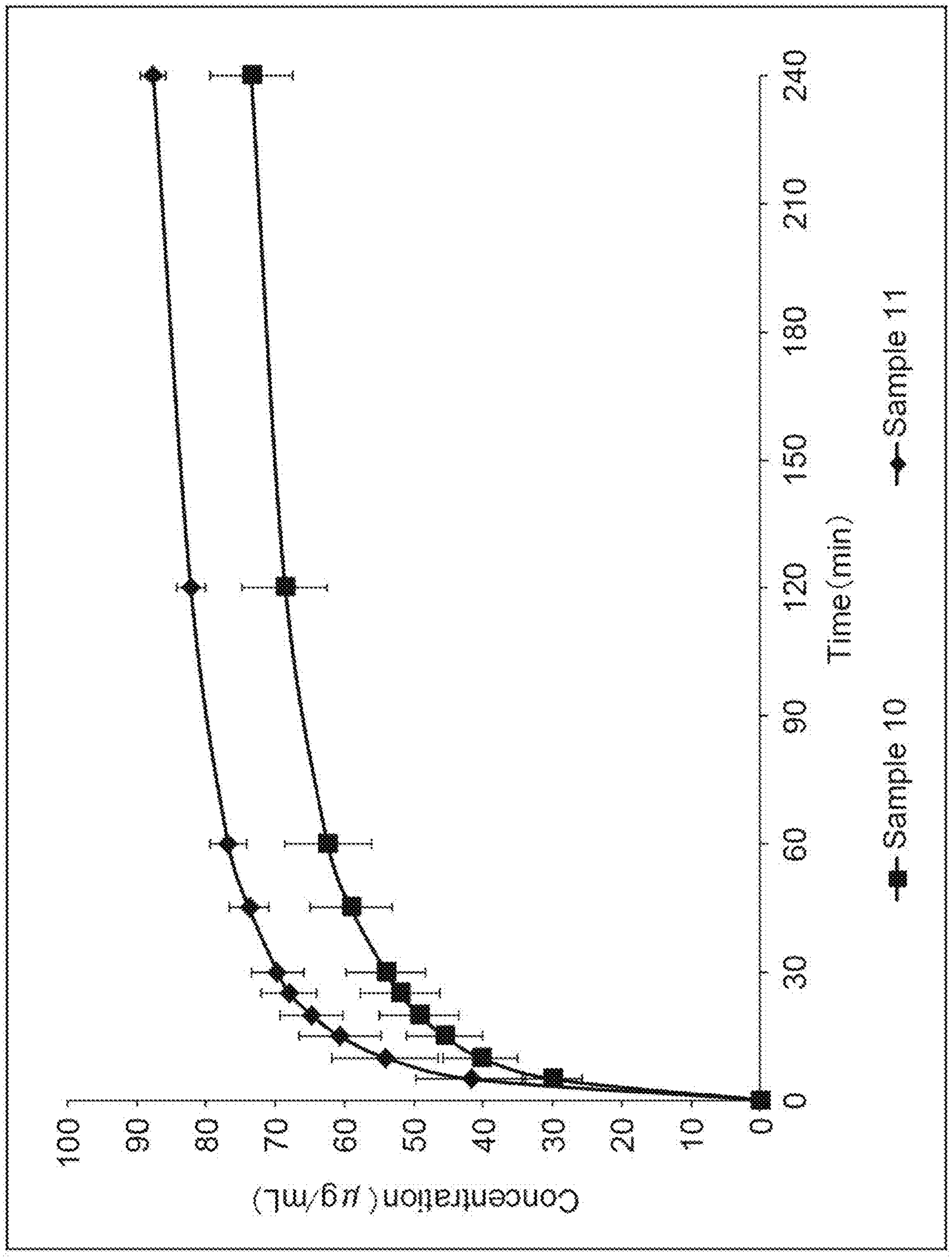
FIG. 16 is a graph showing change over time in concentration (mean±SD) of compound A-1 in a solution obtained by: treating a composition containing a sodium salt of compound A-1 (sample 10 or 11) with Japanese Pharmacopoeia 1st fluid for dissolution test; and thereafter adding FaSSIF thereto, followed by stirring.
Figure 17:
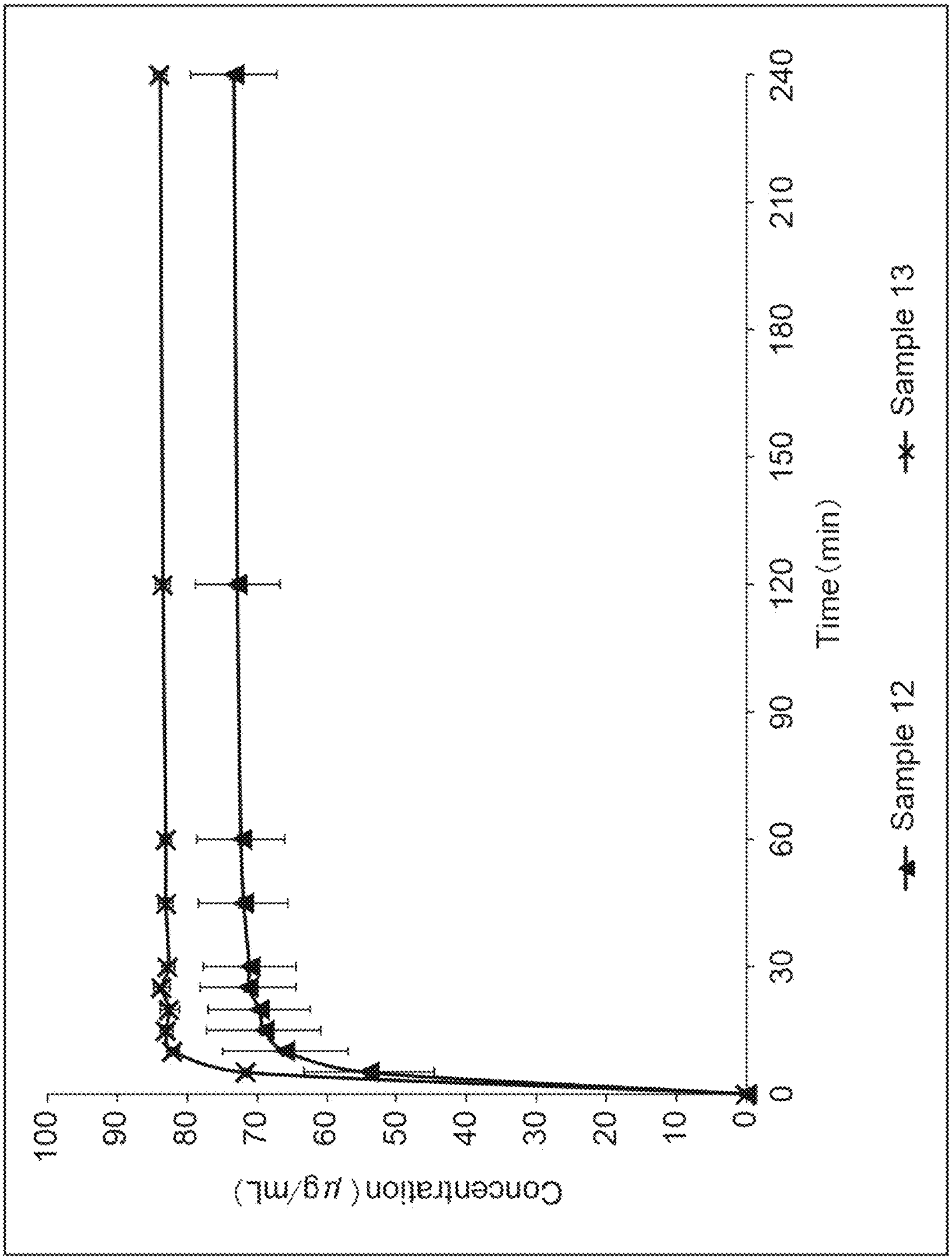
FIG. 17 is a graph showing change over time in concentration (mean±SD) of compound A-1 in a solution obtained by: treating a composition containing a sodium salt of compound A-1 (sample 12 or 13) with Japanese Pharmacopoeia 1st fluid for dissolution test; and thereafter adding FaSSIF thereto, followed by stirring.
Figure 18:
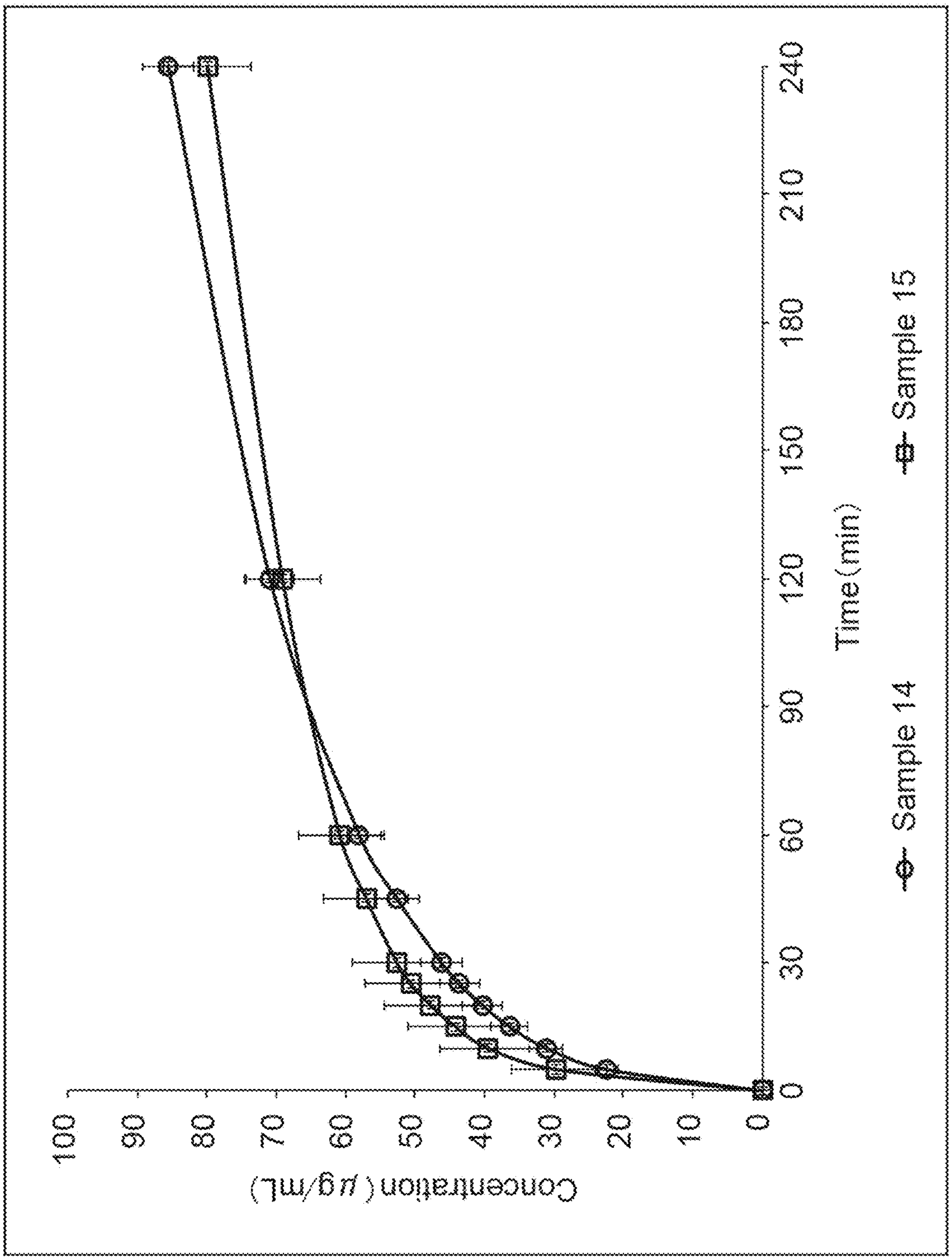
FIG. 18 is a graph showing change over time in concentration (mean±SD) of compound A-1 in a solution obtained by: treating a composition containing a sodium salt of compound A-1 (sample 14 or 15) with Japanese Pharmacopoeia 1st fluid for dissolution test; and thereafter adding FaSSIF thereto, followed by stirring.

The results are shown in FIGS. 16 to 18. In the graphs of FIGS. 16 to 18, the horizontal axis (X axis) represents the time (minutes) after the addition of FaSSIF and the vertical axis (Y axis) represents the concentration (μg/mL) of compound A-1 in the solution.

As is clear from FIGS. 16 to 18, samples 10 to 15 exhibited high performance with respect to the dissolution of the sodium salt of compound A-1 into FaSSIF.

Test Example 10

Effect of a Dispersant on the Dissolution of an Aryl Amide Derivative

The compositions described in Table 5 below (samples 16 to 19) were investigated for the dissolution of the sodium salt of compound A-1 into FaSSIF after treatment with Japanese Pharmacopoeia 1st fluid for dissolution test in the same manner as in Test Example 8. Table 5 shows the ingredients of each composition and their amounts (mg).

TABLE 5

| | Sample 16 | Sample 17 | Sample 18 | Sample 19 |
|---|---|---|---|---|
| Sodium salt of compound A-1 | 5 | 5 | 5 | 5 |
| Polyvinyl alcohol | 25 | 25 | — | — |
| Methylcellulose | — | — | 25 | 25 |
| Meglumine | — | 5 | — | 5 |
| Mannitol | 69.5 | 64.5 | 69.5 | 64.5 |
| Magnesium stearate | 0.5 | 0.5 | 0.5 | 0.5 |
| Total | 100 | 100 | 100 | 100 |

Figure 19:
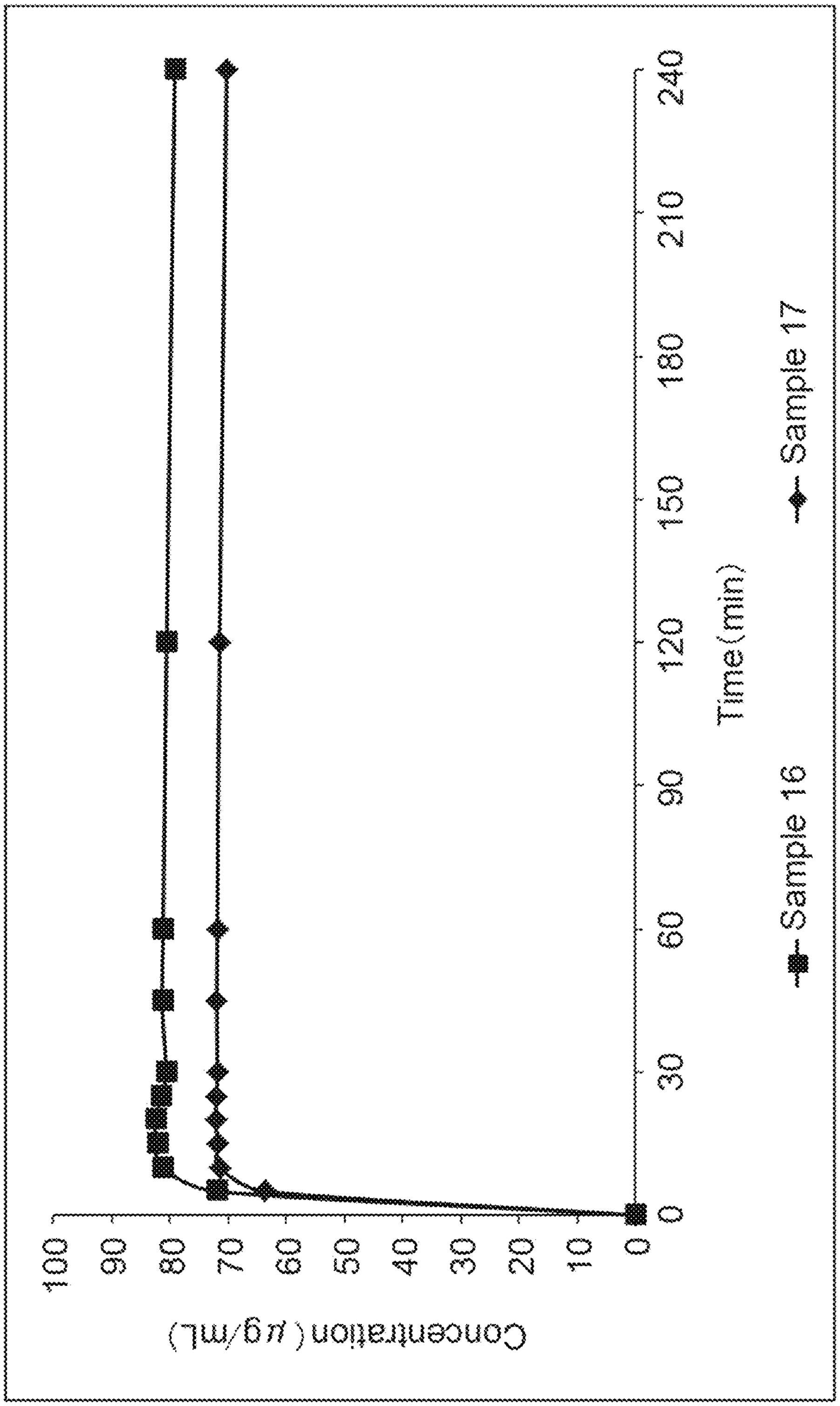
FIG. 19 is a graph showing change over time in concentration (mean±SD) of compound A-1 in a solution obtained by: treating a composition containing a sodium salt of compound A-1 (sample 16 or 17) with Japanese Pharmacopoeia 1st fluid for dissolution test; and thereafter adding FaSSIF thereto, followed by stirring.
Figure 20:
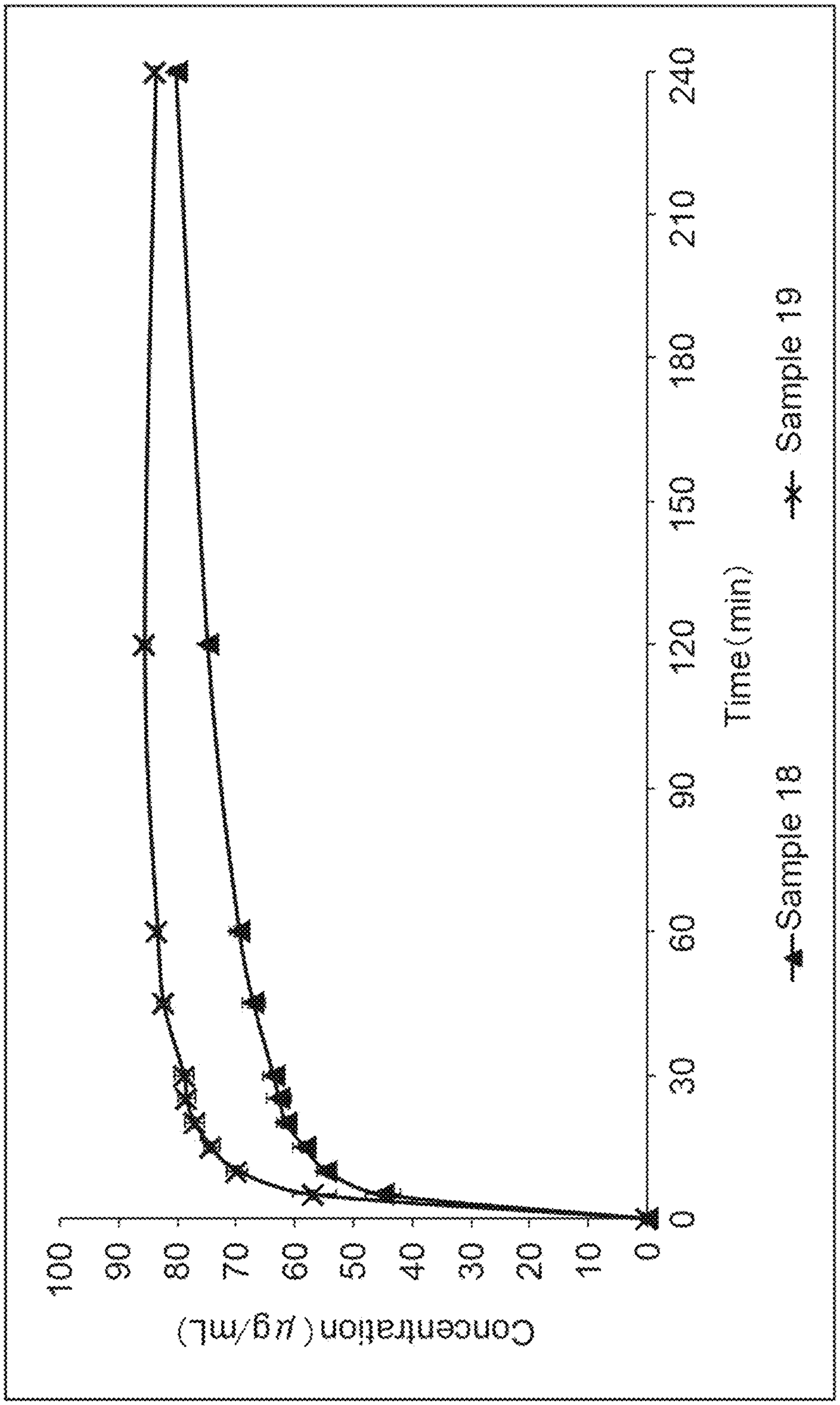
FIG. 20 is a graph showing change over time in concentration (mean±SD) of compound A-1 in a solution obtained by: treating a composition containing a sodium salt of compound A-1 (sample 18 or 19) with Japanese Pharmacopoeia 1st fluid for dissolution test; and thereafter adding FaSSIF thereto, followed by stirring.

The results are shown in FIGS. 19 and 20. In the graphs of FIGS. 19 and 20, the horizontal axis (X axis) represents the time (minutes) after the addition of FaSSIF and the vertical axis (Y axis) represents the concentration (μg/mL) of compound A-1 in the solution.

As is clear from FIGS. 19 and 20, samples 16 to 19 exhibited high performance with respect to the dissolution of the sodium salt of compound A-1 into FaSSIF.

Test Example 11

Effect of a Dispersant on the Dissolution of an Aryl Amide Derivative

The compositions described in Table 6 below (samples 20 to 23) were investigated for the dissolution of the sodium salt of compound A-1 into FaSSIF after treatment with Japanese Pharmacopoeia 1st fluid for dissolution test in the same manner as in Test Example 8. Table 6 shows the ingredients of each composition and their amounts (mg).

TABLE 6

| | Sample 20 | Sample 21 | Sample 22 | Sample 23 |
|---|---|---|---|---|
| Sodium salt of compound A-1 | 5 | 5 | 5 | 5 |
| Methylcellulose | 1 | 3 | 5 | 10 |
| Meglumine | 5 | 5 | 5 | 5 |
| Mannitol | 88 | 86 | 84 | 79 |
| Magnesium stearate | 1 | 1 | 1 | 1 |
| Total | 100 | 100 | 100 | 100 |

Figure 21:
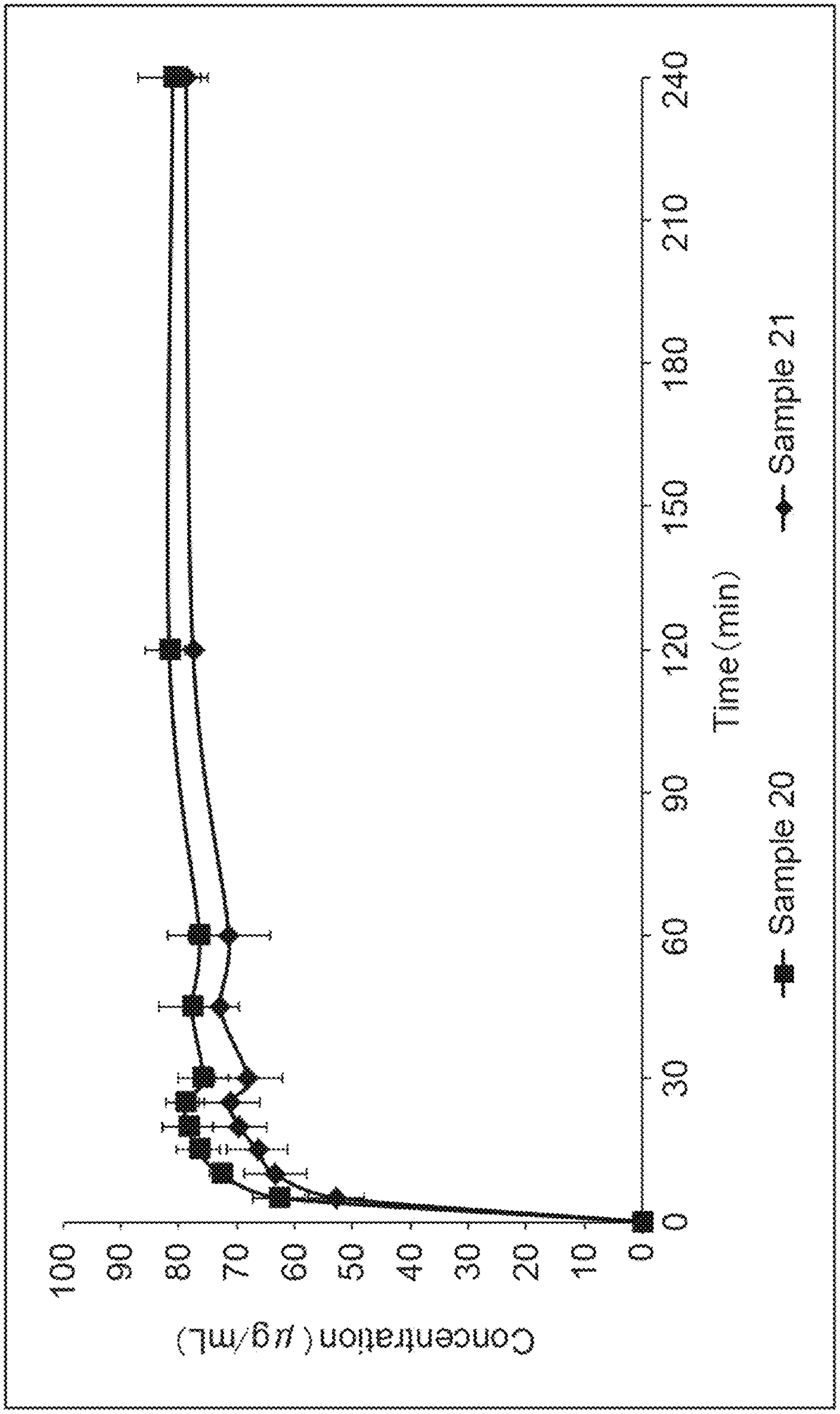
FIG. 21 is a graph showing change over time in concentration (mean±SD) of compound A-1 in a solution obtained by: treating a composition containing a sodium salt of compound A-1 (sample 20 or 21) with Japanese Pharmacopoeia 1st fluid for dissolution test; and thereafter adding FaSSIF thereto, followed by stirring.
Figure 22:
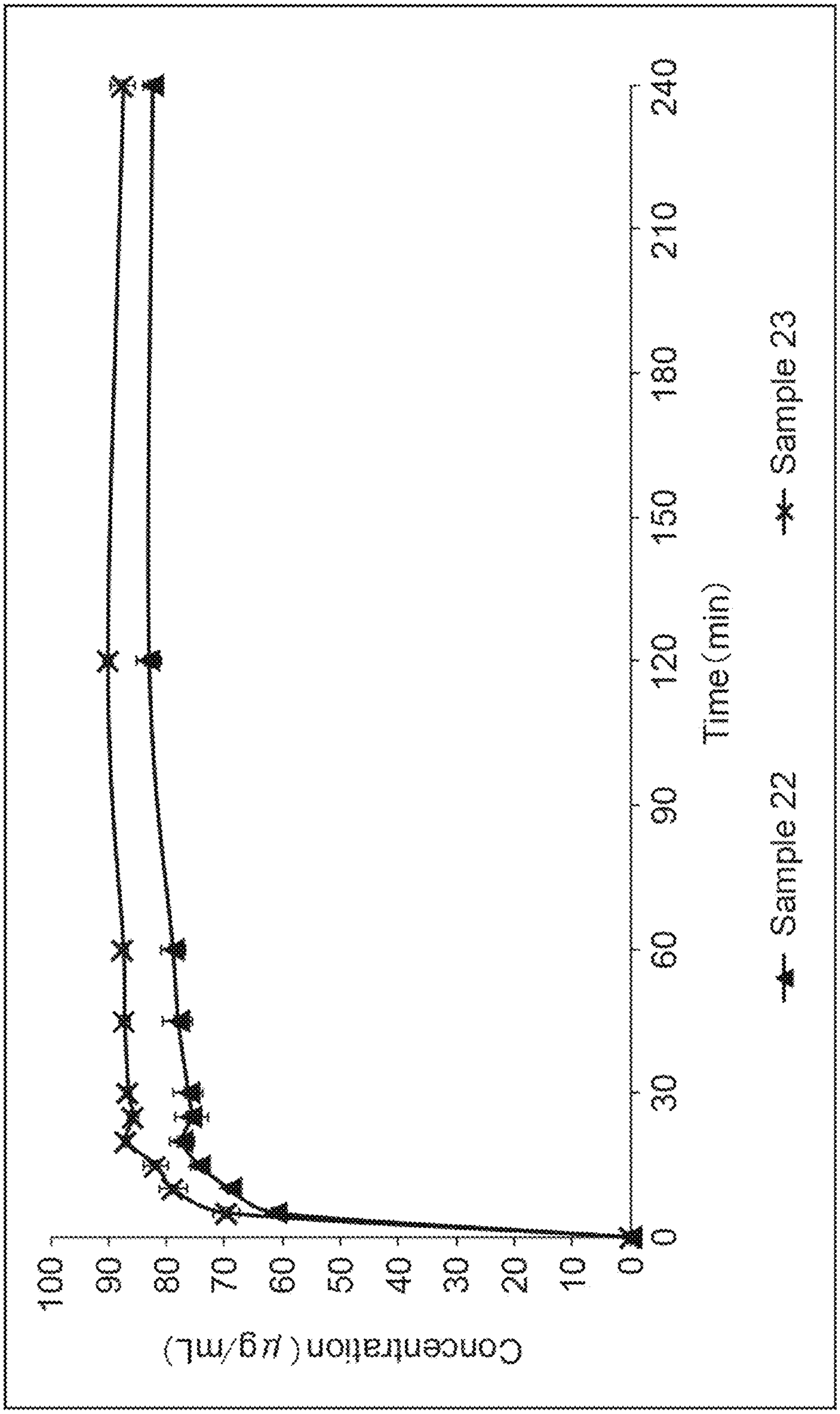
FIG. 22 is a graph showing change over time in concentration (mean±SD) of compound A-1 in a solution obtained by: treating a composition containing a sodium salt of compound A-1 (sample 22 or 23) with Japanese Pharmacopoeia 1st fluid for dissolution test; and thereafter adding FaSSIF thereto, followed by stirring.

The results are shown in FIGS. 21 and 22. In the graphs of FIGS. 21 and 22, the horizontal axis (X axis) represents the time (minutes) after the addition of FaSSIF and the vertical axis (Y axis) represents the concentration (gig/mL) of compound A-1 in the solution.

As is clear from FIGS. 21 and 22, samples 20 to 23 exhibited high performance with respect to the dissolution of the sodium salt of compound A-1 into FaSSIF.

Test Example 12

Effect of Abasic Compound on the Stability of an Aryl Amide Derivative

The compositions described in Table 7 below (samples 24 to 32) were investigated as described below for the stability of the sodium salt of compound A-1 in the compositions. Table 7 shows the ingredients of each composition and their amounts (mg).

TABLE 7

| | Sample 24 | Sample 25 | Sample 26 | Sample 27 | Sample 28 |
|---|---|---|---|---|---|
| Sodium salt of compound A-1 | 20 | 20 | 20 | 20 | 20 |
| Mannitol | 970 | 930 | 880 | 930 | 930 |
| Meglumine | 10 | 50 | 100 | — | — |
| Arginine | — | — | — | 50 | — |
| Histidine | — | — | — | — | 50 |
| Magnesium oxide | — | — | — | — | — |
| Calcium silicate | — | — | — | — | — |
| Magnesium stearate | — | — | — | — | — |
| Hydroxypropyl-methylcellulose | 300 | 300 | 300 | 300 | 300 |

TABLE 7-continued

| | Sample 29 | Sample 30 | Sample 31 | Sample 32 |
|---|---|---|---|---|
| Sodium salt of compound A-1 | 20 | 20 | 20 | 20 |
| Mannitol | 930 | 930 | 930 | 980 |
| Meglumine | — | — | — | — |
| Arginine | — | — | — | — |
| Histidine | — | — | — | — |
| Magnesium oxide | 50 | — | — | — |
| Calcium silicate | — | 50 | — | — |
| Magnesium stearate | — | — | 50 | — |
| Hydroxypropyl-methylcellulose | 300 | 300 | 300 | 300 |

The ingredients shown in Table 7 were mixed in a mortar, and the mixture was stored tightly stoppered at 80° C. for 2 weeks. The mixture at the start of storage and the mixture at the end of storage were analyzed in the following manner for the contents of the sodium salt of compound A-1, a hydrolysis product of compound A-1 represented by formula (X) below, and other degradation products derived from compound A-1. The mixture was dissolved in a liquid mixture of dimethylformamide/acetonitrile (6:1). This was filtered and the filtrate was subjected to high-performance liquid chromatography (HPLC) analysis under the analysis conditions I shown in Table 29 below.

[Chemical Formula 332]

(X)

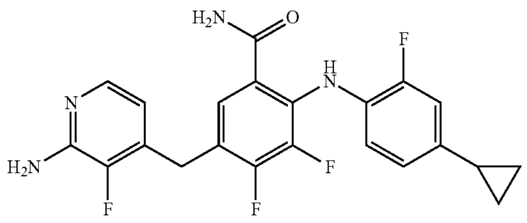

The results are shown in Table 8 below. Table 8 shows the relative peak areas of compound A-1, the hydrolysis product represented by formula (X) above, and other degradation products derived from compound A-1 when the sum of the peak areas of compound A-1, the hydrolysis product, and the other degradation products is taken as 100.

TABLE 8

| | Sample 24 | | Sample 25 | | Sample 26 | | Sample 27 | | Sample 28 | |
|---|---|---|---|---|---|---|---|---|---|---|
| | Start | End | Start | End | Start | End | Start | End | Start | End |
| Compound A-1 | 98.52 | 96.63 | 98.75 | 97.14 | 98.81 | 97.41 | 98.8 | 97.26 | 98.66 | 93.83 |
| Hydrolysis product of compound A-1 (Compound of formula (X)) | 0.1 | 2.67 | 0.1 | 2.26 | 0.09 | 2.06 | 0.11 | 2.2 | 0.11 | 5.46 |
| Other degradation products | 1.38 | 0.7 | 1.15 | 0.6 | 1.1 | 0.53 | 1.09 | 0.54 | 1.23 | 0.71 |

| | Sample 29 | | Sample 30 | | Sample 31 | | Sample 32 | |
|---|---|---|---|---|---|---|---|---|
| | Start | End | Start | End | Start | End | Start | End |
| Compound A-1 | 98.57 | 95.63 | 98.53 | 95.23 | 98.5 | 93.8 | 98.53 | 92.3 |
| Hydrolysis product of compound A-1 (Compound of formula (X)) | 0.11 | 3.6 | 0.12 | 3.98 | 0.11 | 4.97 | 0.11 | 6.57 |
| Other degradation products | 1.32 | 0.77 | 1.35 | 0.79 | 1.39 | 1.23 | 1.36 | 1.13 |

As is clear from Table 8, samples 24 to 31 exhibited decreased degradation of the sodium salt of compound A-1 compared with sample 32.

Test Example 13

Effect of Abasic Compound on the Stability of an Aryl Amide Derivative

The compositions described in Table 9 below (samples 33 and 34) were investigated as described below for the stability of the sodium salt of compound A-1 in the compositions. Table 9 shows the ingredients of each composition and their amounts (mg).

TABLE 9

| | Sample 33 | Sample 34 |
|---|---|---|
| Sodium salt of compound A-1 | 2 | 2 |
| Mannitol | 198 | 198 |
| Meglumine | — | 30 |
| Total | 200 | 230 |

The ingredients shown in Table 9 were mixed in a mortar, and the mixture was stored tightly stoppered at 80° C. for 2 weeks. The mixture at the start of storage and the mixture at the end of storage were analyzed in the following manner for the content of the sodium salt of compound A-1. The mixture was dissolved in a liquid mixture of dimethylformamide/acetonitrile (6:1). This was filtered and the filtrate was subjected to high-performance liquid chromatography (HPLC) analysis under the analysis conditions I shown in Table 29 below.

The results are shown in Table 10 below. Table 10 shows the relative peak area of compound A-1 when the sum of the peak areas of compound A-1, the hydrolysis product represented by formula (X) above, and other degradation products derived from compound A-1 is taken as 100.

TABLE 10

| | Start of storage | End of storage |
|---|---|---|
| Sample 33 | 98.4 | 70.3 |
| Sample 34 | 97.7 | 89.7 |

As is clear from Table 10, sample 34 exhibited remarkably decreased degradation of the sodium salt of compound A-1 compared with sample 33.

Test Example 14

Effect of a Basic Compound on the Stability of an Aryl Amide Derivative

The compositions described in Table 11 below (samples 35 and 36) were investigated as described below for the stability of the sodium salt of compound A-1 in the compositions. Table 11 shows the ingredients of each composition and their amounts (mg).

TABLE 11

| | Sample 35 | Sample 36 |
|---|---|---|
| Sodium salt of compound A-1 | 0.25 | 0.25 |
| Methylcellulose | 1.25 | 1.25 |
| Meglumine | — | 5 |
| Mannitol | 98 | 93 |
| Magnesium stearate | 0.5 | 0.5 |
| Total | 100 | 100 |

The ingredients shown in Table 11 were mixed in a mortar, and the mixture was stored tightly stoppered at 40° C. for 3 months. The mixture at the start of storage and the mixture at the end of storage were analyzed in the following manner for the content of the sodium salt of compound A-1. The mixture was dissolved in a liquid mixture of dimethylformamide/acetonitrile (6:1). This was filtered and the filtrate was subjected to high-performance liquid chromatography (HPLC) analysis under the analysis conditions I shown in Table 29 below.

The results are shown in Table 12 below. Table 12 shows the relative peak area of compound A-1 when the sum of the peak areas of compound A-1, the hydrolysis product represented by formula (X) above, and other degradation products derived from compound A-1 is taken as 100.

TABLE 12

| | Start of storage | End of storage |
|---|---|---|
| Sample 35 | 95.7 | 90.5 |
| Sample 36 | 96.5 | 95.0 |

As is clear from Table 12, sample 36 exhibited remarkably decreased degradation of the sodium salt of compound A-1 compared with sample 35.

Test Example 15

Capsules (1) Production of Capsules

Capsules (samples 37 to 39) were produced in the following manner in accordance with the prescriptions shown in Table 13 below. The sodium salt of compound A-1 and D-mannitol were mixed and sieved, and the remaining ingredients (methylcellulose, meglumine, and magnesium stearate) were then added and mixed. The resulting mixture was filled into a capsule shell to give a capsule. Table 13 shows the amounts (mg) of the composition and its ingredients per capsule.

TABLE 13

| | Sample 37 | Sample 38 | Sample 39 |
|---|---|---|---|
| Sodium salt of compound A-1 | 0.10 | 0.83 | 2.08 |
| D-Mannitol | 93.90 | 93.17 | 91.92 |
| Methylcellulose | 5.00 | 5.00 | 5.00 |
| Meglumine | 5.00 | 5.00 | 5.00 |
| Magnesium stearate | 1.00 | 1.00 | 1.00 |
| Total | 105.00 | 105.00 | 105.00 |

(2) Testing of Capsules (2-1) Tightly Stoppered Storage

The capsule was put into a bottle with silica gel and stored tightly stoppered under the conditions (a), (b) or (c) below for 6 months.

(a) 5° C.

(b) 30° C./75% RH (c) 40° C./75% RH

The capsule at the start of storage and the capsule at the end of storage were analyzed in the following manner for the content of degradation products of compound A-1. The capsule was dissolved in a liquid mixture of dimethylformamide/acetonitrile (6:1). This was filtered and the filtrate was subjected to high-performance liquid chromatography (HPLC) analysis under the analysis conditions I shown in Table 29 below.

The results are shown in Table 14 below. Table 14 shows the relative peak area of degradation products of compound A-1 when the sum of the peak areas of compound A-1 and the degradation products is taken as 100.

TABLE 14

| | Start of storage | End of storage 5° C. | End of storage 30° C., 75% RH | End of storage 40° C., 75% RH |
|---|---|---|---|---|
| Sample 37 | 0.3 | 0.2 | 0.2 | 0.6 |
| Sample 38 | 0.3 | 0.3 | 0.3 | 0.4 |
| Sample 39 | 0.3 | 0.3 | 0.3 | 0.3 |

The capsule at the start of storage and the capsule at the end of storage were investigated in the following manner for the dissolution of the sodium salt of compound A-1. Dissolution testing was conducted using the paddle method under the conditions below, and the solution collected 15 minutes, 30 minutes or 60 minutes after the start of the test was subjected to high-performance liquid chromatography (HPLC) analysis under the analysis conditions J shown in Table 29 below.

Medium: McIlvaine's buffer (pH 7.5) containing 0.1% Tween 80

Volume of medium: 900 mL

Temperature: 37° C.

Rotational speed: 50 rpm

The results are shown in Tables 15 to 17 below. Tables 15 to 17 show the dissolution (%) (mean±SD) of the sodium salt of compound A-1.

Sample 37:

TABLE 15

| | | 15 min | 30 min | 60 min |
|---|---|---|---|---|
| Start of storage | | 100 ± 1.6 | 102 ± 2.0 | 102 ± 1.7 |
| End of storage | 5° C. | 96 ± 7.6 | 101 ± 3.1 | 100 ± 2.6 |
| | 30° C., 75% RH | 99 ± 1.9 | 99 ± 1.7 | 99 ± 1.9 |
| | 40° C., 75% RH | 98 ± 1.5 | 100 ± 1.1 | 99 ± 1.2 |

Sample 38:

TABLE 16

| | | 15 min | 30 min | 60 min |
|---|---|---|---|---|
| Start of storage | | 93 ± 5.4 | 101 ± 0.8 | 101 ± 0.7 |
| End of storage | 5° C. | 99 ± 1.2 | 101 ± 1.2 | 100 ± 1.2 |
| | 30° C., 75% RH | 98 ± 4.7 | 100 ± 1.5 | 100 ± 1.5 |
| | 40° C., 75% RH | 99 ± 2.2 | 100 ± 1.7 | 100 ± 1.8 |

Sample 39:

TABLE 17

| | | 15 min | 30 min | 60 min |
|---|---|---|---|---|
| Start of storage | | 90 ± 4.8 | 95 ± 2.9 | 96 ± 2.9 |
| End of storage | 5° C. | 91 ± 3.3 | 96 ± 3.4 | 97 ± 3.5 |
| | 30° C., 75% RH | 91 ± 4.9 | 97 ± 4.4 | 97 ± 4.3 |
| | 40° C., 75% RH | 89 ± 8.7 | 95 ± 4.8 | 96 ± 4.5 |

As is clear from the above results (Tables 14 to 17), no large influence of storage on product quality was observed in any of the capsules.

(2-2) Unstoppered Storage

The capsule was put into a bottle with silica gel and stored unstoppered at 40° C./75% RH for 4 weeks.

The capsule at the start of storage and the capsule at the end of storage were analyzed for the content of degradation products of compound A-1 in the same manner as in (2-1) above. The results are shown in Table 18 below. Table 18 shows the relative peak area of degradation products of compound A-1 when the sum of the peak areas of compound A-1 and the degradation products is taken as 100.

TABLE 18

| | Start of storage | End of storage |
|---|---|---|
| Sample 37 | 0.2 | 3.8 |
| Sample 38 | 0.3 | 1.3 |
| Sample 39 | 0.3 | 0.7 |

The capsule at the start of storage and the capsule at the end of storage were investigated for the dissolution of the sodium salt of compound A-1 in the same manner as in (2-1) above. The results are shown in Table 19 below. Table 19 shows the dissolution (%) (mean±SD) of the sodium salt of compound A-1.

TABLE 19

| | | 15 min | 30 min | 60 min |
|---|---|---|---|---|
| Sample 37 | Start of storage | 100 ± 1.6 | 102 ± 2.0 | 102 ± 1.7 |
| | End of storage | 88 ± 4.6 | 94 ± 1.6 | 95 ± 1.3 |
| Sample 38 | Start of storage | 93 ± 5.4 | 101 ± 0.8 | 101 ± 0.7 |
| | End of storage | 92 ± 7.8 | 99 ± 2.3 | 99 ± 1.6 |
| Sample 39 | Start of storage | 90 ± 4.8 | 95 ± 2.9 | 96 ± 2.9 |
| | End of storage | 91 ± 5.2 | 96 ± 2.5 | 97 ± 2.3 |

As is clear from the above results (Tables 18 and 19), although the amount of degradation products generated during storage in sample 37 was larger compared with sample 38 or 39, no large influence of storage on product quality was observed in any of the capsules.

Test Example 16

Capsules (1) Production of Capsules

Capsules (samples 40 to 42) were produced in the following manner in accordance with the prescriptions shown in Table 20 below. The sodium salt of compound A-1 and D-mannitol were mixed and sieved, and the remaining ingredients (methylcellulose, meglumine, and magnesium stearate) were then added and mixed. The resulting mixture was filled into a capsule shell to give a capsule. Table 20 shows the amounts (mg) of the composition and its ingredients per capsule.

TABLE 20

| | Sample 40 | Sample 41 | Sample 42 |
|---|---|---|---|
| Sodium salt of compound A-1 | 0.10 | 0.83 | 2.08 |
| D-Mannitol | 93.90 | 93.17 | 91.92 |
| Methylcellulose | 5.00 | 5.00 | 5.00 |
| Meglumine | 5.00 | 5.00 | 5.00 |
| Magnesium stearate | 1.00 | 1.00 | 1.00 |
| Total | 105.00 | 105.00 | 105.00 |

(2) Testing of Capsules

The capsule was put into a bottle with silica gel and stored tightly stoppered at 30° C./75% RH for 6 months.

The capsule at the start of storage and the capsule at the end of storage were analyzed for the content of degradation products of compound A-1 in the same manner as in Test Example 15. The results are shown in Table 21 below. Table 21 shows the relative peak area of degradation products of compound A-1 when the sum of the peak areas of compound A-1 and the degradation products is taken as 100.

TABLE 21

| | Start of storage | End of storage |
|---|---|---|
| Sample 40 | 0.4 | 0.5 |
| Sample 41 | 0.4 | 0.6 |
| Sample 42 | 0.4 | 0.6 |

The capsule at the start of storage and the capsule at the end of storage were investigated for the dissolution of the sodium salt of compound A-1 in the same manner as in Test Example 15. The results are shown in Table 22 below. Table 22 shows the dissolution (%) (mean±SD) of the sodium salt of compound A-1.

TABLE 22

| | | 15 min | 30 min | 60 min |
|---|---|---|---|---|
| Sample 40 | Start of storage | 99 ± 1.7 | 100 ± 1.7 | 99 ± 1.6 |
| | End of storage | 88 ± 22.8 | 99 ± 2.7 | 99 ± 2.3 |
| Sample 41 | Start of storage | 99 ± 2.7 | 101 ± 2.1 | 101 ± 2.1 |
| | End of storage | 98 ± 1.8 | 100 ± 1.3 | 100 ± 1.4 |
| Sample 42 | Start of storage | 99 ± 1.8 | 100 ± 1.4 | 100 ± 1.5 |
| | End of storage | 92 ± 3.1 | 97 ± 2.1 | 97 ± 2.0 |

As is clear from the above results (Tables 21 and 22), no large influence of storage on product quality was observed in any of the capsules.

Test Example 17

Tablets

Tablets were produced in the following manner in accordance with the prescription of sample 39 that is shown in Table 13 above. The sodium salt of compound A-1 and D-mannitol were mixed and sieved, and the remaining ingredients (methylcellulose, meglumine, and magnesium stearate) were then added and mixed. The resulting mixture was tableted at a load of 7.5 kN or 5.5 kN with a compaction simulator to form a tablet.

The ejection stress of the tablets at the time of tableting was measured. Also, the hardness of the tablets was measured with a hardness tester and converted to tensile strength. The results are shown in Table 23 below.

TABLE 23

| | | |
|---|---|---|
| Load (kN) | 7.5 | 5.5 |
| Ejection stress (MPa) | 15.43 | 10.56 |
| Tensile strength (MPa) | 4.77 | 3.62 |

It is stated that it is preferred in terms of manufacturability that the ejection stress be 5 MPa or less and the tensile strength be 2 MPa or more (see Int J Pharm. 2016; 510(1): 195-202). From such a viewpoint, it can be said that both of the above tablets have good tensile strength but high ejection stress.

Test Example 18

Tablets (1) Production of Tablets

Tablets (samples 43 and 44) were produced in the following manner in accordance with the prescriptions shown in Table 24 below. Table 24 shows the amounts (mg) of the composition and its ingredients per tablet.

TABLE 24

| | Sample 43 | Sample 44 |
|---|---|---|
| Sodium salt of compound A-1 | 2.0 | 2.0 |
| D-Mannitol | 92.0 | 92.0 |
| Methylcellulose | 5.0 | 5.0 |
| Meglumine | 5.0 | 5.0 |
| Magnesium stearate | 1.0 | 0.5 |
| Magnesium stearate (tableting lubricant) | — | 1.0 |

Sample 43:

The sodium salt of compound A-1 and D-mannitol were mixed and sieved, and the mixture was then put into a mortar with methylcellulose, meglumine, and magnesium stearate, and mixed. The resulting mixture was dry granulated and sized, and this was then tableted at a load of 7.5 kN with a compaction simulator to form a tablet.

Sample 44:

The sodium salt of compound A-1 and D-mannitol were mixed and sieved, and the mixture was then put into a mortar with methylcellulose, meglumine, and magnesium stearate (not including the amount to be used as a tableting lubricant), and mixed. The resulting mixture was dry granulated and sized, magnesium stearate (the amount to be used as a tableting lubricant) was then added, and it was tableted at a load of 5.5 kN with a compaction simulator to form a tablet.

The ejection stress of the tablets at the time of tableting was measured. Also, the hardness of the tablets was measured with a hardness tester and converted to tensile strength. The results are shown in Table 25 below.

TABLE 25

| | Sample 43 | Sample 44 |
|---|---|---|
| Ejection stress (MPa) | 10.31 | 3.56 |
| Tensile strength (MPa) | 4.35 | 3.00 |

As is clear from Table 25, both tablets had remarkably low ejection stress compared with the tablets of Test Example 17. Also, they had good tensile strength, like the tablets of Test Example 17. In particular, the tablet of sample 44 had good ejection stress and good tensile strength, and had excellent manufacturability.

(2) Testing of Tablets (2-1) Dissolution Testing

The tablets (samples 43 and 44) were investigated for the dissolution of the sodium salt of compound A-1 in the same manner as in Test Example 15. The results are shown in Table 26 below. Table 26 shows the dissolution (%) (mean±SD) of the sodium salt of compound A-1.

TABLE 26

| | 15 min | 30 min | 60 min |
|---|---|---|---|
| Sample 43 | 99.5 ± 0.35 | 100.2 ± 0.12 | 100.0 ± 0.10 |
| Sample 44 | 99.9 ± 0.0 | 100.1 ± 0.1 | 100.0 ± 0.1 |

As is clear from Table 26, both tablets exhibit good dissolution of the sodium salt of compound A-1.

(2-2) Purity Testing

The tablet of sample 44 was stored tightly stoppered at 40° C. for 1 month. The capsule at the start of storage and the capsule at the end of storage were analyzed for the content of degradation products of compound A-1 in the same manner as in Test Example 15. The relative peak area of degradation products of compound A-1 when the sum of the peak areas of compound A-1 and the degradation products is taken as 100 is shown below.

Start of storage: 0.55

End of storage: 0.47

As is clear from the above results, no decrease in purity due to storage was observed.

Test Example 19

Tablets

Tablets (samples 45 and 46) were produced in the following manner in accordance with the prescriptions shown in Table 27 below. Table 27 shows the amounts (mg) of the composition and its ingredients per tablet.

TABLE 27

| | Sample 45 | Sample 46 |
|---|---|---|
| Sodium salt of compound A-1 | 0.2 | 0.2 |
| D-Mannitol | 93.8 | 93.8 |
| Methylcellulose | 5.0 | 5.0 |
| Meglumine | 5.0 | 5.0 |
| Magnesium stearate | 0.5 | 0.5 |
| Magnesium stearate (tableting lubricant) | 1.0 | — |
| Sodium stearyl fumarate (tableting lubricant) | — | 1.0 |

Sample 45:

The sodium salt of compound A-1 and D-mannitol were mixed and sieved, and the mixture was then put into a mortar with methylcellulose, meglumine, and magnesium stearate (not including the amount to be used as a tableting lubricant), and mixed. The resulting mixture was dry granulated and sized, magnesium stearate (the amount to be used as a tableting lubricant) was then added, and it was tableted at a load of 5.5 kN with a compaction simulator to form a tablet.

Sample 46:

The sodium salt of compound A-1 and D-mannitol were mixed and sieved, and the mixture was then put into a mortar with methylcellulose, meglumine, and magnesium stearate, and mixed. The resulting mixture was dry granulated and sized, sodium stearyl fumarate (tableting lubricant) was then added, and it was tableted at a load of 5.5 kN with a compaction simulator to form a tablet.

The ejection stress of the tablets at the time of tableting was measured. Also, the hardness of the tablets was measured with a hardness tester and converted to tensile strength. Also, friability testing was conducted to determine friability. The results are shown in Table 28 below.

TABLE 28

| | Sample 45 | Sample 46 |
|---|---|---|
| Ejection stress (MPa) | 4.26 | 4.33 |
| Tensile strength (MPa) | 2.50 | 3.44 |
| Friability (%) | 0.12 | 0.13 |

As is clear from Table 28, both tablets had good ejection stress and good tensile strength, and had excellent manufacturability. Also, it is stated that it is preferred that the friability be 1 or less (see Japanese Pharmacopoeia), it can be said that the results of the friability testing were extremely good.

(HPLC Analysis Conditions)

The HPLC analysis conditions H to J used in the test examples above are shown in Table 29 below. In Table 29 below, "TFA" stands for trifluoroacetic acid.

TABLE 29

| Analysis conditions | Apparatus | Column | Column temperature | Detection wavelength (UV) |
|---|---|---|---|---|
| H | Acquity UPLC (Waters) | Acquity UPLC BEH Shield RP18 2.1 × 50 mm, 1.7 μm (Waters) | 40° C. | 279 nm |
| I | Acquity UPLC (Waters) | ZORBAX ECLIPSE Plus C18 Rapid Resolution HD 2.1 × 50 mm, 1.8 μm (Agilent Technologies) | 35° C. | 278 nm |
| J | Acquity UPLC (Waters) | ZORBAX ECLIPSE Plus C18 2.1 × 50 mm, 1.8 μm (Agilent Technologies) | 40° C. | 278 nm |

| Analysis | | Gradient | | Flow rate |
|---|---|---|---|---|
| conditions | Mobile phase | Time after injection (min) | A/B | (mL/min) |
| H | A) 0.05% TFA/$H_2O$ | 0-0.95 | 95.0/5.0 → 2.0/98.0 | 1.0 |
| | B) 0.05% TFA/$CH_3CN$ | 0.95-1.40 | 2.0/98.0 | |
| | | 1.40-1.41 | 2.0/98.0 → 95.0/5.0 | |
| I | A) 0.05% TFA/$H_2O$ | 0-0.15 | 95.0/5.0 | 0.9 |
| | B) 0.05% TFA/$CH_3CN$ | 0.15-0.25 | 95.0/5.0 → 67.0/33.0 | |
| | | 0.25-2.8 | 67.0/33.0 → 61.0/39.0 | |
| | | 2.8-7.8 | 61.0/39.0 → 57.7/42.3 | |
| | | 7.8-9.2 | 57.7/42.3 → 4.0/96.0 | |
| | | 9.2-10.4 | 4.0/96.0 | |
| | | 10.4-10.5 | 4.0/96.0 → 95.0/5.0 | |
| | | 10.5-13.0 | 95.0/5.0 | |
| J | A) 0.05% TFA/$H_2O$ | 0-2.7 | 56.0/44.0 → 52.8/47.2 | 0.9 |
| | B) 0.05% TFA/$CH_3CN$ | 2.7-2.8 | 52.8/47.2 → 56.0/44.0 | |
| | | 2.8-3.5 | 56.0/44.0 | |

INDUSTRIAL APPLICABILITY

Compositions according to the present disclosure can be utilized for the treatment or prevention of a cell proliferative disorder, particularly a cancer.

The invention claimed is:

1. A composition comprising a compound represented by general formula (1) below or a pharmaceutically acceptable salt thereof, or a pharmaceutically acceptable solvate of said compound or salt, and a dispersant:

(1)

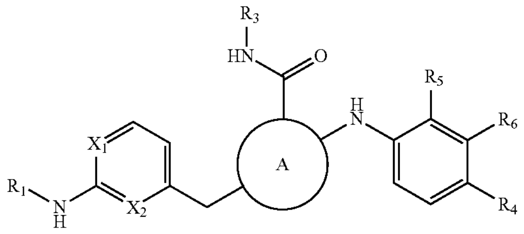

wherein:

ring A is a group represented by general formula (2) or (5) below, where the bonds denoted by *,  and * are bonded to —NH—, —CONH— and —$CH_2$—, respectively:

(2)

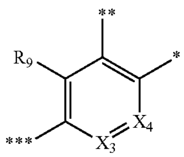

-continued (5)

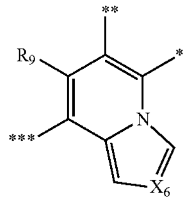

$X_1$, $X_2$, $X_3$, $X_4$, and $X_6$ are each independently —$CR_2$= or —N=;

$R_2$ is a hydrogen atom, a halogen atom, or a C1-6 alkyl group;

$R_1$ is —S(=O) 2-NH—$R_8$ or —$S(=O)_2$—$R_8$;

$R_8$ is a hydrogen atom; a C1-6 alkyl group that is optionally substituted with a halogen atom, a hydroxy group, a C1-6 alkoxy group, a C3-6 cycloalkyl group or a C3-6 heterocycloalkyl group; a monocyclic or bicyclic C3-6 cycloalkyl group that is optionally substituted with a C1-6 alkyl group or a C1-6 alkoxy group; or a monocyclic or bicyclic C3-6 heterocycloalkyl group;

$R_3$ is a hydrogen atom; a C1-6 alkyl group that is optionally substituted with a halogen atom, a hydroxy group or a C1-6 alkoxy group; a C3-6 cycloalkyl group that is optionally substituted with a halogen atom or a C1-6 alkyl group; or a C1-6 alkoxy group that is optionally substituted with a halogen atom, a hydroxy group or a C1-6 alkoxy group;

$R_5$ is a halogen atom or a C1-6 alkyl group;

$R_6$ is a hydrogen atom, a halogen atom or a C1-6 alkyl group, and $R_4$ is a hydrogen atom, a halogen atom, a C1-6 alkyl group, a C2-7 alkenyl group, a C2-7 alkynyl group, a C3-6 cycloalkyl group or a C1-6 alkylthio group, or $R_6$ and $R_4$ form an unsaturated hetero 5-membered ring together with the carbon atoms to which they are bonded; and $R_9$ is a hydrogen atom, a halogen atom, or a C1-6 alkyl group.

2. The composition according to claim 1, wherein said dispersant is at least one selected from methylcellulose, polyvinyl alcohol, hydroxypropylcellulose, copolyvidone, hydroxypropylmethylcellulose, methacrylic acid copolymer, polyvinylpyrrolidone, and hypromellose acetate succinate.

3. The composition according to claim 1, wherein said dispersant is methylcellulose.

4. The composition according to claim 1, wherein the content of said dispersant is 0.1 to 20 parts by weight relative to 1 part by weight of said compound of general formula (1), said salt or said solvate.

5. The composition according to claim 1, further comprising a basic compound.

6. A composition comprising a compound represented by general formula (1) below or a pharmaceutically acceptable salt thereof, or a pharmaceutically acceptable solvate of said compound or salt, and a basic compound:

(1)

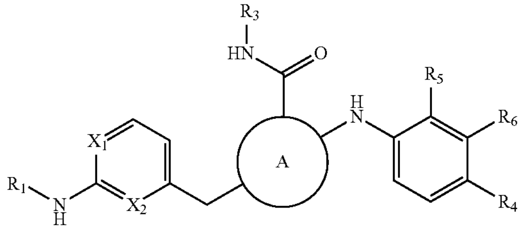

wherein:

ring A is a group represented by general formula (2), or (5) below, where the bonds denoted by *,  and * are bonded to —NH—, —CONH— and —$CH_2$—, respectively:

(2)

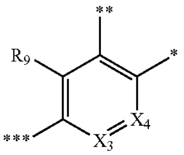

(5)

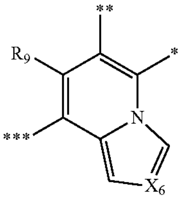

$X_1$, $X_2$, $X_3$, $X_4$ and $X_6$ are each independently —$CR_2$= or —N=;

$R_2$ is a hydrogen atom, a halogen atom, or a C1-6 alkyl group;

$R_1$ is —S(=O) 2-NH—$R_8$ or —$S(=O)_2$—$R_8$;

$R_8$ is a hydrogen atom; a C1-6 alkyl group that is optionally substituted with a halogen atom, a hydroxy group, a C1-6 alkoxy group, a C3-6 cycloalkyl group or a C3-6 heterocycloalkyl group; a monocyclic or bicyclic C3-6 cycloalkyl group that is optionally substituted with a C1-6 alkyl group or a C1-6 alkoxy group; or a monocyclic or bicyclic C3-6 heterocycloalkyl group;

$R_3$ is a hydrogen atom; a C1-6 alkyl group that is optionally substituted with a halogen atom, a hydroxy group or a C1-6 alkoxy group; a C3-6 cycloalkyl group that is optionally substituted with a halogen atom or a C1-6 alkyl group; or a C1-6 alkoxy group that is optionally substituted with a halogen atom, a hydroxy group or a C1-6 alkoxy group;

$R_5$ is a halogen atom or a C1-6 alkyl group;

$R_6$ is a hydrogen atom, a halogen atom or a C1-6 alkyl group, and $R_4$ is a hydrogen atom, a halogen atom, a C1-6 alkyl group, a C2-7 alkenyl group, a C2-7 alkynyl group, a C3-6 cycloalkyl group or a C1-6 alkylthio group, or $R_6$ and $R_4$ form an unsaturated hetero 5-membered ring together with the carbon atoms to which they are bonded; and $R_9$ is a hydrogen atom, a halogen atom, or a C1-6 alkyl group.

7. The composition according to claim 6, wherein said basic compound is at least one selected from meglumine, arginine, histidine, magnesium oxide, calcium silicate, and magnesium stearate.

8. The composition according to claim 6, wherein said basic compound is meglumine.

9. The composition according to claim 6, wherein the content of said basic compound is 0.2 to 40 parts by weight relative to 1 part by weight of said compound of general formula (1), said salt or said solvate.

10. The composition according to claim 1, wherein:

ring A is a group represented by general formula (2);

$R_8$ is a hydrogen atom; a C1-6 alkyl group that is optionally substituted with a halogen atom, a hydroxy group or a C1-6 alkoxy group; or a monocyclic C3-6 cycloalkyl group that is optionally substituted with a C1-6 alkyl group;

$R_3$ is a hydrogen atom; a C1-6 alkyl group; a C3-6 cycloalkyl group; or a C1-6 alkoxy group that is optionally substituted with a hydroxy group;

$R_6$ is a hydrogen atom, a halogen atom or a C1-6 alkyl group, and $R_4$ is a halogen atom or a cyclopropyl group.

11. The composition according to claim 1, wherein said compound of general formula (1) is 2-(4-cyclopropyl-2-fluoroanilino)-3,4-difluoro-5-[[3-fluoro-2-(methylsulfamoylamino)pyridin-4-yl]methyl]benzamide.

12. The composition according to claim 1, further comprising a pharmaceutically acceptable excipient.

13. The composition according to claim 1, in the form of a capsule or a tablet.

14. A method for producing the composition according to claim 1, the method comprising providing a mixture containing: said compound of general formula (1), said salt or said solvate; and said dispersant.

15. A composition comprising 2-(4-cyclopropyl-2-fluoroanilino)-3,4-difluoro-5-[[3-fluoro-2-(methylsulfamoylamino)pyridin-4-yl]methyl]benzamide or a pharmaceutically acceptable salt thereof, or a pharmaceutically acceptable solvate of said compound or salt, together with a compound represented by formula (X) below, wherein the content of said compound of formula (X) is 3.0% by weight or less with respect to the content of said 2-(4-cyclopropyl-2-fluoroanilino)-3,4-difluoro-5-[[3-fluoro-2-(methylsulfamoylamino)pyridin-4-yl]methyl]benzamide, said salt, or said solvate (X)

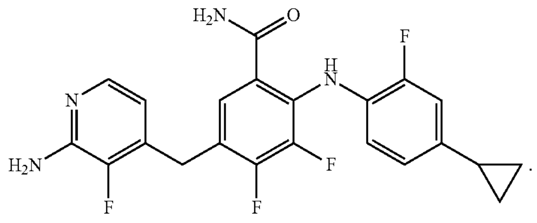

16. The composition according to claim 6, wherein:

ring A is a group represented by general formula (2);

$R_8$ is a hydrogen atom; a C1-6 alkyl group that is optionally substituted with a halogen atom, a hydroxy group or a C1-6 alkoxy group; or a monocyclic C3-6 cycloalkyl group that is optionally substituted with a C1-6 alkyl group;

$R_3$ is a hydrogen atom; a C1-6 alkyl group; a C3-6 cycloalkyl group; or a C1-6 alkoxy group that is optionally substituted with a hydroxy group;

$R_6$ is a hydrogen atom, a halogen atom or a C1-6 alkyl group; and $R_4$ is a halogen atom or a cyclopropyl group.

17. The composition according to claim 6, wherein said compound of general formula (1) is 2-(4-cyclopropyl-2-fluoroanilino)-3,4-difluoro-5-[[3-fluoro-2-(methylsulfamoylamino)pyridin-4-yl]methyl]benzamide.

18. The composition according to claim 6, further comprising a pharmaceutically acceptable excipient.

19. The composition according to claim 6, in the form of a capsule or a tablet.

20. A method for producing the composition according to claim 6, the method comprising providing a mixture containing: said compound of general formula (1), said salt or said solvate; and said basic compound.

21. The composition according to claim 1, wherein: said composition comprises a sodium salt of 2-(4-cyclopropyl-2-fluoroanilino)-3,4-difluoro-5-[[3-fluoro-2-(methylsulfamoylamino)pyridin-4-yl]methyl]benzamide as said salt of the compound of general formula (1); and said dispersant is methylcellulose.

22. The composition according to claim 6, wherein: said composition comprises a sodium salt of 2-(4-cyclopropyl-2-fluoroanilino)-3,4-difluoro-5-[[3-fluoro-2-(methylsulfamoylamino)pyridin-4-yl]methyl]benzamide as said salt of the compound of general formula (1); and said basic compound is meglumine.

23. The composition according to claim 5, wherein: said composition comprises a sodium salt of 2-(4-cyclopropyl-2-fluoroanilino)-3,4-difluoro-5-[[3-fluoro-2-(methylsulfamoylamino)pyridin-4-yl]methyl]benzamide as said salt of the compound of general formula (1); said dispersant is methylcellulose; and said basic compound is meglumine.

* * * * *